(12) United States Patent
De Jong et al.

(10) Patent No.: US 11,180,572 B2
(45) Date of Patent: Nov. 23, 2021

(54) DIMERIC PROTEIN WITH TRIPLE MUTATIONS

(71) Applicant: GENMAB B.V., Utrecht (NL)

(72) Inventors: Rob N. De Jong, Utrecht (NL); Frank Beurskens, Utrecht (NL); Paul Parren, Utrecht (NL); Aran Frank Labrijn, Utrecht (NL); Janine Schuurman, Utrecht (NL); Arjen Vlug, Utrecht (NL); Sandra Verploegen, Utrecht (NL)

(73) Assignee: GENMAB B.V., Utrecht (NL)

( * ) Notice: Subject to any disclaimer, the term of this patent is extended or adjusted under 35 U.S.C. 154(b) by 223 days.

(21) Appl. No.: 14/413,178

(22) PCT Filed: Jul. 5, 2013

(86) PCT No.: PCT/EP2013/064330
§ 371 (c)(1),
(2) Date: Mar. 17, 2015

(87) PCT Pub. No.: WO2014/006217
PCT Pub. Date: Jan. 9, 2014

(65) Prior Publication Data
US 2015/0175707 A1 Jun. 25, 2015

Related U.S. Application Data

(60) Provisional application No. 61/751,045, filed on Jan. 10, 2013.

(30) Foreign Application Priority Data

Jul. 6, 2012 (WO) .................. PCT/EP2012/063339
Jan. 10, 2013 (DK) ................................. 2013 00019

(51) Int. Cl.
| | |
|---|---|
| *C07K 16/00* | (2006.01) |
| *A61K 39/395* | (2006.01) |
| *C07K 16/28* | (2006.01) |
| *C07K 16/30* | (2006.01) |
| *C07K 16/40* | (2006.01) |
| *C07K 16/32* | (2006.01) |
| *C07K 16/10* | (2006.01) |
| *C07K 16/36* | (2006.01) |
| *C07K 16/12* | (2006.01) |
| *A61K 39/00* | (2006.01) |

(52) U.S. Cl.
CPC .............. *C07K 16/40* (2013.01); *C07K 16/00* (2013.01); *C07K 16/1063* (2013.01); *C07K 16/1271* (2013.01); *C07K 16/2809* (2013.01); *C07K 16/2863* (2013.01); *C07K 16/2887* (2013.01); *C07K 16/2896* (2013.01); *C07K 16/32* (2013.01); *C07K 16/36* (2013.01); *A61K 2039/505* (2013.01); *C07K 2317/24* (2013.01); *C07K 2317/31* (2013.01); *C07K 2317/41* (2013.01); *C07K 2317/51* (2013.01); *C07K 2317/515* (2013.01); *C07K 2317/524* (2013.01); *C07K 2317/526* (2013.01); *C07K 2317/53* (2013.01); *C07K 2317/71* (2013.01); *C07K 2317/732* (2013.01); *C07K 2317/734* (2013.01); *C07K 2317/74* (2013.01); *C07K 2317/75* (2013.01); *C07K 2317/77* (2013.01); *C07K 2317/90* (2013.01); *C07K 2317/92* (2013.01)

(58) Field of Classification Search
CPC C07K 16/32; C07K 16/2863; C07K 16/2887; C07K 16/2896; C07K 2317/92; C07K 2317/41; C07K 2317/74; C07K 2317/732; C07K 2317/734; C07K 2317/24; C07K 2317/71; C07K 2317/75; C07K 2317/90; C07K 2317/77; C07K 2317/51; C07K 2317/515; C07K 2317/53; C07K 2317/31; C07K 2317/524; C07K 2317/526; A61K 2039/505; A61P 7/00; A61P 37/06; A61P 37/02; A61P 35/00; A61P 33/00; A61P 31/12; A61P 31/04; A61P 31/00; A61P 29/00
See application file for complete search history.

(56) References Cited

U.S. PATENT DOCUMENTS

| | | |
|---|---|---|
| 4,801,687 A | 1/1989 | Ngo |
| 4,816,567 A | 3/1989 | Cabilly et al. |
| 5,151,504 A | 9/1992 | Croze |
| 5,731,168 A | 3/1998 | Carter et al. |

(Continued)

FOREIGN PATENT DOCUMENTS

| | | |
|---|---|---|
| EP | 0120694 A2 | 10/1984 |
| EP | 0314161 A1 | 5/1989 |

(Continued)

OTHER PUBLICATIONS

Ai-Lazikani B. et al., "Standard conformations for the canonical structures of immunoglobulins," J Mol Biol., vol. 273 (4):927-9488 (1997).

(Continued)

*Primary Examiner* — Phuong Huynh
(74) *Attorney, Agent, or Firm* — Nelson Mullins Riley & Scarborough LLP; Jane E. Remillard, Esq.; Christopher L. Frank

(57) ABSTRACT

The present invention relates to dimeric proteins comprising amino acids at three different positions which are different from those present in a human IgG1. Six of said dimeric proteins are capable of forming a hexameric structure in solution.

45 Claims, 63 Drawing Sheets

Specification includes a Sequence Listing.

(56) References Cited

U.S. PATENT DOCUMENTS

| | | | |
|---|---|---|---|
| 5,834,237 | A | 11/1998 | Jacobs et al. |
| 6,004,940 | A | 12/1999 | Marasco et al. |
| 6,737,056 | B1 | 5/2004 | Presta |
| 7,740,847 | B2 * | 6/2010 | Allan ............... C07K 16/2887 424/133.1 |
| 8,309,690 | B2 * | 11/2012 | Allan ............... A61K 39/39591 424/130.1 |
| 10,759,867 | B2 | 9/2020 | Parren et al. |
| 2004/0110226 | A1 * | 6/2004 | Lazar ..................... C07K 16/00 435/7.1 |
| 2007/0148164 | A1 * | 6/2007 | Farrington ............. C07K 16/00 424/133.1 |
| 2008/0089892 | A1 * | 4/2008 | Allan ..................... C07K 16/00 424/143.1 |
| 2009/0098124 | A1 * | 4/2009 | Stavenhagen ........ C07K 16/283 424/136.1 |
| 2009/0136936 | A1 * | 5/2009 | Georgiou ............... C07K 16/00 435/6.16 |
| 2010/0015133 | A1 | 1/2010 | Igawa et al. |
| 2010/0105873 | A1 | 4/2010 | Allan et al. |
| 2010/0184959 | A1 | 7/2010 | Guler-Gane et al. |
| 2011/0044998 | A1 * | 2/2011 | Bedian ............. A61K 39/39558 424/158.1 |
| 2011/0123440 | A1 | 5/2011 | Hansen et al. |
| 2013/0115208 | A1 | 5/2013 | Ho et al. |
| 2014/0242075 | A1 * | 8/2014 | Parren .................... C07K 16/00 424/136.1 |
| 2015/0139996 | A1 | 5/2015 | De Kruif et al. |
| 2015/0196637 | A1 | 7/2015 | De Kruif et al. |
| 2015/0353636 | A1 | 12/2015 | Parren et al. |
| 2016/0177364 | A1 | 6/2016 | De Kruif et al. |
| 2020/0017600 | A1 | 1/2020 | Goeij et al. |
| 2020/0165352 | A1 | 5/2020 | Goeij et al. |
| 2021/0163619 | A1 | 6/2021 | Parren et al. |

FOREIGN PATENT DOCUMENTS

| | | |
|---|---|---|
| EP | 0481790 A2 | 4/1992 |
| EP | 0523949 A1 | 1/1993 |
| EP | 0814159 A2 | 12/1997 |
| EP | 1439234 A1 | 7/2004 |
| EP | 2 147594 A1 | 1/2010 |
| JP | H 11-500915 A | 1/1999 |
| JP | 2006-109711 A | 4/2006 |
| JP | 2011/508604 A | 3/2011 |
| WO | 00/422072 A2 | 7/2000 |
| WO | 00/63403 A2 | 10/2000 |
| WO | 03/004704 A2 | 1/2003 |
| WO | 2003/107218 A1 | 12/2003 |
| WO | 2004/061104 A2 | 7/2004 |
| WO | 2005/047327 A2 | 5/2005 |
| WO | 2005/070963 A1 | 8/2005 |
| WO | 06/020114 A2 | 2/2006 |
| WO | 06/053301 A2 | 5/2006 |
| WO | 06/105062 A2 | 10/2006 |
| WO | 2006/104989 A2 | 10/2006 |
| WO | 2006105062 A2 | 10/2006 |
| WO | 2007/005612 A2 | 1/2007 |
| WO | 07/039818 A2 | 4/2007 |
| WO | 2008/090958 A1 | 7/2008 |
| WO | 2008/114011 A2 | 9/2008 |
| WO | 2009/006520 A1 | 1/2009 |
| WO | 2010/0451943 A1 | 4/2010 |
| WO | 2012/058768 A1 | 5/2010 |
| WO | 2010/106180 A2 | 9/2010 |
| WO | 2011/091078 A2 | 7/2011 |
| WO | 2011/131746 A2 | 10/2011 |
| WO | 2012/058768 A1 | 5/2012 |
| WO | 2012/125850 A1 | 9/2012 |
| WO | 2013/004842 A2 | 1/2013 |

OTHER PUBLICATIONS

Attaelmannan M. et al., "Understanding and identifying monoclonal gammopathies," Clin. Chem., vol. 46(8 Pt 2):1230-1238 (2000).

Bendig, MM., "The production of foreign proteins in mammalian cells," Genet Eng., (7):91-127 (1988).

Bostrom, J., "Variants of the antibody herceptin that interact with HER2 and VEGF at the antigen binding site," Science, vol. 323(5921):1610-1614 (2009).

Capelle, MA et al., "Spectroscopic characterization of; antibodies adsorbed to aluminium adjuvants: correlation with antibody vaccine immunogenicity," Vaccine, vol. 23(14):1686-1694 (2005).

Coligan JE, "Commonly used detergents," Curr Protoc Protein Sci., Appendix 1:Appendix 1B (1998).

De Kruif, J. et al., "Generation of stable cell clones expressing mixtures of human antibodies," Biotechnol Bioeng, vol. 106(5): 741-750 (2010).

Devries, SJ. et al., "The HADDOCK web server for data driven biomolecular docking," Nature Protocols, vol. 5(5):883-897 (2010).

Demeule, B., "Characterization of protein aggregation: the case of a therapeutic immunoglobulin," Biochem Biophys. Acta., vol. 1774(1):146-153 (2007).

Demeule, B., "Detection and characterization of protein aggregates by fluorescence microscopy," Int J. Pharm, vol. 329(1-2):37-45 (2007).

Farnan, D. et al., "Multiproduct high-resolution monoclonal antibody charge variant separations by pH gradient ion-exchange chromatography," Anal Chem, vol. 81(21): 8846-8857 (2009).

Idusogie, EE, "Mapping of the C1q binding site on rituxan, a chimeric antibody with a human IgG1 Fc," J Immunol., vol. 164(8):4178-4184 (2000).

Ionescu, RM. et al, "Contribution of variable domains to the stability of humanized IgG1 monoclonal antibodies," J. Pharm Sci., vol. 97(4): 1414-1426 (2008).

Kabat, EA., et al., "Identical V region amino acid sequences and segments of sequences in antibodies of different specificities. Relative contributions of VH and VL genes, mini genes, and complementarity-determining regions to binding of antibody-combining sites," J Immunol., vol. 147(5):1709-1719 (1991).

Lee, B. et al., "The interpretation of protein structures: estimation of static accessibility," J Mol Biol.,vol. 55(3), 379-400 (1971).

Schaefer, G. et al, "A two-in-one antibody against HER3 and EGFR has superior inhibitory activity compared with monospecific antibodies," Cancer Cell, vol. 20(4): 472-486 (2011).

Tahallah, N., "The effect of the source pressure on the abundance of ions of noncovalent protein assemblies in an electrospray ionization orthogonal time-of-flight instrument," Rapid Commun Mass Spectrom, vol. 15(8):596-601 (2001).

Burton, D.R., "Antibody: the flexible adaptor molecule," Trends Biochem Sci., vol. 15(2): 64-69. (1990).

Burton, D.R., "Immunoglobulin G: functional sites," Mol Immunol., vol. 22(3): 161-206 (1985).

Dall'Acqua, W.F. et al., "Modulation of the effector functions of a human IgG1 through engineering of its hinge region," J Immunol., vol. 177(2):1129-1138. (2006).

Desjarlais, Jr. et al., "Modulation of antibody effector function," Exp Cell Res, vol. 317(9): 1278-1285 (2011).

Finstein, A. et al., "Immunoglobulin flexibility in complement activation," Immunology Today, vol. 7(6): 169-174 (1986).

Hornick, J.L. et al., "Single Amino Acid Substitution in the Fc Region of Chimeric TNT-3 Antibody Accelerates Clearance and improves Immunoscintigraphy of solid tumors," Journal of Nuclear Medicine, vol. 41(2): 355-362 (2000).

Hughes-Jones, N.C. et al., "Reaction between the isolated globular sub-units of the complement component C1q and IgG-complexes," Mol Immunol., vol. 16(9): 697-701 (1979).

Idusogie, E.E., et al., "Engineered Antibodies with Increased Activity to Recruit Complement," J Immunol., vol. 166 (4):2571-25755 (2001).

Idusogie, E.E., et al., "Mapping of the C1q binding Site on Rituxan, a Chimeric Antibody with a Human IgG1 Fc," J Immunol., vol. 164(8):4178-4184. (2000).

International Preliminary Report on Patentability, PCT/EP2012/063339, dated Jan. 7, 2014, 16 pages.

(56) References Cited

OTHER PUBLICATIONS

International Preliminary Report on Patentability, PCT/EP2013/064330, dated Jan. 6, 2015, 7 pages.
International Search Report and Written Opinion, PCT/EP2012/063339, dated Jan. 25, 2013, 24 pages.
International Search Report and Written Opinion, PCT/EP2013/064330, dated Sep. 12, 2013, 11 pages.
Kaneko, E. et al, "Optimizing Therapeutic Antibody Function: Progress with Fc domain Engineering," BioDrugs, vol. 25(1):1-11 (2011).
Kubota, T., et al., "Engineered therapeutic antibodies with improved effector functions," Cancer Sci., vol. 100(9): 1566-1572. (2009).
Kuznetsov, Y., "Chimeric Human-Simian Anti-CD4 Antibodies Form Crystalline High Symmetry Particles," Journal of Structural Biology, vol. 131(2): p. 108-115 (2000).
Lazar, G.A., et al., "Engineered antibody Fc variants with enhanced effector function," PNAS, vol. 103(11): 4005-4010 (2006).
Mekhaiel, D.N., et al., "Polymeric human Fc-fusion proteins with modified effector functions," Sci Rep., vol. 1(124) 1-11(2011).
Michaelsen, T.E., et al., "Structural Difference in the Complement Activation Site of Human IgG1 and IgG3," Scandinavian Journal of Immunology, vol. 70(6): 553-564 (2009).
Moller, N.P. et al., "Fc-mediated immune precipitation. II. Analysis of precipitating immune complexes by rate-zonal ultracentrifugation," Immunology, vol. 38(3): 641-648. (1979).
Moore, G.L., et al., "Engineered Fc variant antibodies with enhanced ability to recruit complement and mediate effector functions," MAbs, vol. 2(2): 181-189. (2010).
Natsume, A. et al., "Improving effector functions of antibodies for cancer treatment: Enhancing ADCC and CDC," Drug Des Devel Ther., vol. 3: 7-16 (2009).
Natsume, A., et al., Engineered anti-CD20 Antibodies with Enhanced Complement-activating Capacity Mediate Potent Anti-lymphoma Activity, Cancer Sci., vol. 100(12):2411-2418 (2009).
Natsume, A., et al., Engineered Antibodies of IgG1/IgG3 Mixed Isotype with Enhanced Cytotoxic Activities, Cancer Res, vol. 68(10): 3863-3872 (2008).
Parren, P. et al., "Fc-Fc Interactions and Complement Activation," FASEB Summer Research Conference, Snowmass, Co., Jul. 5-10, 2010, 39 pages.
Perkins, S.J., "Molecular modelling of human complement subcomponent C1q and its complex with C1r2C1s2 derived from neutron-scattering curves and hydrodynamic properties," Biochem J., vol. 228(1):13-26 (1985).
Pinteric, L. et al., "Ultrastructure of the Fc fragment of human immunoglobulin G," Immunochemistry, vol. 8(11): 1041-1045 (1971).
Poon, P.H. et al., "Conformation and restricted segmental flexibility of C1, the first component of human complement," J Mol Biol., vol. 8(3):563-577 (1983).
Reid, K.B., "Proteins involved in the activation and control of the two pathways of human complement," Biochem Soc Trans., vol. 11(1):1-12 (1983).
Saphire, E.O. et al., "Crystal structure of a neutralizing human IgG against HIV-1: A template for vaccine design," Science, vol. 293(5532):1155-1159 (2011).
Sato, F., et al., "A complement-dependent cytotoxicity-enhancing anti-CD20 antibody mediating potent antitumor activity in the humanized NOD/Shi-scid, IL-2Rgamma(null) mouse lymphoma model," Cancer Immunol Immunother., vol. 59(12): 1791-1800. (2010).
Shields, Robert L. et al., "High Resolution Mapping of the Binding Site on Human IgG1 for FcgammaRI, FcgammaRII, FcgammaRIII and FcRn and design of IgG1 variants with improved binding to the FcgammaR," The Journal of Biological Chemistry, vol. 276(9):6591-6604 (2001).
Sledge, C.R. et al., "Binding properties of the human complement protein C1q," J Biol Chem., vol. 248(8): 2818-2823. (1973).
Smith, R.I. et al., "Recombinant Polymeric IgG: an approach to engineering more potent antibodies," Biotechnology (N Y), ol. 12(7): 683-638(1994).
Smith, R.I., et al., "Addition of a u-tailpiece to IgG Results in Polymeric Antibodies with Enhanced Effector Functions Including Complement-mediated cytolysis by IgG4," J Immunol., vol. 154(5): 2226-2236 (1995).
Tao, M.H., et al., "Structural features of human immunoglobulin G that determine isotype-specific differences in complement activation," J Exp Med., vol. 178(2):661-667. (1993).
Thommesen, J.E., et al., "Lysine 322 in the human IgG3 C(H)2 domain is crucial for antibody dependent complement activation," Mol Immunol., vol. 37(16): 995-1004 (2000).
Tschopp, J., et al., "Antigen-independent binding of IgG dimers to C 1 q as studied by sedimentation equilibrium, complement fixation and electron microscopy," Eur J Immunol., vol. 10(7): 529-535. (1980).
Weiss, V., et al., "Functional model of subcomponent C1 of human complement," J Mol Biol., vol. 189(3): 573-581 (1986).
Xu, Y., et al., "Residue at position 331 in the IgG1 and IgG4 CH2 domains contributes to their differential ability to bind and activate complement," J Biol Chem., vol. 269(5): 3469-3474 (1994).
Yamaguchi, A. et al., "Current Technological Development of Antibody Therapeutics," Immun., Endoc.& Metab. Agents in Med. Chem., vol. 11:21-32. (2011).
U.S. Appl. No. 14/760,135, filed Jul. 9, 2015, Paul Parren.
U.S. Appl. No. 14/760,135, Jan. 24, 2018.
U.S. Appl. No. 14/760,135, Oct. 5, 2017.
U.S. Appl. No. 14/130,543, filed May 5, 2014, Paul Parren.
U.S. Appl. No. 14/130,543, Jan. 11, 2019.
U.S. Appl. No. 14/130,543, May 23, 2018.
U.S. Appl. No. 14/130,543, Dec. 6, 2017.
U.S. Appl. No. 14/130,543, Jun. 23, 2017.
U.S. Appl. No. 14/130,543, Mar. 9, 2017.
U.S. Appl. No. 14/130,543, Nov. 18, 2016.
U.S. Appl. No. 14/130,543, Jul. 29, 2016.
U.S. Appl. No. 14/130,543, Aug. 23, 2019.
U.S. Appl. No. 14/760,135, Jul. 10, 2019.
U.S. Appl. No. 14/760,135, Sep. 13, 2018.
U.S. Appl. No. 16/786,563, filed Feb. 10, 2020, Bart De Goeij.
U.S. Appl. No. 16/512,206, filed Jul. 15, 2019, Bart De Goeij.
U.S. Appl. No. 16/786,563, dated Jun. 29, 2020, M. Allen.
U.S. Appl. No. 16/786,563, dated Mar. 6, 2020, M. Allen.
U.S. Appl. No. 16/512,206, dated Apr. 8, 2020, M. Allen.
U.S. Appl. No. 16/512,206, dated Oct. 7, 2019, M. Allen.
U.S. Appl. No. 14/760,135, filed Jul. 6, 2020, Paul Parren.
U.S. Appl. No. 14/760,135, dated Dec. 24, 2020, C. Dahle.
U.S. Appl. No. 14/130,543, dated Apr. 7, 2020, C. Dahle.
U.S. Appl. No. 16/786,563, dated Dec. 3, 2020, M. Allen.
U.S. Appl. No. 16/512,206, dated Dec. 30, 2020, M. Allen.

* cited by examiner

IgG molecules in hexamer formation

Figure 2

```
IgG1    247 PKDTLMISRTPEVTCVVVDVSHEDPEVKFNWYVDGVEVHNAKTKPREEQYNSTYRVVSVL 306
IgG1f       PKDTLMISRTPEVTCVVVDVSHEDPEVKFNWYVDGVEVHNAKTKPREEQYNSTYRVVSVL
IgG2        PKDTLMISRTPEVTCVVVDVSHEDPEVQFNWYVDGVEVHNAKTKPREEQFNSTFRVVSVL
IgG3        PKDTLMISRTPEVTCVVVDVSHEDPEVQFKWYVDGVEVHNAKTKPREEQYNSTFRVVSVL
IgG4        PKDTLMISRTPEVTCVVVDVSQEDPEVQFNWYVDGVEVHNAKTKPREEQFNSTYRVVSVL
IgE         SPEDLFIRKSPTITCLVVDLAPSKGTVNLTWSRASGKPVNHSTRKEEKQRNGTLTVTSTL
IgA1        ALEDLLLGSEANLTCTLTGLRDASG-VTFTWTPSSGKSAVQGP--PERDLCGCYSVSSVL
IgA2        ALEDLLLGSEANLTCTLTGLRDASG-ATFTWTPSSGKSAVQGP--PERDLCGCYSVSSVL
IgM         SFASIFLTKSTKLTCLVTDLTTYDS-VTISWTRQNGEAVKTHTNISESHPNATFSAVGEA
IgD         AVQDLWLRDKATFTCFVVGSDLKDAHLTWEVAG-KVPTGGVEEGLLERHSNGSQSQHSRL

IgG1    307 TVLHQDWLNGKEYKCKVSNKALPAPIEKTIS-KAKGQPREPQVYTLPPSRDELTK-NQVS 364
IgG1f       TVLHQDWLNGKEYKCKVSNKALPAPIEKTIS--KAKGQPREPQVYTLPPSREEMTK-NQVS
IgG2        TVVHQDWLNGKEYKCKVSNKGLPAPIEKTIS--KTKGQPREPQVYTLPPSREEMTK-NQVS
IgG3        TVLHQDWLNGKEYKCKVSNKALPAPIEKTIS--KTKGQPREPQVYTLPPSREEMTK-NQVS
IgG4        TVLHQDWLNGKEYKCKVSNKGLPSSIEKTIS--KAKGQPREPQVYTLPPSQEEMTK-NQVS
IgE         PVGTRDWIEGETYQCRVTHPHLPRALMRSTT-KTSGPRAAPEVYAFATPEWPGSR-DKRT
IgA1        PGCAEPWNHGKTFTCTAAYPESKTPLTATLS--KSGNTFRPEVHLLPPPSEELALNELVT
IgA2        PGCAQPWNHGETFTCTAAHPELKTPLTANIT--KSGNTFRPEVHLLPPPSEELALNELVT
IgM         SICEDDWNSGERFTCTVTHTDLPSPLKQTISRPKGVALHRPDVYLLPPAREQLNLRESAT
IgD         TLPRSLWNAGTSVTCTLNHPSLPPQRLMALREPAAQAPVKLSLNLLASSDPPEAA----SW

IgG1    365 LTCLVKGFYPSDIAVEWESNGQ--PENNYKTTPPVLDS---DGSFFLYSKLTVDKSRWQQ 419
IgG1f       LTCLVKGFYPSDIAVEWESNGQ--PENNYKTTPPVLDS---DGSFFLYSKLTVDKSRWQQ
IgG2        LTCLVKGFYPSDIAVEWESNGQ--PENNYKTTPPMLDS---DGSFFLYSKLTVDKSRWQQ
IgG3        LTCLVKGFYPSDIAVEWESSGQ--PENNYNTTPPMLDS----DGSFFLYSKLTVDKSRWQQ
IgG4        LTCLVKGFYPSDIAVEWESNGQ--PENNYKTTPPVLDS---DGSFFLYSRLTVDKSRWQE
IgE         LACLIQNFMPEDISVQWLHNEVQLPDARHSTTQPRKTK---GSGFFVFSRLEVTRAEWEQ
IgA1        LTCLARGFSPKDVLVRWLQGSQELPREKYLTWASRQEPSQGTTTFAVTSILRVAAEDWKK
IgA2        LTCLARGFSPKDVLVRWLQGSQELPREKYLTWASRQEPSQGTTTFAVTSILRVAAEDWKK
IgM         ITCLVTGFSPADVFVQWMQRGQPLSPEKYVTSAPMPEP-QAPGRYFAHSILTVSEEEWNT
IgD         LLCEVSGFSPPNILLMWLEDQREVNTSGFAPARPPPQP--GSTTFWAWSVLRVPAPPSPQ

IgG1    420 GNVFSCSVMHEALHN-HYTQKSLSLSPGK------------------- 447
IgG1f       GNVFSCSVMHEALHN-HYTQKSLSLSPGK-------------------
IgG2        GNVFSCSVMHEALHN-HYTQKSLSLSPGK-------------------
IgG3        GNIFSCSVMHEALHN-RFTQKSLSLSPGK-------------------
IgG4        GNVFSCSVMHEALHN-HYTQKSLSLSLGK-------------------
IgE         KDEFICRAVHEAASPSQTVQRAVSVNPGK-------------------
IgA1        GDTFSCMVGHEALPL-AFTQKTIDRLAGKPTHVNVSVVMAEVDGTCY
IgA2        GDTFSCMVGHEALPL-AFTQKTIDRLAGKPTHVNVSVVMAEVDGTCY
IgM         GETYTCVA-HEALPN-RVTERTVDKSTGKPTLYNVSLVMSDTAGTCY
IgD         PATYTCVVSHEDSRTLLNASRSLEVSYVTDHGPMK-------------
```

Figure 2 (continued)

```
IgG1  = aa 130-330 of Uniprot entry P01857
IgG1f= IgG1 allotypic variant "f"
IgG2  = aa 126-326 of Uniprot entry P01859
IgG3  = aa 177-377 of Uniprot entry P01860
IgG4  = aa 127-327 of Uniprot entry P01861
IgE   = aa 225-428 of Uniprot entry P01854
IgA1  = aa 133-353 of Uniprot entry P01876
IgA2  = aa 120-340 of Uniprot entry P01877
IgM   = aa 230-452 of Uniprot entry P01871
IgD   = aa 176-384 of Uniprot entry P01880
```

```
              3         3                   3          3                          3               3   3 3        3   4
              0         1                   3          4                          5               6   8 9        9   0
              123456789012345678901 2 3456 78901 234567890123456789012345678901234567 89012345678901 234567 890123456789
ED
2F8-G1        RVVSVLTVLHQDWLNGKEYKCKVSNKALPAPI-EKTI-SKAKG-QPREPQVYTLPPSKDE--LTKNQVSLTCLVKGFYPSDIAV--EWESN-GQ----PENNYKTTPPVLDS
2F8-G4        KVVSVLTVLHQDWLNGKEYKCKVSNKGLPSSI-EKTI-SKAKG-QPREPQVYTLPPSQEE--MTKNQVSLTCLVKGFYPSDIAV--EWESN-GQ----PENNYKTTPPVLDS
KABAT         3         3                   3          3                          3               3   3 3            4
              2         3                   4          5                          6               7   8 9            2
              0123456789012345678901234567890123456789012345678901234567890123456789012345678901234567890123456789012345678
                                                       A 4         4                   4
              0         1                   2
              1 23456789012345678901234567890123456
ED
2F8-G1        -D---GSFFLYSKLTVDKSRWQQGNVFSCSVMHEALHNHYTQKSLSLSPGK
2F8-G4        -D---GSFFLYSRLTVDKSRWQEGNVFSCSVMHEALHNHYTQKSLSLSLGK
KABAT         4         4                   4         4
              3         4                   5         6
              901234567890123456789012345678901234567 8
```

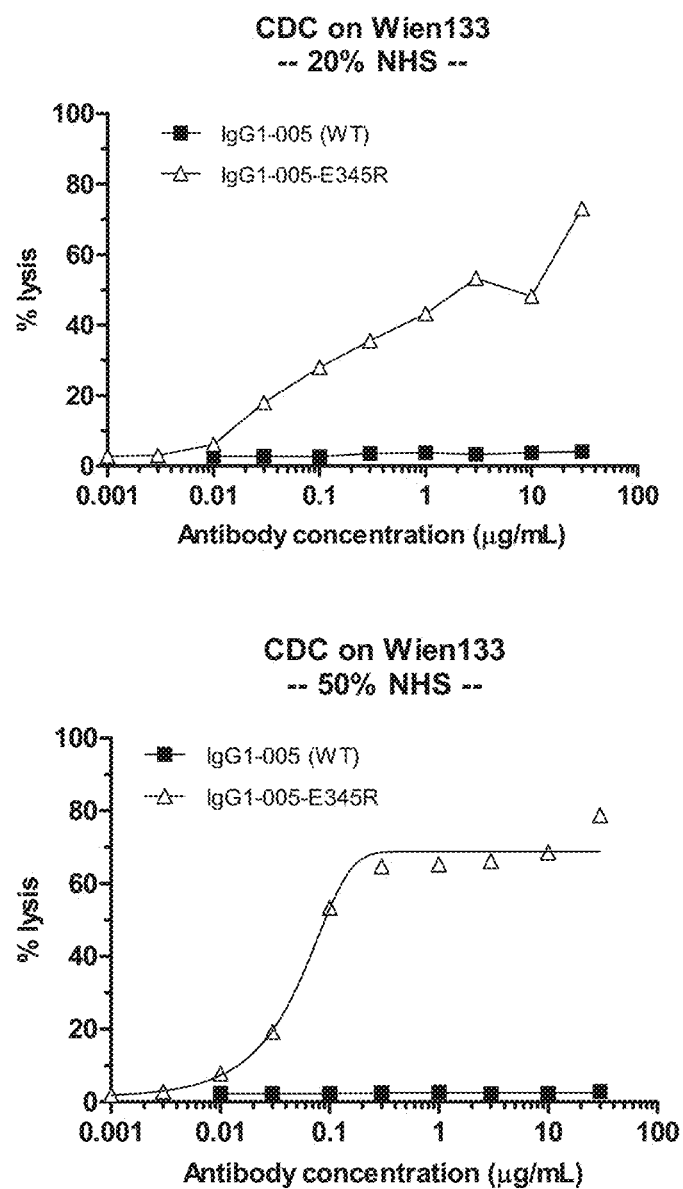

Figure 5D
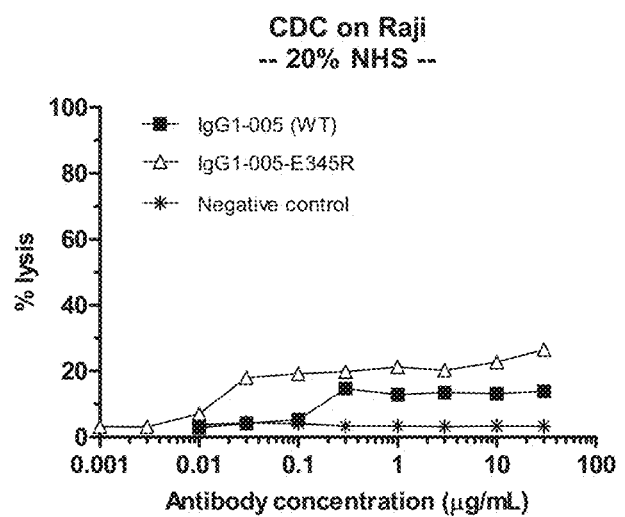
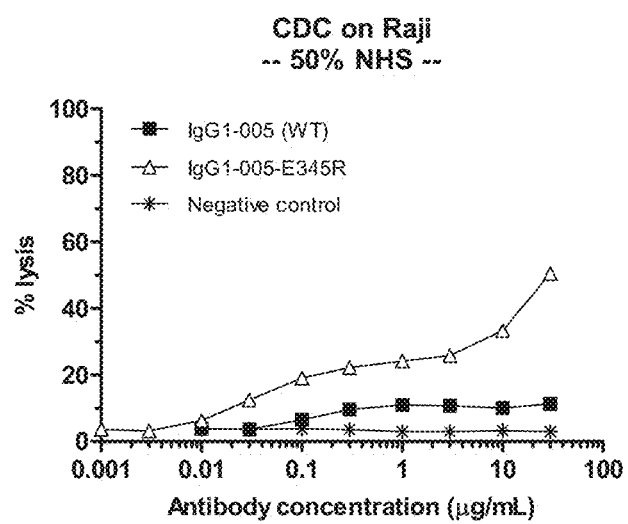

Figure 5D cont'd
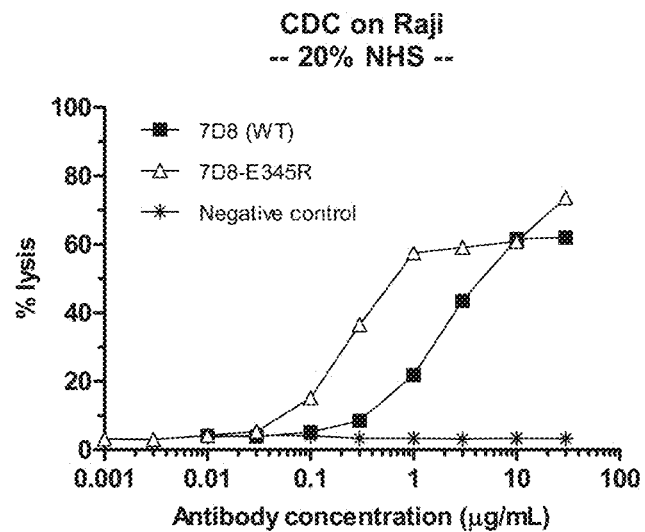
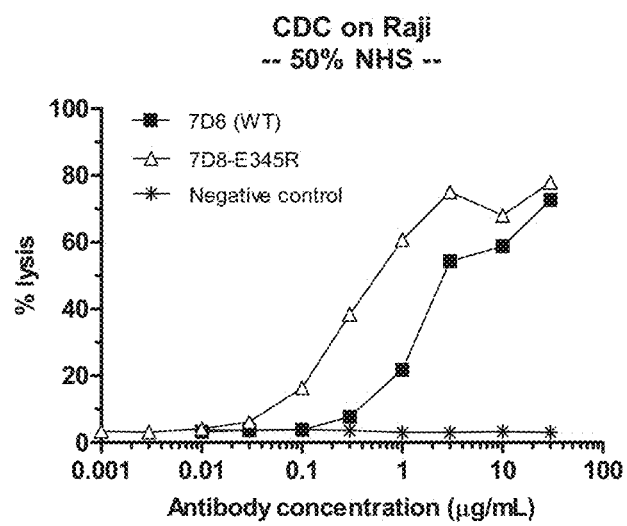

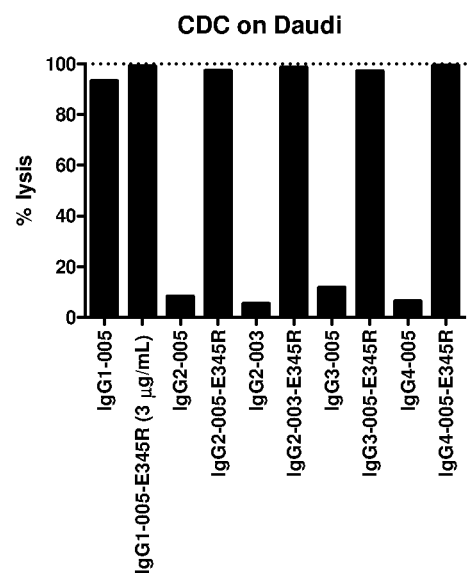 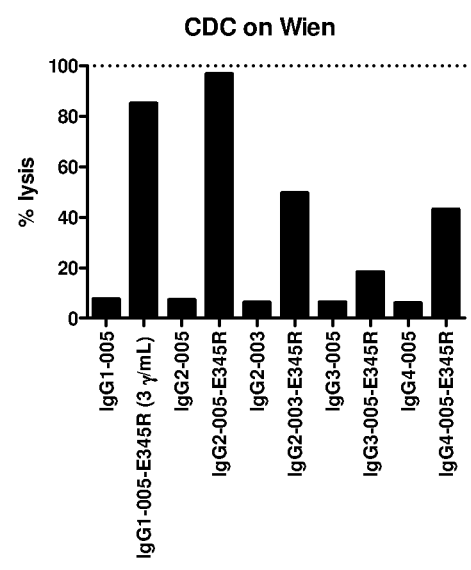
Figure 19A — CDC on Daudi
Figure 19B — CDC on Wien

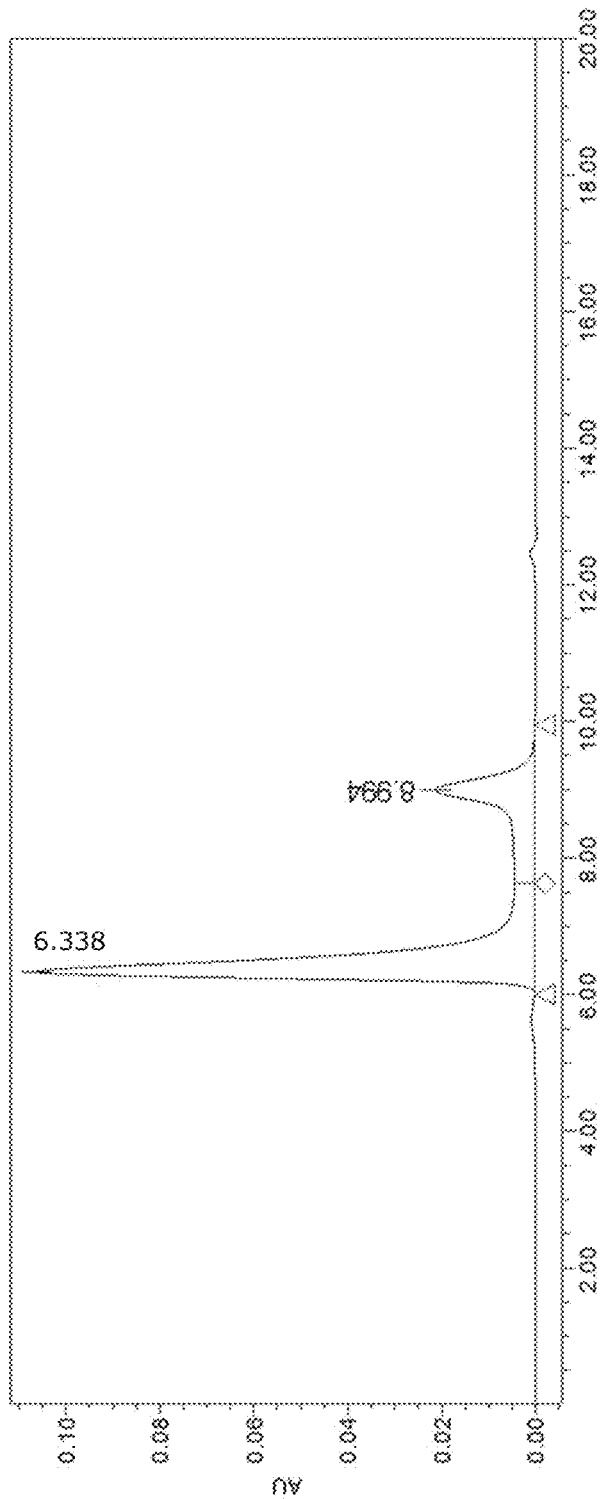

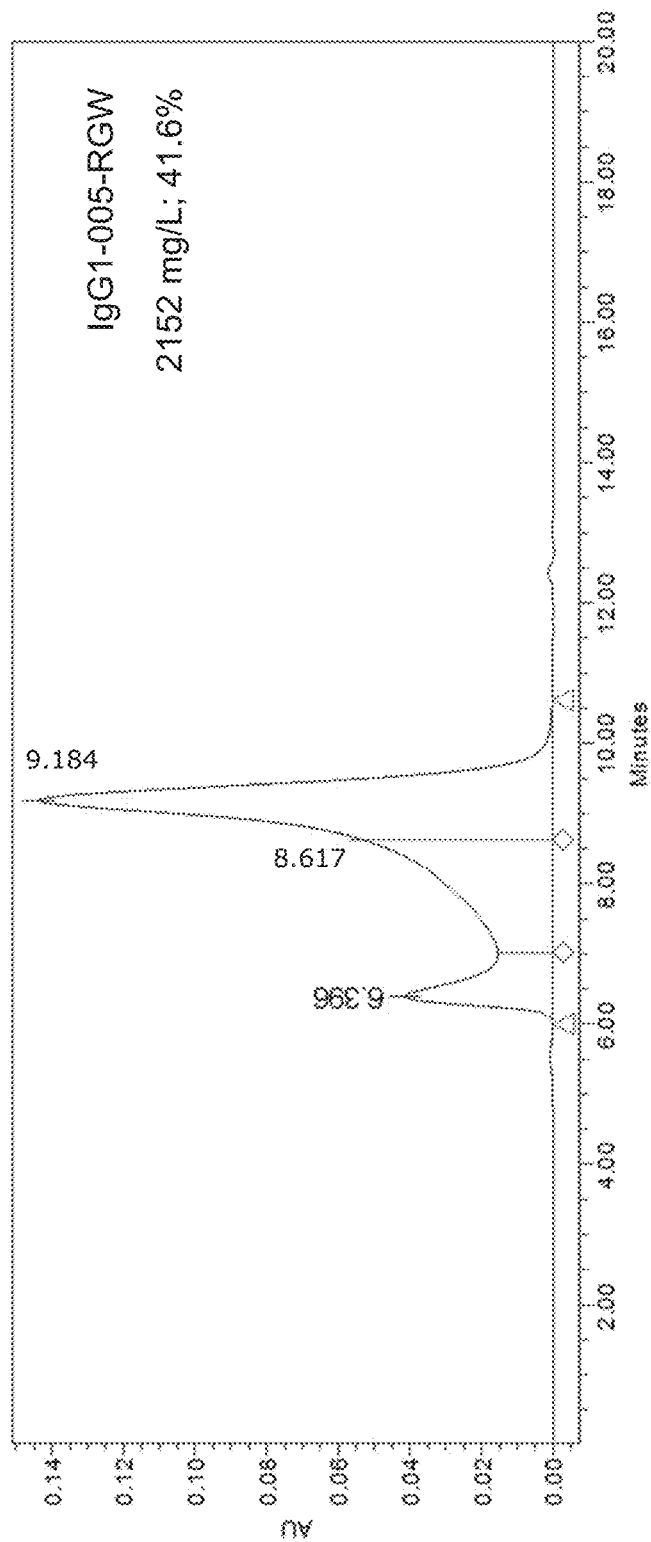

SEQUENCE LISTING

<160> NUMBER OF SEQ ID NOS: 15

<210> SEQ ID NO 1
<211> LENGTH: 330
<212> TYPE: PRT
<213> ORGANISM: HOMO SAPIENS

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: HOMO SAPIENS

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 3
<211> LENGTH: 377
<212> TYPE: PRT
<213> ORGANISM: HOMO SAPIENS

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

-continued

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 4
<211> LENGTH: 327
<212> TYPE: PRT
<213> ORGANISM: HOMO SAPIENS

<400> SEQUENCE: 4

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 330
<212> TYPE: PRT
<213> ORGANISM: HOMO SAPIENS

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                    115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 6
<211> LENGTH: 201
<212> TYPE: PRT
<213> ORGANISM: HOMO SAPIENS

<400> SEQUENCE: 6

Pro Lys Asp Thr Leu Met Ile Ser Arg Thr Pro Glu Val Thr Cys Val
1               5                   10                  15

Val Val Asp Val Ser His Glu Asp Pro Glu Val Lys Phe Asn Trp Tyr
                20                  25                  30

Val Asp Gly Val Glu Val His Asn Ala Lys Thr Lys Pro Arg Glu Glu
            35                  40                  45

Gln Tyr Asn Ser Thr Tyr Arg Val Val Ser Val Leu Thr Val Leu His
        50                  55                  60

Gln Asp Trp Leu Asn Gly Lys Glu Tyr Lys Cys Lys Val Ser Asn Lys
65                  70                  75                  80

Ala Leu Pro Ala Pro Ile Glu Lys Thr Ile Ser Lys Ala Lys Gly Gln
                85                  90                  95

Pro Arg Glu Pro Gln Val Tyr Thr Leu Pro Pro Ser Arg Asp Glu Leu
            100                 105                 110
```

```
Thr Lys Asn Gln Val Ser Leu Thr Cys Leu Val Lys Gly Phe Tyr Pro
            115                 120                 125

Ser Asp Ile Ala Val Glu Trp Glu Ser Asn Gly Gln Pro Glu Asn Asn
        130                 135                 140

Tyr Lys Thr Thr Pro Pro Val Leu Asp Ser Asp Gly Ser Phe Phe Leu
145                 150                 155                 160

Tyr Ser Lys Leu Thr Val Asp Lys Ser Arg Trp Gln Gln Gly Asn Val
                165                 170                 175

Phe Ser Cys Ser Val Met His Glu Ala Leu His Asn His Tyr Thr Gln
                180                 185                 190

Lys Ser Leu Ser Leu Ser Pro Gly Lys
            195                 200

<210> SEQ ID NO 7
<211> LENGTH: 201
<212> TYPE: PRT
<213> ORGANISM: HOMO SAPIENS

<400> SEQUENCE: 7

Pro Lys Asp Thr Leu Met Ile Ser Arg Thr Pro Glu Val Thr Cys Val
1               5                   10                  15

Val Val Asp Val Ser His Glu Asp Pro Glu Val Lys Phe Asn Trp Tyr
            20                  25                  30

Val Asp Gly Val Glu Val His Asn Ala Lys Thr Lys Pro Arg Glu Glu
        35                  40                  45

Gln Tyr Asn Ser Thr Tyr Arg Val Val Ser Val Leu Thr Val Leu His
    50                  55                  60

Gln Asp Trp Leu Asn Gly Lys Glu Tyr Lys Cys Lys Val Ser Asn Lys
65                  70                  75                  80

Ala Leu Pro Ala Pro Ile Glu Lys Thr Ile Ser Lys Ala Lys Gly Gln
                85                  90                  95

Pro Arg Glu Pro Gln Val Tyr Thr Leu Pro Pro Ser Arg Glu Glu Met
            100                 105                 110

Thr Lys Asn Gln Val Ser Leu Thr Cys Leu Val Lys Gly Phe Tyr Pro
            115                 120                 125

Ser Asp Ile Ala Val Glu Trp Glu Ser Asn Gly Gln Pro Glu Asn Asn
        130                 135                 140

Tyr Lys Thr Thr Pro Pro Val Leu Asp Ser Asp Gly Ser Phe Phe Leu
145                 150                 155                 160

Tyr Ser Lys Leu Thr Val Asp Lys Ser Arg Trp Gln Gln Gly Asn Val
                165                 170                 175

Phe Ser Cys Ser Val Met His Glu Ala Leu His Asn His Tyr Thr Gln
                180                 185                 190

Lys Ser Leu Ser Leu Ser Pro Gly Lys
            195                 200

<210> SEQ ID NO 8
<211> LENGTH: 201
<212> TYPE: PRT
<213> ORGANISM: HOMO SAPIENS

<400> SEQUENCE: 8

Pro Lys Asp Thr Leu Met Ile Ser Arg Thr Pro Glu Val Thr Cys Val
1               5                   10                  15

Val Val Asp Val Ser His Glu Asp Pro Glu Val Gln Phe Asn Trp Tyr
            20                  25                  30
```

```
Val Asp Gly Val Glu Val His Asn Ala Lys Thr Lys Pro Arg Glu Glu
        35                  40                  45

Gln Phe Asn Ser Thr Phe Arg Val Val Ser Val Leu Thr Val Val His
 50                  55                  60

Gln Asp Trp Leu Asn Gly Lys Glu Tyr Lys Cys Lys Val Ser Asn Lys
 65                  70                  75                  80

Gly Leu Pro Ala Pro Ile Glu Lys Thr Ile Ser Lys Thr Lys Gly Gln
                 85                  90                  95

Pro Arg Glu Pro Gln Val Tyr Thr Leu Pro Pro Ser Arg Glu Glu Met
                100                 105                 110

Thr Lys Asn Gln Val Ser Leu Thr Cys Leu Val Lys Gly Phe Tyr Pro
            115                 120                 125

Ser Asp Ile Ala Val Glu Trp Glu Ser Asn Gly Gln Pro Glu Asn Asn
130                 135                 140

Tyr Lys Thr Thr Pro Pro Met Leu Asp Ser Asp Gly Ser Phe Phe Leu
145                 150                 155                 160

Tyr Ser Lys Leu Thr Val Asp Lys Ser Arg Trp Gln Gln Gly Asn Val
                165                 170                 175

Phe Ser Cys Ser Val Met His Glu Ala Leu His Asn His Tyr Thr Gln
            180                 185                 190

Lys Ser Leu Ser Leu Ser Pro Gly Lys
            195                 200

<210> SEQ ID NO 9
<211> LENGTH: 201
<212> TYPE: PRT
<213> ORGANISM: HOMO SAPIENS

<400> SEQUENCE: 9

Pro Lys Asp Thr Leu Met Ile Ser Arg Thr Pro Glu Val Thr Cys Val
 1               5                  10                  15

Val Val Asp Val Ser His Glu Asp Pro Glu Val Gln Phe Lys Trp Tyr
                 20                  25                  30

Val Asp Gly Val Glu Val His Asn Ala Lys Thr Lys Pro Arg Glu Glu
        35                  40                  45

Gln Tyr Asn Ser Thr Phe Arg Val Val Ser Val Leu Thr Val Leu His
 50                  55                  60

Gln Asp Trp Leu Asn Gly Lys Glu Tyr Lys Cys Lys Val Ser Asn Lys
 65                  70                  75                  80

Ala Leu Pro Ala Pro Ile Glu Lys Thr Ile Ser Lys Thr Lys Gly Gln
                 85                  90                  95

Pro Arg Glu Pro Gln Val Tyr Thr Leu Pro Pro Ser Arg Glu Glu Met
                100                 105                 110

Thr Lys Asn Gln Val Ser Leu Thr Cys Leu Val Lys Gly Phe Tyr Pro
            115                 120                 125

Ser Asp Ile Ala Val Glu Trp Glu Ser Gly Gln Pro Glu Asn Asn
130                 135                 140

Tyr Asn Thr Thr Pro Pro Met Leu Asp Ser Asp Gly Ser Phe Phe Leu
145                 150                 155                 160

Tyr Ser Lys Leu Thr Val Asp Lys Ser Arg Trp Gln Gln Gly Asn Ile
                165                 170                 175

Phe Ser Cys Ser Val Met His Glu Ala Leu His Asn Arg Phe Thr Gln
            180                 185                 190

Lys Ser Leu Ser Leu Ser Pro Gly Lys
            195                 200
```

<210> SEQ ID NO 10
<211> LENGTH: 201
<212> TYPE: PRT
<213> ORGANISM: HOMO SAPIENS

<400> SEQUENCE: 10

```
Pro Lys Asp Thr Leu Met Ile Ser Arg Thr Pro Glu Val Thr Cys Val
1               5                   10                  15

Val Val Asp Val Ser Gln Glu Asp Pro Glu Val Gln Phe Asn Trp Tyr
            20                  25                  30

Val Asp Gly Val Glu Val His Asn Ala Lys Thr Lys Pro Arg Glu Glu
        35                  40                  45

Gln Phe Asn Ser Thr Tyr Arg Val Val Ser Val Leu Thr Val Leu His
    50                  55                  60

Gln Asp Trp Leu Asn Gly Lys Glu Tyr Lys Cys Lys Val Ser Asn Lys
65                  70                  75                  80

Gly Leu Pro Ser Ser Ile Glu Lys Thr Ile Ser Lys Ala Lys Gly Gln
                85                  90                  95

Pro Arg Glu Pro Gln Val Tyr Thr Leu Pro Pro Ser Gln Glu Glu Met
            100                 105                 110

Thr Lys Asn Gln Val Ser Leu Thr Cys Leu Val Lys Gly Phe Tyr Pro
        115                 120                 125

Ser Asp Ile Ala Val Glu Trp Glu Ser Asn Gly Gln Pro Glu Asn Asn
    130                 135                 140

Tyr Lys Thr Thr Pro Pro Val Leu Asp Ser Asp Gly Ser Phe Phe Leu
145                 150                 155                 160

Tyr Ser Arg Leu Thr Val Asp Lys Ser Arg Trp Gln Glu Gly Asn Val
                165                 170                 175

Phe Ser Cys Ser Val Met His Glu Ala Leu His Asn His Tyr Thr Gln
            180                 185                 190

Lys Ser Leu Ser Leu Ser Leu Gly Lys
        195                 200
```

<210> SEQ ID NO 11
<211> LENGTH: 204
<212> TYPE: PRT
<213> ORGANISM: HOMO SAPIENS

<400> SEQUENCE: 11

```
Ser Pro Phe Asp Leu Phe Ile Arg Lys Ser Pro Thr Ile Thr Cys Leu
1               5                   10                  15

Val Val Asp Leu Ala Pro Ser Lys Gly Thr Val Asn Leu Thr Trp Ser
            20                  25                  30

Arg Ala Ser Gly Lys Pro Val Asn His Ser Thr Arg Lys Glu Glu Lys
        35                  40                  45

Gln Arg Asn Gly Thr Leu Thr Val Thr Ser Thr Leu Pro Val Gly Thr
    50                  55                  60

Arg Asp Trp Ile Glu Gly Glu Thr Tyr Gln Cys Arg Val Thr His Pro
65                  70                  75                  80

His Leu Pro Arg Ala Leu Met Arg Ser Thr Thr Lys Thr Ser Gly Pro
                85                  90                  95

Arg Ala Ala Pro Glu Val Tyr Ala Phe Ala Thr Pro Glu Trp Pro Gly
            100                 105                 110

Ser Arg Asp Lys Arg Thr Leu Ala Cys Leu Ile Gln Asn Phe Met Pro
        115                 120                 125
```

Glu Asp Ile Ser Val Gln Trp Leu His Asn Glu Val Gln Leu Pro Asp
            130                 135                 140

Ala Arg His Ser Thr Thr Gln Pro Arg Lys Thr Lys Gly Ser Gly Phe
145                 150                 155                 160

Phe Val Phe Ser Arg Leu Glu Val Thr Arg Ala Glu Trp Glu Gln Lys
                165                 170                 175

Asp Glu Phe Ile Cys Arg Ala Val His Glu Ala Ala Ser Pro Ser Gln
            180                 185                 190

Thr Val Gln Arg Ala Val Ser Val Asn Pro Gly Lys
        195                 200

<210> SEQ ID NO 12
<211> LENGTH: 221
<212> TYPE: PRT
<213> ORGANISM: HOMO SAPIENS

<400> SEQUENCE: 12

Ala Leu Glu Asp Leu Leu Leu Gly Ser Glu Ala Asn Leu Thr Cys Thr
1               5                   10                  15

Leu Thr Gly Leu Arg Asp Ala Ser Gly Val Thr Phe Thr Trp Thr Pro
            20                  25                  30

Ser Ser Gly Lys Ser Ala Val Gln Gly Pro Pro Glu Arg Asp Leu Cys
        35                  40                  45

Gly Cys Tyr Ser Val Ser Ser Val Leu Pro Gly Cys Ala Glu Pro Trp
    50                  55                  60

Asn His Gly Lys Thr Phe Thr Cys Thr Ala Ala Tyr Pro Glu Ser Lys
65                  70                  75                  80

Thr Pro Leu Thr Ala Thr Leu Ser Lys Ser Gly Asn Thr Phe Arg Pro
                85                  90                  95

Glu Val His Leu Leu Pro Pro Ser Glu Glu Leu Ala Leu Asn Glu
            100                 105                 110

Leu Val Thr Leu Thr Cys Leu Ala Arg Gly Phe Ser Pro Lys Asp Val
            115                 120                 125

Leu Val Arg Trp Leu Gln Gly Ser Gln Glu Leu Pro Arg Glu Lys Tyr
        130                 135                 140

Leu Thr Trp Ala Ser Arg Gln Glu Pro Ser Gln Gly Thr Thr Thr Phe
145                 150                 155                 160

Ala Val Thr Ser Ile Leu Arg Val Ala Ala Glu Asp Trp Lys Lys Gly
                165                 170                 175

Asp Thr Phe Ser Cys Met Val Gly His Glu Ala Leu Pro Leu Ala Phe
            180                 185                 190

Thr Gln Lys Thr Ile Asp Arg Leu Ala Gly Lys Pro Thr His Val Asn
        195                 200                 205

Val Ser Val Val Met Ala Glu Val Asp Gly Thr Cys Tyr
    210                 215                 220

<210> SEQ ID NO 13
<211> LENGTH: 221
<212> TYPE: PRT
<213> ORGANISM: HOMO SAPIENS

<400> SEQUENCE: 13

Ala Leu Glu Asp Leu Leu Leu Gly Ser Glu Ala Asn Leu Thr Cys Thr
1               5                   10                  15

Leu Thr Gly Leu Arg Asp Ala Ser Gly Ala Thr Phe Thr Trp Thr Pro
            20                  25                  30

```
Ser Ser Gly Lys Ser Ala Val Gln Gly Pro Pro Glu Arg Asp Leu Cys
        35                  40                  45

Gly Cys Tyr Ser Val Ser Val Leu Pro Gly Cys Ala Gln Pro Trp
 50                  55                  60

Asn His Gly Glu Thr Phe Thr Cys Thr Ala Ala His Pro Glu Leu Lys
 65                  70                  75                  80

Thr Pro Leu Thr Ala Asn Ile Thr Lys Ser Gly Asn Thr Phe Arg Pro
                 85                  90                  95

Glu Val His Leu Leu Pro Pro Ser Glu Glu Leu Ala Leu Asn Glu
                100                 105                 110

Leu Val Thr Leu Thr Cys Leu Ala Arg Gly Phe Ser Pro Lys Asp Val
                115                 120                 125

Leu Val Arg Trp Leu Gln Gly Ser Gln Glu Leu Pro Arg Glu Lys Tyr
        130                 135                 140

Leu Thr Trp Ala Ser Arg Gln Glu Pro Ser Gln Gly Thr Thr Thr Phe
145                 150                 155                 160

Ala Val Thr Ser Ile Leu Arg Val Ala Ala Glu Asp Trp Lys Lys Gly
                165                 170                 175

Asp Thr Phe Ser Cys Met Val Gly His Glu Ala Leu Pro Leu Ala Phe
                180                 185                 190

Thr Gln Lys Thr Ile Asp Arg Leu Ala Gly Lys Pro Thr His Val Asn
        195                 200                 205

Val Ser Val Val Met Ala Glu Val Asp Gly Thr Cys Tyr
        210                 215                 220

<210> SEQ ID NO 14
<211> LENGTH: 223
<212> TYPE: PRT
<213> ORGANISM: HOMO SAPIENS

<400> SEQUENCE: 14

Ser Phe Ala Ser Ile Phe Leu Thr Lys Ser Thr Lys Leu Thr Cys Leu
1               5                  10                  15

Val Thr Asp Leu Thr Thr Tyr Asp Ser Val Thr Ile Ser Trp Thr Arg
                20                  25                  30

Gln Asn Gly Glu Ala Val Lys Thr His Thr Asn Ile Ser Glu Ser His
        35                  40                  45

Pro Asn Ala Thr Phe Ser Ala Val Gly Glu Ala Ser Ile Cys Glu Asp
 50                  55                  60

Asp Trp Asn Ser Gly Glu Arg Phe Thr Cys Thr Val Thr His Thr Asp
 65                  70                  75                  80

Leu Pro Ser Pro Leu Lys Gln Thr Ile Ser Arg Pro Lys Gly Val Ala
                 85                  90                  95

Leu His Arg Pro Asp Val Tyr Leu Leu Pro Pro Ala Arg Glu Gln Leu
                100                 105                 110

Asn Leu Arg Glu Ser Ala Thr Ile Thr Cys Leu Val Thr Gly Phe Ser
        115                 120                 125

Pro Ala Asp Val Phe Val Gln Trp Met Gln Arg Gly Gln Pro Leu Ser
130                 135                 140

Pro Glu Lys Tyr Val Thr Ser Ala Pro Met Pro Glu Pro Gln Ala Pro
145                 150                 155                 160

Gly Arg Tyr Phe Ala His Ser Ile Leu Thr Val Ser Glu Glu Glu Trp
                165                 170                 175

Asn Thr Gly Glu Thr Tyr Thr Cys Val Ala His Glu Ala Leu Pro Asn
```

```
                    180                 185                 190
Arg Val Thr Glu Arg Thr Val Asp Lys Ser Thr Gly Lys Pro Thr Leu
                195                 200                 205
Tyr Asn Val Ser Leu Val Met Ser Asp Thr Ala Gly Thr Cys Tyr
        210                 215                 220

<210> SEQ ID NO 15
<211> LENGTH: 209
<212> TYPE: PRT
<213> ORGANISM: HOMO SAPIENS

<400> SEQUENCE: 15

Ala Val Gln Asp Leu Trp Leu Arg Asp Lys Ala Thr Phe Thr Cys Phe
1               5                   10                  15

Val Val Gly Ser Asp Leu Lys Asp Ala His Leu Thr Trp Glu Val Ala
            20                  25                  30

Gly Lys Val Pro Thr Gly Gly Val Glu Glu Gly Leu Leu Glu Arg His
        35                  40                  45

Ser Asn Gly Ser Gln Ser Gln His Ser Arg Leu Thr Leu Pro Arg Ser
    50                  55                  60

Leu Trp Asn Ala Gly Thr Ser Val Thr Cys Thr Leu Asn His Pro Ser
65                  70                  75                  80

Leu Pro Pro Gln Arg Leu Met Ala Leu Arg Glu Pro Ala Ala Gln Ala
                85                  90                  95

Pro Val Lys Leu Ser Leu Asn Leu Leu Ala Ser Ser Asp Pro Pro Glu
            100                 105                 110

Ala Ala Ser Trp Leu Leu Cys Glu Val Ser Gly Phe Ser Pro Pro Asn
            115                 120                 125

Ile Leu Leu Met Trp Leu Glu Asp Gln Arg Glu Val Asn Thr Ser Gly
        130                 135                 140

Phe Ala Pro Ala Arg Pro Pro Pro Gln Pro Gly Ser Thr Thr Phe Trp
145                 150                 155                 160

Ala Trp Ser Val Leu Arg Val Pro Ala Pro Pro Ser Pro Gln Pro Ala
                165                 170                 175

Thr Tyr Thr Cys Val Val Ser His Glu Asp Ser Arg Thr Leu Leu Asn
            180                 185                 190

Ala Ser Arg Ser Leu Glu Val Ser Tyr Val Thr Asp His Gly Pro Met
            195                 200                 205

Lys
```

DIMERIC PROTEIN WITH TRIPLE MUTATIONS

RELATED APPLICATIONS

This application is a 35 U.S.C. 371 national stage filing of International Application PCT/EP2013/064330, filed on Jul. 5, 2013, which claims priority to International Application PCT/EP2012/063339, filed on Jul. 6, 2012, U.S. Patent Application No. 61/751,045, filed on Jan. 10, 2013, and Danish Patent Application PA201300019, filed on Jan. 10, 2013. The contents of the aforementioned applications are hereby incorporated by reference.

FIELD OF THE INVENTION

The present invention relates to dimeric proteins, e.g. antibodies, comprising at least three mutations as compared to a parent dimeric protein. More particularly, the present invention relates to such dimeric proteins which are capable of forming oligomeric, e.g hexameric structures in solution. The present invention also relates to uses of such dimeric proteins and compositions comprising such dimeric proteins.

BACKGROUND OF THE INVENTION

The effector functions mediated by the Fc region of an antibody allow for the destruction of foreign entities, such as the killing of pathogens and the clearance and degradation of antigens. Antibody-dependent cell-mediated cytotoxicity (ADCC) and antibody-dependent cell-mediated phagocytosis (ADCP) is initiated by binding of the Fc region to Fc receptor (FcR)-bearing cells, whereas complement-dependent cytotoxicity (CDC) is initiated by binding of the Fc region to C1q, which initiates the classical route of complement activation.

Each IgG antibody contains two binding sites for C1q, one in each heavy chain constant (Fc) region. A single molecule of IgG in solution, however, does not activate complement as the affinity of monomeric IgG for C1q is quite weak ($K_d \sim 10^{-4}$ M) (Sledge et al., 1973 J. Biol. Chem. 248, 2818-13; Hughes-Jones et al., 1979 Mol. Immunol. 16, 697-701). Antigen-driven association of IgG can lead to much tighter binding of the multivalent C1q molecule ($K_d \sim 10^{-8}$ M) and complement activation (Burton et al., 1990 Mol. Immunol. 22, 161-206). In contrast, IgM exists naturally in covalently bound penta- or hexamers, and upon binding of cellular expressed or immobilized antigen IgM pentamers and hexamers can efficiently elicit CDC. Antigen-binding is a requirement to induce a conformational change in IgM to expose the C1q binding sites (Feinstein et al., 1986, Immunology Today, 169-174).

It has been suggested that also IgG can achieve complement activation by the formation of hexameric ring structures, through interaction of the CH2/CH3 domains of the Fc region (Burton et al., 1990 Trends in Biochem. Sci. 15, 64-69). Evidence supporting the existence of such hexameric IgG structures has been found in two dimensional (Reidler et al., 1986 I Handbook of Experimental Immunology 4$^{th}$ edit. (Weir, D. M. ed.), pp 17.1-17.5. Blackwell, Edinburgh; Pinteric et al., 1971 Immunochem. 8, 1041-5) and three dimensional crystals, as well as for IgG1, IgG2a and IgG4 and human Fc in solution (Kuznetsov et al., 2000 J Struct. Biol. 131, 108-115). A hexameric ring formation was also observed in the crystal structure of the b12 human IgG1κ antibody directed against HIV-1 gp120 (1HZH in PDB) (Saphire et al., Science 2001 Aug. 10; 293(5532), 1155-9). In the b12 hexamer ring, six accessible C1q binding sites were presented at the hexamer surface, one from each of the six antibodies, while the other six binding sites faced downwards.

C1q resembles a bunch of tulips with six globular heads, containing the antibody combining regions, tethered to six collagenous stalks [Perkins et al., 1985 Biochem J. 228, 13-26; Poon et al., 1983 J Mol Biol. 168, 563-77; Reid et al., 1983 Biochem Soc Trans 11, 1-12; Weiss et al., 1986 J. Mol. Biol. 189, 573-81]. C1q was found to fit onto the b12 hexameric assembly of the 1HZH crystal structure, so that each of the six globular heads were in contact with one of the six C1q binding sites (Parren, FASEB Summer Research Conference, Snowmass, Co., 5-10 Jul. 2010; "Crystal Structure of an intact human IgG: implications for HIV-1 neutralization and effector Function", Thesis by Erica Ollmann Saphire, for the Scripps Research Institute, La Jolla, Calif. November 2000). Mutations in selected amino acids in the Fc interfaces observed between symmetry-related b12 antibodies in the crystal structure were observed to decrease the binding avidity of C1q, indicating the contribution of these amino acids to the intermolecular Fc:Fc interaction.

Mekhaiel D N A et al, Nature Scientific Reports, 1:124, 19 Oct. 2011, disclose polymeric human Fc-fusion proteins with modified effector functions.

WO0042072 disclose polypeptide variants with altered effector functions.

US20080089892 disclose Fc region variants.

WO2006105062 disclose altered antibody Fc regions and uses thereof.

The present invention relates to dimeric proteins comprising certain amino acid residues, wherein six of said dimeric proteins are capable of forming non-covalent hexameric forms in solution.

SUMMARY OF THE INVENTION

In one aspect the present invention relates to a dimeric protein comprising a first and a second polypeptide, each polypeptide comprising at least $C_H2$ and $C_H3$ regions of an immunoglobulin heavy chain, wherein in said first and/or second polypeptides
the amino acids in the positions corresponding to E345 and E430 in a human IgG1 heavy chain are not E and the amino acid in at least one position selected from the group consisting of S440, Y436, D/E356, T359, E382, N434, Q438, I253 and S254 is Y, K, R, or W; not Y; not D or E; not T; not E; not N; not Q; not I; and not S, for each position, respectively.

In another aspect the present invention relates to an oligomer comprising at least two non-covalently associated dimeric proteins of the present invention.

In another aspect the present invention relates to a hexamer comprising six non-covalently associated dimeric of the present invention.

In another aspect the present invention relates to a composition comprising the dimeric protein of the present invention, one or more antibodies, and a pharmaceutically acceptable carrier.

In another aspect the present invention relates to a composition comprising a first dimeric protein according to the present invention, a second dimeric protein according to the present invention, and optionally a pharmaceutically acceptable carrier.

In another aspect the present invention relates to a method of increasing oligomerization in solution and/or an effector function of a dimeric protein comprising a first and second polypeptide, each comprising at least CH2 and CH3 regions of an immunoglobulin heavy chain, the method comprising introducing into said first and/or second polypeptide, amino acid substitutions in at least the positions corresponding to E345, E430 and in a position selected from the group consisting of S440, Y436, D/E356, T359, E382, N434, Q438, I253 and S254 in a human IgG1 heavy chain.

In another aspect the present invention relates to a variant dimeric protein prepared by the method of the present invention.

In another aspect the present invention relates to a kit-of-parts comprising a first dimeric protein according to the present invention and a second dimeric protein according to the present invention for simultaneous, separate or sequential use in imaging, diagnostics or therapy.

In another aspect the present invention relates to a method for imaging of at least a part of the body of a human or other mammal, comprising administering a dimeric protein, oligomer, hexamer, composition or kit-of-parts according to the present invention.

In another aspect the present invention relates to a method for treating a bacterial, viral or parasitic infection, for imaging of at least a part of the body of human or other mammal, or for modulating clearance of a target molecule from the body of a human or other mammal, comprising administering a dimeric protein, oligomer, hexamer, composition or kit-of-parts according to the present invention.

In another aspect the present invention relates to a method for preventing or treating a disease, such as cancer, auto-immune diseases, organ transplant rejections, and C1q depletion in the humoral system, comprising administration of a dimeric protein, oligomer, hexamer, composition, kit-or-parts according to the present invention.

BRIEF DESCRIPTION OF THE DRAWINGS

FIG. 2: Sequence alignment of the human IgG1, IgG1f, IgG2, IgG3, IgG4, IgA1, IgA2, IgD, IgE and IgM Fc segments corresponding to residues P247 to K447 in the IgG1 heavy chain, using Clustal 2.1 software, as numbered by the Eu index as set forth in Kabat. The sequence of the shown IgG1 (SEQ ID NO:6) represents residues 130 to 330 of the human IgG1 heavy chain constant region (SEQ ID NO:1; UniProt accession No. P01857) and the sequence of the shown IgG1m(f) (SEQ ID NO:7) represents residues 130 to 330 of the allotypic variant IgG1m(f) (SEQ ID NO:5); the sequence of the shown IgG2 (SEQ ID NO:8) represents residues 126 to 326 of the IgG2 heavy chain constant region (SEQ ID NO:2; UniProt accession No. P01859); and the sequence of the shown IgG3 (SEQ ID NO:9) represents residues 177 to 377 of the IgG3 heavy chain constant region (SEQ ID NO:3; UniProt accession No. P01860); and the sequence of the shown IgG4 (SEQ ID NO:10) represents residues 127 to 327 of the IgG4 heavy chain constant region (SEQ ID NO:4; UniProt accession No. P01861); and the sequence of the shown IgE (SEQ ID NO:11) represents residues 225-428 of the IgE constant region (Uniprot accession No. P01854); and the sequence of the shown IgA1 (SEQ ID NO:12) represents residues 133-353 of the IgA1 constant region (Uniprot accession No. P01876); and the sequence of the shown IgA2 (SEQ ID NO:13) represents residues 120-340 of the IgA2 constant region (SEQ ID NO:8; Uniprot accession No. P01877); and the sequence of the shown IgM (SEQ ID NO:14) represents residues 230-452 of the IgM constant region (Uniprot accession No. P01871); and the sequence of the shown IgD (SEQ ID NO:15) represents residues 176-384 of the IgD constant region (Uniprot accession No. P01880).

FIGS. 3A and 3B: Sequence alignment of anti-EGFr antibody 2F8 in an IgG1 (SEQ ID NO:3), IgG4 (SEQ ID NO:5) and (partial) IgG3 (SEQ ID NO:6) backbone. Amino acid numbering according to Kabat and according to the Eu-index are depicted (both described in Kabat et al., Sequences of Proteins of Immunological Interest, 5th Ed. Public Health Service, National Institutes of Health, Bethesda, Md. (1991)).

FIGS. 5A-5D: CDC mediated by mutants of CD38 antibody HuMAb 005 on CD38-positive cells. (FIG. 5A) CDC efficacy on Daudi cells by a concentration series of 005 mutants. (FIG. 5B) CDC efficacy on Raji cells by a concentration series of HuMAb 005 mutants. (FIG. 5C) CDC efficacy of E345R mutant of HuMAb 005 with either 20% or 50% NHS on Wien133 cells. (FIG. 5D) CDC efficacy of E345R mutants of HuMAb 005 and 7D8 with either 20% or 50% NHS on Raji cells. Unpurified antibody samples isolated from transient transfections were tested. As a negative control, supernatant of mock-transfected cells was used.

FIGS. 19A and 19B: CDC efficacy of IgG1, IgG2, IgG3 and IgG4 isotype antibodies containing the E345R mutation.

FIGS. 34A-34D: HP-SEC analysis of triple mutant antibodies IgG1-005-RGY, IgG-7D8-RGY, IgG1-ritux-RGY, IgG1-2F8-RGY and IgG1-M1-RGY.

FIGS. 38A-38D: HP-SEC analysis of IgG1-005-KGY (FIG. 38A), IgG1-005-RSY (FIG. 38B), IgG1-005-RGW (FIG. 38C) and IgG1-005-RGI (FIG. 38D).

DETAILED DESCRIPTION OF THE INVENTION

Definitions

Figure 1:
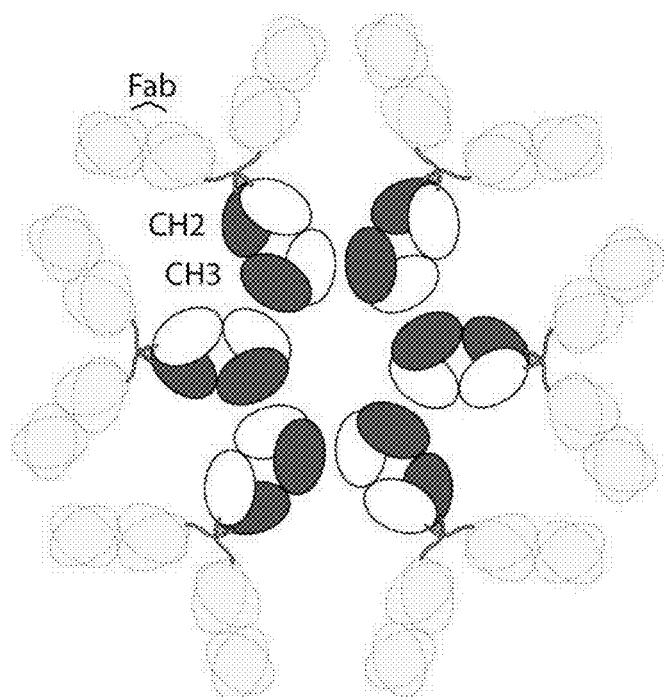
FIG. 1: (A) Schematic representation of IgG molecules in hexamer formation.

The term "immunoglobulin" refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are interconnected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, the amino acids of the constant region sequences are herein numbered according to the Eu-index or numbering (described in Kabat, E. A. et al., Sequences of proteins of immunological interest. 5th Edition—US Department of Health and Human Services, NIH publication No. 91-3242, pp 662,680,689 (1991)).

The term "hinge region" as used herein is intended to refer to the hinge region of an immunoglobulin heavy chain. Thus, for example the hinge region of a human IgG1 antibody corresponds to amino acids 216-230 according to the Eu numbering as set forth in Kabat.

The term "CH2 region" or "CH2 domain" as used herein is intended to refer the CH2 region of an immunoglobulin heavy chain. Thus, for example the CH2 region of a human IgG1 antibody corresponds to amino acids 231-340 according to the Eu numbering system. However, the CH2 region may also be any of the other subtypes as described herein.

The term "CH3 region" or "CH3 domain" as used herein is intended to refer the CH3 region of an immunoglobulin heavy chain. Thus for example the CH3 region of a human IgG1 antibody corresponds to amino acids 341-447 according to the Eu numbering system. However, the CH3 region may also be any of the other subtypes as described herein.

"Fc region", "Fc fragment" or "Fc domain", which may be used interchangeably herein, refers to an antibody region comprising, in the direction from the N- to C-terminal, at least a hinge region, a CH2 domain and a CH3 domain. An Fc region of an IgG1 antibody can, for example, be generated by digestion of an IgG1 antibody with papain.

The term "Fab fragment" in the context of the present invention, refers to a fragment of an immunoglobulin molecule, which comprises the variable regions of the heavy chain and light chain as well as the constant region of the light chain and the CH1 region of an immunoglobulin. The "CH1 region" refers e.g. to the region of a human IgG1 antibody corresponding to amino acids 118-215 according to the Eu numbering system. Thus, the Fab fragment comprises the binding region of an immunoglobulin.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about eight hours, at least about 12 hours, about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The antibody of the present invention comprises an Fc-domain of an immunoglobulin and an antigen-binding region. An antibody generally contains two CH2-CH3 regions and a connecting region, e.g. a hinge region, e.g. at least an Fc-domain. Thus the antibody of the present invention may comprise an Fc region and an antigen-binding region. The variable regions of the heavy and light chains of the immunoglobulin molecule contain a binding domain that interacts with an antigen. The constant or "Fc" regions of the antibodies may mediate the binding of the immunoglobulin to host tissues or factors, including various cells of the immune system (such as effector cells) and components of the complement system such as C1q, the first component in the classical pathway of complement activation. An antibody may also be a multispecific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104), strand-exchange engineered domain (SEED or Seed-body) which are asymmetric and bispecific antibody-like molecules (Merck, WO2007110205); Triomab (Fresenius, Lindhofer et al. (1995 J Immunol 155:219); FcΔAdp (Regeneron, WO2010151792), Azymetric Scaffold (Zymeworks/Merck, WO2012/058768), mAb-Fv (Xencor, WO2011/028952), Dual variable domain immunoglobulin (Abbott, DVD-Ig, U.S. Pat. No. 7,612,181); Dual domain double head antibodies (Unilever; Sanofi Aventis, WO20100226923), Di-diabody (ImClone/Eli Lilly), Knobs-into-holes antibody formats (Genentech, WO9850431); DuoBody (Genmab, WO 2011/131746); Electrostatic steering antibody formats (Amgen, EP1870459 and WO 2009089004; Chugai, US201000155133; Oncomed, WO2010129304A2); bispecific IgG1 and IgG2 (Rinat neurosciences Corporation, WO11143545), CrossMAbs (Roche, WO2011117329), LUZ-Y (Genentech), Biclonic (Merus), Dual Targeting domain antibodies (GSK/Domantis), Two-in-one Antibodies recognizing two targets (Genentech, NovImmune), Cross-linked Mabs (Karmanos Cancer Center), CovX-body (CovX/Pfizer), IgG-like Bispecific (ImClone/Eli Lilly, Shen, J., et al. J Immunol Methods, 2007. 318(1-2): p. 65-74), and DIG-body and PIG-body (Pharmabcine), and Dual-affinity retargeting molecules (Fc-DART or Ig-DART, by Macrogenics, WO/2008/157379, WO/2010/080538), Zybodies (Zyngenia), approaches with common light chain (Crucell/Merus, U.S. Pat. No. 7,262, 028) or common heavy chains (κλBodies by NovImmune), as well as fusion proteins comprising a polypeptide sequence fused to an antibody fragment containing an Fc-domain like scFv-fusions, like BsAb by ZymoGenetics/BMS), HERCULES by Biogen Idec (U.S. Ser. No. 00/795, 1918), SCORPIONS by Emergent BioSolutions/Trubion, Ts2Ab (MedImmune/AZ (Dimasi, N., et al. J Mol Biol, 2009. 393(3): p. 672-92), scFv fusion by Novartis, scFv fusion by Changzhou Adam Biotech Inc (CN 102250246), TvAb by Roche (WO 2012025525, WO 2012025530), mAb$^2$ by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), and antibody-like polypeptides, such as chimeric antibodies and humanized antibodies. An antibody as generated can potentially possess any isotype.

The term "full-length antibody" when used herein, refers to an antibody (e.g., a parent or variant antibody) which contains all heavy and light chain constant and variable domains corresponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a particular epitope. Accordingly, the term "human monoclonal antibody" refers to Abs displaying a single binding specificity which have variable and constant regions derived from human germline immunoglobulin sequences. The human mAbs may be generated by a hybridoma which includes a B cell obtained from a transgenic or transchromosomal non-human animal, such as a transgenic mouse, having a genome comprising a human heavy chain transgene repertoire and a light chain transgene repertoire, rearranged to produce a functional human antibody and fused to an immortalized cell.

As used herein, "isotype" refers to the immunoglobulin class (for instance IgG1, IgG2, IgG3, IgG4, IgD, IgA1, IgA2, IgE, or IgM or any allotypes thereof such as IgG1m(za) and IgG1m(f)) that is encoded by heavy chain constant region genes. Further, each heavy chain isotype can be combined with either a kappa (κ) or lambda (λ) light chain.

The term "monovalent antibody" means in the context of the present invention that an antibody molecule is only capable of binding with one binding domain of the antibody to an antigen, e.g. has a single antigen-antibody interaction, and thus is not able of antigen crosslinking.

A "binding region" as used herein may be a polypeptide sequence, such as a protein, protein ligand, receptor, an antigen-binding region, or a ligand-binding region capable of binding to a target associated with a cell, bacterium, virion, or the like. A binding region may, for example, comprise part of a receptor, receptor ligand or antigen-binding region of an immunoglobulin or antibody.

As used herein, the term "target" is in the context of the present invention to be understood as a molecule to which the binding region of the polypeptide comprising a CH2, CH3, and optionally a hinge region, and a binding region binds. When used in the context of the binding of an antibody includes any antigen towards which the raised antibody is directed. The term "antigen" and "target" may in relation to an antibody be used interchangeably and constitute the same meaning and purpose with respect to any aspect or embodiment of the present invention.

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-19}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$K_D$" (M), as used herein, refers to the dissociation equilibrium constant of a particular antibody-antigen interaction.

A "variant" of the present invention denotes a molecule, e.g. dimeric protein or which comprises one or more mutations as compared to a "parent molecule", e.g. "parent dimeric protein", such as a "parent antibody". For an antibody variant, exemplary parent antibody formats include, without limitation, a wild-type antibody, a full-length antibody or Fc-containing antibody fragment, a bispecific antibody, a human antibody, or any combination thereof. Exemplary mutations include amino acid deletions, insertions, and substitutions of amino acids in the parent amino acid sequence. Amino acid substitutions may exchange a native amino acid for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |

| -continued | |
|---|---|
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

In the context of the present invention, a substitution in a variant is indicated as:

Original amino acid—position—substituted amino acid;

Referring to the well-recognized nomenclature for amino acids, the three letter code, or one letter code, are used, including the codes Xaa and X to indicate amino acid residue. Accordingly, the notation "E345R" or "Glu345Arg" means, that the variant comprises a substitution of Glutamic acid with Arginine in the variant amino acid position corresponding to the amino acid in position 345 in the parent antibody, when the two are aligned as indicated below.

Where a position as such is not present in an antibody, but the variant comprises an insertion of an amino acid, for example:

Position—substituted amino acid; the notation, e.g., "448E" is used.

Such notation is particular relevant in connection with modification(s) in a series of homologous polypeptides or antibodies.

Similarly when the identity of the substitution amino acid residues(s) is immaterial:

Original amino acid—position; or "E345".

For a modification where the original amino acid(s) and/or substituted amino acid(s) may comprise more than one, but not all amino acid(s), the substitution of Glutamic acid for Arginine, Lysine or Tryptophan in position 345:

"Glu345Arg,Lys,Trp" or "E345R,K,W" or "E345R/K/W" or "E345 to R, K or W" may be used interchangeably in the context of the invention.

Furthermore, the term "a substitution" embraces a substitution into any one of the other nineteen natural amino acids, or into other amino acids, such as non-natural amino acids. For example, a substitution of amino acid E in position 345 includes each of the following substitutions: 345A, 345C, 345D, 345G, 345H, 345F, 345I, 345K, 345L, 345M, 345N, 345Q, 345R, 345S, 345T, 345V, 345W, 345P, and 345Y. This is, by the way, equivalent to the designation 345X, wherein the X designates any amino acid other than the original amino acid. These substitutions can also be designated E345A, E345C, etc, or E345A,C, etc, or E345A/C/etc. The same applies by analogy to each and every position mentioned herein, to specifically include herein any one of such substitutions.

The terms "amino acid" and "amino acid residue" may be used interchangeably.

The reference to "D/E356" refers in the present context to allotypic variants in the sequence of human IgG1. In the IgG1m(za) allotype of human IgG1 the amino acid in position 356 is D, while in the IgG1m(f) allotype of human IgG1 the amino acid in position 356 is E.

Unless otherwise stated or contradicted by the context, reference to an amino acid position number refers to the amino acid position number in a human IgG1 heavy chain.

An amino acid or segment in one sequence that "corresponds to" an amino acid or segment in another sequence is one that (i) aligns with the other amino acid or segment using a standard sequence alignment program such as ALIGN, ClustalW or similar, typically at default settings and (ii) has a sequence identity to SEQ ID NO:1 of at least 50%, at least 80%, at least 90%, or at least 95%. For example, the sequence alignments shown in FIGS. 2 and 3 can be used to identify any amino acid in the shown immunoglobulin Fc sequences that corresponds to a particular amino acid in the IgG1 Fc sequence.

Figure 3A:
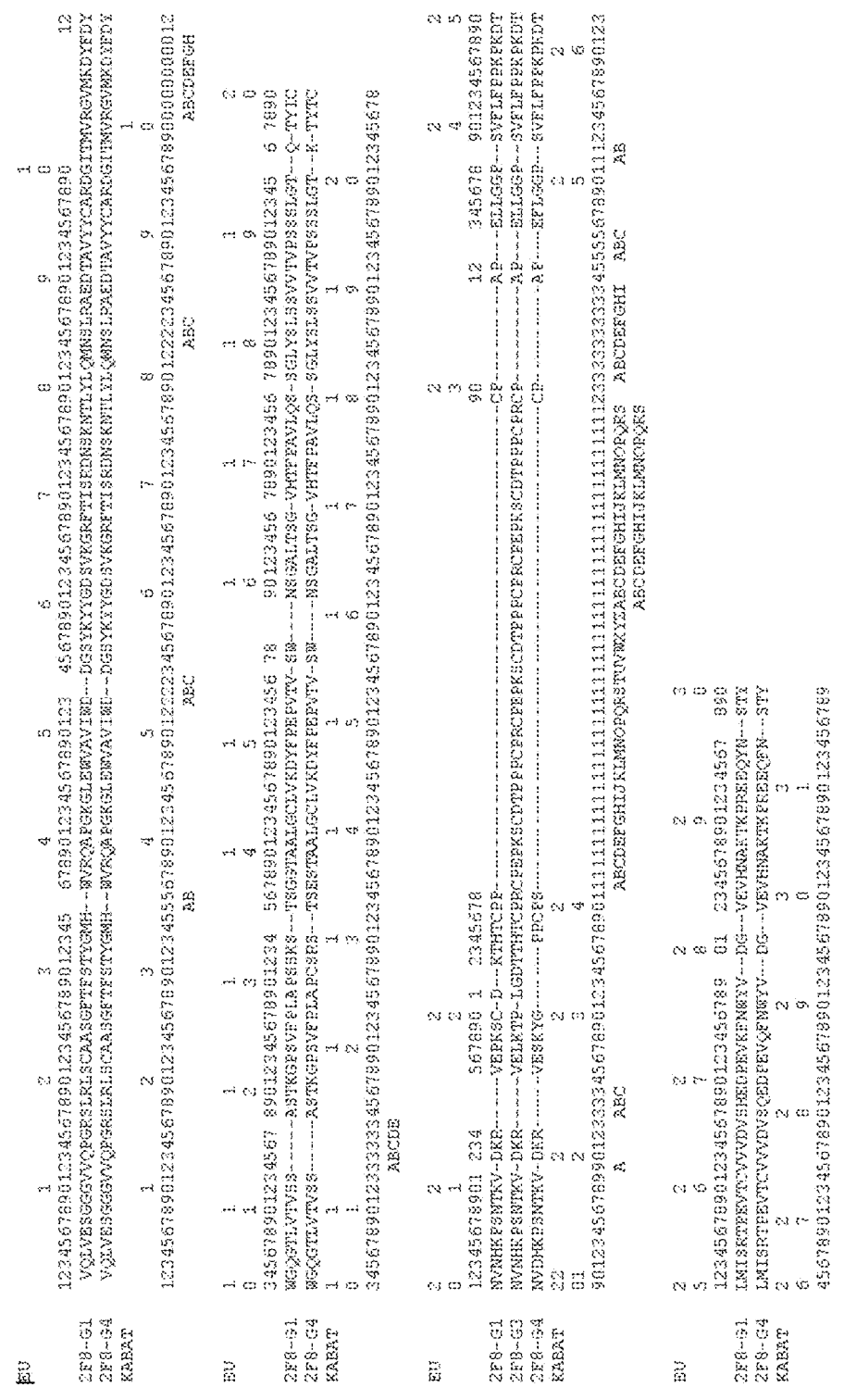

For purposes of the present invention, an amino acid at a position in an amino acid sequence which corresponds to a specific position in another, reference amino acid sequence, as well as the degree of identity between two amino acid or nucleotide sequences, can determined by alignment of the two sequences. Herein, unless otherwise indicated or contradicted by context, the reference amino acid sequence is the amino acid sequence of the human IgG1 heavy chain. The program "Align" which is a Needleman-Wunsch alignment (i.e. a global alignment) can be used for alignment of polypeptide, as well as nucleotide sequences. The default scoring matrix BLOSUM50 or BLOSUM62 can be used for polypeptide alignments, and the default identity matrix can be used for nucleotide alignments, the penalty of the first residue of a gap is −12 for polypeptides and −16 for nucleotides. The penalties for further residues of a gap are −2 for polypeptides, and −4 for nucleotides. "Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biolo. 147:195-197). Representative alignments between Fc regions of immunoglobulin heavy chains are shown in FIGS. 2 and 3.

The term "vector," as used herein, is intended to refer to a nucleic acid molecule capable of inducing transcription of a nucleic acid segment ligated into the vector. One type of vector is a "plasmid", which is in the form of a circular double stranded DNA loop. Another type of vector is a viral vector, wherein the nucleic acid segment may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NS0 cells, and lymphocytic cells, and prokaryotic cells such as E. coli and other eukaryotic hosts such as plant cells and fungi.

The term "transfectoma", as used herein, includes recombinant eukaryotic host cells expressing the Ab or a target antigen, such as CHO cells, PER.C6, NS0 cells, HEK-293 cells, plant cells, or fungi, including yeast cells.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcRs, are involved in specific killing of target cells and presenting antigens to other components of the immune system, or binding to cells that present antigens. In some embodiments the ADCC can be further enhanced by antibody driven classical complement activation resulting in the deposition of activated C3 fragments on the target cell. C3 cleavage products are ligands to complement receptors (CRs), such as CR3, expressoid on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell. The expression of a particular FcR or complement receptor on an effector cell may be regulated by humoral factors such as cytokines. For example, expression of FcγRI has been found to be up-regulated by interferon γ (IFN γ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytosis by effector cells or indirectly by enhancing antibody mediated phagocytosis.

As used herein, the term "effector functions" refers to functions that are a consequence of binding a dimeric protein, such as an antibody, to its target, such as an antigen, optionally on a cell, on a cell membrane, on a virion, or on another particle. Examples of effector functions include (i) C1q-binding, (ii) complement activation, (iii) complement-dependent cytotoxicity (CDC), (iv) oligomer formation, (v) oligomer stability, (vi) antibody-dependent cell-mediated cytotoxity (ADCC), (vii) FcRn-binding, (viii) Fc-gamma receptor-binding, (ix) antibody-dependent cellular phagocytosis (ADCP), (x) complement-dependent cellular cytotoxicity (CDCC), (xi) complement-enhanced cytotoxicity, (xii) binding to complement receptor of an opsonized antibody mediated by the antibody, (xiii) internalization, (xiv) down-modulation, (xv) induction of apoptosis, (xvi) opsonisation, (xvii) proliferation modulation, such as proliferation reduction, inhibition or stimulation, and (xii) a combination of any of (i) to (xvi).

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen binding sites of antibodies simultaneously interacting with a target or e.g. between antibody and C1q. When more than one binding interactions are present, the two structures will only dissociate when all binding sites dissociate, and thus, the dissociation rate will be slower than for the individual binding sites, and thereby providing a greater effective total binding strength (avidity) compared to the strength of binding of the individual binding sites (affinity).

As used herein, the term "oligomer" refers to a structure that consists of more than one but a limited number of units of a specific type of molecule (such as, e.g., antibody or other dimeric protein molecules according to the invention) in contrast to a polymer which, at least in principle, consists of an unlimited number of units. Thus, an oligomer according to the invention consists of a limited number of dimeric proteins according to any aspect or embodiment of the present invention. Exemplary oligomers are dimers, trimers, tetramers, pentamers, hexamers, and dodecamers. Greek prefixes are often used to designate the number of monomer units in the oligomer, for example a tetramer being composed of four units and a hexamer of six units. Likewise, the term "oligomerization", as used herein, is intended to refer to a process that converts molecules to a finite degree of polymerization. Herein, it is observed, that antibodies and/or other dimeric proteins according to the invention can form oligomers, such as hexamers, via non-covalent association of Fc-domains in solution under certain pH conditions, as described in Example 31, or, in the case of dimeric proteins comprising target-binding regions, after target binding, e.g., at a cell surface. Oligomerization in solution can be evaluated, e.g., as described in Example 20. In a particular embodiment, the oligomerization in solution may be determined by performing HP-SEC (high pressure size exclusion chromatography) fractionation using a suitable size exclusion chromatography resin with a porse size capable of separating molecules in the range of 50 kDa to 1000 kDa, connected to an absorbance detector; separating into 50 μL samples containing 1.25 μg/mL protein at 1 mL/min in 0.1 M $Na_2SO_4$/0.1 M sodium phosphate buffered at pH 6.8; using a suitable software to process results; and expressing per peak as percentage of total peak area. The oligomerization of antibodies after antigen-binding can be evaluated (e.g. using a complement dependent cytotoxicity as described in Examples 3, 6, and 21). In a particular embodiment, CDC may be determined by pre-incubating suspension cells at a concentration of $1\times10^6$ cells/mL in round-bottom 96-well plates with an antibody at a final concentration ranging from 0.0003 to 30.0 μg/mL in a total volume of 100 μL for 15 min on a shaker at room temperature; adding normal human serum at a final concentration of 20%, 30% or 50%; incubating at 37° C. for 45 min; putting the plates on ice; adding 10 μL propidium iodide; and determining cell lysis by FACS analysis.

The term "C1q binding", as used herein, is intended to refer to the binding of C1q in the context of the binding of C1q to an antibody bound to its antigen. The antibody bound to its antigen is to be understood as happening both in vivo and in vitro in the context described herein. C1q binding can be evaluated for example by using immobilized antibody on artificial surface (e.g. plastic in plates for ELISA, as described in example 21). In a particular embodiment, C1q binding may be determined by coating 96-well ELISA plates overnight at 4° C. with antibody in PBS at a concentration ranging from 0.007 to 25.0 μg/mL; washing the plates; blocking with 0.5×PBS/0.025% Tween 20/0.1% gelatin; sequentially incubating for 1 h at 37° C. plates with 3% pooled human serum, rabbit anti-human C1q, swine anti-rabbit IgG-HRP, by in-between washing; developing the plates for about 30 min with 1 mg/mL 2,2'-azino-bis 3-ethylbenzothiazoline-6-sulfonic acid; adding 100 μL 2% oxalic acid; and measuring the absorbance at 405 nm in a microplate reader. The binding of C1q to an antibody oligomer is to be understood herein as a multivalent interaction resulting in high avidity binding.

As used herein, the term "complement activation" refers to the activation of the classical complement pathway, which is triggered by the binding of complement component C1q to an antibody bound to its antigen. C1q is the first protein in the early events of the classical complement cascade that involves a series of cleavage reactions that culminate in the formation of an enzymatic activity called C3 convertase, which cleaves complement component C3 into C3b and C3a. C3b binds covalently to C5 on the membrane to form C5b that in turn triggers the late events of complement activation in which terminal complement components C5b, C6, C7, C8 and C9 assemble into the membrane attack complex (MAC). The complement cascade results in the creation of pores due to which causes cell lysis, also known as CDC. Complement activation can be evaluated by using, CDC kinetics (as described in example 14, 15 and 16), CDC assays (as described in examples 3 and 21) or by the method Cellular deposition of C3b and C4b described in Beurskens et al Apr. 1, 2012 vol. 188 no. 7 3532-3541.

The term "complement-dependent cytotoxicity" ("CDC"), as used herein, is intended to refer to the process of antibody-mediated complement activation leading to lysis of a cell or virion as a result of pores in the membrane that are created by MAC assembly, when the antibody is bound to its target on said cell or virion. CDC can be evaluated by in vitro assays such as a CDC assay in which normal human serum is used as a complement source, as described above, e.g. in example 3 and 21.

The term "antibody-dependent cell-mediated cytotoxicity" ("ADCC") as used herein, is intended to refer to a mechanism of killing of antibody-coated target cells or virions by cells expressing Fc receptors that recognize the constant region of the bound antibody. ADCC can be determined using methods such as, e.g., the ADCC assay described in example 21. In a particular embodiment, ADCC may be determined by incubating cells with antibody at a concentration ranging from 0.5 to 250 ng/mL; and quantifying ADCC activity with a ADCC bioluminescent reporter assay kit.

The term "antibody-dependent cellular phagocytosis" ("ADCP") as used herein is intended to refer to a mechanism of elimination of antibody-coated target cells or virions by internalization by phagocytes. The internalized antibody-coated target cell or virion is contained in a vesicle called a phagosome, which then fuses with one or more lysosomes to form a phagolysosome. ADCP may be evaluated by using an in vitro cytotoxicity assay with marcophages as effector cells and video microscopy as described by van Bij et al. in Journal of Hepatology Volume 53, Issue 4, October 2010, Pages 677-685 or as described in example 24 for e.g. *S. aureus* phagocytos by PMN.

The term "complement-dependent cellular cytotoxicity" ("CDCC") as used herein is intended to refer to a mechanism of killing of target cells or virions by cells expressing complement receptors that recognize complement 3 (C3) cleavage products that are covalently bound to the target cells or virions as a result of antibody-mediated complement activation. CDCC may be evaluated in a similar manner as described for ADCC, but in the presence of complement C5 depleted normal human serum.

The term "downmodulation", as used herein, is intended to refer to a process that decreases the number of molecules, such as antigens or receptors, on a cellular surface, e.g. by binding of an antibody to a receptor.

The term "internalization", as used herein, is intended to refer to any mechanism by which a dimeric protein of the present invention, e.g. an antibody or Fc-containing polypeptide, is internalized into a target-expressing cell from the cell-surface and/or from surrounding medium, e.g., via endocytosis. The internalization of an antibody can be evaluated using a direct assay measuring the amount of internalized antibody (such as, e.g., the lysosomal co-localization assay described in Example 12).

The term "programmed cell-death" or "PCD", as used herein refers to the death of a cell in any form mediated by an intracellular signalling. Three forms of PCD are found; apoptosis, autophagy and necrosis/oncosis. In a particular embodiment, any of the three forms of programmed cell death may be determined by culturing $1.0\times10^5$ cells for 24 hours in 96-well U-bottom plates in the presence of antibody at a concentration ranging from 0.0025 to 10 μg/mL; staining dead cells with annexin V-FITC using a suitable annexin binding assay kit according to the manufacturer's instructions; and determining the amount of annexin V-FITC-positive cells using by FACS analysis.

The term "apoptosis", as used herein, refers to the best-characterized type of programmed cell death because of its importance in development and homeostasis, and in the pathogenesis of different diseases, such as cancer. Apoptotic cells die in a controlled fashion in response to a variety of extrinsic or intrinsic signals (e.g., activation of tumor necrosis factor (TNF) receptors, DNA damage, mitochondrial pathways). Biochemical events lead to characteristic cell changes (morphology) and death. The hallmarks of apoptotic cell death include blebbing, exposure of phosphatidylserine on the extracellular face of the plasma membrane, activation of caspases, disruption of mitochondrial membrane potential, cell shrinkage, chromatin condensation, DNA fragmentation and DNA condensation. Binding of an antibody to a certain receptor may induce apoptosis.

The term "autophagy", as used herein, refers to a selective degradation of intracellular molecules or structures, such as misfolded proteins and damaged organelles, and is an important homeostatic function. Autophagy performs in concert with the Ubiquitin-Proteasome System (UPS) to degrade aggregated/misfolded proteins that are ubiquitinated, labelling them for degradation by autophagy. The ubiquitinated cargo is carried to the phagophore and surrounds its cargo forming a double membrane vesicle, the autophagosome. The lyososome fuses to the autophagosome and the cargo is degraded inside the autolysosome.

The term "necrosis" or "oncosis", as used herein, refers to an uncontrolled cell death characterized by cell swelling, as well as destruction of the plasma membrane and subcellular organelles, without nuclear fragmentation and condensation. Necrotic cell death is considered a heterogeneous phenomenon including both programmed and accidental cell death.

The term "proliferation", as used herein refers to an increase in the number of cells as a result of cell growth and cell division.

The term "antibody-drug conjugate", as used herein refers to a dimeric protein of the present invention, e.g. an antibody or Fc-containing polypeptide, having specificity for at least one type of malignant cell, a drug, and a linker coupling the drug to e.g. the antibody. The linker is cleavable or non-cleavable in the presence of the malignant cell; wherein the antibody-drug conjugate kills the malignant cell.

The term "antibody-drug conjugate uptake", as used herein refers to the process in which antibody-drug conjugates are bound to a target on a cell followed by uptake/engulfment by the cell membrane and thereby is drawn into the cell. Antibody-drug conjugate uptake may be evaluated as "antibody-mediated internalization and cell killing by anti-TF ADC in an in vitro killing assay" as described in WO 2011/157741.

The term "FcRn", as used herein is intended to refer to neonatal Fc receptor which is an Fc receptor. It was first discovered in rodents as a unique receptor capable of transporting IgG from mother's milk across the epithelium of newborn rodent's gut into the newborn's bloodstream. Further studies revealed a similar receptor in humans. In humans, however, it is found in the placenta to help facilitate transport of mother's IgG to the growing fetus and it has also been shown to play a role in monitoring IgG turnover. FcRn binds IgG at acidic pH of 6.0-6.5 but not at neutral or higher pH. Therefore, FcRn can bind IgG from the intestinal lumen (the inside of the gut) at a slightly acidic pH and ensure efficient unidirectional transport to the basolateral side (inside the body) where the pH is neutral to basic (pH 7.0-7.5). This receptor also plays a role in adult salvage of IgG through its occurrence in the pathway of endocytosis in endothelial cells. FcRn receptors in the acidic endosomes bind to IgG internalized through pinocytosis, recycling it to the cell surface, releasing it at the basic pH of blood, thereby preventing it from undergoing lysosomal degradation. This mechanism may provide an explanation for the greater half-life of IgG in the blood compared to other isotypes.

The term "Protein A", as used herein, is intended to refer to a 56 kDa MSCRAMM surface protein originally found in the cell wall of the bacterium *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It is composed of five homologous Ig-binding domains that fold into a three-helix bundle. Each domain is able to bind proteins from many mammalian species, most notably IgGs. It binds the heavy chain Fc region of most immunoglobulins (overlapping the conserved binding site of FcRn receptors) and also interacts with the Fab region of the human VH3 family. Through these interactions in serum, IgG molecules bind the bacteria via their Fc region instead of solely via their Fab regions, by which the bacteria disrupts opsonization, complement activation and phagocytosis.

The term "Protein G", as used herein is intended to refer to an immunoglobulin-binding protein expressed in group C and G Streptococcal bacteria much like Protein A but with differing specificities. It is a 65-kDa (G148 protein G) and a 58 kDa (C40 protein G) cell surface protein that has found application in purifying antibodies through its binding to the Fc region.

Dimeric Protein

The present invention relates in one aspect to a dimeric protein comprising a first and a second polypeptide, each polypeptide comprising at least $C_H2$ and $C_H3$ regions of an immunoglobulin heavy chain, wherein in said first and/or second polypeptide the amino acids in the positions corresponding to E345 and E430 in a human IgG1 heavy chain are not E, and the amino acid in at least one position selected from the group consisting of S440, Y436, D/E356, T359, E382, N434, Q438, I253 and S254 is Y, K, R or W; not Y; not D or E; not T; not E; not N; not Q; not I; and not S, for each position, respectively. Each of positions S440, Y436, D/E356, T359, E382, N434, Q438, I253 and S254 corresponds to the position in a human IgG1 heavy chain.

In one embodiment, in each of said first and second polypeptides the amino acids in the positions corresponding to E345 and E430 in a human IgG1 heavy chain are not E, and the amino acid in at least one position selected from the group consisting of S440, Y436, D/E356, T359, E382, N434, Q438, I253 and S254 is Y, K, R or W; not Y; not D or E; not T; not E; not N; not Q; not I; and not S, for each position, respectively. Each of positions S440, Y436, D/E356, T359, E382, N434, Q438, I253 and S254 corresponds to the position in a human IgG1 heavy chain.

The first and second polypeptides of the dimeric protein according to the invention dimerize by forming covalent or non-covalent interaction. Such an interaction may be found in any region of the polypeptides. Examples of covalent interaction are any CxxC peptide interaction, wherein the "x" represents any amino acid and the "C" represents cysteine residues. Another example is a TCRalpha chain constant domain and a TCRbeta chain constant domain. Examples on non-covalent interaction may be a leucine zipper such as described in Moll et al, Prot. Science, 2001, 10:649-655. In one embodiment, said first and/or second polypeptide may further comprise a region capable of covalent binding between said first and second polypeptide.

In one embodiment, the first and/or second polypeptides further comprise a hinge region.

For certain purposes of the present invention a part of the hinge region, such as amino acid positions corresponding to 226-230, suffices. Thus, in one embodiment, the first and/or second polypeptide may further comprise amino acids at positions corresponding to positions 226-230 in a human IgG1 heavy chain.

In one embodiment, in said first and second polypeptide the amino acid in the positions corresponding to E345 and E430 in a human IgG1 heavy chain, are not E, and the amino acid in at least one position selected from the group consisting of S440, Y436, D/E356, T359, E382, N434, Q438, I253 and S254 is Y or W; not Y; not D or E; not T; not E; not N; not Q; not I; and not S, for each position, respectively.

In one embodiment, in said first and second polypeptide the amino acid in the positions corresponding to E345 and E430 in a human IgG1 heavy chain, are not E, and the amino acid in at least one position selected from the group consisting of S440, Y436, E356, T359, E382, N434, Q438, I253 and S254 is Y, K, R or W; not Y; not E; not T; not E; not N; not Q; not I; and not S, for each position, respectively.

Thus, one embodiment the present invention relates to the dimeric protein comprising a first and a second polypeptide, each polypeptide comprising at least $C_H2$, $C_H3$ and hinge regions of an immunoglobulin heavy chain, wherein the amino acids in the positions corresponding to E345 and E430 in a human IgG1 heavy chain are not E and the amino acid in at least one position selected from the group consisting of S440, Y436, E356, T359, E382, N434, Q438, I253 and S254 is Y or W; not Y; not E; not T; not E; not N; not Q; not I; and not S, for each position, respectively.

In one embodiment, the first and second polypeptides are interconnected via hinge region disulphide binds.

Unless otherwise stated or contradicted by context, the amino acid positions mentioned refer to an amino acid position in a human IgG1 heavy chain in any aspect or embodiment of the present invention.

Furthermore, unless otherwise stated or contradicted by context, the amino acid numbering is according to Eu numbering as set forth in Kabat, as described above.

The dimeric protein may be prepared from a parent dimeric protein, and thereby be regarded as a variant dimeric protein, by introducing mutations in the positions corresponding to E345 and E430 in a human IgG1 heavy chain, and in at least one position selected from the group consisting of the positions corresponding to S440, Y436, D/E356, T359, E382, N434, Q438, I253 and S254 in a human IgG1 heavy chain, wherein the amino acid introduced in the position corresponding to S440 is Y, K, R or W. At the other amino acid positions any amino acid may be introduced, e.g. any naturally occurring amino acid.

In one embodiment, the amino acid at the position corresponding to E345 is, for one or both, such as each, of said first and second polypeptides of the dimeric protein, selected, e.g. separately, from the group consisting of R, Q, N, K, Y, A, C, D, F, G, H, I, L, M, P, S, T, V and W, such as from the group consisting of R, Q, N, K and Y.

In a further embodiment, the amino acid at the position corresponding to E345 is, for one or both, such as each, of said first and/or second polypeptides of the dimeric protein, selected, e.g. separately, from the group consisting of R, Q, K and Y.

In a further embodiment, the amino acid at the position corresponding to E345 is, for one or both, such as each, of said first and/or second polypeptides of the dimeric protein, R.

In one embodiment, the amino acid at the position corresponding to E430 is, for one or both, such as each, of said first and/or second polypeptides of the dimeric protein, selected, e.g. separately from the group consisting of G, T, S, F, H, A, C, D, I, K, L, M, N, P, Q, R, V, W and Y, such as from the group consisting of G, T, S, F and H.

In a further embodiment, the amino acid at the position corresponding to E430 is, for one or both, such as each, of said first and/or second polypeptides of the dimeric protein, selected, e.g. separately from the group consisting of G, T, S and F.

In a further embodiment, the amino acid at the position corresponding to E430 is, for one or both, such as each, of said first and/or second polypeptides of the dimeric protein, G.

In one embodiment the amino acid in the position corresponding to S440 is, for one or both, such as each, of said first and/or second polypeptides of the dimeric protein, selected, e.g. separately from the group consisting of Y or W.

In one embodiment the amino acid in the position corresponding to S440 is, for one or both, such as each, of said first and/or second polypeptides of the dimeric protein, W.

In one embodiment the amino acid in the position corresponding to S440 is, for one or both, such as each, of said first and/or second polypeptides of the dimeric protein, Y.

In one embodiment, the amino acid in a position selected from the group consisting of Y436, D/E356, T359, E382, N434, Q438, I253 and S254 is, in one or both, such as each, of said first and/or second polypeptides of the dimeric protein, (a) I, N, Q, S, T, R, A, E, F, H, K, L, M or V, such as I, N, Q or S;

(b) R, G, T, I, L, M, K, H, S, V, Y, Q, N, W, F, A, or C;

(c) R;

(d) V, L, M, D, Q, K, R, N, H, S, T, W or Y, such as V, L or M;

(e) W, H, K, Q, R, D, E, S, T, or Y, such as W, H, K, Q or R;

(f) N, S, T, A, E, G, H, K, Q, R, W or Y, such as N, S or T;

(g) V, L, N, Q, E, S or T, such as V, L, N or Q;

(h) L, G, I or V;

for each position, respectively.

The amino acid at the positions corresponding to E345 and E430 in a human IgG1 heavy chain, and at a position corresponding to a position selected from the group consisting of S440, Y436, D/E356, T359, E382, N434, Q438, I253 and S254, may in one embodiment be the same in the first and second polypeptide; or they may be different. The amino acids at said positions may be different, e.g. if the dimeric protein is a heterodimeric protein, such as a bispecific antibody described herein.

The amino acids at the positions corresponding to E345, E430 and S440 may, for one or both, such as each, of said first and/or second polypeptides of the dimeric protein be one of the following non-limiting examples; E345R/E430G/S440Y, E345R/E430G/S440W, E345K/E430G/S440Y, E345K/E430G/S440W, E345Q/E430G/S440Y, E345Q/E430G/S440W, E345N/E430G/S440Y, E345N/E430G/S440W, E345Y/E430G/S440Y, E345Y/E430G/S440W, E345R/E430T/S440Y, E345R/E430T/S440W, E345K/E430T/S440Y, E345K/E430T/S440W, E345Q/E430T/S440Y, E345Q/E430T/S440W, E345N/E430T/S440Y, E345N/E430T/S440W, E345Y/E430T/S440Y, E345Y/E430T/S440W, E345R/E430S/S440Y, E345R/E430S/S440W, E345K/E430S/S440Y, E345K/E430S/S440W, E345Q/E430S/S440Y, E345Q/E430S/S440W, E345N/E430S/S440Y, E345N/E430S/S440W, E345Y/E430S/S440Y, E345Y/E430S/S440W, E345R/E430F/S440Y, E345R/E430F/S440W, E345K/E430F/S440Y, E345K/E430F/S440W, E345Q/E430F/S440Y, E345Q/E430F/S440W, E345N/E430F/S440Y, E345N/E430F/S440W, E345Y/E430F/S440Y, E345Y/E430F/S440W, E345R/E430G/S440K, E345R/E430G/S440R, E345K/E430G/S440K, E345K/E430G/S440R, E345Q/E430G/S440K, E345Q/E430G/S440R, E345N/E430G/S440K, E345N/E430G/S440R, E345Y/E430G/S440K, E345Y/E430G/S440R, E345R/E430T/S440K, E345R/E430T/S440R, E345K/E430T/S440K, E345K/E430T/S440R, E345Q/E430T/S440K, E345Q/E430T/S440R, E345N/E430T/S440K, E345N/E430T/S440R, E345Y/E430T/S440K, E345Y/E430T/S440R, E345R/E430S/S440K, E345R/E430S/S440R, E345K/E430S/S440K, E345K/E430S/S440R, E345Q/E430S/S440K, E345Q/E430S/S440R, E345N/E430S/S440K, E345N/E430S/S440R, E345Y/E430S/S440K, E345Y/E430S/S440R, E345R/E430F/S440K, E345R/E430F/S440R, E345K/E430F/S440K, E345K/E430F/S440R, E345Q/E430F/S440K, E345Q/E430F/S440R, E345N/E430F/S440K, E345N/E430F/S440R, E345Y/E430F/S440K, and E345Y/E430F/S440R.

In one embodiment, the amino acids in the positions corresponding to E345, E430 and S440 are, for one or both, such as each, of said first and/or second polypeptides of the dimeric protein, R, G and Y, respectively.

In an alternative embodiment, the amino acids in the positions corresponding to E345, E430 and S440 are, for said first and/or second polypeptides of the dimeric protein, K, G, and Y, respectively.

In an alternative embodiment, the amino acids in the positions corresponding to E345, E430, and S440 are, for said first and/or second polypeptides of the dimeric protein, R, S, and Y, respectively.

In an alternative embodiment, the amino acids in the positions corresponding to E345, E430 and S440 are, for said first and/or second polypeptides of the dimeric protein, R, G, and W, respectively.

In an alternative embodiment, the amino acids in the positions corresponding to E345, E430 and Y436 are, for said first and/or second polypeptides of the dimeric protein, R, G, and I, respectively.

In an alternative embodiment, the amino acids in the positions corresponding to E345, E430, Y436 and S440 are, for said first and/or second polypeptides of the dimeric protein, R, G, I, and K, respectively.

In one embodiment, the amino acids in the positions corresponding to E345, E430 and S440 are, for said first and/second polypeptides of the dimeric proteins, R, G, and K, respectively.

As described herein, the present invention inter alia relates to dimeric proteins comprising amino acids at three positions which are different from those naturally present in the CH2/CH3 region of a human IgG1 heavy chain.

In one embodiment, said first and second polypeptides of the dimeric protein are interconnected via hinge region disulphide bonds.

In one embodiment the isotype of the immunoglobulin heavy chain is selected from the group consisting of IgG1, IgG2, IgG3, IgG4, IgA1, IgA2, IgD, IgE and IgM. The isotype of the first and second polypeptide may be different, but in a particular embodiment, they are the same. In one embodiment, the isotype of the first and second polypeptide is different, such as the isotype of said first polypeptide may be an IgG1 immunoglobulin heavy chain and the isotype of said second polypeptide may be an IgG4 immunoglobulin heavy chain. The example is not to be understood limiting and thus, other combinations of isotypes is considered comprised in the present invention.

Any amino acid position, or mutation in an amino acid position, described herein as corresponding to an amino acid position in a human IgG1 heavy chain, can be identified or introduced at its equivalent position in IgG2, IgG3, IgG4, IgA1, IgA2, IgE, IgD and IgM as defined by the alignment in FIG. 2 to obtain a dimeric protein according to the invention.

In a particular embodiment the isotype of the immunoglobulin heavy chain is selected from the group consisting of IgG1, IgG2, IgG3, and IgG4, such as IgG1.

In another embodiment, the isotype of the immunoglobulin heavy chain is selected from the group consisting of IgA1 and IgA2.

In another embodiment, the isotype of the immunoglobulin heavy chain is selected from the group consisting of IgE, IgD and IgM.

In one embodiment, the immunoglobulin heavy chain is of mammalian origin.

In one embodiment the immunoglobulin heavy chain is of primate or murine origin, such as human origin.

In one embodiment, at least one of the polypeptides of the dimeric protein comprises a binding region which specifically binds to a target.

In a further embodiment, both the first and second polypeptide comprises a binding region, such as an antigen-binding region, specifically binding to a target. The binding region, such as an antigen-binding region, of the first and second polypeptide may bind to the same target, optionally to different epitopes of the same target, or they may bind to different targets.

The binding regions of the first and/or second polypeptide may be antigen binding regions.

Said binding region may bind any target, wherein the target may e.g. be a molecule present on a cell, bacterium, parasite or virion.

In a particular embodiment the target may be an antigen.

In a further embodiment said antigen may be expressed on the surface of a cell, such as a human tumor cell.

In one embodiment, said antigen is associated with a cell membrane.

In another embodiment, said antigen is associated with a virion, optionally wherein the antigen is comprised in the protein coat or a lipid envelope of the virion.

In a further embodiment, the target to which a binding regions binds may be an antigen expressed on the surface of a bacterial cell or a virion.

In another embodiment, the bacterial cell is selected from the group consisting of *S. aureus, S. epidermidis, S. pneumonia, Bacillus anthracis, Pseudomonas aeruginosa, Chlamydia trachomatis, E. coli, Salmonella, Shigella, Yersinia, S. typhimurium, Neisseria meningitides*, and *Mycobacterium tuberculosis*.

Examples of targets or antigens include but are not limited to: 5T4; ADAM-10; ADAM-12; ADAM17; AFP; alpha/beta T cell receptor (TCR); AXL; ANGPT2 anthrax antigen; antidrug antibody (ADA) BSG; CAIX; CAXII; CA 72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD55$^{SC1}$; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; CRF-1; Cripto; DLL4; Death receptor 4; Death receptor 5; ED-B; EFNA2; EGFR; Endothelin B receptor; ENPP3; EPCAM; ERBB2; ERBB3; FAP alpha; FAS (aka APO-1, CD95); Fc gamma RI; FCER2; FGFR3; fibrin II beta chain; FLT1; FOLH1;

FOLR1; FRP-1; G-28 glycolipid; GD1a; GD-2; GM-1; GD3 ganglioside; GM3; GDF2; GLP1R; Glypican-3; GPNMB; GRP78; *Haemophilus* influenza; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human anti-human antibodies (HAHA); human anti-murine antibodies (HAMA); human respiratory syncytial virus, glycoprotein F; ICAM1; IFNA1; IFNA1; IFNB1 bispecific; IgE, IgE Fc; IGF1R; IGHE connecting region; IL12B; IL13; IL15; IL17A; IL1A; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-x; Lewis-y; lipid A, domain of lipopolyaccharide LPS; LTA; lipid A; Mannan (*Candida albicans*); MET; microbial proteases such as *Staphylococcus aureus* gluV8 and *Streptococcus pyogenes* IdeS; MMP14; MMp15; MST1R; MSTN; MUC1; MUC4; MUC16; MUC5AC; myelin; NCA-90 granulocyte cell antigen; Nectin 4; *Neisseria meningitides*, NGF; non-POU domain-containing octomer binding protein (NONO); NRP; NY-ESO-1; O-glycan; OX40L; PLAC-1; PLGF; PDGFRA; PD1; PDL1; PSCA; phosphatidylserine; PTK-7; *Pseudomonas aeruginosa* serotype IATS 011; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; *Streptococcus pneumonia*; TAF-15; T cell receptor alpha_beta; Tissue Factor (TF); TGFB1; TGFB2; TMEFF2; TNC; TNF; TNFRSF10A; TNFRSF10B; TNFRSF12A; TNFSF13; TNFSF14; TNFSF2; TNFSF7; TRAILR2; TROP2; TYRP1; VAP-1; Vimentin; erbB1 (EGFR); erbB2 (HER2); erbB3; erbB4; MUC-1; CXCR5; c-Met; HERV-envelop protein; periostin; Bigh3; SPARC; BCR; and MRP3.

In a further embodiment, the antigens may be selected from CD20, EGFr and CD38, optionally, the dimeric protein of the present invention may be selected from 7D8, 2F8, 003 and 005 as described herein comprising the amino acid positions as defined by the present invention. Thus, 7D8, 2F8, 003, and 005, may be used as a parent dimeric protein according to the present invention.

In one embodiment, at least one of the polypeptides, of the dimeric protein, comprises an immunoglobulin heavy chain variable region.

In one embodiment, the dimeric protein of the present invention is an antibody.

In a further embodiment, wherein the dimeric protein is an antibody, one or both, such as each, of the first and second polypeptides comprises immunoglobulin heavy and light chain variable regions to form a first and a second antigen-binding region, optionally binding the same antigen.

In another embodiment, wherein the dimeric protein is an antibody, one or both, such as each, of the first and second polypeptides comprises an immunoglobulin heavy-chain variable region associated with an immunoglobulin light chain sequence comprising light chain variable and constant regions to form a first and a second antigen-binding region, optionally binding the same antigen. In such an embodiment, it is understood that said first and second polypeptides comprising immunoglobulin heavy-chain variable and constant regions are associated with an immunoglobulin light chain sequence comprising light chain variable and constant regions by interchain disulfide bonds between the constant domains of said heavy chain and said light chain, and thereby forming a first and a second antigen-binding region, optionally binding the same antigen.

In a further embodiment, wherein the dimeric protein is an antibody, one or both polypeptides comprise a full-length heavy chain constant region, such as a full-length human IgG1 heavy chain constant region.

The CH2 and CH3 regions of the first and/or second polypeptides may except for the amino acid positions defined by the present invention, comprise amino acids 114-223 and 224-330, respectively, of SEQ ID NO:1; amino acids 111-219 and 220-326, respectively, of SEQ ID NO:2; amino acids 161-270 and 271-377, respectively, of SEQ ID NO:3; amino acids 111-220 and 221-327, respectively, of SEQ ID NO:4; or amino acids 114-223 and 224-330, respectively, of SEQ ID NO:5.

Said first and/or second polypeptides may further comprise a hinge region, wherein said hinge region comprise amino acids 99-113 of SEQ ID NO:1; amino acids 99-110 of SEQ ID NO:2; amino acids 99-160 of SEQ ID NO:3; amino acids 99-110 of SEQ ID NO:4; or amino acids 99-113 of SEQ ID NO:5.

The first and/or second polypeptide may except for the amino acid positions defined by the present invention comprise a sequence according to any of SEQ ID NOs: 1, 2, 3, 4, and 5.

The dimeric protein of the present invention may in a particular embodiment as described above be an antibody. Furthermore, the dimeric protein, e.g. an antibody, may also be prepared by introducing mutations into a parent dimeric protein, e.g. a parent antibody, in the amino acids in the positions corresponding to E345 and E430 in a human IgG1 heavy chain, and an amino acid in at least one position selected from the group consisting of S440, Y436, D/E356, T359, E382, N434, Q438, I253 and S254. The examples of antibodies may thus refer to "an antibody of the present invention" or "a variant antibody of the present invention", and a "parent antibody".

Examples of suitable antibodies include but are not limited to monovalent antibodies heavy-chain antibodies, consisting only of two heavy chains and naturally occurring in e.g. camelids (e.g., Hamers-Casterman (1993) Nature 363: 446); ThioMabs (Roche, WO2011069104), strand-exchange engineered domain (SEED or Seed-body) which are asymmetric and bispecific antibody-like molecules (Merck, WO2007110205); Triomab (Fresenius, Lindhofer et al. (1995 J Immunol 155:219); FcΔAdp (Regeneron, WO2010151792), Azymetric Scaffold (Zymeworks/Merck, WO2012/058768), mAb-Fv (Xencor, WO2011/028952), Dual variable domain immunoglobulin (Abbott, DVD-Ig, U.S. Pat. No. 7,612,181); Dual domain double head antibodies (Unilever; Sanofi Aventis, WO20100226923), Di-diabody (ImClone/Eli Lilly), Knobs-into-holes antibody formats (Genentech, WO9850431); DuoBody (Genmab, WO 2011/131746); Electrostatic steering antibody formats (Amgen, EP1870459 and WO 2009089004; Chugai, US201000155133; Oncomed, WO20100129304A2); bispecific IgG1 and IgG2 (Rinat neurosciences Corporation, WO11143545), CrossMAbs (Roche, WO2011117329), LUZ-Y (Genentech), Biclonic (Merus), Dual Targeting domain antibodies (GSK/Domantis), Two-in-one Antibodies recognizing two targets (Genentech, NovImmune), Cross-linked Mabs (Karmanos Cancer Center), CovX-body (CovX/Pfizer), IgG-like Bispecific (ImClone/Eli Lilly, Shen, J., et al. J Immunol Methods, 2007. 318(1-2): p. 65-74), and DIG-body and PIG-body (Pharmabcine), and Dual-affinity retargeting molecules (Fc-DART or Ig-DART, by Macrogenics, WO/2008/157379, WO/2010/080538), Zybodies (Zyngenia), approaches with common light chain (Crucell/Merus, U.S. Pat. No. 7,262,028) or common heavy chains (κλBodies by NovImmune), as well as fusion proteins comprising a polypeptide sequence fused to an antibody fragment containing an Fc-domain like scFv-fusions, like BsAb by ZymoGenetics/BMS), HERCULES by Biogen Idec (U.S. Ser. No. 00/795,1918), SCORPIONS by Emergent BioSolutions/Trubion, Ts2Ab (MedImmune/AZ (Dimasi, N., et al. J Mol Biol, 2009. 393(3): p. 672-92), scFv fusion by Novartis, scFv fusion by Changzhou Adam Biotech Inc (CN 102250246), TvAb by Roche (WO 2012025525, WO 2012025530), mAb$^2$ by f-Star (WO2008/003116) dual scFv-fusions, a mini-antibody, and a Dual Targeting (DT)-Ig antibody. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), and antibody-like polypeptides, such as chimeric antibodies and humanized antibodies. An antibody as generated can potentially possess any isotype.

The parent antibody or an antibody of the present invention may be prepared from wild-type antibodies or non-naturally occurring antibody formats as any of those described herein, e.g. heterodimeric proteins, which are used as starting material into which the relevant modifications according to the present invention are introduced. The antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624 628 (1991) and Marks et al., J. Mol. Biol. 222, 581 597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rabbits, rats, dogs, primates, etc.

The antibody may be e.g. a chimeric or humanized antibody. In another embodiment, the antibody is a human antibody. Human monoclonal antibodies may be generated using transgenic or transchromosomal mice, e.g. HuMAb mice, carrying parts of the human immune system rather than the mouse system. The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., Nature 368, 856 859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49 101 (1994), Lonberg, N. and Huszar, D., Intern. Rev. Immunol. Vol. 13 65 93 (1995) and Harding, F. and Lonberg, N. Ann. N.Y. Acad. Sci 764 536 546 (1995)). The preparation of HuMAb mice is described in detail in Taylor, L. et al., Nucleic Acids Research 20, 6287 6295 (1992), Chen, J. et al., International Immunology 5, 647 656 (1993), Tuaillon et al., J. Immunol. 152, 2912 2920 (1994), Taylor, L. et al., International Immunology 6, 579 591 (1994), Fishwild, D. et al., Nature Biotechnology 14, 845 851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187. Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, mammalian display, yeast display and other techniques known in the art, and the resulting molecules may be subjected to additional maturation, such as affinity maturation, as such techniques are well known in the art.

The antibody is not limited to antibodies which have a natural, e.g. a human Fc domain but it may also be an antibody having other mutations than those of the present invention, such as e.g. mutations that affect glycosylation, C1q binding, Fc receptor binding, or enables the antibody to be a bispecific antibody. By the term "natural antibody" is meant any antibody which does not comprise any genetically introduced mutations. An antibody which comprises naturally occurring variations, e.g. different allotypes, is thus to be understood as a "natural antibody" in the sense of the present invention. Such antibodies may serve as a template or starting material, e.g. parent antibody, for introducing the mutations according to the present invention, and thereby providing the antibodies of the invention. An example of an antibody comprising other mutations than those of the present invention is a bispecific antibody as described in WO2011/131746 (Genmab), utilizing reducing conditions to promote half-molecule exchange of two antibodies comprising IgG4-like matched CH3 regions, thus forming bispecific antibodies without concomitant formation of aggregates. Other examples of antibodies include but are not limited to bispecific antibodies such as heterodimeric bispecifics: Triomabs (Fresenius); bispecific IgG1 and IgG2 (Rinat Neurosciences Corporation); FcΔAdp (Regeneron); Knobs-into-holes (Genentech); Electrostatic steering (Amgen, Chugai, Oncomed); SEEDbodies (Merck); Azymetric scaffold (Zymeworks); mAb-Fv (Xencor); and LUZ-Y (Genentch). Other exemplary antibody formats include, without limitation, a wild-type antibody, a full-length antibody or Fc-containing antibody fragment, a human antibody, or any combination thereof.

Monoclonal antibodies for use in the present invention, may be produced, e.g., by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody is a human antibody. Human monoclonal antibodies directed against any antigen may be generated using transgenic or transchromosomal mice carrying parts of the human immune system rather than the mouse system. Such transgenic and transchromosomic mice include mice referred to herein as HuMAb® mice and KM mice, respectively, and are collectively referred to herein as "transgenic mice".

The HuMAb® mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb® mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/C mice can be generated by crossing HCo12 to KCo5[J/K](Balb) as described in WO/2009/097006. Splenocytes from these transgenic mice may be used to generate hybridomas that secrete human monoclonal antibodies according to well-known techniques.

Further, any antigen-binding regions of the present invention may be obtained from human antibodies or antibodies from other species identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

The dimeric protein, e.g. antibody of the present invention may comprise human IgG1 heavy chain comprising except for the mutations described herein the sequence of SEQ ID NO: 1 (UniProt accession No. P01857), such as comprising the relevant segment, I253 to K447, e.g. P247 to K447, corresponding to the underlined residues 136 to 330, e.g. 130 to 330, of the human IgG1 heavy chain constant region; SEQ ID NO:1:

```
  1 astkgpsvfp lapsskstsg gtaalgclvk dyfpepvtvs
    wnsgaltsgv 51 htfpavlqss glyslssvvt vpssslgtqt yicnvnhkps
    ntkvdkkvep 101 kscdkthtcp pcpapellgg psvflfppkp kdtlmisrtp
    evtcvvvdvs 151 hedpevkfnw yvdgvevhna ktkpreeqyn styrvvsvlt
    vlhqdwlngk 201 eykckvsnka lpapiektis kakgqprepq vytlppsrde
    ltknqvsltc 251 lvkgfypsdi avewesnggp ennykttppv ldsdgsffly
    skltvdksrw 301 qqgnvfscsv mhealhnhyt qkslslspgk
```

The allotype of the above-referenced IgG1 is IgG1m(za). The CH1 domain, hinge region, CH2 domain, and CH3 domain in SEQ ID NO:1 are for the present invention amino acids 1-98, 99-113, 114-223 and 224-330, respectively. The CH1 domain, hinge region, CH2 domain, and CH3 domain when numbered according to Eu numbering as set forth in Kabat are numbered as amino acids 118-215, 216-230, 231-340, and 340-447, respectively.

The dimeric protein, e.g. antibody of the present invention can also comprise a human IgG2 heavy chain comprising except for the mutations described herein the sequence of SEQ ID NO:2. Amino acid residues I253 to K447, e.g. P247 to K447, of the IgG1 heavy chain correspond to the underlined residues 132 to 326, e.g. 126 to 326, of the IgG2 heavy chain constant region (accession number P01859; SEQ ID NO:2)

```
  1 astkgpsvfp lapcsrstse staalgclvk dyfpepvtvs
    wnsgaltsgv 51 htfpavlqss glyslssvvt vpssnfgtqt ytcnvdhkps
    ntkvdktver 101 kccvecppcp appvagpsvf lfppkpkdtl misrtpevtc
    vvvdvshedp 151 evqfnwyvdg vevhnaktkp reeqfnstfr vvsvltvvhq
    dwlngkeykc 201 kvsnkglpap iektisktkg qpregavytl ppsreemtkn
    qvsltclvkg 251 fypsdiavew esnggpenny kttppmldsd gsfflysklt
    vdksrwqqgn 301 vfscsvmhea lhnhytqksl slspgk
```

The CH1 domain, hinge region, CH2 domain, and CH3 domain in SEQ ID NO:2 are for the present invention amino acids 1-98, 99-110, 111-219 and 220-326, respectively.

The dimeric protein, e.g. antibody, of the present invention can also comprise a human IgG3 heavy chain comprising except for the mutations described herein the sequence of SEQ ID NO:3. Amino acid residues I253 to K447, e.g. P247 to K447, of the IgG1 heavy chain correspond to residues 183 to 377, e.g. 177 to 377, of the IgG3 heavy chain constant region (UniProt accession No. P01860, SEQ ID NO:3), underlined in the following:

```
  1 astkgpsvfp lapcsrstsg gtaalgclvk dyfpepvtvs
    wnsgaltsgv 51 htfpavlqss glyslssvvt vpssslgtqt ytcnvnhkps
    ntkvdkrvel 101 ktplgdttht cprcpepksc dtpppcprcp epkscdtppp
    cprcpepksc 151 dtpppcprcp apellggpsv flfppkpkdt lmisrtpevt
    cvvvdvshed 201 pevqfkwyvd qvevhnaktk preeqynstf rvvsvltvlh
    qdwlngkeyk 251 ckvsnkalpa piektisktk ggprepqvyt lppsreemtk
    nqvsltclvk 301 gfypsdiave wessggpenn ynttppmlds dgsfflyskl
    tvdksrwqqg 351 nifscsvmhe alhnrftqks lslspgk
```

The CH1 domain, hinge region, CH2 domain, and CH3 domain in SEQ ID NO:3 are for the present invention amino acids 1-98, 99-160, 161-270 and 271-377, respectively.

The dimeric protein, e.g. antibody, of the present invention can also comprise a human IgG4 heavy chain comprising except for the mutations described herein the sequence of SEQ ID NO:4. Amino acid residues I253 to K447, e.g. P247 to K447, of the IgG1 heavy chain correspond to the underlined residues 133 to 327, e.g. 127 to 327, of the IgG4 heavy chain constant region (accession number P01859, SEQ ID NO:4)

```
  1 astkgpsvfp lapcsrstse staalgclvk dyfpepvtvs
    wnsgaltsgv 51 htfpavlqss glyslssvvt vpssslgtkt ytcnvdhkps
    ntkvdkrves
```

```
101 kygppcpscp apeflggpsv flfppkpkdt lmisrtpevt
    cvvvdvsqed 151 pevqfnwyvd qvevhnaktk preeqfnsty rvvsvltvlh
    qdwlngkeyk 201 ckvsnkqlps siektiskak gqprepqvyt lppsqeemtk
    nqvsltclvk 251 gfvpsdiave wesnggpenn ykttppvlds dqsfflysrl
    tvdksrwqeg 301 nvfscsvmhe alhnhytqks lslslgk
```

The CH1 domain, hinge region, CH2 domain, and CH3 domain in SEQ ID NO:4 are for the present invention amino acids 1-98, 99-110, 111-220 and 221-327, respectively.

The dimeric protein, e.g. antibody, of the present invention can also comprise a human IgG1m(f) allotype heavy chain comprising except for the mutations described herein the sequence of SEQ ID NO:5. Amino acid residues I253 to K447 of the IgG1m(f) allotype heavy chain correspond to the underlined residues 136-330 of SEQ ID NO:5

```
  1 astkgpsvfp lapsskstsg gtaalgclvk dyfpepvtvs
    wnsgaltsgv 51 htfpavlqss glyslssvvt vpssslgtqt yicnvnhkps
    ntkvdkrvep 101 kscdkthtcp pcpapellgg psvflfppkp kdtlmisrtp
    evtcvvvdvs 151 hedpevkfnw yvdgvevhna ktkpreeqyn styrvvsvlt
    vlhqdwlngk 201 eykckvsnka lpapiektis kakgqprepq vytlppsree
    mtknqvsltc 251 lvkgfypsdi avewesnggp ennykttppv ldsdgsffly
    skltvdksrw 301 qqgnvfscsv mhealhnhyt qkslslspgk
```

The CH1 domain, hinge region, CH2 domain, and CH3 domain in SEQ ID NO:5 are for the present invention amino acids 1-98, 99-113, 114-223 and 224-330, respectively.

The dimeric protein of the present invention may be of another allotype of human IgG1 immunoglobulins, such as IgG1m(a), IgG1m(z), and IgG1m(x). Such allotypes have been described to contain different amino acid in one or more positions corresponding to positions 214, 356, 358, and 431 according to Eu numbering as set forth in Kabat.

An alignment of the respective segments of the IgG1, IgG2, IgG3, IgG4, IgG1m(f), IgA1, IgA2, IgE, IgD and IgM constant regions is shown in FIG. 2. Accordingly, any amino acid position, or mutation in an amino acid position, described herein as corresponding to an amino acid position in a human IgG1 heavy chain, can be identified or introduced at its equivalent position in IgG2, IgG3, IgG4, IgG1m(f), IgA1, IgA2, IgE, IgD and IgM as defined by the alignment in FIG. 2 to obtain a dimeric protein according to the invention.

In any aspect or embodiment of a dimeric protein of the present invention, the first and/or second polypeptide of the dimeric protein may comprise the sequence of residues 130 to 330 of SEQ ID NO:1, residues 126 to 326 of SEQ ID NO:2, residues 177 to 377 of SEQ ID NO:3, residues 127 to 327 of SEQ ID NO:4, or residues 130 to 330 of SEQ ID NO:5.

In one embodiment, the first and/or second polypeptide of the dimeric protein comprises a sequence selected from SEQ ID No.: 1-5, such as SEQ ID No.:1, SEQ ID No.:2, SEQ ID No.:3, SEQ ID No.:4, or SEQ ID No.:5.

In one embodiment the antibody is a human full-length antibody, such as a human full-length IgG1 antibody.

In one embodiment, the antibody is a human IgG1 antibody, e.g. the IgG1m(za) or IgG1m(f) allotype, optionally wherein the first and/or second polypeptide, e.g. both polypeptides, comprises except for the mutations described herein, SEQ ID NO:1 or 5, In one embodiment, the antibody is a human antibody which may be any of the allotypes known within that isotype.

In one embodiment, the antibody is a human IgG2 antibody, optionally wherein the first and/or second polypeptide, e.g. both polypeptides, comprises SEQ ID NO:2.

In one embodiment, the antibody is a human IgG3 antibody, optionally wherein the first and/or second polypeptide, e.g. both polypeptides, comprises SEQ ID NO:3.

In one embodiment, the antibody is a human IgG4 antibody, optionally wherein the first and/or second polypeptide, e.g. both polypeptides, comprises SEQ ID NO:4.

In particular embodiments of any dimeric protein of the present invention, the first and/or second polypeptide, e.g. both polypeptides, of the dimeric protein comprises an amino acid sequence which has a degree of identity to amino acids P247 to K447, e.g. I253 to K447, of SEQ ID Nos: 1, 2, 3, 4, and 5 of at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, or of at least about 99%, except for the amino acid positions defined by the present invention.

Thus, the first and/or second polypeptide, e.g. both polypeptides, of the dimeric protein may comprise a sequence according to SEQ ID No:1, SEQ ID No:2, SEQ ID No:3, SEQ ID No: 4, or SEQ ID No:5 except for any amino acid residues of the present invention and defined herein.

The inventors of the present invention have found that six antibodies in which the amino acids E, E and S at the positions corresponding to E345, E430 and S440 of a human IgG1 heavy chain, have been substituted with the amino acids R, G and Y, respectively, are capable of forming non-covalent hexameric structures in solution.

Hence, in one embodiment, the dimeric protein of the present invention is predominantly in oligomeric form, such as hexameric form, in a phosphate buffer at a pH of about 6.8.

Hence, in one embodiment a dimeric protein of the present invention is capable of forming a non-covalent hexameric structure under the conditions described in Example 20 or 23, e.g. in a solution of 12.6 mM sodium phosphate, 140 mM NaCl at pH 7.4, or in a solution of 0.1 M $Na_2SO_4$, 0.1 M sodium phosphate at pH 6.8, or in a solution of 0.15 M NaCl, 0.1M citrate buffer at pH 6.8. In the context of the present invention the term "capable of forming non-covalent hexameric structure" means that more than 30%, such as more than 40%, or more than 50%, or more than 60%, or more than 70%, or more than 80%, or more than 85%, or more than 90%, or more than 95% of the dimeric proteins, e.g. antibodies are in a non-covalent hexameric structure when determined as described in Example 20. In a further embodiment the dimeric protein of the present invention is not capable of forming non-covalent structure in a solution of 0.15 M NaCl, 0.1M citrate buffer at pH 5.0. The term "is not able to form non-covalent hexameric structure" means in the context of the present invention that less than 10%, such as less than 8%, or less than 7%, or less than 6%, or less than 5%, or less than 4%, or less than 3%, or less than 2%, or less than 1%, or less than 0.5% of the dimeric proteins, e.g. antibodies, are in a non-covalent hexameric structure when determined as described in Example 20. Thus, in one embodiment, the hexameric structure may be determined by performing HP-SEC (high pressure size exclusion chromatography) fractionation using a suitable size exclusion chromatography resin with a pore size capable of separating molecules in the range of 50 kDa to 1000 kDa, connected to an absorbance detector; separating in 50 µL samples containing 1.25 µg/mL protein at 1 mL/min in 0.1 M $Na_2SO_4$/0.1 M sodium phosphate buffered at pH 6.8; using suitable software to process results; and expressing per peak as percentage of total peak area.

The ability of a dimeric protein of the present invention of forming an oligomeric, e.g. a hexameric structure makes the dimeric protein suitable for binding targets not only present on a cell but also soluble targets. Thus, the dimeric protein of the present invention may e.g. be used to remove soluble factors, e.g. bacterial toxins, or other unwanted factors, from the blood stream, such as complement components, e.g. C1q.

Phenotyping of erythrocytes, such as determination of the Rhesus D status, is important in case of blood transfusions and to determine the risk of hemolytic disease of a newborn. For the phenotyping of erythrocytes currently monoclonal human IgG antibodies are used in a laboratory test, e.g. Coombs test. However, many of the IgGs used in these assays induce poor agglutination. In stead of IgG, oligomeric structures, e.g. hexameric structures, of the dimeric proteins of the present invention may be used as reagent in phenotyping assays. Using a stable oligomeric, such as a hexameric, structure of the dimeric proteins of the present invention for erythrocyte phenotyping may have several advantages, such as the oligomeric structure could by itself induce crosslinking of cells bypassing need for a secondary antibody, could improve the sensitivity of the assay, and two or more dimeric proteins having different binding regions could be used for phenotyping multiple erythrocyte antigens simultaneously. Thus, in one embodiment, the dimeric protein of the present invention may be used for phenotyping erythrocytes. In one embodiment, two or more, such as three, four, five or six, dimeric proteins of the present invention having different binding regions may be used for phenotyping of multiple erythrocyte antigens.

In a further embodiment the dimeric protein of the present invention has an increased effector function compared to a parent dimeric protein. The dimeric protein of the present invention may be regarded as a variant of a parent dimeric protein wherein the variant comprises amino acid mutations in the positions 345, 430, and an amino acid mutation in at least one position selected from the group consisting of S440, Y436, D/E356, T359, E382, N434, Q438, I253 and S254, compared to the parent dimeric protein. A parent dimeric protein is in this context a dimeric protein in which the amino acids of said first and/or second polypeptides correspond to those of a human IgG1 heavy chain at positions E345, E430 and amino acid in at least one position selected from the group consisting of S440, Y436, D/E356, T359, E382, N434, Q438, I253 and S254, wherein the amino acid position selected from the group consisting of S440, Y436, E356, T359, E382, N434, Q438, I253 and S254, corresponds to those of a human IgG1 heavy chain at that position. As described above, the parent dimeric protein may be any isotype.

For an antibody, typically, the efficacy of the antibody may be expressed by the EC50 value, which is the concentration of the antibody necessary to obtain 50% of the maximal effect. This similarly applies to a dimeric protein of the present invention.

Maximal effect is the effect obtained when a saturating amount of the antibody is used, in which saturating is intended to refer to the amount of antibody at which all antigens for the antibody are bound by the antibody. This similarly applies to a dimeric protein of the present invention.

The term "increasing an effector function" or "improving an effector function" refers in the context of the present invention to a decrease in the EC50 value of the dimeric protein of the present invention compared to the parent dimeric protein. The decrease in the EC50 value may e.g. be at least or about 2-fold, such as at least or about 3-fold, or at least or about 5-fold, or at least or about 10-fold. Alternatively, "increasing an effector function" or "improving an effector function" means that there is an increase in the maximal amount of cells lysed (where the total amount of cells is set at 100%) by e.g. from 10% to 100% of all cells, such as by about 10%, about 20%, about 30%, about 40%, about 50%, about 60%, about 70%, about 80%, about 90%, and about 100% under conditions where the parent dimeric protein lyses less than 100% of all cells.

A dimeric protein could be tested for increased or improved effector function by cloning the variable domain of the IgG1-005 or IgG1-7D8 heavy chain into the dimeric protein and test its efficacy in CDC assays, such as described for Daudi (Example 3) and Wien (Example 6). In one embodiment, CDC efficacy may be determined by pre-incubating suspension cells at a concentration of $1 \times 10^6$ cells/mL in round-bottom 96-well plates with an antibody in the range from 0.0003 to 30.0 μg/mL final concentration in a total volume of 100 μL for 15 min on a shaker at room temperature, adding normal human serum at a concentration of 20%, 30% or 50% final concentration, incubating at 37° C. for 45 min, putting the plates on ice, adding 10 μL propidium iodide, and determining cell lysis by FACS analysis.

Using an IgG1-7D8 HC variable domain and Daudi cells, an increase would be defined by a more than 2 fold lower EC50 than the EC50 of IgG1-7D8 under the studied condition, such as about 2-fold, about 3-fold, about 5-fold, about 10-fold or a more than 10-fold lower EC50 value, the concentration at which half-maximal lysis is observed. Using an IgG1-005 HC variable domain and Daudi cells, an increase would be defined by a more than 2 fold lower EC50 than the EC50 of IgG1-005 under the studied condition, such as about 2-fold, about 3-fold, about 5-fold, about 10-fold or a more than 10-fold lower EC50 value, the concentration at which half-maximal lysis is observed. Using an IgG1-7D8 HC variable domain and Wien133 cells, an increase would be defined by a more than 2 fold lower EC50 than the EC50 of IgG1-7D8 under the studied condition, such as about 2-fold, about 3-fold, about 5-fold, about 10-fold or a more than 10-fold lower EC50 value, the concentration at which half-maximal lysis is observed. Using an IgG1-005 HC variable domain and Wien133 cells, an increase would be defined by an increase in the maximal lysis ranging from 10% to 100% of all cells, such as by about 10%, about 20%, about 30%, about 40%, about 50%, about 60%, about 70%, about 80%, about 90%, and about 100%. An increase in CDC efficacy could also be defined by a more than 2-fold lower EC50 than the EC50 of IgG1-005 under the studied condition, such as about 2-fold, about 3-fold, about 5-fold, about 10-fold or a more than 10-fold lower EC50 value, the concentration at which half-maximal lysis is observed under conditions where lysis of Wien133 cells is detectable.

The inventors of the present invention have found that an antibody wherein the amino acids in positions corresponding to E345, E430 and S440 in a human IgG1 heavy chain are not E, E and S, respectively have a lower EC50 value for binding to C1q and a lower EC50 value for CDC (see example 21) compared to the same antibody wherein the amino acids at said positions are E, E and S, respectively.

In a further embodiment, an effector function, such as CDC, of the dimeric protein of the present invention may be increased when the dimeric protein is bound to its target on a cell or virion where the target is present on the virion or cell membrane, as compared to the parent dimeric protein.

Other Amino Acid Position(s)

The first and/or second polypeptide of the dimeric protein of the present invention may further comprise other specific amino acids at indicated position(s). As described herein, a dimeric protein of the present invention, e.g. an antibody, may be prepared by introducing mutations at the amino acid positions as specified by the present invention.

Examples of such further other amino acids positions, or mutations, include amino acids positions where the specific amino acid affects one or more effector functions of the dimeric protein. Examples of such amino acids include amino acid residues which are capable of enhancing CDC, C1q binding, Fc-gamma receptor binding or FcRn-binding and/or improving Fc-gamma receptor-mediated effector functions.

Examples of effector functions include (i) C1q-binding, (ii) complement activation, (iii) CDC, (iv) oligomer formation, (v) oligomer stability, (vi) antibody-dependent cell-mediated cytotoxity (ADCC), (vii) FcRn-binding, (viii) Fc-gamma receptor-binding, (ix) antibody-dependent cellular phagocytosis (ADCP), (x) complement-dependent cellular cytotoxicity (CDCC), (xi) complement-enhanced cytotoxicity, (xii) binding to complement receptor of an opsonized antibody mediated by the antibody, (xiii) internalization, (xiv) downmodulation, (xv) induction of apoptosis, (xvi) opsonisation, (xvii) proliferation modulation, such as proliferation reduction, inhibition, and stimulation, and (xvii) a combination of any of (i) to (xvi), of a dimeric protein, such as an antibody when e.g. bound to its antigen on a cell, on a cell membrane, on a virion, or on another particle.

In one embodiment, a dimeric protein according to the invention further comprises an amino acid residue, or a modification of an amino acid residue, which is known as enhancing CDC e.g., an exchange of segments between IgG isotypes to generate chimeric IgG molecules (Natsume et al., 2008 Cancer Res 68(10), 3863-72); one or more amino acid substitutions in the hinge region (Dall'Acqua et al., 2006 J Immunol 177, 1129-1138), and/or one or more amino acid substitutions in or near the C1q-binding site in the CH2 domain, centered around residues D270, K322, P329, and P331 (Idusogie et al., 2001 J Immunol 166, 2571-2575; Michaelsen et al., 2009 Scand J Immunol 70, 553-564; WO 99/51642; Moore et al., 2010 mAbs 2(2), 181-189). For example, in one embodiment, a dimeric protein according to the invention further comprises a combination of any of the amino acid substitutions S267E, H268F, S324T, S239D, G236A and I332E, providing enhanced effector function via CDC or ADCC (Moore et al., 2010 mAbs 2(2), 181-189 and WO 2011/091078 A2). Other Fc mutations affecting binding to Fc-receptors (described in WO 2006/105062, WO 00/42072, U.S. Pat. Nos. 6,737,056 and 7,083,784) or physical properties of the antibodies (described in WO 2007/005612 A1) can also be used in the variants of the invention.

Hence, in one embodiment, the amino acid in at least one position corresponding to S267, H268, S324, S239, G236 and I332, may be E, F, T, D, A and E, respectively.

In one embodiment, a dimeric protein according to the invention further comprises modifications enhancing Fc-gamma receptor binding and/or Fc-gamma receptor-mediated effector function. Such modifications include (i) reducing the amount of fucose in the CH2 attached glycosylation (glyco-engineering) (Umana P, et al., Nat Biotechnol 1999; 17: 176-80; Niwa R, et al., Clin Cancer Res 2004; 10: 6248-55.)), and (ii) site-directed mutagenesis of amino acids in the hinge or CH2 regions of antibodies (protein-engineering) (Lazar G A, et al., Proc Natl Acad Sci USA 2006; 103: 4005-10).

In another embodiment such further mutations may be mutations which inhibit or reduce the effector functions of the dimeric protein. In clinical applications where engagement of the immune system is not required and may even cause unwanted side-effects the first and/or second polypeptide of the dimeric protein may then be further mutated in the CH2 domain to abolish C1q and/or FcGammaReceptor interactions.

Some amino acid residues in the Fc-domain that play a dominant role in the interactions with C1q and the FcGammaReceptors have been identified. Positions 234 and 235 were shown to have a strong modulating effect on human Fc binding to human CD64 (Canfield & Morrison, 1991; Chappel et al., 1991; Hezareh et al., 2001), CD32A (Hezareh et al., 2001; Armour et al., 2003), CD16 (Hezareh et al., 2001) and C1q (Xu et al., 2000; Hezareh et al., 2001). The CH2 position 331 was shown to be a major determinant for human IgG binding to human CD64 (Canfield & Morrison, 1991, J Exp Med.; 173:1483-91) and C1q (Tao et al., 1993; Idusogie et al., 2000) and a triple mutation L234F/L235E/P331S causes a profound decrease in binding to human CD64, CD32A, CD16 and C1q.

Based on this knowledge several variants were described to make Fc-domain inactive for interactions with Fcgamma receptors and C1q for therapeutic antibody development.

For IgG1 mutating L234A and L235A and P331S were described (Hezareh M, et al., J Virol 2001, 75:12161-12168, Xu D et al. Cell Immunol 2000, 200:16-26, Shields R L, et al. J Biol Chem 2001, 276:6591-6604) and L234A combined with L235A was used in the clinic (Herold K C, et al. Diabetes 2005, 54:1763-1769). Hence, in one embodiment, the amino acid in at least one position corresponding to L234, L235 and P331, may be A, A and S, respectively.

Also mutating these same positions to L234F and L235E was described to result in Fc-domains with abrogated interactions with FcGammaReceptors and C1q (Oganesyan Acta Cryst. (2008). D64, 700-704, Canfield & Morrison, 1991 J Exp Med.; 173:1483-91., Duncan, 1988 Nature 332:738-40). Hence, in one embodiment, the amino acids in the positions corresponding to L234 and L235, may be F and E, respectively.

Mutating position D265A showed decreased binding to all FcγReceptors and prevented ADCC (Shields R L et al. *J Biol Chem* 2001, 276:6591-6604). Hence, in one embodiment, the amino acid in a position corresponding to D265, may be A.

Binding to C1q could be abrogated by mutating positions D270, K322, P329, and P331 (Idusogie et al., J Immunol 2000, 164:4178-4184). Mutating these positions to either D270A or K322A or P329A or P331A made the antibody deficient in CDC activity. Hence, in one embodiment, the amino acids in at least one position corresponding to D270, K322, P329 and P331, may be A, A, A, and A, respectively.

An alternative approach to minimize the interaction of the Fc-domain with FcgammaReceptors and C1q is by removal of the glycosylation site of an antibody. Mutating position N297 to eg Q, A, and E removes a glycosylation site which is critical for IgG-Fcgamma receptor interactions (Tao and Morrison, J Immunol. 1989 Oct. 15; 143(8):2595-601, Bolt S et al., *Eur J Immunol* 1993, 23:403-411). Hence, in one embodiment, the amino acid in a position corresponding to N297, may be Q, A or E.

Alternatively, human IgG2 and IgG4 subclasses are naturally compromised in their interactions with C1q and FcgammaReceptors. However, residual interactions with FcγReceptors (FcgammaReceptors) have been described (Parren et al., J Clin Invest 1992, 90:1537-1546.). Mutations abrogating these residual interactions have been described for both isotypes and result in reduction of unwanted side-effects associated with FcR binding. For IgG2 mutating L234A and G237A was described (Cole M S et al. J Immunol 1997, 159:3613-3621 and for IgG4 L235E was described (Reddy M P et al., J Immunol 2000, 164:1925-1933). Hence, in one embodiment, the amino acid in a position corresponding to L234 and G237 in a human IgG2 heavy chain, may be A and A, respectively. In one embodiment, the amino acid in a position corresponding to L235 in a human IgG4 heavy chain, may be E.

Other approaches to further minimize the interaction with FcgammaReceptors and C1q IgG2 antibodies were described in WO 2011/066501 A1 (PCT/US2010/058188) and Lightle, S., et al.; Protein Science (19):753-62 (2010).

Alternatively, the hinge region of the antibody is of importance with respect of interactions with FcgammaReceptors and complement. Mutations in the hinge region have been described to influence effector functions of an antibody (Brekke et al., J Immunol 2006, 177:1129-1138, Dall'Acqua W F, et al. J Immunol 2006, 177:1129-1138. Either mutating or deleting the hinge region will affect Fc effector functions of an antibody.

Hence, in one embodiment the first and/or second polypeptide of the dimeric protein of the present invention may further comprise any of the above mentioned mutations which inhibit or reduce one or more effector functions of the dimeric protein.

Combining sets of mutations described above may result in an even more inert Fc-domain, for instance combining mutations L234F, L235E, D265A; or L234F, L235E, N297Q and D265A in an IgG1 Fc-domain or other variations generated by the information described above. Hence, in one embodiment, the amino acids in at least one or a combination of positions corresponding to L234, L235, D265; or L234, L235, N297 and D265, may be F, E, A, F, E, Q and A, respectively.

In one embodiment the first and/or second polypeptide, e.g. both polypeptides of the dimeric protein of the present invention may further comprise any combination of the above mentioned mutations which inhibit or reduce one or more effector functions of the dimeric protein.

Typically, the effect of an antibody on an effector function may be measured by the EC50 value, which is the concentration of the antibody necessary to obtain half the value of the maximal lysis. This similarly applies to a dimeric protein of the present invention.

Maximal lysis is the effect obtained when a saturating amount of the antibody is used in which saturating is intended to refer to the amount of antibody at which all antigens for the antibody are bound by the antibody. This similarly applies to a dimeric protein of the present invention.

Thus, in one embodiment, the first and/or second polypeptides of the dimeric protein may further comprise amino acid substitutions in the amino acid positions corresponding to L234, L235 and D265 in a human IgG1 heavy chain, which are F, E, and A, respectively.

The term "decreasing an effector function" refers in the context of the present invention that there is an increase in the EC50 value of the dimeric protein compared to the parent dimeric protein, wherein parent dimeric protein has the meaning as described above. The increase in the EC50 value may e.g. be at least or about 2-fold, such as at least or about 3-fold, or at least or about 5-fold, or at least or about 10-fold. Alternatively, "decreasing an effector function" means that there is a decrease in the maximal amount of cells lysed by e.g. from 10% to 100% of all cells, such as about 10%, about 20%, about 30%, about 40%, about 50%, about 60%, about 70%, about 80%, about 90%, and about 100% under conditions where the parent dimeric protein lyses less than 100% of all cells.

A dimeric protein could be tested for decreased effector function by cloning the variable domain of the IgG1-005 or IgG1-7D8 heavy chain into the dimeric protein and test its efficacy in CDC assays, such as described for Daudi (Example 3) and Wien (Example 6). Using an IgG1-7D8 HC variable domain and Daudi cells, a decrease would be defined by a more than 2 fold higher EC50 than the EC50 of IgG1-7D8 under the studied condition, such as about 2-fold, about 3-fold, about 5-fold, about 10-fold or a more than 10-fold higher EC50 value, the concentration at which half-maximal lysis is observed. Using an IgG1-005 HC variable domain and Daudi cells, a decrease would be defined by a more than 2-fold higher EC50 than the EC50 of IgG1-005 under the studied condition, such as about 2-fold, about 3-fold, about 5-fold, about 10-fold or a more than 10-fold higher EC50 value, the concentration at which half-maximal lysis is observed. Using an IgG1-7D8 HC variable domain and Wien133 cells, a decrease would be defined by a more than 2 fold higher EC50 than the EC50 of IgG1-7D8 under the studied condition, such as about 2-fold, about 3-fold, about 5-fold, about 10-fold or a more than 10-fold higher EC50 value, the concentration at which half-maximal lysis is observed. Using an IgG1-005 HC variable domain and Wien133 cells, a decrease would be defined by a decrease in the maximal lysis ranging from 10% to 100% of all cells, such as by about 10%, about 20%, about 30%, about 40%, about 50%, about 60%, about 70%, about 80%, about 90%, and about 100%. A decrease in CDC efficacy could also be defined by a more than 2-fold higher EC50 than the EC50 of IgG1-005 under the studied condition, such as about 2-fold, about 3-fold, about 5-fold, about 10-fold or a more than 10-fold higher EC50 value, the concentration at which half-maximal lysis is observed under conditions where lysis of Wien133 cells is detectable.

FcRn is a major histocompatibility complex class I-related receptor and plays a role in the passive delivery of immunoglobulin (Ig)Gs from mother to young and in the regulation of serum IgG levels by protecting IgG from intracellular degradation (Ghetie V et al., Annu Rev Immunol. 18, 739-66 (2000)). As FcRn is responsible for the extended persistence of IgG and other Fc-conjugated proteins in the serum, modulating the FcRn-Fc interaction will allow the deliberate control of the half-life of these agents in the circulation to various ends.

In one embodiment, the dimeric protein may comprise other amino acid residues or further, such as amino acid substitutions, which affect the pharmacokinetic profile, e.g. by affecting binding to FcRn.

In one embodiment, the plasma clearance of hexameric forms of dimeric proteins according to the present invention is decreased, for example to allow lower dosing and minimize adverse reactions caused by high doses, decrease frequency of injection, maximize transcytosis to specific tissue sites, enhance efficiency of trans-placental delivery, or decrease production costs.

In a further embodiment, the first and/or second polypeptide, e.g. both polypeptides, of the dimeric protein according to the present invention have been further modified e.g. in the CH2 and/or CH3 region, for example, to improve the pharmacokinetic profile, e.g. via improving the binding to FcRn, e.g. at pH 6.0. These modifications include, but are not limited to, mutations at any one or more of amino acid positions P238, T250, M252, I253, S254, R255, T256, D265, E272, N286, K288, V303, V305, T307, L309, H310, Q311, D312, K317, K340, D356, K360, Q362, D376, A378, E380, E382, Q386, E388, S400, D413, S415, S424, M428, H433, N434, H435, Y436, K439 or K447 of the Fc region, wherein the numbering of the residues in the Fc region is that of the EU index as in Kabat (Shields, R. L., et al, J Biol Chem. 9, 6591-604 (2001), Dall'Acqua, W. F., et al, J Immunol. 9, 5171-80 (2002), Hinton, P., et al, J Biol Chem. 8, 6213-6 (2004), Dall'Acqua, W. F., et al, J Biol Chem. 33, 23514-24 (2006), Petkova, S. B., et al, Int Immunol. 12, 1759-69 (2006), Datta-Mannan, A., et al, J Biol Chem. 3, 1709-17 (2007), Yeung, Y. A., J Immunol. 12, 7663-71 (2009), Kabat, E. A. in US Department of Health and Human Services, NIH publication n° 91-3242, 5th edition 662, 680, 689 (1991)). Hence, in one embodiment, in the first and/or second, such as both, polypeptides of the dimeric protein, an amino acid in at least one position corresponding to a position selected from the group consisting of P238, T250, M252, I253, S254, R255, T256, D265, E272, N286, K288, V303, V305, T307, L309, H310, Q311, D312, K317, K340, D356, K360, Q362, D376, A378, E380, E382, Q386, E388, S400, D413, S415, S424, M428, H433, N434, H435, Y436, K439 or K447; is not P, not T, not M, not I, not S, not R, not T, not D, not E, not N, not K, not V, not V, not T, not L, not H, not Q, not D, not K, not K, not D, not K, not Q, not D, not A, not E, not E, not Q, not E, not S, not D, not S, not S, not M, not H, not N, not H, not Y, not K or not K, for each position, respectively.

In an even further embodiment, the first and/or second polypeptide, e.g. both polypeptides, of the dimeric protein according to the present invention have been further modified to improve the pharmacokinetic profile, via improving the binding to FcRn by the specific mutations N434A (Shields, R. L., et al, J Biol Chem. 9, 6591-604 (2001)), T307A/E380A/N434A (Shields, R. L., et al, J Biol Chem. 9, 6591-604 (2001)), T250Q/M428L (Hinton, P., et al, J Biol Chem. 8, 6213-6 (2004)) or M252Y/S254T/T256E (Dall'Acqua, W. F., et al, J Immunol. 9, 5171-80 (2002)), wherein the numbering of the residues in the Fc region is that of the EU index as in Kabat (Kabat, E. A. in US Department of Health and Human Services, NIH publication n° 91-3242, 5th edition 662, 680, 689 (1991). Hence, in one embodiment, an amino acid in position corresponding to N434 may be A. In another embodiment, amino acids in positions corresponding to T307, E380 and N434 may be A, A and A, respectively. In another embodiment, amino acids in positions corresponding to positions T250 and M428 may be Q and L, respectively. In another embodiment, amino acids in positions in positions corresponding to M252, S254 and T256 may be Y, T and E, respectively. Thus, in one embodiment, said first and/or second polypeptides of the dimeric protein, may comprise amino acid substitutions in the amino acid positions corresponding to E345, E430, N434, and S440 in a human IgG1 heavy chain, which are not E; not E; A; and Y or W, respectively.

In one embodiment the dimeric protein may comprise a substitution of one or more of P238, T256, T307, Q311, D312, E380, E382, and N434 into an alanine residue improving FcRn binding (Shields R L, et al. J. Biol. Chem. 2001; 276:6591); or an amino acid substitution or combination of amino acid substitutions selected from M252Y/S254T/T256E, M252W, M252Y, M252Y/T256Q, M252F/T256D, V308T/L309P/Q311S, G385D/Q386P/N389S, G385R/Q386T/P387R/N389P, H433K/N434F/Y436H, N434F/Y436H, H433R/N434Y/Y436H, M252Y/S254T/T256E-H433K/N434F/Y436H or M252Y/S254T/T256E-G385R/Q386T/P387R/N389P in IgG1, increasing the affinity for FcRn (Dall'Acqua et al., supra). Hence, in one embodiment, one or more amino acids in position(s) corresponding to positions to those selected from the group consisting of P238, T256, T307, Q311, D312, E380, E382 and N434 may, for each polypeptide of the dimeric protein, be an A for each position, respectively. In another embodiment the amino acids in a positions corresponding to M252, S254 and T256, may be Y, T and E, respectively; or in position corresponding to M252 may be W; or in a position corresponding to M252 may be Y; or in positions corresponding to M252 and T256 may be Y and Q, respectively; or in positions corresponding to M252 and T256 may be F and D, respectively; or in positions corresponding to V308, L309 and Q311 may be T, P and S, respectively; or in positions corresponding to G385, Q386 and N389 may be D, P and S, respectively; or in positions corresponding to G385, Q386, P387 and N389 may be R, T, R and P, respectively; or in positions corresponding to H433, N434 and Y436 may be K, F and H, respectively; or in positions corresponding to N434 and Y436 may be F and H, respectively; or in positions corresponding to H433, N434 and Y436 may be R, Y and H, respectively; or in positions corresponding to M252, S254, T256, H433, N434 and Y436 may be Y, T, E, K, F and H, respectively; or in positions corresponding to M252, S254, T256, G385, Q386, P387 and N389 may be Y, T, E, R, T, R and P, respectively.

In one embodiment, the half-life of hexameric forms of the dimeric proteins according to the present invention is shortened, for example to ensure rapid clearance of dimeric proteins used for imaging and/or radioimmunotherapy, or promote clearance of pathogenic target molecules.

In a further embodiment, the first and/or second polypeptide, e.g. both polypeptides, of the dimeric protein according to the present invention have been further modified e.g. in the CH2 and/or CH3 region, for example, to modulate the pharmacokinetic profile, e.g. via reducing or abrogating the binding to FcRn. These modifications include, but are not limited to, mutations at any one or more of amino acid positions P238, T250, M252, I253, S254, R255, T256, D265, E272, N286, K288, V303, V305, T307, L309, H310, Q311, D312, K317, K340, D356, K360, Q362, D376, A378, E380, E382, Q386, E388, S400, D413, S415, S424, M428, H433, N434, H435, Y436, K439 or K447 of the Fc region, wherein the numbering of the residues in the Fc region is that of the EU index as in Kabat (Shields, R. L., et al, J Biol Chem. 9, 6591-604 (2001), Dall'Acqua, W. F., et al, J Immunol. 9, 5171-80 (2002), Hinton, P., et al, J Biol Chem. 8, 6213-6 (2004), Dall'Acqua, W. F., et al, J Biol Chem. 33, 23514-24 (2006), Petkova, S. B., et al, Int Immunol. 12, 1759-69 (2006), Datta-Mannan, A., et al, J Biol Chem. 3, 1709-17 (2007), Yeung, Y. A., J Immunol. 12, 7663-71 (2009), Kabat, E. A. in US Department of Health and Human Services, NIH publication n° 91-3242, 5th edition 662, 680, 689 (1991)). Hence, in one embodiment an amino acid in at least one position corresponding to a position selected from the group consisting of P238, T250, M252, I253, S254, R255, T256, D265, E272, N286, K288, V303, V305, T307, L309, H310, Q311, D312, K317, K340, D356, K360, Q362, D376, A378, E380, E382, Q386, E388, S400, D413, S415, S424, M428, H433, N434, H435, Y436, K439 or K447; is not P; not T; not M; not I; not S; not R; not T; not D; not E; not N; not K; not V; not V; not T; not L; not H; not Q; not D; not K; not K; not D; not K; not Q; not D; not A; not E; not E; not Q; not E; not S; not D; not S; not S; not M; not H; not N; not H; not Y; not K or not K, for each position, respectively.

In an even further embodiment, the first and/or second polypeptide, e.g. both polypeptides, of the dimeric protein according to the present invention have been further modified to improve the pharmacokinetic profile, via reducing or abrogating the binding to FcRn by the specific mutations I253A, H310A, H433A, H435A, Y436A, mutations I253A/H310A/H435A (Kim, J. K. et al. Eur. J. Immunol. 29, 2819-2825 (1999), Shields, R. L., et al, J Biol Chem. 9, 6591-604 (2001)), wherein the numbering of the residues in the Fc region is that of the EU index as in Kabat (Kabat, E. A. in US Department of Health and Human Services, NIH publication n° 91-3242, 5th edition 662, 680, 689 (1991)). Hence, in one embodiment, an amino acid in at least one position corresponding to a position selected from the group consisting of I253, H310, H433, H435 and Y436, may be A for each position, respectively. In another embodiment, the amino acids in positions corresponding to I253, H310A and H435A may each be A.

Another example of other amino acid positions where the specific amino acid may be relevant, e.g. where a parent dimeric protein is mutated to change the amino acid, may be amino acids which affect the interaction in the Fc-region between dimeric proteins, e.g. antibodies. Such mutations may be used to minimize the interaction of a therapeutic dimeric protein, e.g. therapeutic antibody, with antibodies naturally present in a patient to whom the therapeutic dimeric protein, e.g. therapeutic antibody, is administered.

Such amino acid residues or mutations have previously been described in PCT/EP12/063339, and include combinations of two amino acid residues or mutations which individually decrease an effector function but when used together, e.g. by combining two dimeric proteins each comprising one of said amino acid residues or mutations the effector function is similar to a parent dimeric protein where said amino acid residue is not mutated, thus it corresponds to that of a human IgG1 heavy chain. When such two dimeric proteins, each comprising one of such a pair of mutations, are used together, the specificity for interaction between said two dimeric proteins may be increased compared to the interaction between two dimeric proteins comprising only one of the mutations of such a pair of mutations. Similarly, the interaction between two dimeric proteins each comprising one of such a pair of mutations, may also be stronger than the interaction between a dimeric protein comprising only one of the mutations of such a pair with a dimeric protein not comprising any of the mutations of the pair.

Hence, in one embodiment the first and/or second polypeptide of the dimeric protein of the present invention may further comprise a mutation or amino acid residue according to this aspect.

Thus, without being bound by any theory, it is foreseen that by including such two mutations in a therapeutic dimeric protein, the induction of C1q binding in a patient will be limited to oligomeric complexes containing therapeutic dimeric protein, e.g. antibodies, comprising such a combination or pair of amino acids. This may allow a reduction of any potential side-effects caused by interaction of the therapeutic dimeric protein with the patients own antibodies which do not comprise such mutations.

In a particular embodiment, a dimeric protein may be used in combination with another dimeric protein, wherein each of the dimeric proteins comprises one of the amino acids of such a "pair" of amino acids. Thus, in one embodiment the present invention relates to a dimeric protein comprising one of the amino acids of such a "pair" in the first and/or second polypeptides. Such a dimeric protein, e.g. first dimeric protein, comprising one amino acid of such a "pair" may be used together with a second dimeric protein comprising in the first and/or second polypeptide the other amino acid of such a "pair". Examples of such amino acids include those of Table 1. Thus, in a further embodiment, an amino acid in a position corresponding to K439, S440, K447, 448 and 449 may be, for each polypeptide of the dimeric protein of the present invention, as described in Table 1.

TABLE 1

| Amino acid position (IgG1) | Exemplary substitutions | Preferred substitutions |
| --- | --- | --- |
| K439 | 439DER | 439E |
| S440 | 440DEKR | 440K |
| K447 | 447DE | 447E |
| K447/448 | 447KRH/448P | 447/448P |
| K447 | 447DE | 447E |
| K447/448/449 | 447KRH/448KRH/449P | 447/448K/449P |

Specific combinations of dimeric protein comprising such amino acids may be as described herein.

Thus, in a further aspect of the present invention the amino acid in the position corresponding to K439 is, for one or both, such as each, polypeptides of the dimeric protein, not K.

In a further embodiment the amino acid in the position corresponding to K439 is E or D.

In a further embodiment the amino acid in the position corresponding to K439 is E.

In a further embodiment the amino acid in the position corresponding to K439 is D.

In one embodiment, in the first or second polypeptide of the dimeric protein, the amino acid in positions corresponding to E345, E430, K439, and S440, in a human IgG1 heavy chain, are R, K, Q, N or Y; G, S, T, F, or H; E or D; and Y or W, respectively.

In one embodiment, in said first and/or second polypeptide, the amino acids in the positions corresponding to E345, E430, K439, and S440 in a human IgG1 heavy chain, are R; G; E; and Y, respectively.

In one embodiment, in said first and/or second polypeptide, the amino acid in the position corresponding to S440 in a human IgG1 heavy chain is K or R.

In one embodiment, the amino acid in the position corresponding to S440 is K.

In one embodiment, the amino acid in the position corresponding to S440 is R.

In one embodiment, in said first and/or second polypeptide the amino acid in the position corresponding to E345, E430, and S440 in a human IgG1 heavy chain are R; G; and K, respectively.

In a further embodiment of the present invention at least one amino acid in a position selected from the group consisting of Y436, D/E356, T359, E382, N434, Q438, I253 and S254 is, for one or both, such as each, polypeptides of the dimeric protein not Y; D or E; T; E; N; Q; I; and S, for each position, respectively, and the amino acid in the position corresponding to S440 is K or R.

In a further embodiment, the amino acid in the position corresponding to Y436 is I, and the amino acid corresponding to S440 is K.

In one embodiment, in said first and/or second polypeptide, the amino acids in the positions corresponding to E345, E430, Y436 and S440 in a human IgG1 heavy chain, are R; G; I; and K, respectively.

In one embodiment, the pair of K439D/E/R and S440D/E/K/R substitutions are used. Thus, in one embodiment, the first polypeptide comprises K439D/E/R, and the second polypeptide comprises S440D/E/K/R, or vice versa, and wherein in the first and/or second polypeptide the amino acids corresponding to the positions E345 and E430 are not E. In a further embodiment in the polypeptide comprising S440D/E/K/R one of the amino acids corresponding to the positions selected from the group consisting of Y436, D/E356, T359, E382, N434, Q438, I253 and S254 is not Y; D or E; T; E; N; Q; I; and S, for each position, respectively. Thus, in another aspect of the present invention, at least one amino acid in a position selected from the group consisting of Y436, D/E356, T359, E382, N434, Q438, I253 and S254 is, for one or both, such as each, polypeptides of the dimeric protein not Y; D or E; T; E; N; Q; I; and S, for each position, respectively, and the amino acid in the position corresponding to S440 is not S, Y or W.

In another embodiment the amino acid residue in the position corresponding to K447 is, for one or both, such as each, polypeptides of the dimeric protein D or E.

In a further embodiment, the amino acid in a position corresponding to K447 is D.

In a further embodiment, the amino acid in a position corresponding to K447 is E.

In another embodiment the amino acid residue in the position corresponding to K447 is, for one or both, such as each, of the polypeptides of the dimeric protein, K, R or H and the polypeptides comprise
  (a) an amino acid residue in position 448 which is P; or
  (b) an amino acid residue in position 448 which is K, R or H and an amino acid residue in position 449 which is P.

In a further embodiment, the amino acid in the position corresponding to K447 is K.

In a further embodiment, the amino acid in the position corresponding to K447 is R.

In a further embodiment, the amino acid in the position corresponding to K447 is H.

In a further embodiment, the amino acid in the position corresponding to 448 is K.

In a further embodiment, the amino acid in the position corresponding to 448 is R.

In a further embodiment, the amino acid in the position corresponding to 448 is H.

In a further embodiment, the amino acid in the position corresponding to Q386 is, for one or both, such as each, polypeptides in the dimeric protein, K.

Figure 4:
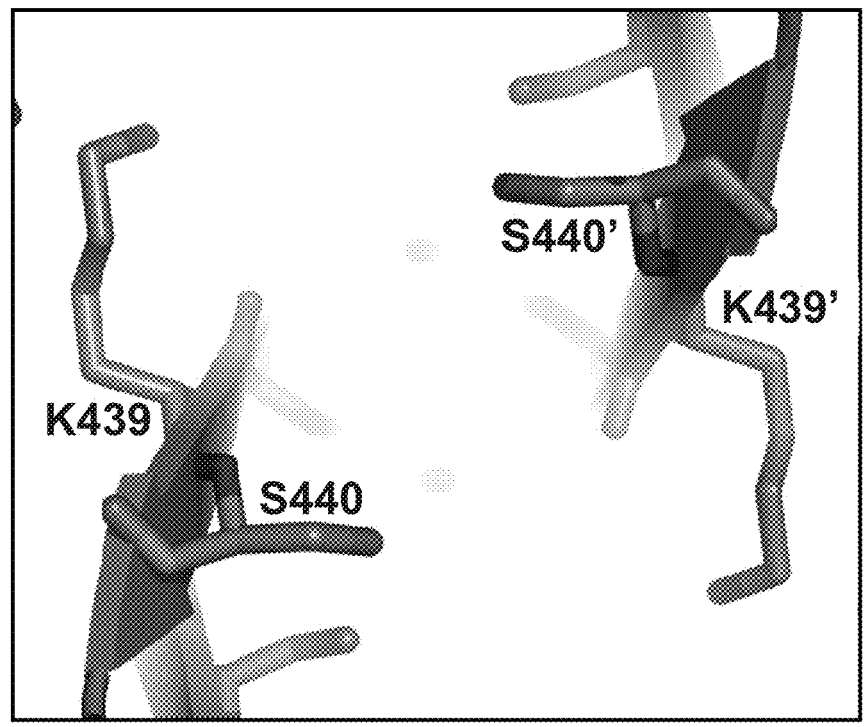
FIG. 4: Detailed view of the K439/S440 interactions between the Fc of adjacent molecules (Fc and Fc', respectively) in an oligomeric (e.g., hexameric) arrangement, illustrating the interaction between wild-type, unmodified Fc and Fc' molecules.

As described in the Examples 3-5, antibody variants comprising only one of the K439E and S440K mutations had a drastically increased $K_D$ for C1q, reflecting a decreased complement activation and/or CDC capability. Surprisingly, it was found that antibody variants of HuMAb 7D8 or 005 comprising both mutations had a restored or increased C1q-binding or CDC. Without being bound by any specific theory, the underlying mechanism could perhaps be explained by the respective mutations sterically compensating for each other, as illustrated in FIG. 4.

In a further embodiment, an amino acid in at least one position corresponding to L234, L235, G236, G237, S239, P238, T250, M252, I253, S254, R255, T256, D265, S267, H268, D270, E272, N286, K288, N297, V303, V305, T307, V308, L309, H310, Q311, D312, K317, K322, S324, P329, P331, I332 K340, D356, K360, Q362, D376, A378, E380, E382, G385, Q386, P387, E388, N389, S400, D413, S415, S424, M428, H433, N434, H435, Y436, K439 or K447, is not, for one or both, such as each, polypeptides of the dimeric protein, L; not L; not G; not G; not S; not P; not T; not M; not I; not S; not R; not T; not D; not S; not H; not D; not E; not N; not K; not N; not V; not V; not T; not V; not L; not H; not Q; not D; not K; not K; not S; not P; not P; not I; not K; not D; not K; not Q; not D; not A; not E; not E; not G; not Q; not P; not E; not N; not S; not D; not S; not S; not M; not H; not N; not H; not Y; not K and not K, respectively.

In one embodiment, the dimeric protein of the present invention is a homodimer. Thus, in one embodiment, both the first and second polypeptides of the dimeric protein comprise the same or identical amino acid substitutions according to any aspect or embodiment of the present invention.

Heterodimeric Format

In another embodiment, the dimeric protein of the present invention is a heterodimer.

In a further embodiment, at least one of the polypeptides comprises a binding region that specifically binds to a target. In a further embodiment, each polypeptide of the heterodimeric protein comprises a binding region specifically binding to a target, optionally the same target.

The target may be any of those described herein.

In a further embodiment the binding regions of the first and second polypeptide of the heterodimeric protein may bind to different epitopes on the same target. In another embodiment the binding regions of the first and second polypeptide of the heterodimeric protein may bind to different targets.

In another embodiment, the binding regions of the first and second polypeptide of the heterodimeric protein may bind to different targets on different cells.

In a particular embodiment, the heterodimeric protein may be a bispecific antibody.

In a further embodiment the binding regions of the first and second polypeptide of said heterodimeric antibody may bind to different epitopes on the same target. In another embodiment the binding regions of the first and second polypeptide of said heterodimeric antibody may bind to different targets.

In another embodiment, the binding regions of the first and second polypeptide of the heterodimeric protein may bind to different targets on different cells.

If the dimeric protein is a heterodimeric protein, the amino acids at the positions corresponding to E345, E430 and at least one position selected from the group consisting of S440, Y436, D/E356, T359, E382, N434, Q438, I253 and S254 in a human IgG1 heavy chain, may in one embodiment be different in the first and second polypeptide, however, they may also in another embodiment be the same.

Said amino acids may for example be different if the heterodimeric protein is produced as described in WO2011/131746.

The bispecific antibody of the present invention is not limited to a particular format and it may be any of those described herein.

Exemplary bispecific antibody molecules which may be used in the present invention comprise (i) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')$_2$ fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab arm exchange (such as described in WO 11/131746) as those described in the present invention.

Examples of different classes of bispecific antibodies include but are not limited to IgG-like molecules with complementary CH3 domains to force heterodimerisation recombinant IgG-like dual targeting molecules, wherein the two sides of the molecule each contain the Fab fragment or part of the Fab fragment of at least two different antibodies;

IgG fusion molecules, wherein full length IgG antibodies are fused to extra Fab fragment or parts of Fab fragment;

Fc fusion molecules, wherein single chain Fv molecules or stabilized diabodies are fused to heavy-chain constant-domains, Fc-regions or parts thereof;

Fab fusion molecules, wherein different Fab-fragments are fused together, fused to heavy-chain constant-domains, Fc-regions or parts thereof;

ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc-regions or parts thereof.

Examples of IgG-like molecules with complementary CH3 domains molecules include but are not limited to the Triomab/Quadroma (Trion Pharma/Fresenius Biotech), the Knobs-into-Holes (Genentech), CrossMAbs (Roche) and the electrostatically-matched (Amgen, Chugai, Oncomed), the LUZ-Y (Genentech), the Strand Exchange Engineered Domain body (SEEDbody)(EMD Serono), the Biclonics (Merus), FcΔAdp (Regeneron), bispecific IgG1 and IgG2 (Pfizer/Rinat), Azymetric scaffold (Zymeworks), mAb-Fv (Xencor), bivalent bispecific antibodies (Roche) and the DuoBody (Genmab A/S).

Examples of recombinant IgG-like dual targeting molecules include but are not limited to Dual Targeting (DT)-Ig (GSK/Domantis), Two-in-one Antibody (Genentech), Cross-linked Mabs (Karmanos Cancer Center), mAb$^2$ (F-Star) and CovX-body (CovX/Pfizer).

Examples of IgG fusion molecules include but are not limited to Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idec) and TvAb (Roche).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China).

Examples of Fab fusion bispecific antibodies include but are not limited to F(ab)$_2$ (Medarex/AMGEN), Dual-Action or Bis-Fab (Genentech), Dock-and-Lock (DNL) (Immuno-Medics), Bivalent Bispecific (Biotecnol) and Fab-Fv (UCB-Celltech).

Examples of ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

In a particular embodiment, the bispecific antibody has the format described in WO 2011/131746.

Thus, in one embodiment the present invention relates to a heterodimeric protein according to the present invention, wherein the amino acid in a position selected from K409, T366, L368, K370, D399, F405, and Y407 is not K, T, L, K, D, F and Y, respectively, in the first polypeptide, and the amino acid in a position selected from F405, T366, L368, K370, D399, Y407, and K409 is not F, T, L, K, D, Y and K, respectively, in the second polypeptide.

In a particular embodiment of the heterodimeric protein, the amino acid in position K409 is R in the first polypeptide, and the amino acid in position F405 is L in the second polypeptide.

Accordingly, in one embodiment, the sequences of said first and second polypeptide contain asymmetrical amino acid residues or mutations, i.e. amino acid residues or mutations at different positions in the first and second polypeptide, e.g. a specific amino acid or mutation at position 405 in one of the polypeptides and a specific amino acid or mutation at position 409 in the other polypeptide. Reference to first and second polypeptide in this respect is not to be understood as limiting, as the amino acid residues or mutations may similarly be present in the opposite polypeptide. Thus, e.g. the amino acid in position F405 is L in said first polypeptide, and the amino acid in position K409 is R in said second polypeptide; or vice versa, the amino acid in position K409 is R in said first polypeptide, and the amino acid in position F405 is L in said second polypeptide.

In one embodiment, the first polypeptide has an amino acid other than Lys, Leu or Met at position 409, such as Arg, His, Asp, Glu, Ser, Thr, Asn, Gln, Gly, Pro, Ala, Val, Ile, Phe, Tyr, Trp, and Cys, and said second polypeptide has an amino acid in a position selected from the group consisting of: 366, 368, 370, 399, 405 and 407, wherein said amino acid is not T, L, K, D, F, and Y. In one such embodiment, said first polypeptide has an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has an amino acid other than Phe at position 405, e.g. Lys, Leu, Met, Arg, His, Asp, Glu, Ser, Thr, Asn, Gln, Gly, Pro, Ala, Val, Ile, Tyr, Trp or Cys. In a further embodiment hereof, said first polypeptide has an amino acid other than Lys, Leu or Met, e.g. Arg, His, Asp, Glu, Ser, Thr, Asn, Gln, Gly, Pro, Ala, Val, Ile, Phe, Tyr, Trp or Cys, at position 409 and said second polypeptide has an amino acid other than Phe, Arg or Gly, e.g. e.g. Lys, Leu, Met, His, Asp, Glu, Ser, Thr, Asn, Gln, Pro, Ala, Val, Ile, Tyr, Trp or Cys, at position 405.

In another embodiment, said first polypeptide comprises a Phe at position 405 and an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide comprises an amino acid other than Phe, e.g. Lys, Leu, Met, Arg, His, Asp, Glu, Ser, Thr, Asn, Gln, Gly, Pro, Ala, Val, Ile, Tyr, Trp or Cys, at position 405 and a Lys at position 409. In a further embodiment hereof, said first polypeptide comprises a Phe at position 405 and an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide comprises an amino acid other than Phe, Arg or Gly at position 405, e.g. Lys, Leu, Met, His, Asp, Glu, Ser, Thr, Asn, Gln, Pro, Ala, Val, Ile, Tyr, Trp or Cys, and a Lys at position 409.

In another embodiment, said first polypeptide comprises a Phe at position 405 and an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide comprises a Leu at position 405 and a Lys at position 409. In a further embodiment hereof, said first polypeptide comprises a Phe at position 405 and an Arg at position 409 and said second polypeptide comprises an amino acid other than Phe, Arg or Gly, e.g. Lys, Leu, Met, His, Asp, Glu, Ser, Thr, Asn, Gln, Pro, Ala, Val, Ile, Tyr, Trp or Cys, at position 405 and a Lys at position 409. In another embodiment, said first polypeptide comprises Phe at position 405 and an Arg at position 409 and said second polypeptide comprises a Leu at position 405 and a Lys at position 409.

In a further embodiment, said first polypeptide comprises an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide comprises a Lys at position 409, a Thr at position 370 and a Leu at position 405. In a further embodiment, said first polypeptide comprises an Arg at position 409 and said second polypeptide comprises a Lys at position 409, a Thr at position 370 and a Leu at position 405.

In an even further embodiment, said first polypeptide comprises a Lys at position 370, a Phe at position 405 and an Arg at position 409 and said second polypeptide comprises a Lys at position 409, a Thr at position 370 and a Leu at position 405.

In another embodiment, said first polypeptide comprises an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide comprises a Lys at position 409 and: a) an Ile at position 350 and a Leu at position 405, or b) a Thr at position 370 and a Leu at position 405.

In another embodiment, said first polypeptide comprises an Arg at position 409 and said second polypeptide comprises a Lys at position 409 and: a) an Ile at position 350 and a Leu at position 405, or b) a Thr at position 370 and a Leu at position 405.

In another embodiment, said first polypeptide comprises a Thr at position 350, a Lys at position 370, a Phe at position 405 and an Arg at position 409 and said second polypeptide comprises a Lys at position 409 and: a) an Ile at position 350 and a Leu at position 405, or b) a Thr at position 370 and a Leu at position 405.

In another embodiment, said first polypeptide comprises a Thr at position 350, a Lys at position 370, a Phe at position 405 and an Arg at position 409 and said second polypeptide comprises an Ile at position 350, a Thr at position 370, a Leu at position 405 and a Lys at position 409.

In another embodiment, said first polypeptide has an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has an amino acid other than Tyr, Asp, Glu, Phe, Lys, Gln, Arg, Ser or Thr at position 407, e.g. His, Asn, Gly, Pro, Ala, Val, Ile, Trp, Leu, Met or Cys. In another embodiment, said first polypeptide has an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has an Ala, Gly, His, Ile, Leu, Met, Asn, Val or Trp at position 407.

In another embodiment, said first polypeptide has an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has a Gly, Leu, Met, Asn or Trp at position 407.

In another embodiment, said first polypeptide has a Tyr at position 407 and an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has an amino acid other than Tyr, Asp, Glu, Phe, Lys, Gln, Arg, Ser or Thr at position 407, e.g. His, Asn, Gly, Pro, Ala, Val, Ile, Trp, Leu, Met or Cys, and a Lys at position 409.

In another embodiment, said first polypeptide has a Tyr at position 407 and an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has an Ala, Gly, His, Ile, Leu, Met, Asn, Val or Trp at position 407 and a Lys at position 409.

In another embodiment, said first polypeptide has a Tyr at position 407 and an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and said second polypeptide has a Gly, Leu, Met, Asn or Trp at position 407 and a Lys at position 409.

In another embodiment, said first polypeptide has a Tyr at position 407 and an Arg at position 409 and said second polypeptide has an amino acid other than Tyr, Asp, Glu, Phe, Lys, Gln, Arg, Ser or Thr at position 407, e.g. His, Asn, Gly, Pro, Ala, Val, Ile, Trp, Leu, Met or Cys and a Lys at position 409.

In another embodiment, said first polypeptide has a Tyr at position 407 and an Arg at position 409 and said second polypeptide has an Ala, Gly, His, Ile, Leu, Met, Asn, Val or Trp at position 407 and a Lys at position 409.

In another embodiment, said first polypeptide has a Tyr at position 407 and an Arg at position 409 and said second polypeptide has a Gly, Leu, Met, Asn or Trp at position 407 and a Lys at position 409.

In one embodiment, the first polypeptide has an amino acid other than Lys, Leu or Met at position 409, e.g. Arg, His, Asp, Glu, Ser, Thr, Asn, Gln, Gly, Pro, Ala, Val, Ile, Phe, Tyr, Trp or Cys, and the second polypeptide has (i) an amino acid other than Phe, Leu and Met at position 368, e.g. Arg, His, Asp, Glu, Ser, Thr, Asn, Gln, Gly, Pro, Ala, Val, Ile, Lys, Tyr, Trp or Cys or (ii) a Trp at position 370, or (iii) an amino acid other than Asp, Cys, Pro, Glu or Gln at position 399, e.g. Arg, His, Ser, Thr, Asn, Gly, Ala, Val, Ile, Phe, Tyr, Trp, Lys, Leu, or Met, or (iv) an amino acid other than Lys, Arg, Ser, Thr, or Trp at position 366, e.g. Leu, Met, His, Asp, Glu, Asn, Glu, Gly, Pro, Ala, Val, Ile, Phe, Tyr or Cys.

In one embodiment, the first polypeptide has an Arg, Ala, His or Gly at position 409, and the second polypeptide has (i) a Lys, Gln, Ala, Asp, Glu, Gly, His, Ile, Asn, Arg, Ser, Thr, Val, or Trp at position 368, or (ii) a Trp at position 370, or (iii) an Ala, Gly, Ile, Leu, Met, Asn, Ser, Thr, Trp, Phe, His, Lys, Arg or Tyr at position 399 or (iv) an Ala, Asp, Glu, His, Asn, Val, Gln, Phe, Gly, Ile, Leu, Met, or Tyr at position 366.

In one embodiment, the first polypeptide has an Arg at position 409, and the second polypeptide has (i) an Asp, Glu, Gly, Asn, Arg, Ser, Thr, Val, or Trp at position 368, or (ii) a Trp at position 370, or (iii) a Phe, His, Lys, Arg or Tyr at position 399, or (iv) an Ala, Asp, Glu, His, Asn, Val, Gln at position 366.

In addition to the above-specified amino-acid substitutions, said first and second polypeptide may contain further amino-acid substitutions, deletion or insertions relative to wild-type Fc sequences.

Such bispecific antibodies according to the invention can be generated as described in Example 8. Furthermore, the effect on CDC killing by the generated heterodimeric proteins can be tested by using an assay as used in Example 9. Thus, in a particular embodiment, CDC killing may be determined by pre-incubating suspension cells at a concentration of $1 \times 10^6$ cells/mL in round-bottom 96-well plates with an antibody in the range from 0.0003 to 30.0 µg/mL final concentration in a total volume of 100 µL for 15 min on a shaker at room temperature, adding normal human serum at a final concentration of 20%, 30% or 50%, incubating at 37° C. for 45 min, putting the plates on ice, adding 10 µL propidium iodide, and determining cell lysis by FACS analysis.

In a particular embodiment of the heterodimeric protein, the amino acid in a position corresponding to K409 is R in the first polypeptide, and the amino acid in a position corresponding to F405 is L in the second polypeptide, and wherein the amino acids of each of said first and second polypeptide in the positions corresponding to E345 and E430 in a human IgG1 heavy chain are not E and an amino acid in at least one position selected from the group consisting of S440, Y436, D/E356, T359, E382, N434, Q438, I253 and S254 is Y or W, not Y, not E, not T, not E, not N, not Q, not I and not S, for each position, respectively.

In a further particular embodiment of the heterodimeric protein, the amino acid in a position corresponding to K409 is R in the first polypeptide, and the amino acid in a position corresponding to F405 is L in the second polypeptide, or vice versa; and wherein the amino acids of the first and second polypeptide at the positions corresponding to E345, E430 and S440 are R, G and Y, respectively.

In a further particular embodiment of the heterodimeric protein, the amino acid in a position corresponding to K409 is R in the first polypeptide, and the amino acid in a position corresponding to F405 is L in the second polypeptide, or vice versa; and wherein the amino acids of the first and/or second polypeptide at the positions corresponding to E345, E430 and S440 are K, G and Y, respectively.

In a further particular embodiment of the heterodimeric protein, the amino acid in a position corresponding to K409 is R in the first polypeptide, and the amino acid in a position corresponding to F405 is L in the second polypeptide, or vice versa; and wherein the amino acids of the first and/or second polypeptide at the positions corresponding to E345, E430 and S440 are R, S and Y, respectively.

In a further particular embodiment of the heterodimeric protein, the amino acid in a position corresponding to K409 is R in the first polypeptide, and the amino acid in a position corresponding to F405 is L in the second polypeptide, or vice versa; and wherein the amino acids of the first and/or second polypeptide at the positions corresponding to E345, E430 and S440 are R, G and W, respectively.

In a further particular embodiment of the heterodimeric protein, the amino acid in a position corresponding to K409 is R in the first polypeptide, and the amino acid in a position corresponding to F405 is L in the second polypeptide, or vice versa; and wherein the amino acids of the first and/or second polypeptide at the positions corresponding to E345, E430 and Y436 are R, G and I, respectively.

In a further embodiment, any other amino acids in the heterodimeric protein may be as further described in the section "Other amino acid positions".

Example 11, shows that introducing the E345R mutation to a bispecific CD20×EGFR antibody enhances the CDC efficacy. Thus, in one embodiment, CDC efficacy may be determined by pre-incubating suspension cells of a concentration of $1 \times 10^6$ cells/mL in round-bottom 96-well plates with an antibody at a final concentration ranging from 0.0003 to 30.0 µg/mL in a total volume of 100 µL for 15 min on a shaker at room temperature, adding normal human serum at a final concentration of 20%, 30% or 50%, incubating at 37° C. for 45 min, putting the plates on ice, adding 10 µL propidium iodide, and determining cell lysis by FACS analysis.

Examples 9, 15 and 16 also describe some of the different bispecific antibodies.

The bispecific antibody may, for example, comprise an antigen-binding region of a CD20 antibody and an antigen-binding region of a CD38 antibody, and the amino acids according to the present invention. Exemplary CD20-binding regions include those of ofatumumab (2F2), 7D8 and 11B8, described in WO2004/035607, which is hereby incorporated by reference in its entirety, and rituximab (WO 2005/103081). Exemplary CD38-binding regions include those of 003 and daratumumab (005), described in WO2006/099875, which is hereby incorporated by reference in its entirety.

In one embodiment, the bispecific antibody binds different epitopes on the same or different target. Thus, the binding region of the first and the second polypeptide may in one embodiment bind to the same target, but different epitopes. In another embodiment the binding region of the first and second polypeptide may bind to different targets.

In another embodiment, the binding region of the first and second polypeptide may bind to different targets on different cells.

In one embodiment, the amino acids in the first and second polypeptide in the positions corresponding to E345, E430 and corresponding to a position selected from the group consisting of S440, Y436, D/E356, T359, E382, N434, Q438, I253 and S254 in a human IgG1 heavy chain, are not D or E; E; S; Y; E; T; E; N; Q; I; and S, respectively, may be the same or different.

In a further embodiment, one or more further amino acids may be as described herein. In a particular embodiment, the amino acid in a position corresponding to K439 is D or E, in each of the polypeptides of the heterodimeric protein. In another particular embodiment, the amino acid in a position corresponding to S440 is K or R. Thus, in a particular embodiment, in said first polypeptide the amino acid in positions corresponding to E345 and E430 in a human IgG1 heavy chain, is not E, the amino acid in at least one position corresponding to a position selected from the group consisting of S440, Y436, D/E356, T359, E382, N434, Q438, I253 and S254 in a human IgG1 heavy chain, is Y, K, R, or W; not Y; not D or E; not T; not E; not N; not Q; not I; and not S, for each position, respectively, and the amino acid in the position corresponding to K439 in a human IgG1 heavy chain is D or E, and in said second polypeptide the amino acid in positions corresponding to E345 and E430 in a human IgG1 heavy chain, is not E, the amino acid in the position S440 in a human IgG1 heavy chain, is K or R.

Fc-Fusion Proteins

In one aspect of the present invention, the dimeric protein according to any aspect or embodiment of the invention is part of a fusion protein. A fusion protein according to the invention may refer to a protein consisting of two or more covalently linked protein fragments which are not naturally expressed as a single protein. Fusion proteins may e.g. be produced by recombinant cloning and expression technologies commonly known in the art, or the method of creating fusion proteins may be post-production. Examples of such processes are intein, protein ligase, or other enzymatic processes commonly known in the art. Thus, a fusion protein according to the present invention is understood to be said dimeric protein comprising a first and a second polypeptide, each comprise at least a CH2 and CH3 region of an immunoglobulin heavy chain, wherein said first and/or second polypeptide may further comprise a binding region.

Thus, the first and/or second polypeptides of the dimeric protein according to the invention may further comprise a binding region. A binding region according to the invention is understood to be a polypeptide sequence which is capable of binding to a target. Thus, the binding region may be a protein, protein ligand, receptor, an antigen-binding region, or a ligand-binding region capable of binding to a target associated with a cell, bacterium, virion, or the like. A binding region may, for example, comprise part of a receptor, receptor ligand, ligand, cytokine, hormone, or antigen-binding region of an immunoglobulin or antibody.

In one embodiment, the binding region is a cytokine which is selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

In one embodiment, the binding region is an antigen-binding region. In some embodiments, said first and/or second polypeptides of said dimeric protein comprise, in addition to the Fc region, one or more or all of the other regions of an antibody, i.e. a CH1 region, a VH region, a CL region and/or a VL region. Thus, in one embodiment, said first polypeptide is a full-length antibody. In another embodiment, said second polypeptide is a full-length antibody.

In another embodiment, the binding region is a toxin, such as a naturally occurring toxin.

Conjugates

In one aspect, the dimeric protein the present invention, further comprises a drug, toxin, radiolabel, radioopaque agent, paramagnetic agent, fluorescent agent, phosphorescent agent, ultrasound enhancing agent, sialylation, or polyethyleneglycol (PEG), optionally conjugated to at least one of the polypeptides via a linker.

In one embodiment said dimeric protein is part of a fusion protein.

In one embodiment, the dimeric protein of the invention comprises a radiolabel.

In one embodiment, the dimeric protein of the invention comprises a radiopaque agent.

In one embodiment, the dimeric protein of the invention comprises a paramagnetic agent.

In one embodiment, the dimeric protein of the invention comprises a fluorescent agent.

In one embodiment, the dimeric protein of the invention comprises a phosphorescent agent.

In one embodiment, the dimeric protein of the invention comprises an ultrasound enhancing agent.

In one embodiment, the dimeric protein of the invention comprises a polyethyleneglycol (PEG).

In another aspect, the dimeric protein of the invention is not conjugated at the C-terminus to another molecule, such as a toxin or label. In one embodiment, the dimeric protein is conjugated to another molecule at another site, typically at a site which does not interfere with oligomer formation. For example, the dimeric protein may, at the other site, be linked to a compound selected from the group consisting of a toxin (including a radioisotope) a prodrug or a drug. Such a compound may make killing of target cells more effective, e.g. in cancer therapy. The resulting dimeric protein is thus an immunoconjugate.

Thus, in a further aspect, the present invention provides a dimeric protein, such as an antibody linked or conjugated to one or more therapeutic moieties, such as a cytotoxin, a chemotherapeutic drug, a cytokine, an immunosuppressant, and/or a radioisotope. Such conjugates are referred to herein as "immunoconjugates" or "drug conjugates". Immunoconjugates which include one or more cytotoxins are referred to as "immuno-toxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, enediyene antitumor antibiotics including neocarzinostatin, calicheamycins, esperamicins, dynemicins, lidamycin, kedarcidin or analogs or derivatives thereof, anthracyclins, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), dolastatin, pyrrolo[2,1-c][1,4] benzodiazepins (PDBs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors) such as monomethyl auristatin E, monomethyl auristatin F, or other analogs or derivatives of dolastatin 10; Histone deacetylase inhibitors such as the hydroxamic acids trichostatin A, vorinostat (SAHA), belinostat, LAQ824, and panobinostat as well as the benzamides, entinostat, CI994, mocetinostat and aliphatic acid compounds such as phenylbutyrate and valproic acid, proteasome inhibitors such as Danoprevir, bortezomib, amatoxins such as alpha-amantin, diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with a dimeric protein of the present invention as described elsewhere herein, such as, e.g., anti-cancer cytokines or chemokines, are also candidates for therapeutic moieties useful for conjugation to a dimeric protein of the present invention.

In one embodiment, the drug conjugates of the present invention comprise a dimeric protein as disclosed herein conjugated to auristatins or auristatin peptide analogs and derivates (U.S. Pat. Nos. 5,635,483; 5,780,588). Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and anti-fungal activity (Pettit et al., (1998) Antimicrob. Agents and Chemother. 42:2961-2965. The auristatin drug moiety may be attached to the dimeric protein via a linker, through the N (amino) terminus or the C (carboxy) terminus of the peptidic drug moiety.

Exemplary auristatin embodiments include the N-terminus-linked monomethyl auristatin drug moieties DE and DF, disclosed in Senter et al., Proceedings of the American Association for Cancer Research. Volume 45, abstract number 623, presented Mar. 28, 2004 and described in US 2005/0238649).

An exemplary auristatin embodiment is MMAE (monomethyl auristatin E). Another exemplary auristatin embodiment is MMAF (monomethyl auristatin F).

In one embodiment, a dimeric protein of the present invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another embodiment, a dimeric protein of the present invention is conjugated to an aptamer or a ribozyme.

In one embodiment, dimeric proteins comprising one or more radiolabeled amino acids are provided. A radiolabeled dimeric protein may be used for both diagnostic and therapeutic purposes (conjugation to radiolabeled molecules is another possible feature). Non-limiting examples of labels for polypeptides include 3H, 14C, 15N, 35S, 90Y, 99Tc, and 125I, 131I, and 186Re. Methods for preparing radiolabeled amino acids and related peptide derivatives are known in the art, (see, for instance Junghans et al., in Cancer Chemotherapy and Biotherapy 655-686 ($2^{nd}$ Ed., Chafner and Longo, eds., Lippincott Raven (1996)) and U.S. Pat. Nos. 4,681,581; 4,735,210; 5,101,827; 5,102,990 (U.S. RE35, 500), U.S. Pat. Nos. 5,648,471 and 5,697,902. For example, a radioisotope may be conjugated by the chloramine-T method.

In one embodiment, the dimeric protein of the present invention is conjugated to a radioisotope or to a radioisotope-containing chelate. For example, the dimeric protein can be conjugated to a chelator linker, e.g. DOTA, DTPA or tiuxetan, which allows for the dimeric protein to be complexed with a radioisotope. The dimeric protein may also or alternatively comprise or be conjugated to one or more radiolabeled amino acids or other radiolabeled molecule. A radiolabeled dimeric protein may be used for both diagnostic and therapeutic purposes. In one embodiment the dimeric protein of the present invention is conjugated to an alpha-emitter. Non-limiting examples of radioisotopes include $^3$H, $^{14}$C, $^{15}$N, $^{35}$S, $^{90}$Y, 99Tc, $^{125}$I, $^{111}$In, $^{131}$I, $^{186}$Re, $^{213}$Bs, $^{225}$Ac and $^{227}$Th.

In one embodiment the dimeric protein of the present invention may be conjugated to a cytokine selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

Dimeric proteins of the present invention may also be chemically modified by covalent conjugation to a polymer to for instance increase their circulating half-life. Exemplary polymers, and methods to attach them to peptides, are illustrated in for instance U.S. Pat. Nos. 4,766,106; 4,179,337; 4,495,285 and 4,609,546. Additional polymers include polyoxyethylated polyols and polyethylene glycol (PEG) (e.g., a PEG with a molecular weight of between about 1,000 and about 40,000, such as between about 2,000 and about 20,000).

Any method known in the art for conjugating the dimeric protein of the present invention to the conjugated molecule (s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such dimeric proteins may be produced by chemically conjugating the other moiety to the N-terminal side or C-terminal side of the dimeric protein or fragment thereof (e.g., an antibody H or L chain) (see, e.g., Antibody Engineering Handbook, edited by Osamu Kanemitsu, published by Chijin Shokan (1994)). Such conjugated dimeric protein derivatives may also be generated by conjugation at internal residues or sugars, where appropriate.

The agents may be coupled either directly or indirectly to a dimeric protein of the present invention. One example of indirect coupling of a second agent is coupling via a spacer or linker moiety to cysteine or lysine residues in a bispecific antibody. In one embodiment, a dimeric protein is conjugated to a prodrug molecule that can be activated in vivo to a therapeutic drug via a spacer or linker. In some embodiments, the linker is cleavable under intracellular conditions, such that the cleavage of the linker releases the drug unit from the dimeric protein in the intracellular environment. In some embodiments, the linker is cleavable by a cleavable agent that is present in the intracellular environment (e. g. within a lysosome or endosome or caveola). For example, the spacers or linkers may be cleavable by tumor-cell associated enzymes or other tumor-specific conditions, by which the active drug is formed. Examples of such prodrug technologies and linkers are described in WO02083180, WO2004043493, WO2007018431, WO2007089149, WO2009017394 and WO201062171 by Syntarga B V, et al. Suitable antibody-prodrug technology and duocarmycin analogs can also be found in U.S. Pat. No. 6,989,452 (Medarex), incorporated herein by reference. The linker can also or alternatively be, e.g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e. g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No. 6,214,345, which describes the synthesis of doxorubicin with the Val-Cit linker and different examples of Phe-Lys linkers). Examples of the structures of a Val-Cit and a Phe-Lys linker include but are not limited to MC-vc-PAB described below, MC-vc-GABA, MC-Phe-Lys-PAB or MC-Phe-Lys-GABA, wherein MC is an abbreviation for maleimido caproyl, vc is an abbreviation for Val-Cit, PAB is an abbreviation for p-aminobenzylcarbamate and GABA is an abbreviation for γ-aminobutyric acid. An advantage of using intracellular proteolytic release of the therapeutic agent is that the agent is typically attenuated when conjugated and the serum stabilities of the conjugates are typically high.

In yet another embodiment, the linker unit is not cleavable and the drug is released by dimeric protein or antibody degradation (see US 2005/0238649). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of dimeric protein drug conjugate compound, are cleaved when the dimeric protein drug conjugate compound is present in an extracellular environment (e.g. plasma). Whether a linker is not substantially sensitive to the extracellular environment can be determined for example by incubating the dimeric protein drug conjugate compound with plasma for a predetermined time period (e.g. 2, 4, 8, 16 or 24 hours) and then quantitating the amount of free drug present in the plasma. Exemplary embodiments comprising MMAE or MMAF and various linker components have the following structures (wherein Ab means antibody and p, representing the drug-loading (or average number of cytostatic or cytotoxic drugs per antibody molecule), is 1 to about 8, e.g. p may be from 4-6, such as from 3-5, or p may be 1, 2, 3, 4, 5, 6, 7 or 8).

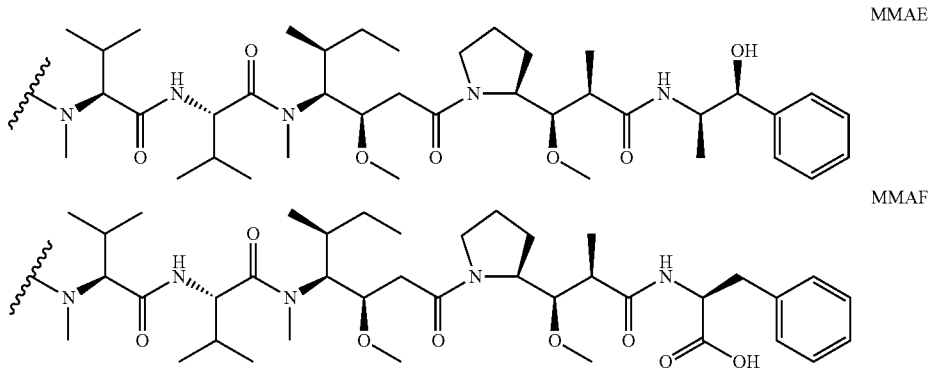

MMAE

MMAF

Examples where a cleavable linker is combined with an auristatin include MC-vc-PAB-MMAF (also designated as vcMMAF) and MC-vc-PAB-MMAE (also designated as vcMMAE), wherein MC is an abbreviation for maleimido caproyl, vc is an abbreviation for the Val-Cit (valine-citruline) based linker, and PAB is an abbreviation for p-aminobenzylcarbamate.

Other examples include auristatins combined with a non-cleavable linker, such as mcMMAF (mc (MC is the same as mc in this context) is an abbreviation of maleimido caproyl).

In one embodiment, the dimeric protein is conjugated to toxins or payloads, such as drugs, which have optimal function at a lower pH than neutral pH.

In one embodiment, both the first and second polypeptide of the dimeric protein is coupled directly or indirectly to the same one or more therapeutic moieties.

In one embodiment, only the first or second polypeptide of the dimeric protein is coupled directly or indirectly to one or more therapeutic moieties.

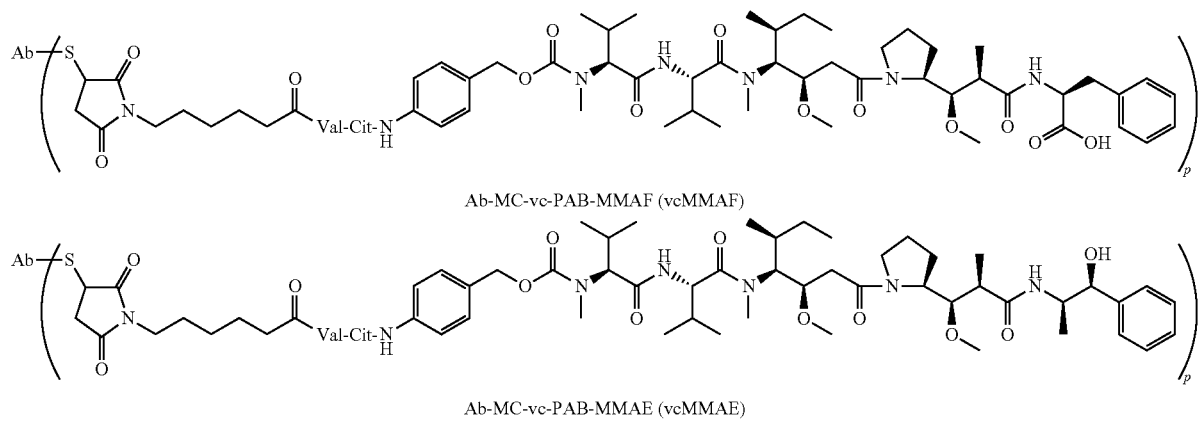

Ab-MC-vc-PAB-MMAF (vcMMAF)

Ab-MC-vc-PAB-MMAE (vcMMAE)

In one embodiment, the drug linker moiety is vcMMAE. The vcMMAE drug linker moiety and conjugation methods are disclosed in WO2004010957, U.S. Pat. Nos. 7,659,241, 7,829,531, 7,851,437 and U.S. Ser. No. 11/833,028 (Seattle Genetics, Inc.), (which are incorporated herein by reference), and the vcMMAE drug linker moiety is bound to the dimeric proteins at the cysteines using a method similar to those disclosed therein.

In one embodiment, the drug linker moiety is mcMMAF. The mcMMAF drug linker moiety and conjugation methods are disclosed in U.S. Pat. No. 7,498,298, U.S. Ser. No. 11/833,954, and WO2005081711 (Seattle Genetics, Inc.), (which are incorporated herein by reference), and the mcMMAF drug linker moiety is bound to the dimeric protein at the cysteines using a method similar to those disclosed in therein.

In one embodiment, the dimeric protein of the present invention is attached to a chelator linker, e.g. tiuxetan, which allows for e.g. a bispecific antibody to be conjugated to a radioisotope.

In one embodiment, the first and second polypeptide of the dimeric protein is coupled directly or indirectly to different therapeutic moieties. For example, in embodiments where the dimeric protein is a bispecific antibody and is prepared by controlled Fab-arm exchange of two different monospecific antibodies, e.g. a first and second antibody such bispecific antibodies can be obtained by using monospecific antibodies which are conjugated or associated with different therapeutic moieties.

Oligomer

The present invention is based, in part, on the discovery that dimeric proteins comprising at least the CH2 and CH3 regions, and optionally a hinge region, of immunoglobulin heavy chains can form oligomers such as hexamers not only when bound to a target molecule but also in solution. The oligomerization occurs via non-covalent association of adjacent Fc-regions, and has in particular been observed for antibodies having mutations in E345, E430 and S440, as described in the Examples.

In one aspect the present invention relates to an oligomer comprising at least two non-covalently associated dimeric proteins, each according to any aspect or embodiment herein described.

In one embodiment, the invention provides a hexamer comprising six non-covalently associated dimeric proteins, each according to any one of the preceding aspects or embodiments. In one embodiment, at least one, such as at least two, at least three, at least four, at least five or six dimeric proteins of the hexamer are antibodies.

In one embodiment, the invention provides an oligomer comprising six non-covalently associated dimeric proteins, at least one of which is a dimeric protein according to any aspect or embodiment of the invention and at least one of which is an antibody comprising an Fc domain comprising at least CH2 and CH3 regions and optionally a hinge region.

In one embodiment, the invention provides a hexamer comprising six non-covalently associated molecules, such as dimeric proteins, at least one of which is of a dimeric protein according to any preceding aspect or embodiment and at least one of which is an antibody comprising an Fc domain comprising at least CH2, CH3 and hinge regions in which at least one of the positions corresponding to E345, E430 and S440 in a human IgG1 heavy chain, is E, E and S, respectively. In one embodiment, the antibody is a monoclonal or polyclonal antibody, the monoclonal antibody optionally selected from the known antibodies denoted "second antibodies" in the section below.

Compositions

The present invention also relates to a composition comprising one or more dimeric proteins of the present invention, optionally in the form of oligomers, such as hexamers according to any preceding aspect or embodiment. The composition of the present invention may be a pharmaceutical composition comprising a dimeric protein of the present invention and a pharmaceutically acceptable carrier. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The composition of the present invention may be a pharmaceutical composition comprising a dimeric protein according to any aspect or embodiments of the present invention, one or more antibodies, and a pharmaceutically acceptable carrier.

In a particular embodiment, the composition comprises a first dimeric protein according to any aspect or embodiment of the invention and a second dimeric protein according to any aspect or embodiment of the invention, and a pharmaceutically acceptable carrier. The pharmaceutically acceptable carriers or diluents as well as any other known adjuvants and excipients should be suitable for the dimeric protein of the present invention and the chosen mode of administration. Suitability for carriers and other components of pharmaceutical compositions is determined based on the lack of significant negative impact on the desired biological properties of the dimeric protein or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars, sugar alcohols such as sorbitol and mannitol, or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a dimeric protein of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the dimeric protein, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The dimeric protein of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the dimeric protein of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the dimeric protein, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be an aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the dimeric protein in the required amount in an appropriate solvent with one or a combination of ingredients e.g. as enumerated above, as required, followed by sterilization microfiltration. Generally, dispersions are prepared by incorporating the dimeric protein into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the dimeric protein in the required amount in an appropriate solvent with one or a combination of ingredients enumerated above, as required, followed by sterilization microfiltration. Generally, dispersions are prepared by incorporating the dimeric protein into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

pH

The compositions of the invention may comprise a suitable buffer system to control the pH and thereby the oligomerization state of the dimeric protein(s) present. For example, at a pH of 6.4 or below, such as at pH 5.0, a dimeric protein according to the invention is typically predominantly in monomeric form, i.e. a single dimeric protein, whereas at above pH 6.4, such as at pH 6.8, a dimeric protein is predominantly in oligomeric form, such as hexamer form. The hexameric form of the dimeric protein, is composed of six dimeric proteins which non-covalently associate with each other to form a hexameric form. The term "monomeric form" in the context of dimeric protein according to the present invention refers to a single, individual dimeric protein, which is composed of dimeric proteins that do not associate non-covalently with each other. Example 31 describes how this can be observed by adjusting pH.

In one embodiment, the composition comprises a pharmaceutically acceptable carrier which is an aqueous buffered solution.

In one embodiment, the pH of the aqueous buffered solution is at least about 6.5, such as from 6.5 to about 9.0, such as from about 7.0 to about 8.0, such as about 7.4. Buffer systems suitable for maintaining a pH in this range and/or near physiological pH include phosphate buffer systems. Thus, in one embodiment, the aqueous buffered solution is a phosphate buffer system. In one embodiment, the dimeric protein is predominantly in oligomeric form, such as hexameric form, in a phosphate buffer at a pH of about 6.8.

In one embodiment, the pH of the aqueous buffered solution is less than pH 6.5, such as from about 4.0 to 6.4, such as from about 5.0 to about 6.0. Buffer systems suitable for maintaining a pH in this range include citrate, acetate, histidine and/or glycine-based buffer systems. Thus, in one embodiment, the buffer system is an acetate, histidine, glycine, citrate, nicotinate, lactate, and/or succinate based buffer system. Such buffer systems may also be a combination of buffer systems. In one embodiment, the dimeric protein is predominantly in monomeric form, i.e. single dimeric protein, at a pH of less than 6.0, such as about 5.0.

As shown in Example 31, the oligomerization of the dimeric protein according to the invention is a reversible process which may be controlled by pH. This could be useful for application in processing during manufacturing of the dimeric protein, such as the purification steps wherein clotting of e.g. purification columns, translaminar flow filtration, dead-end filtration and/or nanofiltration devices can be avoided by lowering the pH without compromising the efficacy of the final product, such as an antibody. Furthermore, lowering the pH below 6.8, e.g. 5.0 and 5.5, during purification can improve purification yields as the dimeric protein is predominantly in monomeric form and thereby less likely to clot than the hexameric form of the dimeric protein, as demonstrated by Example 32. Furthermore, lowering the pH below 6.8 during purification can enable removal of non-specific aggregates by chromatography, such as using weak cation exchange resins. Thus, once the dimeric protein has been purified at a pH below 6.8, the oligomeric, e.g. hexameric, form may be restored by increasing the pH of the solution to a pH around 6.8.

Mixtures

In some aspects, the invention provides compositions comprising a dimeric protein and a second molecule, wherein the second molecule also comprises a first and a second polypeptide, each comprising at least CH2, CH3 and hinge regions of an immunoglobulin heavy chain. Thus, the dimeric protein is to be understood as the dimeric protein according to any aspect or embodiment of the present invention, such as dimeric protein of a parent dimeric protein, such as a variant dimeric protein of a parent dimeric protein.

Advantageously, the relative amounts of the dimeric protein(s) and the second molecule in the compositions can be adjusted to modulate the average number of units of each different dimeric protein in the oligomers/hexamers formed. This, in turn, provides a means for optimizing effector function and/or target-binding properties, when one or more of the dimeric protein(s) and the second molecules bind(s) a target.

Specific aspects and embodiments of compositions comprising mixtures of a dimeric protein and a second molecule are described below. While applicable to all types of dimeric proteins according to the invention and all types of Fc-containing second molecules, including, e.g., Fc-fusion proteins with ligand-binding regions, antibody molecules are particularly contemplated for both components.

In one aspect, the composition of the invention comprises a first dimeric protein according to any aspect or embodiment of the invention, a second dimeric protein according to any aspect or embodiment of the invention, and a pharmaceutically acceptable carrier.

In one aspect, the second molecule is one in which at least one of the amino acids at the positions corresponding to E345, E430 and S440 in a human IgG1 heavy chain is the one normally present at this position in a native IgG1 heavy chain. For example, the heavy-chain polypeptides of the second molecule may comprise E, E and S at each of the positions corresponding to E345, E430 and S440, respectively. According to this aspect, the second molecule may thus comprise, e.g., the native Fc region sequences of a human IgG1, IgG2, IgG3, IgG4, IgA1, IgA2, IgD, IgE or IgM antibody, or in particular at least IgG1, IgG2, IgG3, or IgG4 Fc sequences without amino acid substitutions in all three of E345, E430 and S440.

In one embodiment, the second molecule is an antibody, in particular a well-known antibody already in clinical or pre-clinical use, such as an antibody which has a suitable safety profile. In a further embodiment, said second antibody may have a suitable safety profile but may not be sufficiently efficacious.

In one embodiment, also the dimeric protein is an antibody, so that the composition comprises a first antibody and a second antibody, wherein only the first antibody is a dimeric protein of the invention. The combination of a first antibody which comprises mutations capable of increasing an effector function and a second antibody which does not comprise such a mutation may, as shown in Example 17 provide an increased effector function. Thus, without being bound by theory, it is believed that e.g. this method may be used to combine a therapeutic antibody, as a second antibody, which has been proven to be safe but not efficient enough on its own for a specific application, with a dimeric protein according to the invention, thereby resulting in a combination which is efficacious.

Examples of suitable second antibodies include but are not limited to any of those selected from the group consisting of: (90Y) clivatuzumab tetraxetan; (90Y) tacatuzumab tetraxetan; (99mTc) fanolesomab; (99mTc) nofetumomab Merpentan; (99mTc) pintumomab; 3F8; 8H9; abagovomab; abatacept; abciximab; Actoxumab; adalimumab; adecatumumab; afelimomab; aflibercept; Afutuzumab; alacizumab pegol; albiglutide; ALD518; alefacept; alemtuzumab; Alirocumab; altumomab; Altumomab pentetate; alvircept sudotox; amatuximab; AMG714/HuMax-IL15; anatumomab mafenatox; Anrukinzumab (=IMA-638); apolizumab; arcitumomab; aselizumab; atacicept; atinumab; Atlizumab (=tocilizumab); atorolimumab; baminercept; Bapineuzumab; basiliximab; bavituximab; bectumomab; belatacept; belimumab; benralizumab; bertilimumab; besilesomab; bevacizumab; Bezlotoxumab; biciromab; bifarcept; bivatuzumab; Bivatuzumab mertansine; blinatumomab; blosozumab; brentuximab vedotin; briakinumab; briobacept; brodalumab; canakinumab; cantuzumab mertansine; cantuzumab ravtansine; caplacizumab; capromab; Capromab pendetide; carlumab; catumaxomab; CC49; cedelizumab; certolizumab pegol; cetuximab; Ch.14.18; citatuzumab bogatox; cixutumumab; Clazakizumab; clenoliximab; Clivatuzumab tetraxetan; conatumumab; conbercept; CR6261; crenezumab; dacetuzumab; daclizumab; dalantercept; dalotuzumab; daratumumab; Demcizumab; denosumab; Detumomab; Dorlimomab aritox; drozitumab; dulaglutide; ecromeximab; eculizumab; edobacomab; edrecolomab; efalizumab; efungumab; elotuzumab; elsilimomab; enavatuzumab; enlimomab; enlimomab pegol; enokizumab; ensituximab; epitumomab; epitumomab cituxetan; epratuzumab; erlizumab; ertumaxomab; etanercept; etaracizumab; etrolizumab; exbivirumab; Fanolesomab; faralimomab; farletuzumab; Fasinumab; FBTA05; felvizumab; Fezakinumab; ficlatuzumab; figitumumab; flanvolumab; fontolizumab; foralumab; foravirumab; fresolimumab; fulranumab; galiximab; ganitumab; gantenerumab; gavilimomab; gemtuzumab; Gemtuzumab ozogamicin; gevokizumab; girentuximab; glembatumumab; Glembatumumab vedotin; golimumab; Gomiliximab; GS6624; anti-CD74 antibodies; anti-cMet antibodies as disclosed in WO 2011/110642; anti-Her2 antibodies as disclosed WO 2011/147986 or WO 2011/147982; anti-IL8 antibodies as disclosed in WO 2004/058797; anti-TAC antibodies as disclosed in WO 2004/045512; anti-tissue factor (TF) antibodies as disclosed in WO 2010/066803 or WO 2011/157741; ibalizumab; ibritumomab tiuxetan; icrucumab; igovomab; Imciromab; inclacumab; indatuximab ravtansine; infliximab; inolimomab; inotuzumab ozogamicin; intetumumab; iodine (124I) girentuximab; ipilimumab; iratumumab; itolizumab; ixekizumab; keliximab; labetuzumab; lebrikizumab; lemalesomab; lenercept; lerdelimumab; lexatumumab; libivirumab; lintuzumab; lorvotuzumab mertansine; lucatumumab; lumiliximab; mapatumumab; maslimomab; matuzumab; mavrilimumab; mepolizumab; metelimumab; milatuzumab; minretumomab; mirococept; mitumomab; mogamulizumab; morolimumab; motavizumab; moxetumomab; pasudotox; muromonab-CD3; nacolomab tafenatox; namilumab; naptumomab estafenatox; narnatumab; natalizumab; nebacumab; necitumumab; nerelimomab; nimotuzumab; Nivolumab; Nofetumomab; merpentan; obinutuzumab; Ocaratuzumab; ocrelizumab; odulimomab; ofatumumab; olaratumab; olokizumab; omalizumab; onartuzumab; onercept; oportuzumab monatox; oregovomab; otelixizumab; oxelumab; ozoralizumab; pagibaximab; palivizumab; panitumumab; panobacumab; pascolizumab; pateclizumab; patritumab; pegsunercept; Pemtumomab; pertuzumab; pexelizumab; Pintumomab; Placulumab; ponezumab; priliximab; pritumumab; PRO 140; quilizumab; racotumomab; radretumab; rafivirumab; ramucirumab; ranibizumab; raxibacumab; regavirumab; reslizumab; RG1507/HuMax-IGF1R; RG1512/HuMax-pSelectin; rilonacept; rilotumumab; rituximab; robatumumab; roledumab; romosozumab; rontalizumab; rovelizumab; ruplizumab; samalizumab; sarilumab; satumomab; Satumomab pendetide; secukinumab; sevirumab; sibrotuzumab; sifalimumab; siltuximab; siplizumab; sirukumab; solanezumab; solitomab; Sonepcizumab; sontuzumab; sotatercept; stamulumab; sulesomab; suvizumab; tabalumab; Tacatuzumab tetraxetan; tadocizumab; talizumab; tanezumab; taplitumomab paptox; tefibazumab; telimomab aritox; tenatumomab; teneliximab; teplizumab; teprotumumab; TGN1412; Ticilimumab (=tremelimumab); tigatuzumab; TNX-650; Tocilizumab (=atlizumab); toralizumab; torapsel; tositumomab; tralokinumab; trastuzumab; trastuzumab emtansine; TRBS07; trebananib; tregalizumab; tremelimumab;

tucotuzumab celmoleukin; tuvirumab; ublituximab; urelumab; urtoxazumab; ustekinumab; vapaliximab; vatelizumab; vedolizumab; veltuzumab; vepalimomab; vesencumab; visilizumab; volociximab; Vorsetuzumab mafodotin; votumumab; zalutumumab; zanolimumab; ziralimumab; and zolimomab aritox.

In one aspect, the second molecule is a second dimeric protein according to the invention. Compositions according to this aspect thus comprise a mixture of two or more different dimeric proteins, each according to any aspect or embodiment of the invention, such as described above. Typically, under the right pH and/or target-binding conditions, hexamers comprising two or more different dimeric proteins may then form in the composition, particularly in an aqueous solution or buffer. The first and second dimeric proteins of the present invention will have preference for oligomerization with one another compared to any wildtype or naturally occurring dimeric protein as shown in Example 3.

In one embodiment, the composition comprises a first dimeric protein and a second dimeric protein, optionally further comprising a pharmaceutically acceptable carrier.

In one embodiment the present invention may relate to a composition comprising a first and a second dimeric protein, wherein both the first and the second dimeric proteins comprise a first and a second polypeptide, wherein in one of said first and/or second, such as both, polypeptides of said first and second dimeric protein the amino acids at the positions corresponding to E345 and E430 in a human IgG1 heavy chain, are not E, and the amino acid in at least one position selected from the group consisting of S440, Y436, D/E356, T359, E382, N434, Q438, I253, and S254, corresponding to the position in a human IgG1 heavy chain, is Y, W, K or R; not Y; not D or E; not T; not E; not N; not Q; not I; and not S, for each position, respectively. The first and the second dimeric protein may be any dimeric protein according to the present invention.

In one embodiment, one or both of the first and second dimeric proteins comprise heavy-chain polypeptides wherein, for one or both, such as each, polypeptides, the amino acid at the position corresponding to E345 is selected, e.g. separately, from the group consisting of R, Q, N, K, Y, A, C, D, F, G, H, I, L, M, P, S, T, V and W, such as from the group consisting of R, Q, N, K and Y.

In one embodiment, one or both of the first and second dimeric proteins comprise heavy-chain polypeptides wherein, for one or both, such as each, polypeptides, the amino acid at the position corresponding to E430 is selected, e.g. separately, from the group consisting of G, T, S, F, H, A, C, D, I, K, L, M, N, P, Q, R, V, W and Y, such as from the group consisting of G, T, S, F and H.

In one embodiment, one or both of the first and second dimeric proteins comprise heavy chain polypeptides wherein, for one or both, such as each, polypeptides, the amino acid in at least one of the positions selected from the group consisting of S440, Y436, D/E356, T359, E382, N434, Q438, I253, and S254 corresponds to the position in a human IgG1 heavy chain, is Y, R, K, or W; not Y; not D or E; not T; not E; not N; not Q; not I; and not S, for each position, respectively.

In one embodiment, said first and/or the second, such as both, dimeric proteins comprise heavy chain polypeptides wherein, for one or both, such as each, polypeptide, the amino acids at the positions corresponding to E345, E430 and S440 in a human IgG1 heavy chain, are R, G and Y, respectively.

In one embodiment, in said first and/or second polypeptides of said first and/or second dimeric proteins, the amino acids at the positions corresponding to E345, E430 and S440 in a human IgG1 heavy chain, are K, G and Y, respectively.

In one embodiment, in said first and/or second polypeptides of said first and/or second dimeric proteins, the amino acids at the positions corresponding to E345, E430 and S440 in a human IgG1 heavy chain, are R, S and Y, respectively.

In one embodiment, in said first and/or second polypeptides of said first and/or second dimeric proteins, the amino acids at the positions corresponding to E345, E430 and S440 in a human IgG1 heavy chain, are R, G and W, respectively.

In one embodiment, in said first and/or second polypeptides of said first and/or second dimeric proteins, the amino acids at the positions corresponding to E345, E430 and Y436 in a human IgG1 heavy chain, are R, G and I, respectively.

In another embodiment, one or both of the first and second dimeric proteins comprise heavy chain polypeptides where the amino acids at the positions corresponding to E345, E430 and S440 are R; G; and Y or W, respectively, and where one or at least one of Y436, D/E356, T359, E382, N434, Q438, I253 and S254 is not Y; D or E; T; E; N; Q; I; and S, respectively.

In one embodiment, either said first or the second dimeric protein comprises the indicated amino acids in both said first and second polypeptide, and the other dimeric protein comprises the indicated amino acids in only said first or second polypeptide.

In one embodiment, both said first and second dimeric proteins comprise the indicated amino acids in both said first and second polypeptides.

In some embodiments, the amino acids at certain positions in the heavy chain polypeptides differ between the first and second dimeric proteins to adjust the strength or specificity of the non-covalent association of the two dimeric proteins. This can be achieved, e.g., by using first and/or second dimeric proteins having specific amino acids at the positions corresponding to K439, S440, K447, K448, and/or K449, as described above.

In one embodiment, the polypeptides of the first dimeric protein comprise an amino acid in the position corresponding to K439 which is not K, and the polypeptides of the second dimeric protein comprise an amino acid in the position corresponding to S440 which is not S, with the proviso that the amino acid in S440 is not Y or W. For example, in the first dimeric protein, the amino acid in the position corresponding to K439 can be D or E, and in the second dimeric protein, the amino acid in the position corresponding to S440 can be K, H or R, such as K or R. A similar strategy can be used for combinations of amino acids in the positions corresponding to K447, 448 and 449. Table 2 shows exemplary amino acids for these positions in the first dimeric protein and second dimeric protein to be used together, separated by a "+"-sign. In any one of these aspects and embodiments, one or both of the first and second dimeric proteins can be an antibody (e.g., Ab1 and Ab2, respectively).

TABLE 2

Exemplary positions and amino acids which may further be present in two dimeric proteins (e.g., Ab1 + Ab2)

| Amino acid pair (IgG1) | Exemplary substitutions | Preferred substitutions |
|---|---|---|
| K439 + S440 | 439DER + 440DEKR | 439E + 440K |
| K447 + K447/448 | 447DE + 447KRH/448P | 447E + 447/448P |
| K447 + K447/448/449 | 447DE + 447KRH/ 448KRH/449P | 447E + 447K/448K/449P |

In a further embodiment, in said first and/or second polypeptide of said first dimeric protein the amino acid at the position corresponding to K439 in a human IgG1 heavy chain, is E or D, optionally E, and in said first and/or second polypeptide of said second dimeric protein the amino acid at the position corresponding to S440 in a human IgG1 heavy chain, is K or R, optionally K.

In one embodiment, in said first and/or second polypeptide of said first dimeric protein the amino acid at the positions corresponding to E345, E430, K439, and S440 in a human IgG1 heavy chain, are R, K, Q, N, or Y; G, S, T, F or H; D or E; and Y or W, respectively, and in said first and/or second polypeptide of said second dimeric protein the amino acid at the positions corresponding to E345, E430 and S440 in a human IgG1 heavy chain, are R, K, Q, N, or Y; G, S, T, F or H; and K or R, respectively. In a further embodiment, in said first and/or second polypeptide of the second dimeric protein, the amino acid at the position corresponding to Y436 in a human IgG1 heavy chain, is I.

In one embodiment, in said first and/or second polypeptide of said first dimeric protein the amino acid at the position corresponding to K439 in a human IgG1 heavy chain, is E or D, optionally E, and in said first and/or second polypeptide of said second dimeric protein the amino acid at the position corresponding to S440 in a human IgG1 heavy chain, is K or R, optionally K, and at least one amino acid in a position selected from the group consisting of Y436, D/E356, T359, E382, N434, Q438, I253, and S254 corresponding to the position in a human IgG1 heavy chain, is not Y; D or E; T; E; N; Q; I; and S, respectively.

In one embodiment, in said first and/or second polypeptides of said first dimeric protein the amino acids at the positions corresponding to E345, E430, K439, and S440 in a human IgG1 heavy chain, are R, G, E, and Y, respectively, and in said first and/or second polypeptides of said second dimeric protein the amino acids at the positions corresponding to E345, E430, K439, and S440 in a human IgG1 heavy chain, are R, G, K, and K, respectively.

In one embodiment, in said first and/or second polypeptides of said first dimeric protein the amino acids at the positions corresponding to E345, E430, K439, and S440 in a human IgG1 heavy chain, are R, G, E, and Y, respectively, and in said first and/or second polypeptides of said second dimeric protein the amino acids at the positions corresponding to E345, E430, and S440 in a human IgG1 heavy chain, are R, G, and K, respectively.

In an alternative embodiment, in the first and/or second polypeptides of the first dimeric protein the amino acid at the positions corresponding to E345, E430, and S440 in a human IgG1 human heavy chain, are K, G, and Y, respectively; or alternatively R, G and W, respectively; or alternatively R, G, and K, respectively, or the amino acid in the positions corresponding to E345, E430 and Y436 in a human IgG1 heavy chain, are R, G, and I, respectively. Furthermore, in the first and/or second polypeptide of the second dimeric protein the amino acid at the positions corresponding to E345, E430 and S440 in a human IgG1 heavy chain, are K, G, and K, respectively; or alternatively R, S, and K, respectively; or alternatively R, G, and R, respectively; or alternatively R, S, and R, respectively.

In one embodiment, in said first and/or second polypeptides of the first dimeric protein the amino acids at the positions corresponding to E345, E430, K439, and S440 in a human IgG1 heavy chain, are R, G, E, and Y, respectively, and in said first and/or second polypeptides of said second dimeric protein the amino acids at the positions corresponding to E345, E430, Y436, and S440 in a human IgG1 heavy chain, are R, G, I, and K, respectively.

In a further embodiment, in said first and/or second polypeptides of the first dimeric protein the amino acid at the position corresponding to K447 in a human IgG1 heavy chain, is D or E, and in said first and/or second polypeptides of said second dimeric protein the amino acid at the position corresponding to K447 in a human IgG1 heavy chain, is K, R, or H, and an amino acid at the position corresponding to 448 in a human IgG1 heavy chain, is P.

In one embodiment, in said first and/or second polypeptides of the first dimeric protein the amino acid at the position corresponding to K447 in a human IgG1 heavy chain, is D or E, and in said first and/or second polypeptides of said second dimeric protein the amino acid at the position corresponding to K447 in a human IgG1 heavy chain, is K, R, or H, and amino acid at the position corresponding to 448 in a human IgG1 heavy chain, is K, R, or H, and an amino acid at the position corresponding to 449 in a human IgG1 heavy chain, is P.

In one embodiment, in said first and second polypeptides of the first dimeric protein the amino acids at the positions corresponding to K439 and K447 in a human IgG1 heavy chain, are D or E; and D or E, respectively, and in said first and second polypeptides of said second dimeric protein the amino acids at the positions corresponding to S440, K447, and 448 in a human IgG1 heavy chain, are K or R; K, R, or H; and P, respectively.

In one embodiment, either said first or the second dimeric protein comprises the indicated amino acids in both said first and second polypeptide, and the other dimeric protein comprises the indicated amino acids in only said first or second polypeptide.

In one embodiment, both said first and second dimeric proteins comprise the indicated amino acids in both said first and second polypeptides. In a further embodiment, the first or second dimeric protein may be an antibody, and the other dimeric protein may be a fusion protein or a conjugate as described herein.

In one embodiment, in the first and/or second polypeptide of said first dimeric protein, the amino acid positions corresponding to E345, E430, S440, and K447, in a human IgG1 heavy chain, are R, G, Y, and D/E, respectively, and in the first and/or second polypeptides of said second dimeric protein, the amino acid positions corresponding to E345, E430, S440, K447 and 448, in a human IgG1 heavy chain, are R, G, Y, K/R/H and P, respectively, or vice versa.

In one embodiment, in the first and/or second polypeptide of said first dimeric protein, the amino acid positions corresponding to E345, E430, S440, and K447, in a human IgG1 heavy chain, are R, G, Y, and D/E, respectively, and in the first and/or second polypeptides of said second dimeric protein, the amino acid positions corresponding to E345, E430, S440, K447, 448, and 449, in a human IgG1 heavy chain, are R, G, Y, K/R/H, K/R/H, and P, respectively, or vice versa.

In a particular embodiment, the composition comprising a first and as second dimeric protein, both the first and the second polypeptides of said first and second dimeric proteins comprise the indicated amino acids in the specific positions.

In one embodiment, at least one of said first and second dimeric proteins is an antibody.

In one embodiment, both the first and the second dimeric proteins are antibodies.

In one embodiment, said first and/or second, such as at least one, of said dimeric proteins is a heterodimeric protein, such as a bispecific antibody. It may be any heterodimeric protein described herein.

In one embodiment, said first and second antibodies, bind to the same epitope of the same antigen.

In one embodiment, said first and second antibodies comprise the same variable heavy and light chain region sequences.

In one embodiment, said first and second antibodies bind to different antigens or to different epitopes on the same antigen.

In another embodiment, said first and/or second, such as at least one, of said dimeric proteins is a fusion protein.

The dimeric proteins of the compositions of the preceding aspects or embodiments may contain binding regions binding to a specific target.

In one embodiment, the composition comprises at least one additional dimeric protein according to any aspect or embodiment of the invention, such as three or six, or such as four, five, seven, eight, nine or more dimeric proteins.

In another embodiment, said first and/or second, such as at least one, of said dimeric proteins is an Fc fragment.

In one embodiment, the composition comprises more than two different, such as three, four, five or six, different dimeric proteins according to any aspect or embodiment of the invention.

In one particular embodiment, the composition comprises one or more dimeric proteins and an Fc fragment, wherein said one or more dimeric proteins comprise a first and a second polypeptide, and wherein in the first or second polypeptide the amino acid at the positions corresponding to E345 and E430 in a human IgG1 heavy chain are not E, and the amino acid in at least one position selected from the group consisting of S440, Y436, D/E356, T359, E382, N434, Q438, I253, and S254, corresponding to the position in a human IgG1 heavy chain, is Y, W, K or R; not Y; not D or E; not T; not E; not N; not Q; not I; and not S, for each position, respectively; and wherein said Fc fragment comprises a first and second polypeptide wherein in both said first and second polypeptide, the amino acid at the positions corresponding to E345 and E430 in a human IgG1 heavy chain are not E, and the amino acid in at least one position selected from the group consisting of S440, Y436, D/E356, T359, E382, N434, Q438, I253, and S254, corresponding to the position in a human IgG1 heavy chain, is Y, W, K or R; not Y; not D or E; not T; not E; not N; not Q; not I; and not S, for each position, respectively. In a further embodiment, the one or more dimeric protein and/or Fc fragment may be a fusion protein or a conjugate.

In one embodiment, composition comprises two dimeric proteins according to any aspect or embodiment of the present invention, wherein said first dimeric protein is linked to a first pro-drug, and said second dimeric protein is linked to a second pro-drug. For example, on of the first and second pro-drug may be capable of activation of the other.

In one embodiment, only one of the first and second dimeric proteins comprises a target-binding region. This can be used, e.g., for pharmaceutical compositions where an "Fc only" dimeric protein is conjugated to a therapeutic or diagnostic compound is mixed with a dimeric protein having binding specificity for a target.

In one embodiment, both the first and the second dimeric protein comprise a target-binding region. If the first and second dimeric proteins are heterodimeric proteins, they may bind to the different epitopes on the same target or to different targets. Any combination with respect to such binding is foreseen. By selecting different epitopes and/or targets for each dimeric protein, hexamer formation can be optimized to primarily occur on cells, bacteria or virions expressing both of the epitopes or targets. This provides for a mechanism to guide an immune response towards specific cell types. Additionally, a mixture of dimeric proteins binding to different epitopes on the same target molecule can provide a similar effect as a polyclonal antibody.

In some embodiments, at least one of the first and second dimeric proteins is an antibody as defined herein.

In one embodiment, both of the first and second dimeric proteins are antibodies, representing a first and second antibody. In one embodiment, the antibodies bind the same epitope of the same antigen. Optionally, the antigen-binding regions of the two antibodies are identical, i.e., comprise the same variable heavy and light chain region sequences.

In another embodiment, the first and second antibodies bind to different antigens or to different epitopes on the same antigen.

In another embodiment, the first and second antibodies bind to different antigens on different cells.

In one embodiment the first and second antibodies may each be selected from the group consisting of but not limited to monospecific, bispecific and multispecific antibodies. Further, in any of the above aspects or embodiments, at least one of the first and second dimeric proteins can be an antibody comprising at least the antigen-binding region of a known antibody in clinical or pre-clinical use, e.g., selected from the "second antibodies" listed above.

Non-Limiting Examples of Compositions Include a) a first dimeric protein which comprises a binding region;

b) a first and second dimeric protein, wherein said first and second dimeric proteins bind to different epitopes on the same target or to different targets c) a first dimeric protein of the present invention wherein said first dimeric protein comprises an amino acid in the position corresponding to K439 in a human IgG1 heavy chain which is not K, and the second dimeric protein of the present invention comprises an amino acid in a position corresponding to S440 in a human IgG1 heavy chain which is not S, Y, or W; optionally the amino acid in position K439 is E in the first dimeric protein and the amino acid in position S440 is K in the second dimeric protein.

d) a first dimeric protein of the present invention and a second dimeric protein wherein the amino acid in the second dimeric protein in positions corresponding to E345 and E430 of a human IgG1 heavy chain are not E e) a first dimeric protein of the present invention and a second dimeric protein, e.g. a second antibody, wherein the amino acids in the second dimeric protein in positions corresponding to E345 or E430 of a human IgG1 heavy chain are not E.

f) A first dimeric protein and a second dimeric protein, wherein either the first or second dimeric protein comprises an amino acid mutation which modulates one or more effector functions and/or pharmacokinetic profile of said first or second dimeric protein.

The first and second dimeric proteins may also include combinations of the aspects described in a) to e). For example the first and second dimeric proteins may in particular comprise both the features described in b) and c).

In one embodiment, the specificity is increased when a combination of the first and second dimeric proteins is bound to its target on a cell or virion expressing the target.

In any of the above aspects or embodiments, the composition may comprise at least one additional dimeric protein according to the invention. For example, the composition may comprise three, four, five, six, seven, eight, nine or more dimeric proteins, each according to an aspect or embodiment of the invention. The relative amounts of each dimeric protein can be adjusted to optimize a desired property of the hexamers formed, e.g., target cell specificity, effector function, hexamer avidity and/or stability. Additionally, a composition comprising dimeric proteins binding to different epitopes on the same target may resemble or function as a composition of polyclonal antibodies.

The dimeric protein and the second molecule comprised in each of the above-described compositions may alternatively be provided as a kit of parts, for simultaneous, separate or sequential use in, e.g., imaging or therapy.

Methods

The present invention also relates to a method of increasing oligomerization in solution and/or an effector function of a parent dimeric protein comprising a first and second polypeptide, each comprising at least CH2 and CH3 of an immunoglobulin heavy chain, the method comprising introducing into the first and/or second polypeptides, amino acid substitutions in at least the positions corresponding to E345, E430, and in a position selected from the group consisting of S440, Y436, D/E356, T359, E382, N434, Q438, I253 and S254 in a human IgG1 heavy chain.

In one embodiment, the effector function is complement-dependent cytotoxicity (CDC).

In one embodiment, said first and/or second polypeptide may further comprise a region capable of covalent binding between said first and second polypeptide.

In one embodiment, said first and/or second polypeptides may further comprise a hinge region.

In one embodiment, the method comprises introducing to said first and second polypeptide amino acid substitutions in at least the positions corresponding to E345, E430, and in at least one position selected from the group consisting of S440, Y436, D/E356, T359, E382, N434, Q438, I253 and S254 in a human IgG1 heavy chain.

In one embodiment, the method comprises introducing to said first and second polypeptide amino acid substitutions in at least the positions corresponding to E345, E430, and in at least one position selected from the group consisting of S440, Y436, E356, T359, E382, N434, Q438, I253 and S254 in a human IgG1 heavy chain.

Thus, in one embodiment the present invention also relates to a method of increasing one or both of an effector function or oligomerization in solution of a parent dimeric protein comprising a first and second polypeptide, each comprising at least CH2, CH3, and hinge regions of an immunoglobulin heavy chain, the method comprising introducing into each polypeptide amino acid substitutions in at least the positions corresponding to E345, E430 and S440 in a human IgG1 heavy chain.

In one embodiment, the amino acid substitutions are in at least the positions corresponding to E345, E430 and S440 in a human IgG1 heavy chain.

In one embodiment, the amino acids substitution in the position corresponding to E345 is, for each polypeptide, selected from the group consisting of 345R, 345Q, 345N, 345K, 345Y, 345A, 345C, 345D, 345F, 345G, 345H, 345I, 345L, 345M, 345P, 345S, 345T, 345V and 345W, such as from the group consisting of 345R, 345Q, 345N, 345K and 345Y.

In one embodiment, the amino acid substitution in the position corresponding to E430 is, for each polypeptide, selected from the group consisting of 430G, 430T, 430S, 430F, 430H, 430A, 430C, 430D, 430I, 430K, 430L, 430M, 430N, 430P, 430Q, 430R, 430V, 430W and 430Y, such as from the group consisting of 430G, 430T, 430S, 430F and 430H.

In one embodiment, the amino acid substitution in the position corresponding to S440 is, in each polypeptide, 440Y or 440W.

In one embodiment, the amino acid substitutions in the positions corresponding to E345, E430 and S440 are 345R, 430G and 440Y, respectively.

In one embodiment, the amino acid substitutions in the positions corresponding to E345, E430 and S440 in a human IgG1 heavy chain are 345K, 430G and 440Y, respectively.

In one embodiment, the amino acid substitutions in the positions corresponding to E345, E430 and S440 in a human IgG1 heavy chain are 345R, 430S and 440Y, respectively.

In one embodiment, the amino acid substitutions in the positions corresponding to E345, E430 and S440 in a human IgG1 heavy chain are 345R, 430G and 440W, respectively.

In one embodiment, the amino acid substitutions in the positions corresponding to E345, E430 and Y436 in a human IgG1 heavy chain are 345R, 430G and 436I, respectively.

In one embodiment, the amino acid substitutions in the positions corresponding to E345, E430, Y436, and S440 in a human IgG1 heavy chain are 345R, 430G, 436I, and 440Y respectively.

In any one of the preceding embodiments, the isotype of the heavy chain sequence can selected from the group consisting of IgG1, IgG2, IgG3, IgG4, IgA1, IgA2, IgD, IgM and IgE.

In any one of the preceding embodiments, the heavy chain can be of mammalian origin.

In any one of the preceding embodiments, the heavy chain can be of primate or murine origin, such as of human origin.

In any one of the preceding embodiments, each polypeptide may comprise an immunoglobulin heavy-chain variable region associated with an immunoglobulin light chain sequence comprising light chain variable and constant regions to form a first and a second antigen-binding region, optionally binding the same antigen.

In the preceding embodiment, each polypeptide of the dimeric protein may comprise a full-length heavy chain constant region, such as a full-length human IgG1 heavy chain constant region.

In any one of the preceding embodiments, the parent dimeric protein can be an antibody, such as, for example, a full-length IgG1 antibody.

The invention also provides for any dimeric protein according to any aspect or embodiment herein described, prepared by the method of any one of the preceding embodiments.

The invention also provides for a variant dimeric protein, such as a variant antibody prepared by the method of any one of the preceding embodiments. Specifically, introducing mutations in the designated positions in a parent dimeric protein according to a method of the present invention can result in a dimeric protein of the present invention. The dimeric protein may then be regarded as a variant of the parent dimeric protein, e.g. a variant dimeric protein. Thus, the method(s) of the present invention may be performed so as to obtain any dimeric protein as described herein.

The present invention also relates to a method for purification of a dimeric protein according to the present invention comprising purification on a Protein A or Protein G column at a pH below 6.8, such as between 5.0 and 6.5, e.g. between 5.0 and 6.0, e.g. between 5.0 to 5.5, and subsequently raising the pH above 6.8 or above pH 7.0. Buffers for adjusting the pH may be any of those described herein.

Kit-of-Parts

The present invention also relates to a kit-of-parts comprising a first dimeric protein according to any aspect or embodiment described herein, and a second dimeric protein according to any aspect or embodiment described herein, for simultaneous, separate or sequential use in imaging, diagnostic or therapy.

Uses

As described herein the dimeric protein of the present invention forms hexameric structures in solution, thereby resembling IgM molecules. Furthermore, as described above combinations of a first and second dimeric protein of the present invention, or optionally a second molecule which is not a dimeric protein according to the invention, wherein the different components of the combination bind to different epitopes on the same target is foreseen to create compositions which resemble polyclonal antibody compositions. These features and other features of the dimeric protein of the present invention make it particularly suitable for certain applications.

IgM Like Feature

IgM has a major role in immune response to infectious organisms. It is a potent activator of the classical complement pathway.

Antibodies against carbohydrates are often of IgM isotype. Carbohydrates are potential targets for treatment of bacterial, fungal or viral infections, cancer and autoimmune diseases.

IgM antibodies are described to have immune regulatory properties and to be protective in a number of autoimmune diseases, like lupus (SLE) and multiple sclerosis. IgM would also have a protective role in atherosclerosis, myocardial infarction and stroke, cerebral small vessel disease and Alzheimer's disease. (Groenwall et al 2012, Frontiers in Immunology 3, 1-10)

Naturally occurring antibodies to cancer cells are often of IgM isotype.

IgM (and polymeric IgA) has a function in immune exclusion on the luminal side of mucosal surfaces. For passive immunization, protective levels of IgM (and polymeric IgA) can be delivered directly to mucosal surfaces.

IgM based products are being developed for autoimmune, cancer and infection indications.

The dimeric protein of the present invention could mimic the IgM-like features of listed above when in a pH adjusted, such as pH 6.5 to 7.0, solution, and it is therefore foreseen that the dimeric protein of the invention can be used for treatment of any of said indications.

In addition, by adjusting the pH of the solution, the dimeric proteins of the invention can be in monomeric, i.e. as a single dimeric protein, or hexameric form (as described in Example 32). The term "monomeric form" in the context of dimeric protein according to the present invention refers to a single, individual dimeric protein, which is composed of dimeric proteins that do not associate non-covalently with each other. When referring to a "hexameric form" it is to be understood as a complex of six non-covalently associated single dimeric proteins. It is foreseen that standard production and purification methods used for IgG molecules can be used for the dimeric proteins of the invention when they are in monomeric form, such as, but not limited to, the use of protein A resins and protein A variant resins for purification, and the use of protein A and protein A variant based immunoglobulin domain detection assays for example applied in process control, and the use of cation exchange chromatography for concomitant aggregate removal during protein purification, and the use of nanofiltration for viral clearance, thus avoiding problems often encountered when producing or purifying IgM proteins.

Fast Clearance

The hexameric form of dimeric proteins of the present invention is rapidly cleared unless when combined with technologies preventing rapid clearance as described herein. Fab fragment products, also being cleared rapidly, are being developed/used for treatment of poisoning, poison intoxication, and to deplete excess or abundant ligands and/or soluble factors.

Dimeric proteins of the present invention could have similar applications.

Dimeric proteins of the present invention could also be used to deplete soluble/shedded forms of membrane proteins that would form a sink for cell-targeted therapy.

Polyclonal Aspects

Polyclonal antibody products have the potential of synergistic action (better efficacy), and could overcome acquired therapy resistance.

Polyclonal antibody products are developed/being used for treatment of viral or bacterial infections, envenomation, (immune thrombocytopenic purpura), Digoxin toxicity, renal transplant acute rejection and cancer.

The dimeric protein of the present invention, thus, has similar applications and is therefore suitable for use in the treatment of any of said indications.

Thus, in one embodiment the dimeric proteins of the present invention may be used for treatment of any of the following indications: Autoimmune diseases, including systemic lupus erythematodes (SLE), multiple sclerosis, Neuromyelitis optica, Sjögrens syndrome, CREST syndrome, opsoclonus, Inflammatory myopathy, Mixed connective tissue disease, Systemic sclerosis, Primary biliary cirrhosis, Coeliac disease, Miller-Fisher syndrome, Acute motor axonal neuropathy, Multifocal motor neuropathy MMN, Rheumatoid arthritis, Osteoarthritis, Autoimmune hepatitis, Anti-phospholipid syndrome, Wegener's granulomatosis, Microscopic polyangiitis, Churg-Strauss syndrome, Polymyositis, Scleromyositis, Myasthenia gravis, Lambert-Eaton myasthenic syndrome, Hashimoto's thyroiditis, Graves'disease, Paraneoplastic cerebellar syndrome, Stiff person syndrome, Limbic encephalitis, Sydenham's chorea, PANDAS, Encephalitis, limbic encephalitis, Diabetes mellitus type 1, ataxia, Epilepsia partialis continua, Idiopathic thrombocytopenic purpura, Pernicious anemia, Addison's anemia, Autoimmune gonadal failure, Autoimmune hemolytic diseases, such as hematological auto-immune anemia and HIV-associated thrombocytopenia, *Pemphigus*, Bullous pemphigoid, Dermatitis hepetiformis, Linear IgA dermatosis, Vitiligo, Goodpasture's syndrome, Myocarditis, idiopathic dilated cardiomyopathy, Crohn's disease and ulcerative colitis, cancer, bacterial infections, viral and fungal infections, poisoning and envenomation, or vascular or other diseases.

Examples of cancer, include but are not limited to various cancer types such as: tumors of the central nervous system, head and neck cancer, lung cancer (such as non-small cell lung cancer), breast cancer (such as triple-negative breast cancer), esophageal cancer, stomach cancer, liver and biliary cancer, pancreatic cancer, colorectal cancer, bladder cancer, kidney cancer, prostate cancer, endometrial cancer, ovarian cancer, malignant melanoma, sarcoma (soft tissue eg. bone and muscle), tumors of unknown primary origin (i.e. unknown primaries), leukemia, bone marrow cancer (such as multiple myeloma) acute lymphoblastic leukemia, chronic lymphoblastic leukemia and non-Hodgkin lymphoma, acute myeloid leukemia (AML), skin cancer, glioma, cancer of the brain, uterus, and rectum.

Thus, in one aspect, the present invention relates to a method for preventing or treating a disease, such as cancer, auto-immune diseases, infections, diabetes mellitus, organ transplant rejections, ophthalmological diseases and C1q depletion in the humeral system, comprising administration of a dimeric protein, oligomer, hexamer, composition, kit-of-parts according to any aspect or embodiment of the present invention.

In one embodiment, the cancer is a tumor, such as a brain tumor. The dimeric protein according to the invention may be used to mechanically obstruct blood flow in tumor blood vessels by injection directly into the tumor, such as brain tumors. The dimeric protein according to any aspect or embodiment of the present invention, may be particularly useful to induce mechanical obstruction in tumors due to its capability to form oligomers, such as dimer, trimers, and hexamers. When the dimeric protein, such as an antibody, according to the present invention is used in the treatment of cancer it is particularly useful in overcoming suppression of effector mechanisms due to the low pH of the tumor microenvironment.

In one embodiment, the dimeric protein, oligomer, hexamer, composition or kit-of-parts according to any aspect or embodiment of the present invention, is for use in the treatment of tumors by making use of pH-dependent delivery of toxins or payloads/drugs. In such uses the lower pH at the tumor site can be exploited when the dimeric protein, such as an antibody, of the present invention is fused to a toxin or drug that has optimal function at the lower pH at the tumor site.

In one embodiment, the method comprises the steps of administering to the bloodstream a first dimeric protein according to any aspect or embodiment of the invention linked to a first pro-drug, and a second dimeric protein according to any aspect or embodiment of the invention linked to a second pro-drug.

In one aspect, the present invention relates to a method of inducing an immunomodulatory effector function, such as mediated through CD32b and KIR, wherein the method comprises administration of the dimeric protein, oligomer, hexamer, composition or kit-of-parts according to any aspect or embodiment of the present invention, optionally combined with sialylation of the dimeric protein. In such a method, the dimeric protein of the invention will induce clustering of the target molecules and thereby induce the immunomodulatory effector function. Thus, the dimeric protein according to the invention may be used as an alternative to intravenous immunoglobulin (IVIG).

In one embodiment, the dimeric protein, such as an antibody or Fc-fusion protein, according to any aspect or embodiment of the present invention, may be used to enhance clearance of a target molecule from the bloodstream, such as a ligand, a receptor, a toxin, C1q, IgE, an anti-graft antibody, human anti-human antibodies (HAHA), antidrug antibodies (ADA), human anti murine antibodies (HAMA), human anti chimeric antibodies (HACA), pharmaceutical compounds, and immunomodulatory compounds.

The dimeric protein according to the invention, such as an Fc fragment fused to an antigen, may have improved immunostimulatory effect when in oligomeric form, such as a hexameric molecule, as the oligomer provides antigen complexes that for example stimulate clustering of B-cell receptors directed against said antigen, and facilitate affinity maturation of initial low affinity B-cell receptors by presenting the antigen in a multivalent form. This may be obtained both when the dimeric protein according to the invention is in solution or is presented on the surface of a cell, virion, virus-like particle, embedded in a liposome or in other forms supporting presentation of transmembrane proteins commonly known in the art. Thus, in one embodiment, the dimeric protein, such as an Fc-fragment, according to any aspect or embodiment of the present invention, is for use in vaccination, immunization and immune response stimulation. Thus, in one embodiment the present invention also relates to a method for vaccination, immunization and immune response stimulation comprising administration of the dimeric protein as described herein.

The dimeric protein according to the invention, may be used to create supramolecular structures, that optionally may be assembled in a pH-dependent fashion, both in solution, as well as on a surface, such as, but not limited to, the surface of a cell, virion, virus-like particle, liposome, microchip, solid surface, porous scaffold, or other methods for protein presentation commonly known in the art.

In one embodiment, said first and/or second polypeptide of the dimeric protein may comprise a protein binding domain, such as a Fab domain, specifically binding a Fab domain in a different Fc domain containing polypeptide. The dimeric protein and its target molecule may be used for the formation of supramolecular structures, that may optionally be assembled in a pH controlled fashion.

In one embodiment, the dimeric protein according to any aspect or embodiment of the present invention is for use in protein crystallization. The dimeric protein may be particularly useful due to its capability to form oligomeric structures in a pH controlled fashion.

In one embodiment the present invention relates to a method of using the dimeric protein according any aspect or embodiment herein described for immune complex formation in diagnostical kits, such as an agglutination assay. An example of an agglutination assay is Coombs test.

Examples of bacterial infections, include but are not limited to *Staphylococcus aureus* infection (*S. aureus*), e.g. Methicillin-resistant *Staphylococcus aureus* (MRSA), *Pseudomonas aeruginosa* infection, infections caused by a bacteria selected from the group consisting of *S. epidermidis, S. pneumonia, Bacillus anthracis, Chlamydia trachomatis, E. coli, Salmonella, Shigella, Yersinia, S. typhimurium, Neisseria meningitides*, and *Mycobacterium tuberculosis*. Examples of viral and fungal infections, include but are not limited to West Nile virus, Dengue virus, hepatitis C-virus (HCV), human immunodeficiency virus (HIV), RVS, *Aspergillus, Candida albicans, Cryptococcus, Histoplasma*, human cytomegalovirus (HCMV), herpes simplex virus, human respiratory syncytial virus, human papillomavirus, Epstein-Barr virus, Herpesviruses, poxviruses, and avian influenza virus. Examples of poisoning and envenomation include but are not limited to digoxin, Colchicine, venom from reptiles such as snake venom, venom from insects such as bee, wasp and caterpillar venom, spider venom, Microbial endotoxins and exotoxins, such as botelinum neurotoxins, tetanus toxin, Staphylococcal toxins, alpha toxin, Anthrax toxin, Diphteria toxin, Persussis toxin, Shiga toxin, Shiga-like toxin.

Examples of vascular and other diseases may be e.g. atherosclerosis, myocardial infarction and stroke, cerebral small vessel disease, Alzheimer's disease, and depletion of C1q in high-fat diet induced hepatic insulin resistance and systemic glucose tolerance, and the clearance of anti-graft antibodies before or after organ transplantation.

In one aspect, the present invention relates to the dimeric protein, oligomer, hexamer, composition or kit-of-parts according to any aspect or embodiments described herein, for use in the treatment of a disease, such as a bacterial, viral or parasitic infection, autoimmune disease, cancer, inflammation, and/or reducing the risk for septic shock caused by a bacterial infection.

For the treatment of bacterial infections and/or reducing the risk of septic shock, the dimeric protein of the invention may, for example, comprise a binding region specifically binding to a lipopolysaccharide (LPS), a lipooligosaccharide (LOS), a delta endotoxin, Botulinum toxin, *Corynebacterium diphtheriae* exotoxin, a bacterial superantigen, a heat-stable enterotoxin, cytolysin, a channel-forming toxin, an enzymatically active toxin or a mycotoxin.

In another aspect, the invention provides for the use of the dimeric protein, hexamer, composition or kit-of-parts according to any one of the preceding embodiments in imaging at least a part of the body of a human or other mammal. In one aspect, the present invention relates to a method for imaging of at least a part of the body of a human or other mammal, comprising administering a dimeric protein, oligomer, hexamer, composition or kit-of-parts according to any aspect or embodiments described herein.

In another aspect, the invention relates to a method for treating a bacterial, viral or parasitic infection, for imaging of at least a part of the body of human or other mammal, or for modulating clearance of a target molecule from the body of a human or other mammal, comprising administering a dimeric protein, oligomer, hexamer, composition or kit-of-parts according to any aspect or embodiment described herein.

In another aspect, the invention relates to a method for preventing or treating a disease, such as cancer, autoimmune diseases, organ transplant rejections, and C1q depletion in the humoral system, comprising administration of a dimeric protein, oligomer, hexamer, composition, kit-of-parts according to any aspect or embodiment described herein.

EXAMPLES

Example 1

Design and Generation of CD38 Antibody 005 Mutants

The human monoclonal antibody HuMab 005 is a fully human IgG1,κ antibody described in WO/2006/099875, that is directed against human CD38. Here, it was used as a model antibody to test the capability of Fc mutations to enhance CDC activity. The tested mutations are listed in Table 3.

DNA constructs for the different mutants were prepared and transiently transfected using the heavy chain of HuMab 005 with IgG1m(f) allotype as a template for mutagenesis reactions. Briefly, mutants were prepared using the Quikchange site-directed mutagenesis kit (Stratagene, US). A forward and a reverse primer encoding the desired mutation were used to replicate full length plasmid DNA template encoding the 005 heavy chain with IgG1m(f) allotype. The resulting DNA mixture was digested using DpnI to remove source plasmid DNA and used to transform *E. coli*. Mutant plasmid DNA isolated from resulting colonies was checked by DNA sequencing (Agowa, Germany). Plasmid DNA mixtures encoding both heavy and light chain of antibodies were transiently transfected to Freestyle HEK293F cells (Invitrogen, US) using 293fectin (Invitrogen, US) essentially as described by the manufacturer.

To test the functional relevance of oligomeric Fc-Fc interactions in complement activation and CDC, amino acids in the hydrophobic patch at the Fc:Fc interface were mutated to potentially disrupt the Fc-Fc side-on interaction and CDC efficacy of 005. Mutations I253D and H433A were introduced to change the charge at positions that were chosen based on the 1HZH crystal structure and described to be exposed in hydrophobic patches in the CH2-CH3 domain (Burton Mol Immunol 1985 March; 22(3):161-206)).

The 1HZH crystal structure shows that I253 and H433 bind two different pockets on the opposing Fc positions of the partnering antibody. To exclude the possibility that disruption of direct binding sites for C1q were the cause of the observed effects on CDC, mutants K439E and S440K were generated. As shown in FIG. 4, K439 and S440 face each other on opposite sides at the Fc:Fc interface, so K439E and S440K were designed to induce loss of CDC as single mutant by inhibiting the Fc:Fc interaction, but were expected to restore CDC when interacting with each other, due to restored Fc:Fc interactions in the antibody mixture.

TABLE 3 set of mutations that were introduced in the CH2—CH3 domain of 005 (HuMax-CD38).

| Mutation | Charge WT aa | Charge mutant aa |
|---|---|---|
| I253D | = | − |
| E345R | − | + |
| H433A | δ+ | = |
| K439E | + | − |
| S440K | = | + |

(=) no charge
(−) negative charge
(+) positive charge
(δ+) partial positive charge Example 2

CD38 Binding on Cells by HuMab-005 Mutants

Binding of unpurified antibody samples to CD38-positive Daudi and Raji cells was analyzed by FACS analysis. $10^5$ cells were incubated in 100 μL in polystyrene 96-well round-bottom plates with serial dilutions of antibody preparations (0.01, 0.03, 0.1, 0.3, 1.0, 3.0, 10.0, 30.0 μg/mL) in RPMI1640/0.1% BSA at 4° C. for 30 min. After washing twice in RPMI1640/0.1% BSA, cells were incubated in 50 μL with FITC-conjugated rabbit F(ab')$_2$ anti-human IgG (cat.no. F0056; DAKO; 1:150) at 4° C. for 30 min. Next, cells were washed twice in PBS/0.1% BSA/0.02% azide, resuspended in 100 μL PBS/0.1% BSA/0.02% azide and analyzed on a FACS Cantoll (BD Biosciences). Binding curves were analyzed using GraphPad Prism V5.01 software. As a negative control, supernatant of mock-transfected cells was used.

Binding of HuMab 005 to Daudi cells was not much affected by the introduction of point mutations in the CH2-CH3 domain. All tested antibodies bound Daudi cells in a dose-dependent manner. Binding was similar to wild type HuMab-005 for all tested mutants, with the exception of 005-E345R, which showed slightly decreased binding. However, without being bound by any theory, the lower binding might be a result of decreased binding by the secondary antibody. The actual binding avidity by 005-E345R might be similar or even increased compared 005-WT, however we could not confirm this because of lack of directly labeled antibodies.

Binding of HuMab-005 to Raji cells was also not much affected by the introduction of point mutations in the CH2-CH3 domain. All tested antibodies bound Raji cells in a dose-dependent manner. Maximal binding was similar to that of wild type 005 for the 005-I253D and H433A mutants and lower for the 005-E435R, K439E, S440K mutants and the combination of 005-K439E+005-S440K. However, without being bound by any theory, the lower binding might be a result of decreased binding by the secondary antibody (shielding of the epitope).

Example 3

CDC Assay on CD38-Positive Cells by Mutants of the CD38 Antibody 005

$0.1 \times 10^6$ Daudi or Raji cells were pre-incubated in round-bottom 96-well plates with a concentration series of unpurified antibodies (0.01, 0.03, 0.1, 0.3, 1.0, 3.0, 10.0, 30.0 µg/mL) in a total volume of 100 µL for 15 min on a shaker at RT. Next, 25 µL normal human serum was added as a source of C1q (20% final concentration) and incubated in a 37° C. incubator for 45 min. The reaction was stopped by putting the plates on ice. 10 µL propidium iodide was added and cell lysis was determined by FACS.

The impact of the E435R mutation on CDC was further analyzed on Wien133 cells with different concentration normal human serum (NHS). $0.1 \times 10^6$ Wien133 cells were pre-incubated for 15 min on a shaker at RT in round-bottom 96-well plates with a concentration series of unpurified antibodies (0.001, 0.003, 0.01, 0.03, 0.1, 0.3, 1.0, 3.0, 10.0, 30.0 µg/mL) in a total volume of 50 µL. Next, NHS was added as a source of C1q to reach a final concentration of either 20% or 50% NHS in a total volume of 100 µL. The reaction mixture was incubated in a 37° C. incubator for 45 min. The reaction was stopped by putting the plates on ice. 10 µL propidium iodide was added and cell lysis was determined by FACS.

Figure 5A:
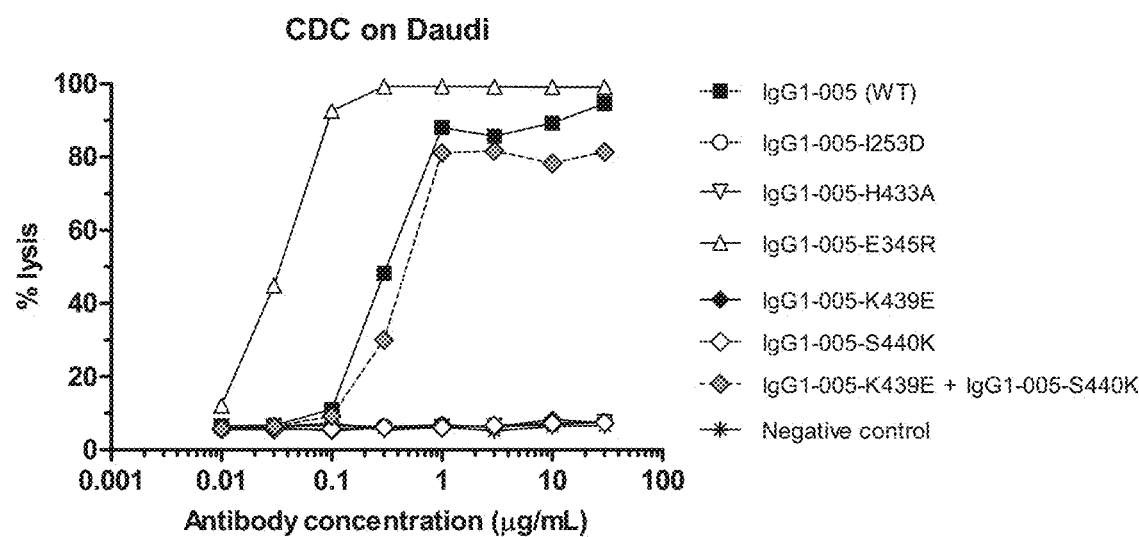
Figure 5B:
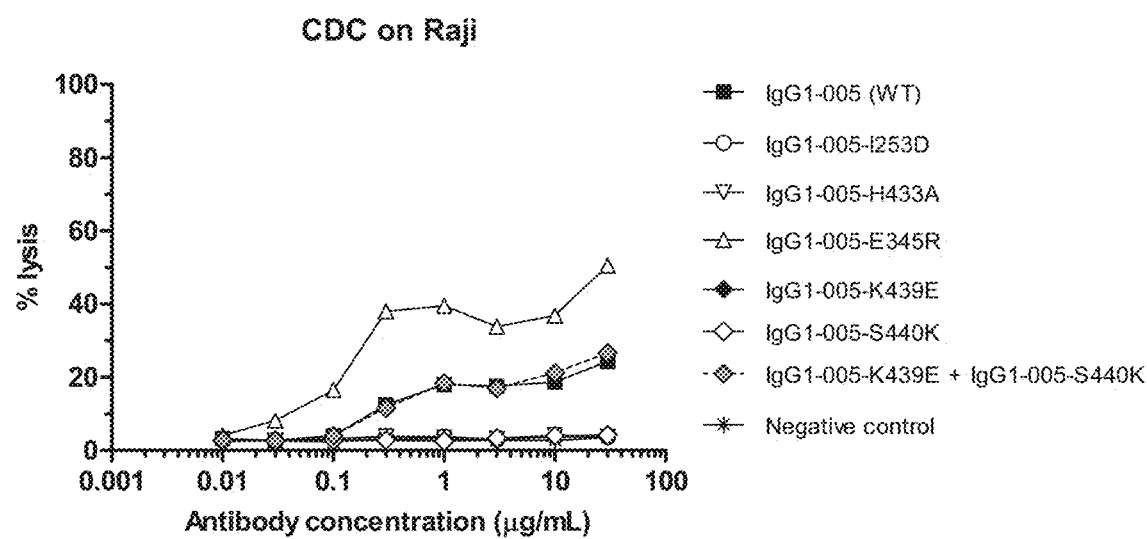

FIG. 5 shows that 005-I253D, H443A, K439E and S440K showed complete loss of CDC activity on both Daudi (FIG. 5A) and Raji (FIG. 5B) cells, whereas the 005-E345R mutant showed strongly enhanced CDC activity on both cell lines. Comparable to 7D8 data, a combination of 005-K439E+005-S440K, which both result in loss of CDC as a single mutant, resulted in restored CDC. Surprisingly, 005-E435R even strongly induced CDC on Wien133 cells, for which wild type 005 is not capable to induce killing by CDC (FIG. 5C). CDC killing by 005-E345R on Wien133 cells was observed with both 20% and 50% serum concentrations (FIG. 5C). On Raji cells, both 7D8-E345R and 005-E345R showed enhanced CDC in vitro in 50% serum, with similar efficacy as in 20% serum (FIG. 5D).

As the E345R mutation in the CH2-CH3 region resulted in enhanced CDC activity in both the tested CD20 antibody 7D8 and CD38 antibody 005, the E345R mutation is considered to be a general antibody modification that can be applied to induce or enhance CDC.

Example 4

IgG1 Antibodies Containing the CDC-Enhancing Mutation E345R are Less Sensitive to Inhibition of CDC by Fc Binding Peptide DCAWHLGELVWCT than Wild Type Antibodies By mutating amino acid positions in the hydrophobic patch at the Fc:Fc interface of IgG, CDC efficacy was found to be either disturbed or enhanced. The involvement of the interactions at the Fc-Fc interface, and thus possibly the formation of an oligomeric (e.g., hexameric ring) structure as observed in the b12 crystal structure, in CDC efficacy was further explored. Therefore, a 13-residue peptide (DCAWHLGELVWCT (SEQ ID NO:7)) was used that targets a consensus binding site in the hydrophobic patch region on the surface of wild type IgG Fc (Delano et al., Science 2000 Feb. 18; 287(5456):1279-83). Indeed, the identification of the consensus binding site on the surface of IgG Fc as an adaptive region that is primed for interaction with a variety of distinct molecules (Delano et al., Science 2000 Feb. 18; 287(5456):1279-83), is consistent with the identification of the core amino acids in the hydrophobic patch that are involved in the Fc-Fc interaction in the IgG1 b12 crystal structure (Saphire et al., Science 2001 Aug. 10; 293(5532):1155-9). Interactions that are present in all of the binding interfaces are mediated by a shared set of six amino acids (Met-252, Ile-253, Ser-254, Asn-434, His-435, and Tyr-436), as well as shared backbone contacts (Delano et al., Science 2000 Feb. 18; 287(5456):1279-83). Accordingly, the Fc binding peptide is expected to affect the Fc-Fc interaction and consequently CDC efficacy.

$0.1 \times 10^6$ Daudi cells were pre-incubated in 75 µL with 1.0 µg/mL unpurified antibody in round-bottom 96-well plates for 10 min at room temperature on a shaker. 25 µL of a concentration series (range 0.06-60 µg/mL final concentration) of the Fc binding peptide DCAWHLGELVWCT was added to the opsonized cells and incubated for 10 min on a shaker at RT. Next, 25 µL NHS was added as a source of complement (20% final concentration) and incubated in a 37° C. incubator for 45 min. The reaction was stopped by adding 25 µL ice cold RPMI medium, supplemented with 0.1% BSA. 15 µL propidium iodide was added and cell lysis was determined by FACS analysis.

Figure 6:
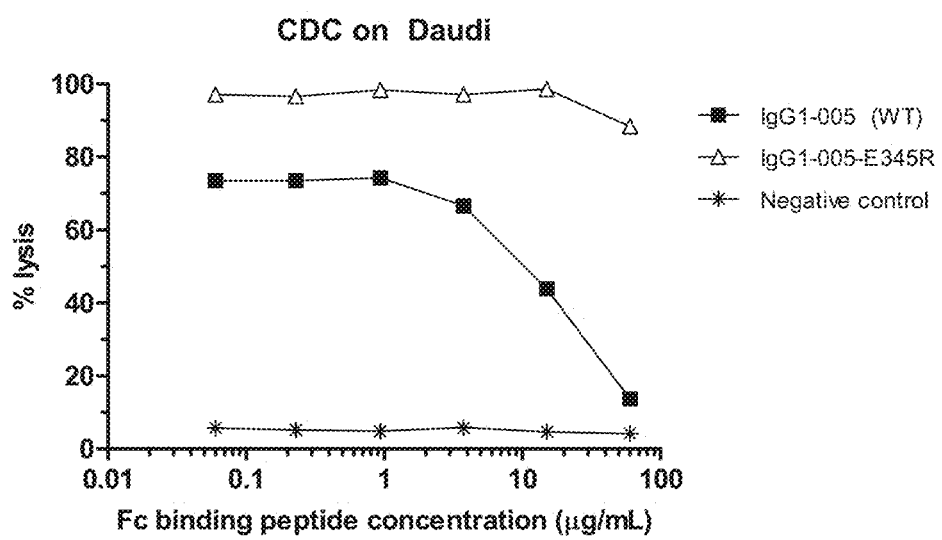
FIG. 6: CDC by wild type and E345R mutants of CD38 antibody HuMAb 005 in a competition experiment with an Fc-binding peptide. Cell lysis was measured after CDC on antibody-opsonized Daudi-cells incubated with a concentration series of the Fc-binding DCAWHLGELVWCT peptide (SEQ ID NO:7). Unpurified antibody samples isolated from transient transfections were used. As a negative control, supernatant of mock-transfected cells was used.

CDC mediated by wild type 005 (FIG. 6) was found to be inhibited by the Fc-binding peptide DCAWHLGELVWCT in a dose-dependent manner. These competition data suggest again the involvement of the Fc-Fc interactions at the hydrophobic patch of IgG in CDC efficacy. The CDC-enhanced IgG1-005-E345R mutant was less sensitive for competition by the Fc-binding peptide compared to the corresponding wild type antibodies, suggesting that the E345R mutation results in increased stability of the Fc-Fc interaction, and consequently increased CDC.

Example 5

Increased Specificity of Enhanced CDC by Combining E345R with Complementary Inhibiting Mutations K439E and S440K in a Mixture of Two Different Monoclonal Antibodies As described in Example 3, CD38 antibody 005 mutations K439E and S440K decreased the CDC efficacy as monoclonal antibodies. Mixing 005 antibodies containing these mutations restored CDC. Efficient CDC was thus restricted to cells bound by both mutant antibodies simultaneously. Similar, data have been found for the CD20 antibody 7D8 described in WO 2004/035607 (data not shown).

It can be advantageous to restrict the enhancement of CDC induction to target cells that express two specific antigens simultaneously, exploiting their combined expression to improve selectivity of enhanced CDC induction. It can also be advantageous to restrict the enhancement of CDC induction to target cells that are bound by mixtures of at least two different antibodies simultaneously, said antibodies binding an identical cell surface antigen at two different epitopes simultaneously, or at two cross-competing, similar, or identical epitopes.

Therefore, to restrict enhanced CDC induction to cells bound by both CD20 and CD38 antibodies simultaneously, the CDC enhancing mutation E345R was combined with CDC inhibiting mutations in the antibodies 7D8-E345R/K439E, 7D8-E345R/S440K, 005-E345R/S440K and 005-E345R/K439E. These antibodies were added separately or mixed 1:1 in CDC experiments as follows. $0.1 \times 10^6$ Wien133 cells (other cell types such as Daudi or Raji cells may also be used) were pre-incubated in round-bottom 96-well plates with a concentration series of unpurified antibodies (final concentration 0.056-10,000 ng/mL in 3-fold dilutions for 7D8-E345R/K439E, 7D8-E345R/S440K, 005-E345R/S440K or 005-E345R/K439E) or antibody mixtures (final concentrations 0.01 µg/mL CD20 antibody mixed with 0-333 ng/mL in 3-fold dilutions CD38 antibody; or 3.3 µg/mL CD38 antibody mixed with 0.0056-1,000 ng/mL in 3-fold dilutions CD20 antibody) in a total volume of 100 µL for 15 min on a shaker at RT. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS.

Figure 7A:
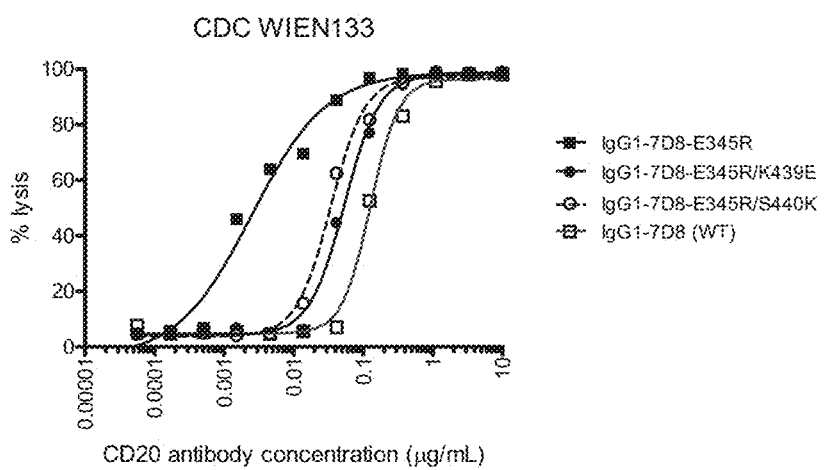
FIGS. 7A-7D: CDC on CD20- and CD38-positive Wien133 cells by CD20 antibody 7D8 mutants (FIG. 7A), CD38 antibody 005 mutants (FIG. 7B), mixtures of CD38 antibody 005 mutants and CD20 antibody 7D8 mutants (FIG. 7C) and (FIG. 7D).
Figure 7B:
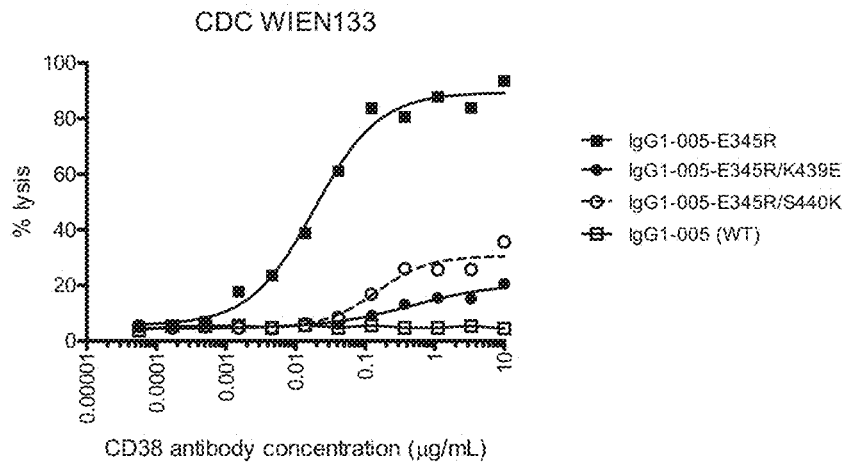
Figure 7C:
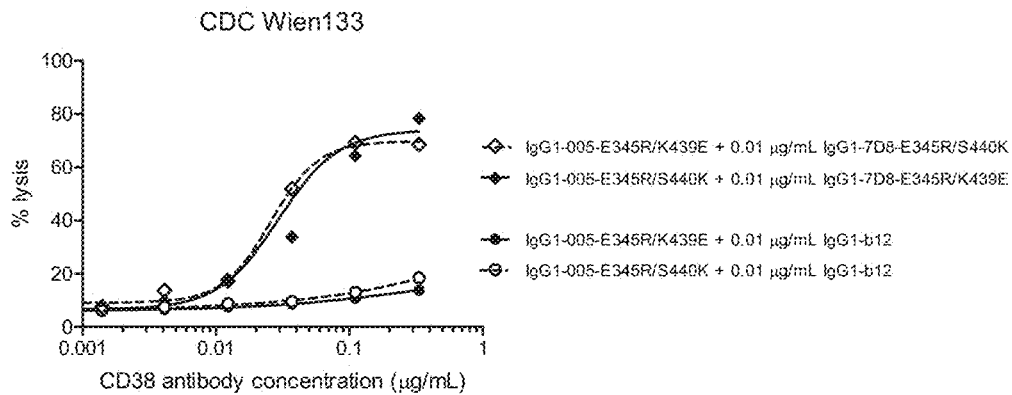

A concentration series of 005-E345R/K439E or 005-E345R/S440K antibody was mixed with a fixed concentration of 0.01 µg/mL 7D8 double mutant antibody (maximal concentration with minimal CDC on Wien133 cells as a single agent as determined from FIG. 7A) to make the complementary combinations 005-E345R/K439E+7D8-E345R/S440K or 005-E345R/S440K+7D8-E345R/K439E. FIG. 7C shows that the 005 double mutant CD38 antibodies induced CDC dose-dependently in the presence of fixed concentration of the complementary 7D8-E345R/K439E or 7D8-E345R/S440K CD20 antibody, respectively. The CDC efficacy by these complementary combinations (FIG. 7C) was comparable to the 005-E345R single mutant (enhancer) antibody as a single agent (FIG. 7B). In contrast, in the presence of irrelevant antibody b12, both 005-E345R/K439E and 005-E345R/S440K showed hardly any CDC in the concentration series tested (comparable to 005-E345R/K439E or 005-E345R/S440K as single agents shown in FIG. 7B).

Figure 7D:
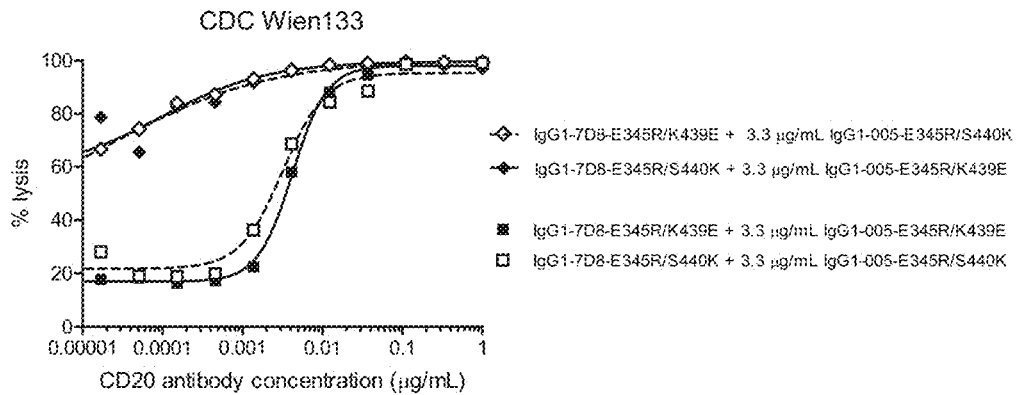

A concentration series of 7D8-E345R/K439E or 7D8-E345R/S440K antibody was mixed with a fixed concentration of 3.3 µg/mL 005 double mutant antibody (showing a little but limited CDC on Wien133 cells as a single agent as determined from FIG. 7B) to make the complementary combinations 7D8-E345R/K439E+005-E345R/S440K or 7D8-E345R/S440K+005-E345R/K439E. FIG. 7D shows that the 7D8 double mutant CD20 antibodies induced CDC very efficiently in the presence of the complementary 005-E345R/K439E or 005-E345R/S440K CD38 antibody respectively, even at the lowest concentrations tested, resembling not more than a few 7D8 double mutant antibody molecules per cell. To eliminate the contribution of increased Fc-tail density on the cell membrane to the observed enhanced CDC by the mixture of 7D8 and 005 antibodies with complementary K439E and S440K mutations, also antibody combinations with non-complementary mutations were tested. FIG. 7D shows that non-complementary combinations showed much lower CDC efficacy than complementary combinations, as a result of less efficient Fc-Fc interaction than the complementary combinations.

These data suggest that the induction of (enhanced) CDC by therapeutic antibodies can be limited to cells that bind simultaneous a mixture of two complementary antibodies, in this case with different antigen specificities, thereby increasing target cell specificity by requiring co-expression of both antigens.

As can be seen in FIGS. 7A and 7B, 7D8-E345R/K439E, 005-E345R/S440K, 7D8-E345R/S440K and 005-E345R/K439E displayed limited CDC efficiency in comparison to 7D8-E345R alone. It is further seen, that the mixture of 7D8-E345R/K439E and 7D8-E345R/S440K enabled CDC with enhanced efficiency compared to wildtype 7D8 antibody as single agent. Likewise, it was observed that the mixture of 005-E345R/K439E and 005-E345R/S440K enabled CDC with enhanced efficiency compared to wildtype 005 antibody as single agent (data not shown).

Example 6

Use of a Mutant Screening Approach to Identify Mutations Stimulating Fc:Fc Interaction Mediated Antibody Oligomerization Detected by a CDC Assay As described in Example 3, amino acid mutations were identified that stimulated CDC for an antibody recognizing the target antigens, CD38, on multiple cell lines expressing variable levels of said antigens. Surprisingly, the single point mutation E345R proved sufficient to endow CDC-dependent cell lysis of Wien133 cells to the anti-CD38 antibody 005, which failed to lyse these cells by CDC in wild type IgG1 format.

Other mutations on or at the periphery of the Fc:Fc interface could stimulate oligomerization and CDC in an analogous fashion. Alternatively, mutations could indirectly stimulate oligomerization, for example by allosterically inducing Fc:Fc interactions.

To determine if other amino acid mutations could stimulate Fc-mediated antibody oligomerization, a library of anti-CD38 IgG1-005 mutants was screened using CDC assays, both individually and mixed in a pairwise fashion to select for example amino acid pairs interacting across the Fc:Fc interface. However, the same strategy can be applied to other antibodies, such as another IgG1 or an IgG3 antibody.

A focused library of mutations at the positions indicated in Table 4 was generated. Mutations were introduced into the IgG1-005 Fc region using the Quikchange site-directed mutagenesis kit (Stratagene, US). Briefly, for each desired mutation position, a forward and a reverse primer encoding a degenerate codon at the desired location were used to replicate full length plasmid DNA template of the 005 heavy chain with IgG1m(f) allotype. The resulting DNA mixtures were digested using DpnI to remove source plasmid DNA and used to transform *E. coli*. Resulting colonies were pooled and cultured and plasmid DNA was isolated from these pools and retransformed into E. coli to obtain clonal colonies. Mutant plasmid DNA isolated from resulting colonies was checked by DNA sequencing (LGC genomics, Berlin, Germany). Expression cassettes were amplified from plasmid DNA by PCR and DNA mixes containing both a mutant heavy and a wildtype light chain of IgG1-005 were transiently transfected to Freestyle HEK293F cells (Invitrogen, US) using 293fectin (Invitrogen, US) essentially as described by the manufacturer. Supernatants of transfected cells containing antibody mutants were collected. Mutant antibody supernatants were screened in CDC assays both individually and in pairwise mixtures as follows.

0.1×10$^6$ Daudi or Wien-133 cells (other cells types such as Raji cells may be used) were pre-incubated in round-bottom 96-well plates with 1.0 ug/ml of unpurified antibodies in a total volume of 100 µL for 15 min on a shaker at RT. Next, 30 µL normal human serum was added as a source of complement (30% final concentration) and incubated in a 37° C. incubator for 45 min. The reaction was stopped by putting the plates on ice. 10 µl propidium iodide was added and cell lysis was determined by FACS.

Mutations described in Table 4, Table 5 and Table 6 were selected for their ability to enhance oligomerization as detected by CDC efficiency, either as a single mutant or when mixed with other mutants for example facing the mutation across the Fc:Fc interface. Mutations can optionally be further screened for their ability to not compromise FcRn, Protein-A or Protein-G binding, ADCC, ADCP or other effector functions mediated by the Fc domain. Combining such stimulating point mutations into one Fc domain can stimulate oligomerization and CDC efficiency even further.

Mutations in the CH2-CH3 region incorporated in the CD38 antibody 005 were tested for their ability to inhibit oligomerization as determined by CDC on Daudi cells. Lysis of the mutant antibody was compared to wild type 005, for which lysis was set to 100%. The cutoff for inhibition was set to 66% lysis. Measured in this way, most of the tested mutations inhibited CDC (see Table 4).

Mutations in the CH2-CH3 region incorporated in the CD38 antibody 005 were tested for their ability to enhance oligomerization as determined by CDC on Wien133 cells (Table 5). Wild type CD38 antibody 005 is not able to induce CDC on Wien133 cells. Mutants displaying ≥39% cell lysis were scored as enhancing. Completely unexpectedly, virtually all obtained substitutions of amino acids E345 and E430 stimulated cell lysis by CDC. To verify this result, amino acids E345, E430 and S440 were substituted with each possible mutation by site directed mutagenesis and tested for their ability to enhance oligomerization as determined by CDC of Wien133 cells using a new human serum batch, yielding slightly more efficient lysis (Table 6). Again, all substitutions of E345 and E430 induced efficient CDC of Wien133 cells.

The following preferred mutations caused 39% cell lysis of Wien133 cells: P247G, I253V, S254L, Q311L, Q311W, E345A, E345C, E345D, E345F, E345G, E345H, E345I, E345K, E345L, E345M, E345N, E345P, E345Q, E345R, E345S, E345T, E345V, E345W, E345Y, D/E356G, D/E356R, T359R, E382L, E382V, Q386K, E430A, E430C, E430D, E430F, E430G, E430H, E430I, E430L, E430M, E430N, E430P, E430Q, E430R, E430S, E430T, E430V, E430W, E430Y, Y436I, S440Y and S440W.

TABLE 4

Percentage lysis of Daudi cells in the presence of 1.0 µg/ml IgG1-005 antibody point mutations. IgG1-005 wildtype lysed 66% of cells under these conditions. For each of the individual positions which have been substituted by another amino acid are given in the outer left column. The substituted amino acid for each particular position is given followed by the measured percentage lysis indicated in paranteses ( ) in the horizontal rows of the individual positions.

| Position | | | | | | | | | | | | | | | | | |
|---|---|---|---|---|---|---|---|---|---|---|---|---|---|---|---|---|---|
| P247 | A (42) | C (67) | D (91) | F (93) | G (95) | H (80) | I (89) | K (96) | L (13) | M (83) | N (78) | R (93) | S (93) | T (10) | V (9) | W (82) | |
| I253 | A (17) | D (12) | K (13) | M (6) | N (5) | R (7) | S (6) | V (94) | | | | | | | | | |
| S254 | E (14) | F (75) | G (100) | H (46) | I (93) | K (86) | L (99) | P (4) | T (8) | W (7) | | | | | | | |
| H310 | K (6) | W (87) | | | | | | | | | | | | | | | |
| Q311 | A (53) | C (72) | E (5) | F (90) | G (68) | H (72) | I (92) | K (93) | L (96) | N (53) | P (97) | R (87) | S (66) | T (54) | W (93) | Y (85) | |
| E345 | A (85) | C (91) | F (95) | G (86) | H (83) | I (96) | K (94) | L (98) | M (94) | N (97) | P (74) | R (98) | S (93) | T (82) | V (92) | W (95) | Y (95) |
| D/E356 | G (88) | I (95) | L (94) | R (97) | T (97) | V (98) | | | | | | | | | | | |
| T359 | G (88) | N (93) | P (87) | R (96) | | | | | | | | | | | | | |
| E382 | F (3) | K (3) | L (99) | M (90) | P (3) | V (96) | W (3) | | | | | | | | | | |
| G385 | D (28) | H (9) | Q (24) | R (27) | S (14) | T (10) | | | | | | | | | | | |
| Q386 | A (56) | C (18) | D (6) | E (9) | F (11) | G (10) | H (26) | I (42) | K (98) | L (15) | N (25) | P (6) | R (10) | S (43) | T (12) | V (53) | W (13) | Y (42) |
| E430 | A (97) | F (97) | G (99) | H (98) | L (95) | P (95) | Q (90) | R (96) | S (94) | V (98) | | | | | | | |
| N434 | D (5) | E (5) | K (5) | R (5) | S (6) | W (98) | | | | | | | | | | | |
| Y436 | I (98) | K (7) | L (10) | R (35) | S (8) | T (7) | W (6) | | | | | | | | | | |
| Q438 | E (5) | K (6) | S (5) | T (8) | W (10) | Y (31) | | | | | | | | | | | |

TABLE 4-continued

Percentage lysis of Daudi cells in the presence of 1.0 μg/ml IgG1-005 antibody point mutations. IgG1-005 wildtype lysed 66% of cells under these conditions. For each of the individual positions which have been substituted by another amino acid are given in the outer left column. The substituted amino acid for each particular position is given followed by the measured percentage lysis indicated in paranteses ( ) in the horizontal rows of the individual positions.

| Position | | | | | | | | | | | |
|---|---|---|---|---|---|---|---|---|---|---|---|
| K439 | A | D | H | L | P | T | Y | | | | |
| | (6) | (5) | (5) | (5) | (8) | (4) | (7) | | | | |
| S440 | A | C | D | E | F | G | I | N | R | T | Y |
| | (61) | (10) | (95) | (24) | (13) | (40) | (8) | (33) | (11) | (28) | (98) |
| K447 | E | *del | | | | | | | | | |
| | (20) | (90) | | | | | | | | | |

*where "del" means that there was a deletion of the amino acid residue at the indicated position.

TABLE 5

Percentage lysis of Wien-133 cells in the presence on 1.0 μg/ml IgG1-005 antibody point mutants. IgG1-005 wildtype lysed 3% of cells under these conditions. For each of the individual positions which have been substituted by another amino acid are given in the outer left column. The substituted amino acid for each particular position is given followed by the measured percentage lysis indicated in paranteses ( ) in the horizontal rows of the individualpositions.

| Position | | | | | | | | | | | | | | | | | |
|---|---|---|---|---|---|---|---|---|---|---|---|---|---|---|---|---|---|
| P247 | A | C | D | F | G | H | I | K | L | M | N | R | S | T | V | W | |
| | (5) | (5) | (12) | (16) | (50) | (11) | (10) | (14) | (4) | (13) | (7) | (10) | (7) | (4) | (3) | (9) | |
| I253 | A | D | K | M | N | R | S | V | | | | | | | | | |
| | (11) | (9) | (3) | (3) | (3) | (4) | (3) | (51) | | | | | | | | | |
| S254 | E | F | G | H | I | K | L | P | T | W | | | | | | | |
| | (14) | (10) | (32) | (2) | (15) | (12) | (65) | (2) | (9) | (9) | | | | | | | |
| H310 | K | W | | | | | | | | | | | | | | | |
| | (3) | (13) | | | | | | | | | | | | | | | |
| Q311 | A | C | E | F | G | H | I | K | L | N | P | R | S | T | W | Y | |
| | (9) | (4) | (3) | (19) | (4) | (6) | (28) | (16) | (55) | (6) | (12) | (18) | (9) | (3) | (41) | (12) | |
| E345 | A | C | F | G | H | I | K | L | M | P | R | S | T | V | W | Y | |
| | (57) | (22) | (48) | (47) | (49) | (59) | (42) | (72) | (67) | (51) | (64) | (60) | (53) | (67) | (52) | (70) | |
| D/E356 | G | I | L | R | T | V | | | | | | | | | | | |
| | (39) | (31) | (30) | (64) | (32) | (13) | | | | | | | | | | | |
| T359 | G | N | P | R | | | | | | | | | | | | | |
| | (2) | (3) | (4) | (40) | | | | | | | | | | | | | |
| E382 | F | K | L | M | P | V | W | | | | | | | | | | |
| | (2) | (2) | (44) | (21) | (3) | (53) | (2) | | | | | | | | | | |
| G385 | D | H | N | Q | R | S | T | | | | | | | | | | |
| | (5) | (4) | (18) | (4) | (14) | (4) | (4) | | | | | | | | | | |
| Q386 | A | C | D | E | F | G | H | I | K | L | N | P | R | S | T | V | W | Y |
| | (3) | (4) | (4) | (4) | (3) | (3) | (3) | (4) | (60) | (3) | (4) | (2) | (4) | (3) | (3) | (3) | (3) | (4) |
| E430 | A | F | G | H | L | P | Q | R | S | V | | | | | | | |
| | (54) | (68) | (55) | (57) | (58) | (56) | (31) | (39) | (20) | (53) | | | | | | | |
| N434 | D | E | K | R | S | W | | | | | | | | | | | |
| | (2) | (2) | (2) | (2) | (3) | (18) | | | | | | | | | | | |
| Y436 | I | K | L | R | S | T | W | | | | | | | | | | |
| | (49) | (3) | (4) | (3) | (3) | (2) | (3) | | | | | | | | | | |
| Q438 | E | K | S | T | W | Y | | | | | | | | | | | |
| | (3) | (3) | (2) | (2) | (2) | (2) | | | | | | | | | | | |
| K439 | A | D | H | L | P | T | Y | | | | | | | | | | |
| | (3) | (2) | (2) | (2) | (2) | (2) | (4) | | | | | | | | | | |
| S440 | A | C | D | E | F | G | I | N | R | T | Y | | | | | | |
| | (3) | (3) | (6) | (2) | (2) | (3) | (2) | (2) | (2) | (3) | (64) | | | | | | |

TABLE 6

Percentage lysis of Wien-133 cells in the presence on 1.0 µg/ml IgG1-005 antibody point mutants. IgG1-005 wildtype lysed 12% of cells under these conditions. Each of the individual positions which have been substituted by another amino acid are given in the outer left column. The substituted amino acid for each particular position is given followed by the measured percentage lysis indicated in parantheses ( ) in the horizontal rows of the individual positions.

| Position | | | | | | | | | | | | | | | | | | | |
|---|---|---|---|---|---|---|---|---|---|---|---|---|---|---|---|---|---|---|---|
| E345 | A | C | D | F | G | H | I | K | L | M | N | P | Q | R | S | T | V | W | Y |
|  | (94) | (87) | (76) | (95) | (95) | (94) | (93) | (97) | (94) | (96) | (93) | (97) | (98) | (94) | (93) | (92) | (96) | (93) | (94) |
| E430 | A | C | D | F | G | H | I | K | L | M | N | P | Q | R | S | T | V | W | Y |
|  | (95) | (79) | (91) | (96) | (96) | (95) | (96) | (83) | (94) | (75) | (95) | (97) | (86) | (92) | (96) | (97) | (96) | (98) | (97) |
| S440 | A | C | D | E | F | G | H | I | K | L | M | N | P | Q | R | T | V | W | Y |
|  | (12) | (8) | (41) | (9) | (7) | (8) | (26) | (7) | (6) | (7) | (8) | (12) | (10) | (21) | (9) | (10) | (7) | (86) | (90) |

Example 7

In Vivo Efficacy of IgG1-005-E345R in a Subcutaneous B Cell Lymphoma Xenograft Model The in vivo anti-tumor efficacy of the IgG1-005-E345R antibody was evaluated in a subcutaneous model with Raji-luc #2D1 cells. These cells show ~150,000 CD38 molecules per cell (determined by QIFIKIT analysis, data not shown) and high complement defense receptor expression. The protocol for tumor inoculation and measurement is basically the same as described in Example 20. At day 0, $5 \times 10^6$ Raji-luc #2D1 cells in 200 µL PBS were s.c. injected in the right flank of SCID mice. When average tumor volume was 100 mm$^3$ (around day 7), the mice were sorted into groups (n=7) and treated by i.p. injection of a single dose of 500 µg antibody per mouse (25 mg/kg). Treatment groups are shown in Table 7. Tumors were measured until an endpoint tumor volume of 1500 mm$^3$ or until tumors showed ulcerations or serious clinical signs were observed to avoid major discomfort.

Figure 8A:
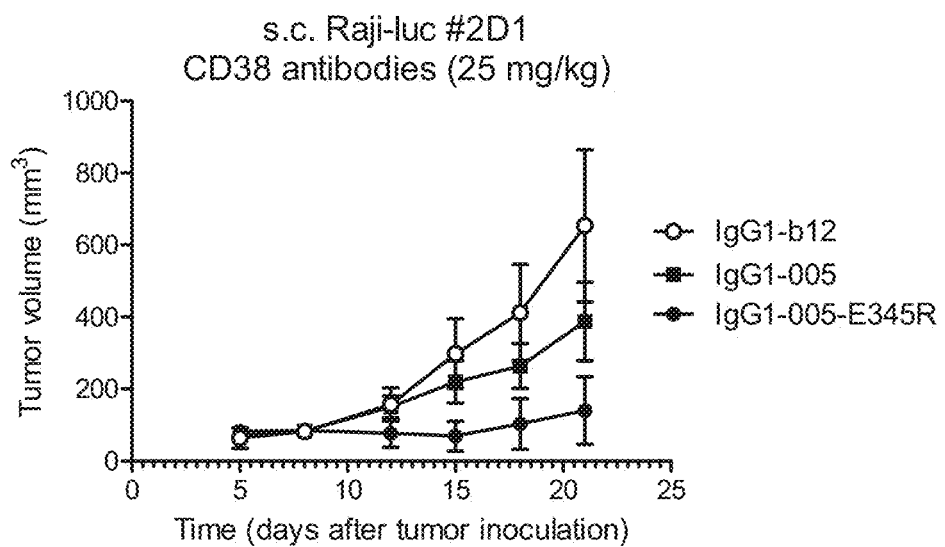
FIGS. 8A and 8B: Evaluation of the in vivo efficacy of IgG1-005-E345R in a subcutaneous xenograft model with Raji-luc #2D1 cells.

FIG. 8A shows mean tumor growth on day 21, when all groups were still complete. Wild type antibody IgG1-005 slightly inhibited tumor growth, although this was not statistically significant. Only IgG1-005-E345R significantly inhibited tumor growth compared to the irrelevant antibody control at day 21 (One-way ANOVA p<0.05).

Figure 8B:
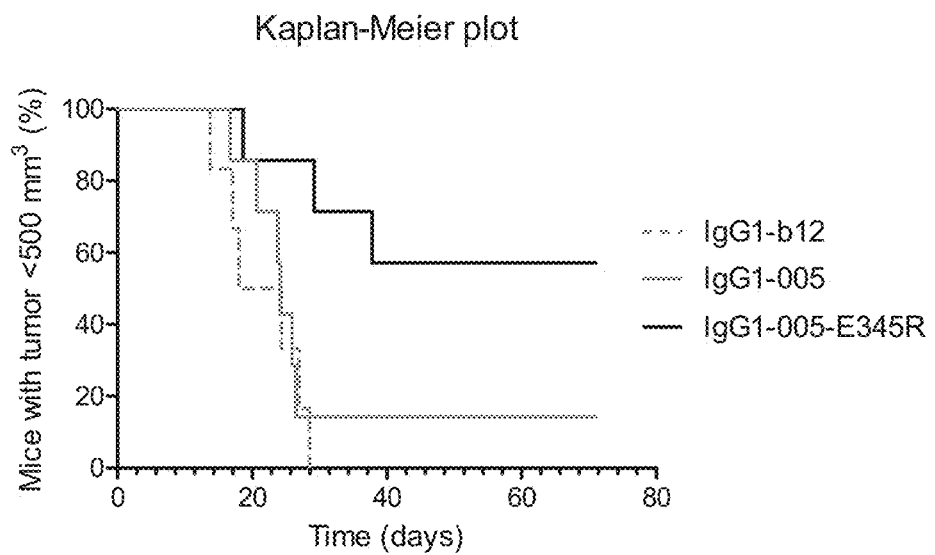

FIG. 8B shows a Kaplan-Meier plot of the percentage mice with tumor sizes smaller than 500 mm$^3$. Tumor formation was significantly delayed in mice treated with IgG1-005-E345R antibody compared to mice treated with negative control antibody IgG1-b12 (Mantel-Cox analysis p<0.001) or wild type IgG1-005 (p<0.05).

These data show that introduction of the E345R mutation in the CD38 antibody 005 resulted in enhanced in vivo anti-tumor activity.

TABLE 7

Treatment groups and dosing.

| Group | Antibody | Dose |
|---|---|---|
| 1. wild type | IgG1-005-WT | 500 µg (=25 mg/kg) |
| 2. CDC-enhancing mutant | IgG1-005-E345R | 500 µg (=25 mg/kg) |
| 3. Irrelevant Ab control | IgG1-b12 | 500 µg (=25 mg/kg) |

Example 8

Monovalent Target Binding Further Enhances the CDC Efficacy of E345R Antibodies A molecular surface of the IgG1 hexameric ring observed in the b12 crystal structure demonstrates that for each IgG in the hexameric ring, one of the two C1q binding sites is facing upwards and the other site is facing downwards of the ring structure, and also one Fab-arm of each antibody is oriented up and one is oriented down, resulting in only one Fab-arm per antibody to take part in antigen binding, suggesting monovalent binding per antibody molecule in the hexameric antibody ring. Monovalency might bring antibodies upon antigen binding in a hexamerization compatible orientation. To test this hypothesis, the CDC efficacy of a bispecific CD38/EGFR antibody with the E345R mutation was tested on CD38-positive, EGFR-negative Wien133 cells, to which this bispecific antibody can only bind monovalently via CD38, and compared to the CDC efficacy of the bivalent binding CD38 antibody, also with the E345R mutation. The human monoclonal antibody HuMax-EGFr (2F8, described in WO 2004/056847) was used as a basis for the EGFR antibodies described in this example.

Bispecific antibodies were generated in vitro according to the DuoBodyn™ platform, i.e. 2-MEA-induced Fab-arm exchange as described in WO 2011/147986. The basis for this method is the use of complementary CH3 domains, which promote the formation of heterodimers under specific assay conditions. To enable the production of bispecific antibodies by this method, IgG1 molecules carrying certain mutations in the CH3 domain were generated: in one of the parental IgG1 antibody the F405L mutation, in the other parental IgG1 antibody the K409R mutation. To generate bispecific antibodies, these two parental antibodies, each antibody at a final concentration of 0.5 mg/mL, were incubated with 25 mM 2-mercaptoethylamine-HCl (2-MEA) in a total volume of 100 µL TE at 37° C. for 90 min. The reduction reaction is stopped when the reducing agent 2-MEA is removed by using spin columns (Microcon centrifugal filters, 30 k, Millipore) according to the manufacturer's protocol.

For the CDC assay, $0.1 \times 10^6$ Wien133 cells were pre-incubated in round-bottom 96-well plates with a concentration series of antibodies (0.01 to 10.0 µg/mL) in a total volume of 100 µL for 15 min on a shaker at RT. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS.

Figure 9:
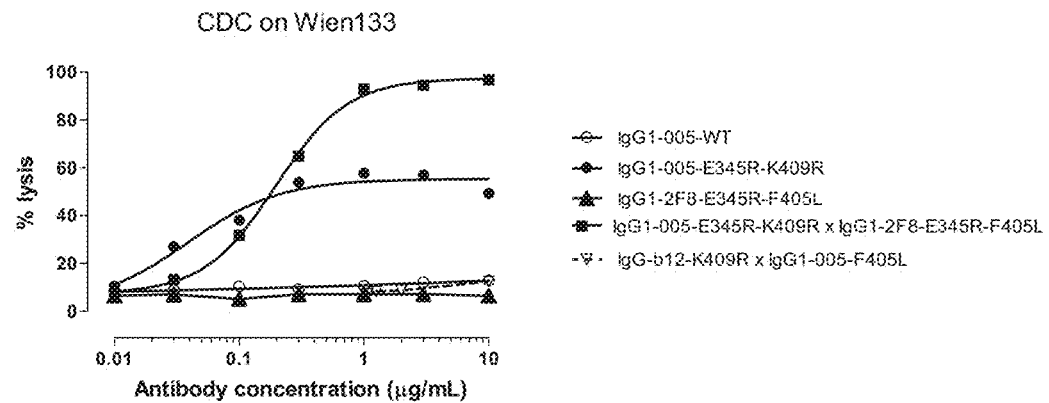
FIG. 9: CDC on CD38-positive, EGFR-negative Wien133 cells by CD38/EGFR bispecific antibody with the E345R mutation.

FIG. 9 shows that, as expected, CD38 antibodies without the E345R mutation (wild type IgG1-005 and IgG-b12-K409R×IgG1-005-F405L) did not induce killing of Wien133 cells. Also the EGFR antibody IgG1-2F8-E345R/F405L, that did not bind the EGFR-negative Wien133 cells (data not shown), did not induce CDC, as expected. The introduction of the K409R mutation did not influence the capacity of the IgG1-005-E345R antibody to induce ~60% killing on Wien133 cells (described in Example 10). Interestingly, the bispecific CD38/EGFR antibody IgG1-005-E345R/K409R×IgG1-2F8-E345R/F405L, which can only bind monovalently to the CD38-positive, EGFR-negative Wien133 cells, showed increased maximal CDC killing (from ~60% to ~100% killing).

These data show that monovalent targeting can further enhance the maximal killing capacity of antibodies containing the CDC enhancing E345R mutation. Furthermore, these data show that the E345R oligomerization enhancing mutation, as measured by enhancing CDC activity, can be applied to other antibody formats, such as DuoBody.

Example 9

The Oligomerization Enhancing E345R Mutation can be Applied to Other Antibody Formats Such as DuoBody™

The effect of the E345R mutation was tested in a bispecific antibody of the DuoBody format. CDC assays were performed with CD20/CD38 bispecific antibodies on CD20-positive, CD38-positive Wien133 and Raji cells.

Bispecific antibodies were generated as described in Example 8. For the CDC assay, $0.1 \times 10^6$ Wien133 or Raji cells were pre-incubated in round-bottom 96-well plates with a concentration series of antibodies (0.01 to 30.0 μg/mL) in a total volume of 100 μL for 15 min on a shaker at RT. Next, 25 μL normal human serum was added as a source of complement (20% final concentration) and incubated in a 37° C. incubator for 45 min. The reaction was stopped by putting the plates on ice. 10 μL propidium iodide was added and cell lysis was determined by FACS.

Figure 10A:
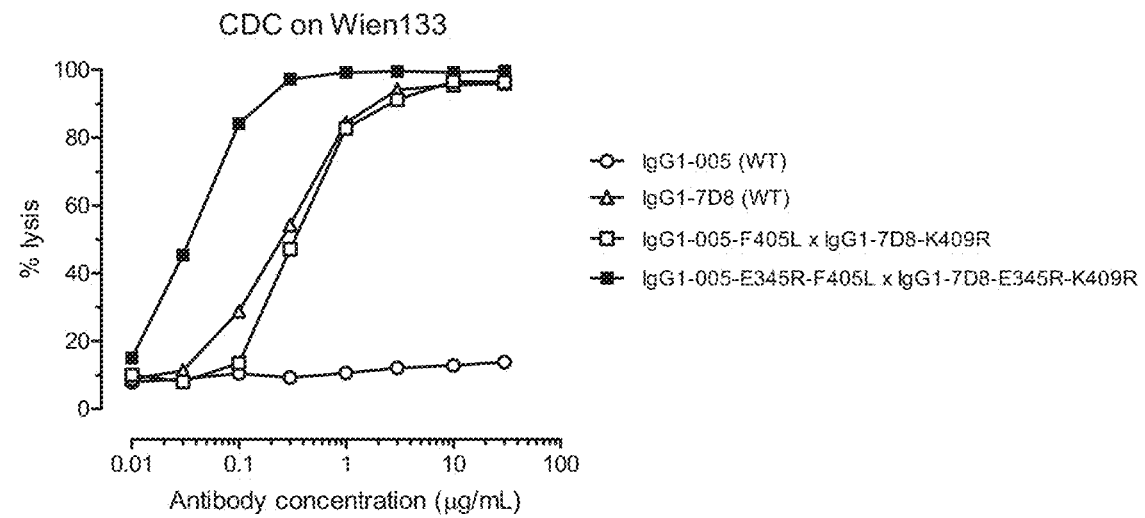
FIGS. 10A and 10B: CDC on CD20-positive, CD38-negative Wien133 cells or Raji cells by CD20/CD38 bispecific antibody with and without the E345R mutation.
Figure 10B:
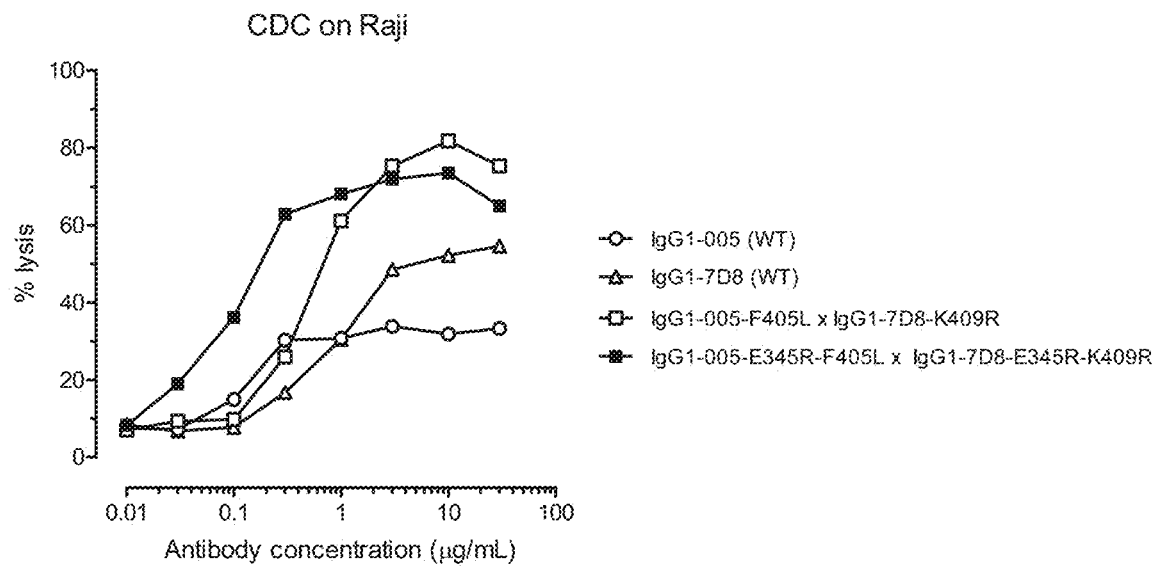

FIG. 10 shows that introduction of the E345R mutation enhanced CDC of the bispecific IgG1-005-F405L×IgG1-7D8-K409R antibody on Wien 133 (FIG. 10A) and Raji (FIG. 10B) cells. These data show that the E345R oligomerization enhancing mutation can be applied to other antibody formats to enhance CDC activity.

Example 10

E345R Rescues CDC by EGFR Antibody 2F8, which can be Further Enhanced by Monovalent Target Binding As described in Examples 3 and 12, E345R enhanced or rescued CDC for antibodies recognizing different hematological tumor targets (CD20 and CD38). To extend the analysis to a solid tumor antigen, the effect of E345R on the CDC capacity of the EGFR antibody 2F8 was tested on A431 epidermoid carcinoma cells. Furthermore, the effect of monovalent EGFR targeting on E345R-mediated CDC induction was tested using a bispecific EGFR×CD20 antibody (IgG1-2F8-E345R/F405L×IgG1-7D8-E345R/K409R) on EGFR-positive, CD20-negative A431 cells.

Bispecific antibodies were generated as described in Example 8. For the CDC assay, $5 \times 10^6$ A431 cells/mL were labeled with 100 μCi $^{51}$Cr for 1 h at 37° C. Cells were washed three times with PBS and resuspended in medium at a concentration of $1 \times 10^5$ cells/mL. 25,000 labeled cells were incubated in round-bottom 96-well plates with a concentration series of unpurified antibodies (0-30 μg/mL in 3-fold dilutions) in a total volume of 100 μL for 15 min at RT. Next, 50 μL normal human serum dilution was added as a source of complement (25% final concentration) and incubated in a 37° C. incubator for 1 h. Cells were spun down (3 min at 300×g) and 25 μL supernatant was added to 100 μL microscint in a white 96 well optiplate (PerkinElmer) for incubation on a shaker (750 rpm) for 15 min. $^{51}$Cr release was determined as counts per minute (cpm) on a scintillation counter. Maximum lysis (100%) was determined by the $^{51}$Cr level measured in the supernatant of Triton X-100-treated cells. Spontaneous lysis was determined by the $^{51}$Cr level measured in the supernatant of cells incubated without antibody. Specific cell lysis was calculated according to the formula: Specific lysis=100×(cpm sample−cpm spont)/(cpm max−cpm spont).

Figure 11:
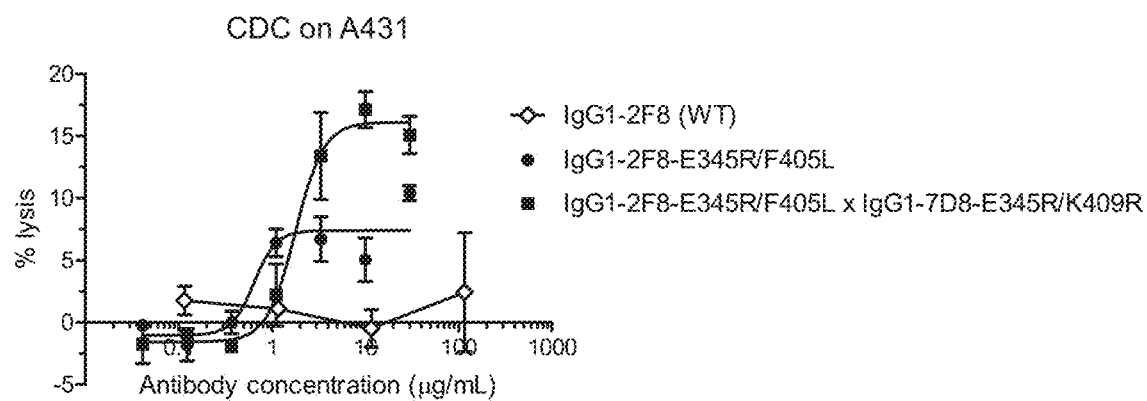
FIG. 11: CDC on EGFR-positive A431 cells by EGFR antibody 2F8 with the E345R mutation.

FIG. 11 shows that IgG1-2F8-E345R/F405L is able to lyse A431 cells by CDC, whereas wild type 2F8 is not capable of killing A431 cells. These data show that CDC activity can be rescued in the EGFR antibody 2F8 by introduction of the E345R mutation. This potentially extends the applicability of the CDC enhancing E345R mutation to antibodies targeting solid tumor antigens.

Bispecific EGFR×CD20 antibody IgG-2F8-E345R/F405L×IgG1-7D8-E345R/K409R, showed further enhancement of CDC on the EGFR-positive, CD20-negative A431 cells.

These data further support the hypothesis that monovalency facilitates the formation of Fc-Fc interactions and subsequent CDC induction as postulated for a CD38 binding antibody described in Example 8.

Example 11

E345R Enhances or Rescues CDC by CD38 Antibody 003 and CD20 Antibodies 11B8 and Rituximab As described in Examples 3 and 12, E345R enhances or induces CDC activity of several antibodies with different target specificities (CD20, CD38 and EGFR), as was tested on multiple cell lines expressing variable levels of said antigens. Therefore, introduction of the E345R mutation was considered to be a general mechanism to enhance or rescues CDC for existing antibodies. To further support this, the effect of the E345R mutation on CDC was tested for more antibodies with variable intrinsic CDC efficacy on Daudi and WIEN133 cells: CD38 antibody 003, described in WO 2006/099875 and CD20 antibodies rituximab (type I) and 11B8 (type II), described in WO 2005/103081. CD20 antibodies can be divided in two subgroups (Beers et al. Seminars in Hematology 47, (2) 2010, 107-114). Type I CD20 antibodies display a remarkable ability to activate complement and elicit CDC by redistributing the CD20 molecules in the plasma membrane into lipid rafts, which cluster the antibody Fc regions and enabling improved C1q binding. Type II CD20 antibodies do not appreciably change CD20 distribution and without concomitant clustering, they are relatively ineffective in CDC.

$0.1 \times 10^6$ Daudi or Raji cells were pre-incubated in round-bottom 96-well plates with a concentration series of unpurified antibodies (0.001, 0.003, 0.01, 0.03, 0.1, 0.3, 1.0, 3.0, 10.0 μg/mL) in a total volume of 70 μL for 15 min on a shaker at RT. Next, 30 μL normal human serum was added as a source of C1q (30% final concentration) and incubated in a 37° C. incubator for 45 min. The reaction was stopped by putting the plates on ice. 10 μL propidium iodide was added and cell lysis was determined by FACS.

Figure 12A:
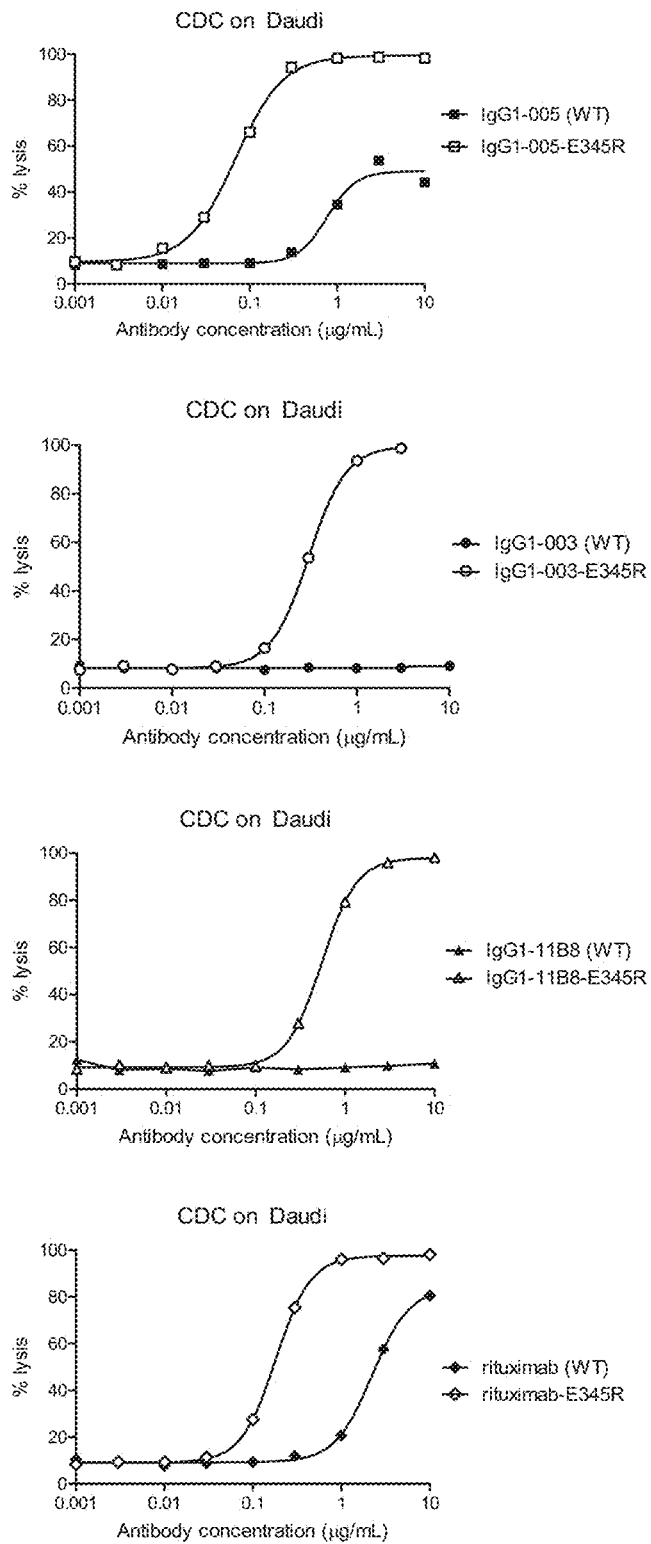
FIGS. 12A and 12B: CDC mediated by E345R mutant antibodies.
Figure 12B:
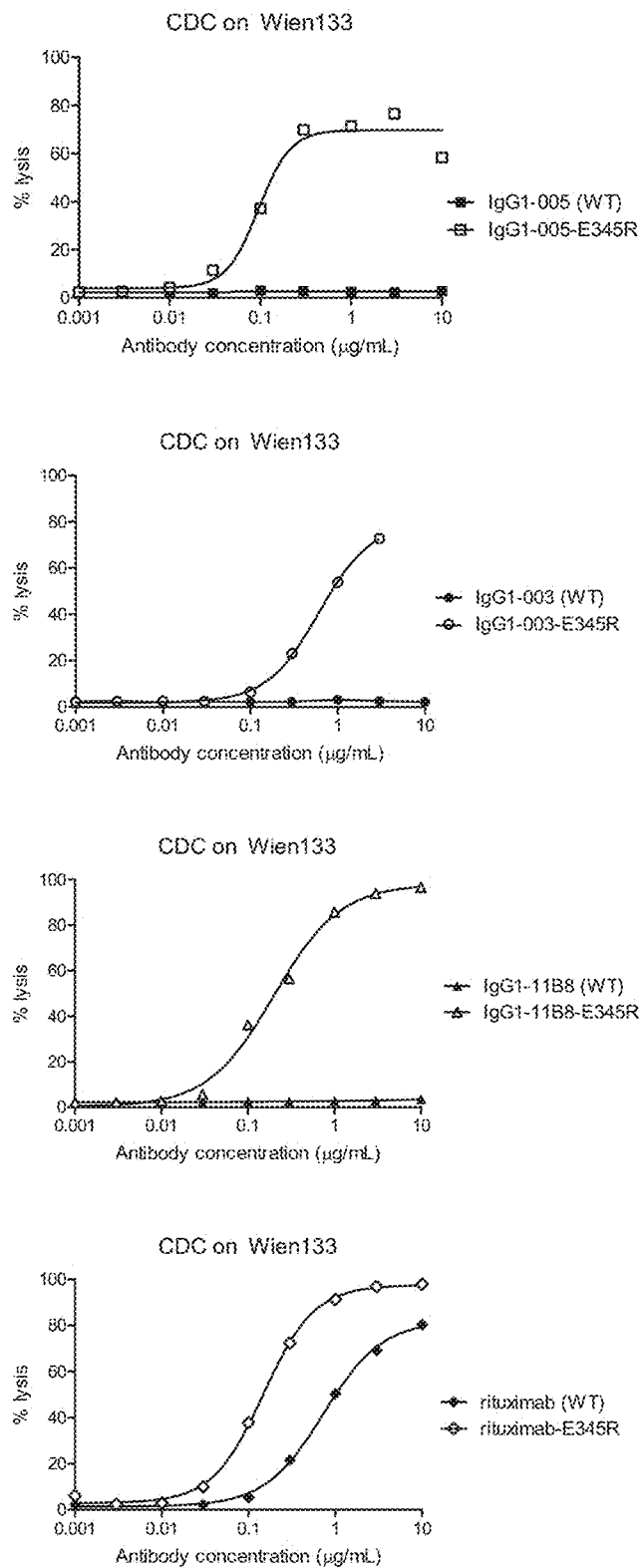

FIG. 12 shows that the E345R mutation enhanced CDC for all tested antibodies on both (A) Daudi and (B) Wien133 cells. Interestingly, at the used concentrations all antibodies that did not induce CDC in the wild type format, induced CDC efficiently after introduction of the E345R mutation: CD38 mAb 003 and CD20 type II mAb 11B8 on Daudi cells, and CD38 mAbs 005 and 003 and CD20 type II mAb 11B8 on Wien133 cells. These data suggest that enhancement of antibody oligomerization, more specifically by introduction of an E345R mutation, is a general mechanism to enhance or rescue CDC by existing antibodies.

Example 12

E345R Enhances Internalization of Tissue Factor Antibodies

To test if enhanced oligomerization can induce increased antibody internalization, colocalization studies of wild type and E345R mutated Tissue Factor (TF) antibodies with the lysosomal marker LAMP1 were performed by confocal microscopy.

SK-OV-3 cells were grown on glass coverslips (thickness 1.5 micron, Thermo Fisher Scientific, Braunschweig, Germany) in standard tissue culture medium at 37° C. for 1 day. Cells were pre-incubated for 1 hour with 50 µg/mL leupeptin (Sigma) to block lysosomal activity, after which 10 µg/mL Tissue Factor (TF) antibody (WO 2010/066803) was added. The cells were incubated for an additional 1, 3 or 16 hours at 37° C. Hereafter, cells were washed with PBS and incubated for 30 minutes at room temperature (RT) with 4% formaldehyde (Klinipath). Slides were washed with blocking buffer (PBS supplemented with 0.1% saponin [Roche] and 2% BSA [Roche]) and incubated for 20 minutes with blocking buffer containing 20 mM $NH_4Cl$ to quench formaldehyde. Slides were washed again with blocking buffer and incubated for 45 minutes at RT with a cocktail of mouse-anti-human CD107a-APC (BD Pharmingen) to identify lysosomal LAMP1 and goat-anti-human IgG-FITC (Jackson) to identify TF antibodies. Slides were washed again with blocking buffer and mounted overnight on microscope slides using 20 µL mounting medium (6 gram Glycerol [Sigma] and 2.4 gram Mowiol 4-88 [Omnilabo] was dissolved in 6 mL distilled water to which 12 mL 0.2M Tris [Sigma] pH8.5 was added followed by incubation for 10 min at 50-60° C.; mounting medium was aliquoted and stored at −20° C.). Slides were imaged with a Leica SPE-II confocal microscope (Leica Microsystems) equipped with a 63×1.32-0.6 oil immersion objective lens and LAS-AF software.

12-bit grayscale TIFF images were analyzed for colocalization using MetaMorph® software (version Meta Series 6.1, Molecular Devices Inc, Sunnyvale Calif., USA). Images were imported as stacks and background was subtracted. Identical thresholds settings were used (manually set) for all FITC images and all APC images. Colocalization was depicted as the pixel intensity of FITC in the region of interest (ROI), were the ROI is composed of all APC positive regions. To compare different slides stained with different TF antibodies, the images were normalized using the pixel intensity of APC. Mouse-anti-human CD107a-APC was used to stain the lysosomal marker LAMP1 (CD107a). The pixel intensity of LAMP1 should not differ between various TF antibodies imaged.

Normalized values for colocalization of FITC and APC are expressed as arbitrary units according to the formula [(TPI FITC×percentage colocalization)/100]×[1/TPI APC]

Percentage colocalization=TPI FITC that colocalizes with an APC pixel/TPI APC

TPI, total pixel Intensity

Figure 13:
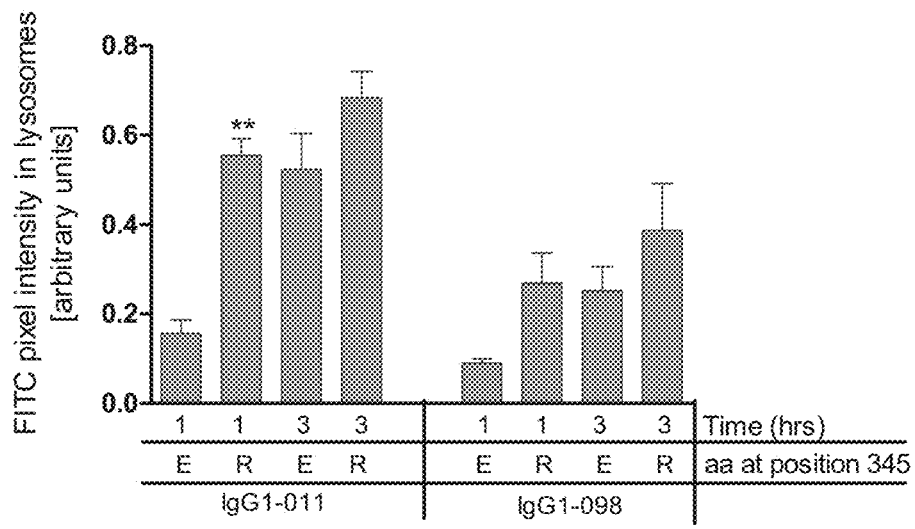
FIG. 13: Colocalization analysis of TF antibodies (FITC) with lysosomal marker LAMP1 (APC).

FIG. 13 depicts the amount of FITC pixel intensity of wild type and E345R mutated TF antibodies that overlap with APC-labeled lysosomal marker. For each antibody or condition tested, three different images were analyzed from one slide containing ~1, 3 or >5 cells. Variation was observed between the different images within each slide. Still, it was evident that the E345R mutation for antibodies 011 and 098 resulted in increased lysosomal colocalization after 1 hour incubation, when compared with wild type 011 and 098. These results indicate that mutation E345R induces more rapid internalization and lysosomal colocalization and could therefore potentiate antibody drug conjugates.

Example 13

Enhanced CDC by E345R Mutation in Rituximab in Different B Cell Lines with Similar CD20 Expression but Different Levels of Membrane-Bound Complement Regulatory Proteins Examples 11 and 14 show that the CDC efficacy of wild type rituximab on Daudi and Wien133 cells was enhanced by introducing the E345R mutation. This enhanced CDC efficacy results from the E345R-mediated stabilization of Fc-Fc interactions. The concomitantly formed hexameric antibody ring structure on the target cell membrane can then promote efficient generation of the membrane attack complex by facilitating the capture and concentration of activated complement components close to the cell membrane. As a result of this efficient complement activation, the inhibiting effects of membrane-bound complement regulatory proteins (mCRP) could be partly overcome. Overexpression of mCRPs, such as CD55, CD46 and CD59, is considered as a barrier for successful immunotherapy with monoclonal anti-tumor antibodies (Jurianz et al., Mol Immunol 1999 36:929-39; Fishelson et al. Mol Immunol 2003 40:109-23, Gorter et al., Immunol Today 1999 20:576-82, Zell et al., Clin Exp Immunol. 2007 December 150(3):576-84). Therefore, the efficacy of rituximab-E345R was compared to that of wild type rituximab on a series of B cell lines with different levels of the mCRPs CD46, CD55 and CD59, but comparable levels of the CD20 target expression.

The B cell lines Daudi, WIL2-S, WSU-NHL, MEC-2 and ARH-77 express comparable amounts of CD20 molecules (~250.000 specific antibody-binding capacity—sABC) as determined by QIFIKIT analysis (data not shown). To compare the expression levels of complement regulatory proteins between these cell lines, QIFIKIT analysis was performed to determine the levels of CD46 (mouse anti-human CD46, CBL488, clone J4.48 Chemicon), CD55 (mouse anti-human CD55, CBL511, Clone BRIC216, Chemicon), and CD59 (mouse anti-human CD59, MCA1054x, clone MEM-43, Serotec).

For the CDC assay, $0.1 \times 10^6$ of cells were pre-incubated in round-bottom 96-well plates with a saturating antibody concentration series (0.002-40.0 µg/mL in 4-fold dilutions) in a total volume of 100 µL for 15 min on a shaker at RT.

Next, 25 μL normal human serum was added as a source of complement (20% final concentration) and incubated in a 37° C. incubator for 45 min. The reaction was stopped by putting the plates on ice. 10 μL propidium iodide was added and cell lysis was determined by FACS. The maximal CDC-mediated killing was calculated from two independent experiments using the top of best-fit values of a non-linear fit in GraphPad PRISM 5.

FIG. 14A-D shows that introduction of E345R in wild type rituximab resulted in enhanced CDC efficacy as observed by an increased maximal lysis and decreased $EC_{50}$ for all tested B cell lines.

Figure 14A:
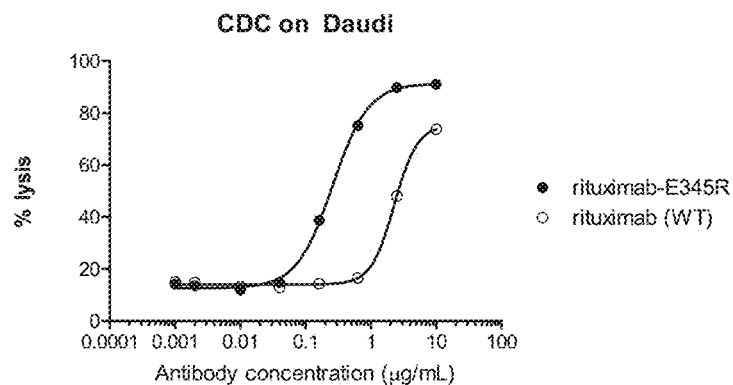
FIGS. 14A-14D: Introduction of E345R resulted in enhanced CDC-mediated killing compared to wild type rituximab tested on different B cell lines.
Figure 14B:
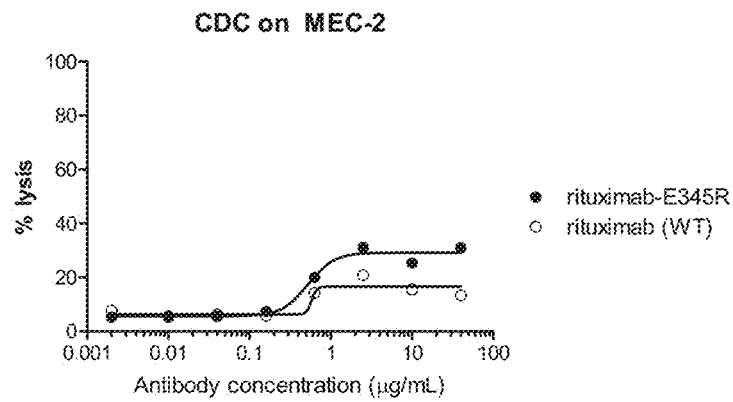
Figure 14C:
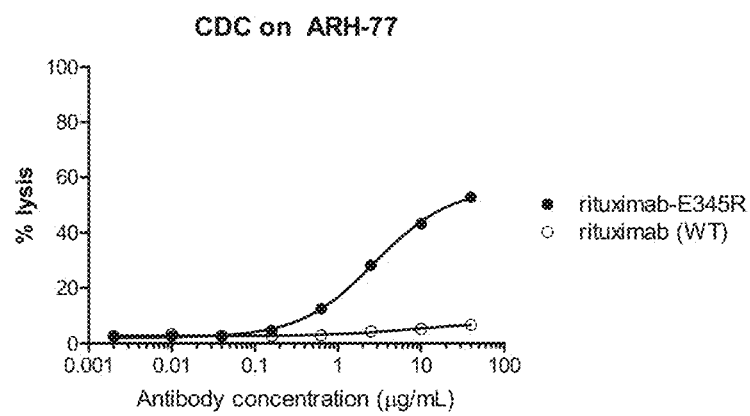
Figure 14D:
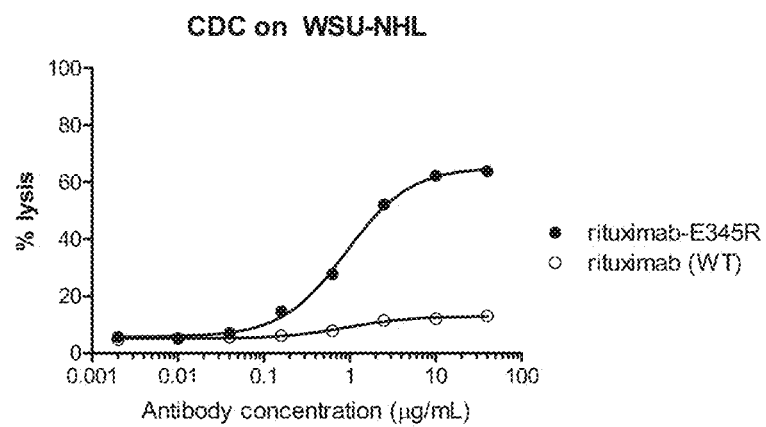
Figure 14E:
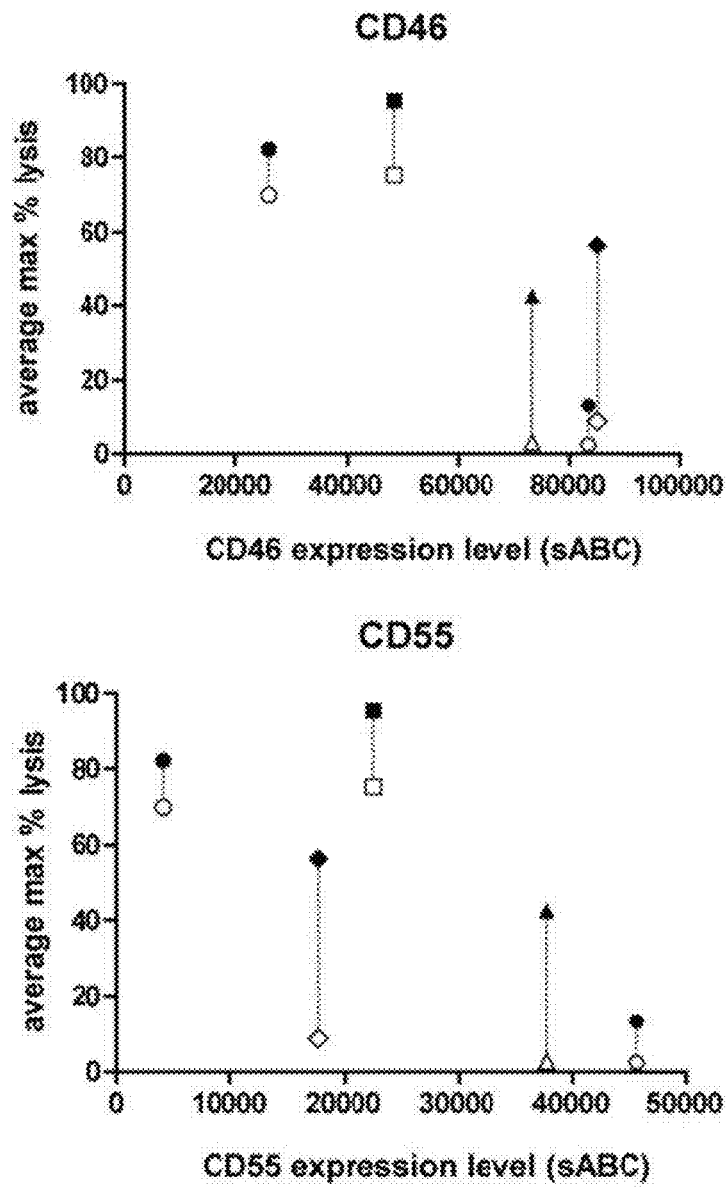
FIG. 14E: Introduction of E345R resulted in increased maximal CDC-mediated killing compared to wild type rituximab, independent of the expression levels of the complement regulatory proteins CD46 (A), CD55 (B) or CD59 (C) in different B cell lines with comparable CD20 expression levels.
Figure 14E:
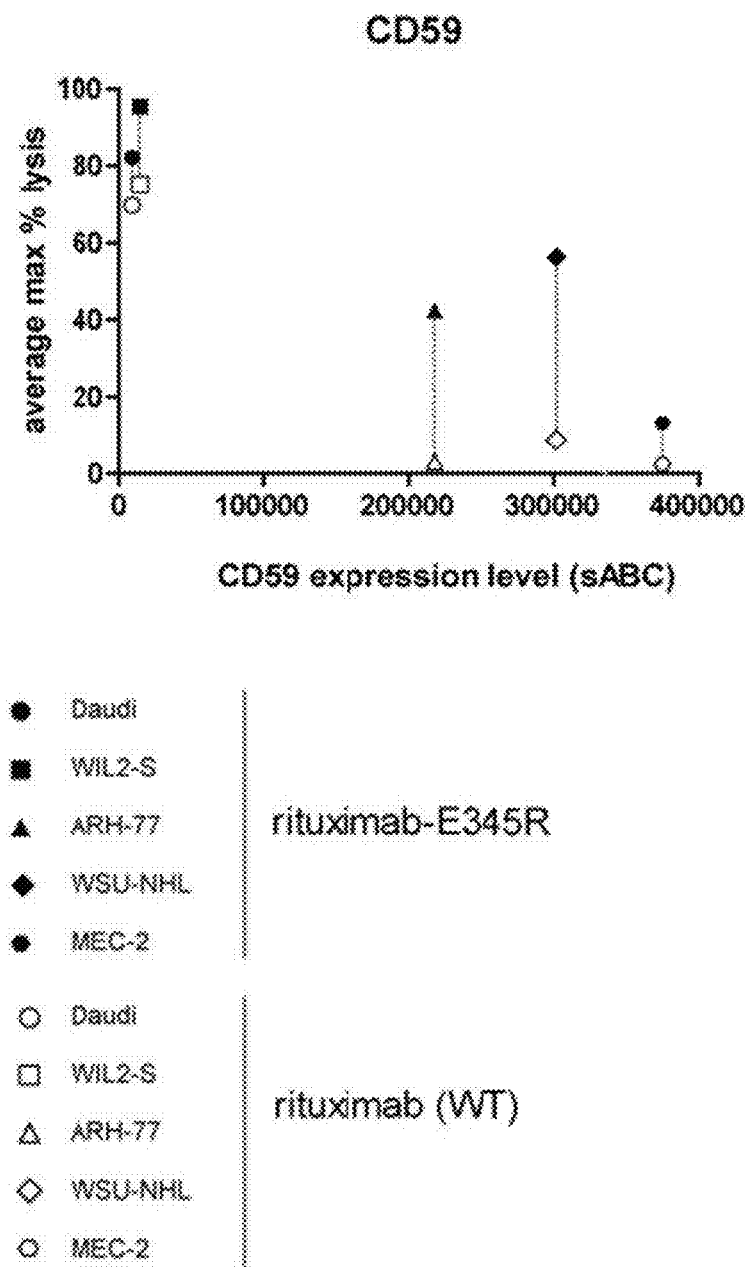

FIG. 14E shows that the maximal CDC-mediated killing induced by the rituximab-E345R mutant was always higher than by wild type rituximab, independent of the expression levels of the membrane-bound complement regulatory proteins. These data indicate that introduction of E345R enhances the therapeutic potential of monoclonal antibodies as the tumor cells are less effective in evading antibody-mediated complement attack by the E345R containing antibodies.

Example 14

Comparison of CDC Kinetics for Wild Type and E345R Antibodies

Introduction of the Fc:Fc interaction stabilizing E345R mutation has been shown to enhance or rescue CDC as observed by decreased $EC_{50}$ values and increased maximal lysis for different antibodies on different cell lines described in Example 3 (CD38 antibody 005 on Daudi, Raji and Wien133) and Example 11 (CD38 antibody 003 and CD20 antibodies rituximab and 11B8 on Daudi and Wien133). Next, the kinetics of the CDC reactions were analyzed to further unravel the difference in CDC efficacy between wild type and E345R antibodies.

$0.1 \times 10^6$ Raji cells were pre-incubated in round-bottom 96-well plates with antibody at a saturating concentration (10.0 μg/mL) in a total volume of 100 μL for 15 min on a shaker at RT. Next, 25 μL normal human serum was added as a source of complement (20% final concentration) and incubated in a 37° C. incubator for different periods of time, varying between 0 and 60 min. The reaction was stopped by putting the plates on ice. 10 μL propidium iodide was added and cell lysis was determined by FACS.

Figure 15A:
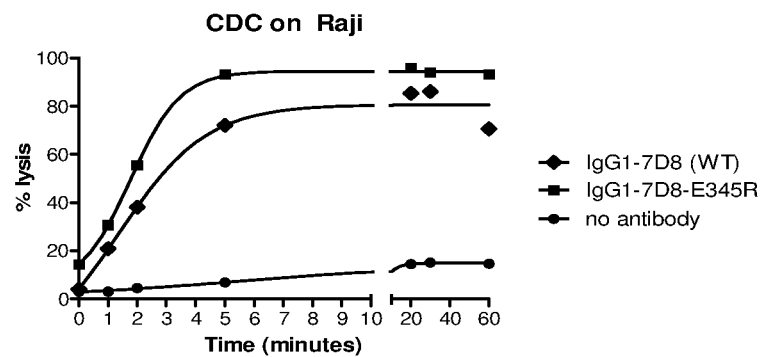
FIGS. 15A-15D: CDC kinetics. E345R antibodies result in more rapid and more substantial target cell lysis by CDC compared to wild type antibodies.

FIG. 15A shows that wild type CD20 antibody IgG1-7D8 showed a maximal CDC-mediated killing of 80% of the Raji cells, which was already reached after 5 min under the tested conditions. However, for IgG-7D8-E345R, 80% killing of Raji cells was observed even faster, after 3 min. Maximal lysis by IgG-7D8-E345R (95%) was also reached after 5 minutes.

Figure 15B:
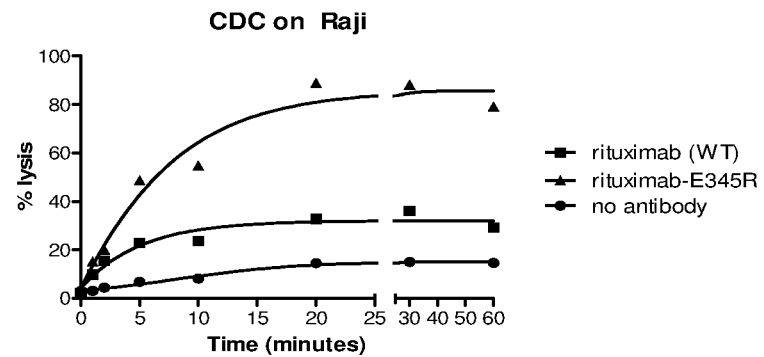

FIG. 15B shows that also for wild type CD20 antibody rituximab, which is less potent than 7D8 to induce CDC on the used Raji cells, introduction of the E345R mutation resulted in faster killing of the target cells. Wild type rituximab showed a maximal CDC-mediated killing of 32%, which was reached after 20 minutes. Rituximab-E345R reached 32% killing already after approximately 3 minutes and remarkably, maximal lysis by rituximab-E345R (85%) was also reached after 20 minutes.

Figure 15C:
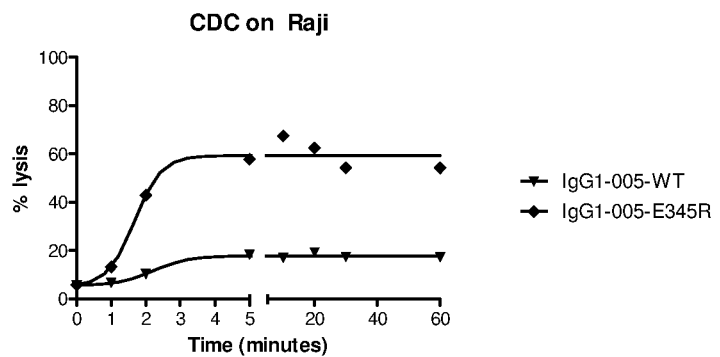
Figure 15D:
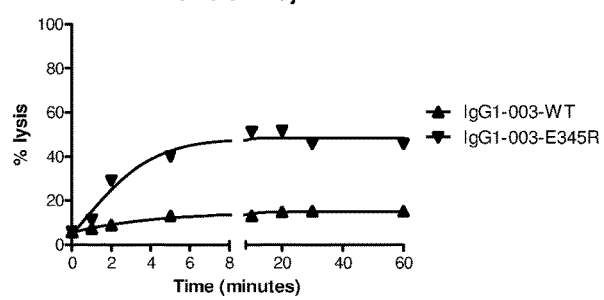

FIG. 15C+D shows that the used Raji cells, which are resistant for CDC-mediated killing by wild type CD38 antibodies IgG1-003 and IgG1-005, could be killed fast by introducing the E345R mutation. IgG1-003-E345R and IgG1-005-E345R showed maximal CDC (50% and 60%, respectively) already after 5 min.

In summary, E345R antibodies are more potent than their wild type counterparts, which results from a combination of higher efficacy (lower $EC_{50}$), increased maximal lysis and a faster kinetics of the CDC reaction.

Example 15

Comparison of CDC Kinetics for Bispecific Antibodies with or without the E345R Mutation In example 9 it is described that the E345R mutation can be applied to the CD38×CD20 bispecific antibody IgG1-005-F405L×IgG1-7D8-K409R that was generated by the DuoBody platform, resulting in an enhanced killing capacity as observed by a decreased $EC_{50}$ in CDC assays on Raji and Wien133 cells. Next, the kinetics of the CDC reaction was analyzed to further unravel the difference in CDC efficacy between the CD38×CD20 bispecific antibodies with and without E345R.

$0.1 \times 10^6$ Raji cells were pre-incubated in round-bottom 96-well plates with antibody at a saturating concentration (10.0 μg/mL) in a total volume of 100 μL for 15 min on a shaker at RT. Next, 25 μL normal human serum was added as a source of complement (20% final concentration) and incubated in a 37° C. incubator for different periods of time, varying between 0 and 60 min. The reaction was stopped by putting the plates on ice. 10 μL propidium iodide was added and cell lysis was determined by FACS.

Figure 16:
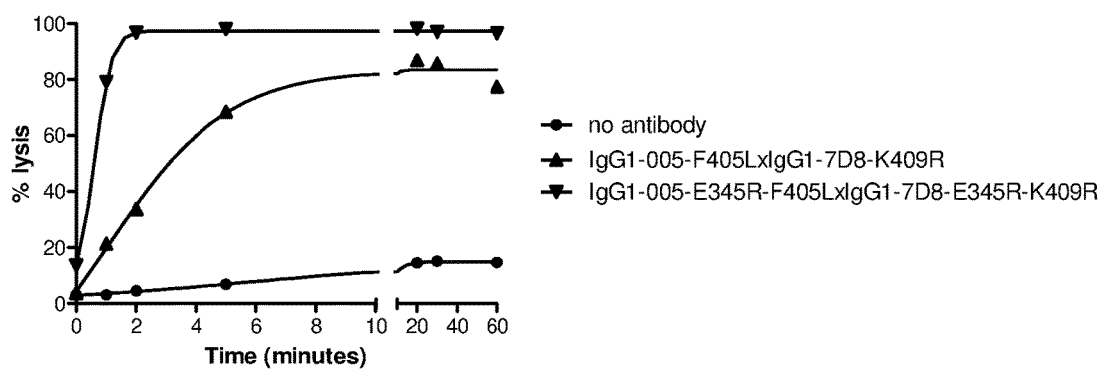
FIG. 16: CDC kinetics. Introduction of the E345R mutation in the bispecific CD38×CD20 antibody results in more rapid and more substantial CDC-mediated target cell lysis.

FIG. 16 shows that the bispecific antibody IgG1-005-F405L×IgG1-7D8-K409R induced a maximal CDC-mediated killing of 83%, which was reached after 10 minutes. Introduction of E345R resulted in an increased maximal killing by IgG1-005-E345R-F405L×IgG1-7D8-E345R-K409R (98%), which was already reached after 2 minutes. These data indicate that introducing the Fc-Fc stabilizing E345R mutation in the bispecific antibody results in an accelerated CDC-mediated killing of the target cells.

Example 16

Comparison of CDC Kinetics for Monovalent Binding Antibodies with and without E345R Example 8 shows that monovalent target binding further enhanced the CDC efficacy of E345R antibodies as observed by increased maximal lysis with a CD38×EGFR bispecific antibody on the CD38-positive, EGFR-negative Wien133 cells. Next, the kinetics of the CDC reaction was analyzed to further unravel the difference in CDC-mediated killing capacity between monovalently binding antibodies with and without E345R.

Bispecific CD38×EGFR and CD20×EGFR antibodies, with or without the E345R mutation, were generated in vitro according to the DuoBody platform as described in Example 8. CDC efficacy of the CD38×EGFR bispecific antibodies was tested on the CD38-positive, EGFR-negative Raji cells, to which the bispecific antibodies can only bind monovalently via CD38. $0.1 \times 10^6$ Raji cells were pre-incubated in round-bottom 96-well plates with antibody at a saturating concentration (10.0 μg/mL) in a total volume of 100 μL for 15 min on a shaker at RT. Next, 25 μL normal human serum was added as a source of complement (20% final concentration) and incubated in a 37° C. incubator for different periods of time, varying between 0 and 60 min. The reaction was stopped by putting the plates on ice. 10 μL propidium iodide was added and cell lysis was determined by FACS.

Figure 17:
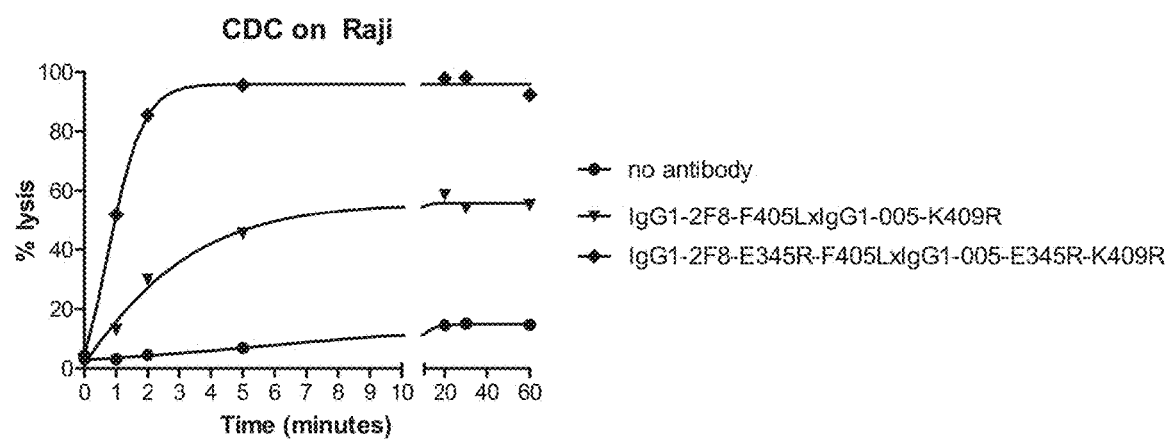
FIG. 17: CDC kinetics. Introduction of the E345R mutation in bispecific antibody EGFRxCD38 that binds monovalently to the EGFR-negative Raji cells, results in more rapid and more substantial CDC-mediated target cell lysis than the bispecific EGFRxCD38 without E345R mutation.

FIG. 17 shows that bispecific antibody CD38×EGFR (IgG1-005-K409R×IgG1-2F8-F405L) induced a maximal CDC-mediated killing of 55%, which was reached after approximately 10 minutes. Introduction of E345R resulted in an increased maximal killing (96%), which was already reached within 5 minutes.

FIG. 17 shows that bispecific antibody CD20×EGFR (IgG1-7D8-K409R×IgG1-2F8-F405L) induced a maximal CDC-mediated killing of 85%, which was reached after approximately 5 minutes. However, with the CD20×EGFR antibody with introduced E345R, 85% lysis was observed faster, after 2 minutes. Maximal lysis by the E345R CD20×EGFR antibody (97%) was also reached after 5 minutes.

In summary, introduction of the E345R mutation in these monovalent binding antibodies resulted in more potent antibodies, which results from a combination of increased maximal lysis and a faster kinetics of the CDC reaction.

Example 17

CDC by a Combination of Therapeutic and E345R/Q386K Antibodies

As described in Example 6, mutant CD38 antibodies derived from IgG1-005 could induce efficient CDC on Wien133 cells when the E345 position of the wild type antibody was substituted to any amino acid other than Glutamate (E). This suggests that oligomerization, as a prerequisite of CDC, is hindered by the presence of the Glutamate side chain at position 345 of the antibody. Since E345 on one Fc is in close proximity to Q386 on the facing second Fc moiety in the hexameric antibody ring structure, the E345-mediated hindrance of oligomerization in a first antibody could possibly be removed by substitutions at the Q386 position of a second antibody. This would then enable E345 in the first antibody to interact better with the mutated 386 position in the second antibody in case both antibodies are combined. To test this hypothesis, CDC assays were performed on Wien133, in which wild type antibodies (IgG1-003, IgG1-005 or IgG1-11B8) were mixed with IgG1-005-E345R/Q386K or IgG1-005-E345R/Q386K/E430G as an example.

$0.1 \times 10^6$ Wien133 cells were pre-incubated in round-bottom 96-well plates with a concentration series of unpurified IgG1-005-E345R/Q386K, IgG1-005-E345R/Q386K/E430G or control antibody (0.0001-20.0 μg/mL in 3.33-fold dilutions) in the presence or absence of 1.0 or 10.0 μg/mL wild type IgG1-003, IgG1-005 or IgG1-11B8 antibody in a total volume of 100 μL for 15 min on a shaker at RT. Next, 25 μL normal human serum was added as a source of complement (20% final concentration) and incubated in a 37° C. incubator for 45 min. The reaction was stopped by putting the plates on ice. 10 μL propidium iodide was added and cell lysis was determined by FACS.

Figure 18A:
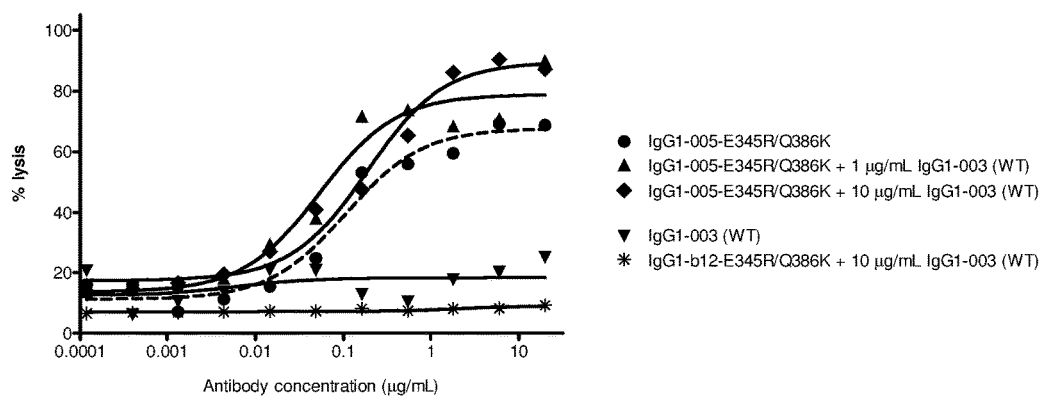
FIGS. 18A-18F: CDC on Wien133 cells by a combination of a wild type antibody with a mutant antibody containing (FIGS. 18A-18C) E345R and Q386K or (FIGS. 18D-18F) E345R, E430G and Q386K. IgG1-b12 mutants do not bind Wien133 cells and were used as negative control antibodies.
Figure 18B:
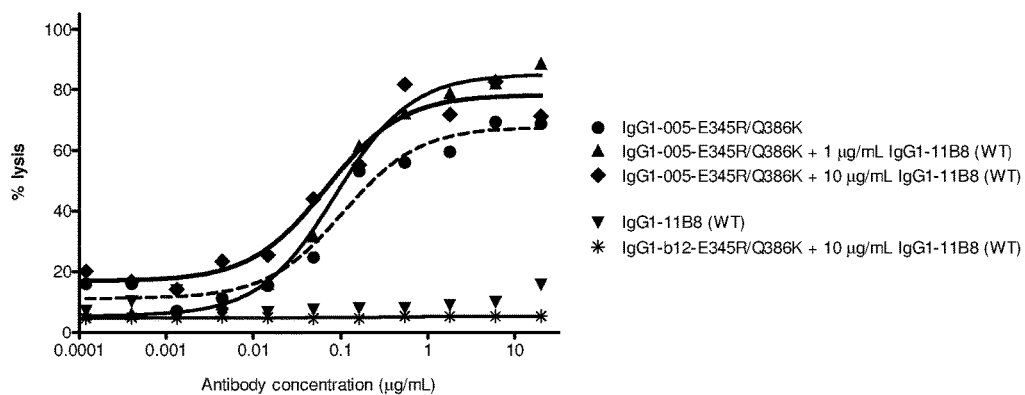
Figure 18C:
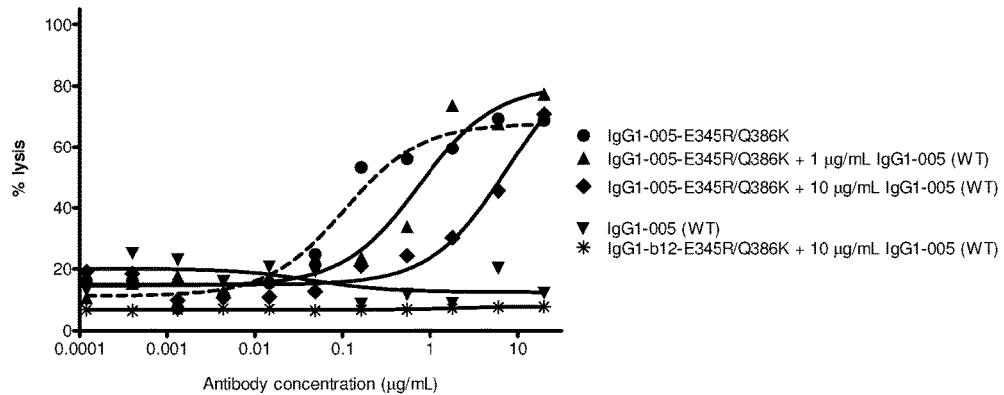

FIG. 18A/B/C shows that CD38 antibody IgG1-005-E345R/Q386K induced CDC-mediated lysis of Wien133 cells in a dose-dependent fashion (dashed line). Combining IgG1-005-E345R/Q386K with 1 or 10 μg/mL wild type CD38 antibody IgG1-003 (FIG. 18A) or wild type CD20 antibody IgG1-11B8 (FIG. 18B) resulted in an increased maximal cell lysis. Combining IgG1-005-E345R/Q386K with wild type IgG1-005 inhibited CDC in a dose-dependent fashion, possibly by competing for the binding site (FIG. 18C).

Figure 18D:
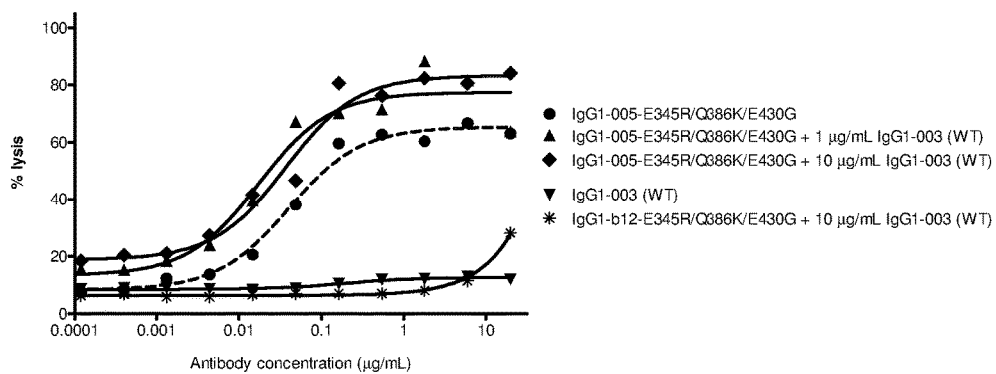
Figure 18E:
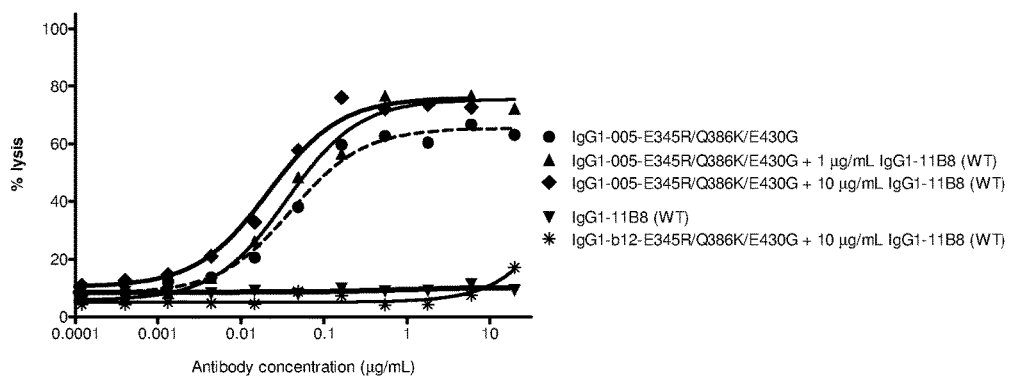
Figure 18F:
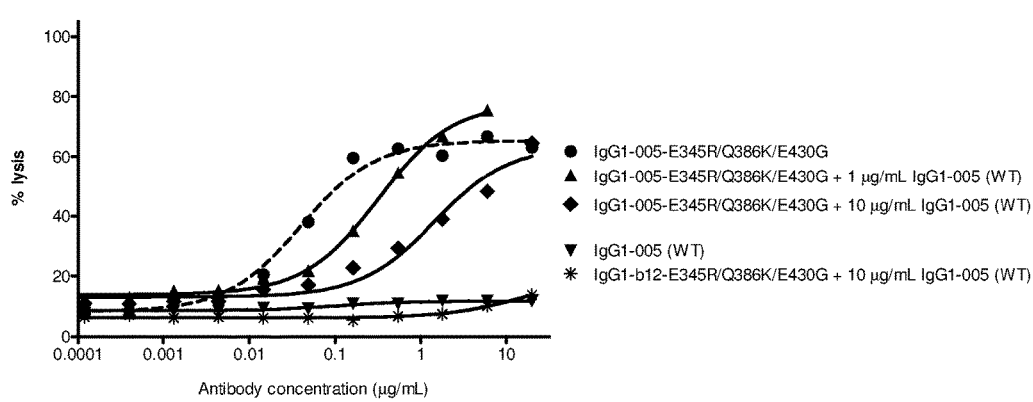

FIG. 18D/E/F shows similar results for CD38 antibody IgG1-005-E345R/Q386K/E430G.

These data indicate that wild type antibodies IgG1-003 and IgG1-11B8 participated in antibody oligomerization and CDC activation when combined with IgG1-005-E345R/Q386K or IgG1-005-E345R/Q386K/E430G. In such combinations, the hindrance of oligomerization by the E345-position that is present in the wild type antibody could be, at least partly, removed by the Q386K substitution in the mutant antibody. This application is in particular interesting to improve therapies with antibodies that are wild type in the E345 position, such as rituximab, ofatumumab, daratumumab or trastuzumab. Also, such oligomerization-inducing antibodies might promote formation of cell-bound complexes with patient-own antibodies directed against target cells like tumor cells or bacteria.

Example 6 describes multiple amino acids in addition to E345 that enhance CDC upon mutation, for example E430 and S440, of which specific mutations induced efficient CDC on Wien133 cells when incorporated in CD38 antibody IgG1-005. With the exception of I253 and Y436 mutants, the identified oligomerization-enhancing mutations contact unmutated amino acids on the facing second Fc moiety in the hexameric ring structure. Therefore, the identified oligomerization-enhancing mutations, both alone or combined, can be expected to also promote oligomerization with unmutated antibodies, and further optimization of such mutants could be achieved by a selection strategy similar to that applied in example 6.

Example 18

E345R Induced CDC in IgG2, IgG3 and IgG4 Antibody Isotypes

To test if the introduction of oligomerization-promoting mutations can stimulate the CDC activity of non-IgG1 antibody isotypes, isotypic variants of the CD38 antibody IgG1-005 were generated with constant domains of human IgG2, IgG3 or IgG4 yielding IgG2-005, IgG3-005 and IgG4-005 by methods known in the art. Furthermore, the oligomerization enhancing E345R mutation was introduced in all these antibodies, yielding IgG2-005-E345R, IgG3-005-E345R and IgG4-005-E345R. In a similar way, also IgG2-003 and IgG2-003-E345R were generated from CD38 antibody IgG1-003. CDC efficacy of the different isotypes was compared in an in vitro CDC assay.

$0.1 \times 10^6$ Wien133 cells were pre-incubated in round-bottom 96-well plates with 10 μg/mL unpurified antibodies in a total volume of 100 μL for 15 min on a shaker at RT. IgG1-005-E345R was added at 3.0 μg/mL. Next, 25 μL normal human serum was added as a source of complement (20% final concentration) and incubated in a 37° C. incubator for 45 min. The reaction was stopped by putting the plates on ice. 10 μL propidium iodide was added and cell lysis was determined by FACS.

FIG. 19 shows that IgG2-005, IgG2-003, IgG3-005 and IgG4-005 were unable to lyse either (A) Daudi or (B) Wien133 cells efficiently under the tested conditions (the observed ~20% lysis was considered as background). Introduction of the E345R mutation enabled potent CDC on Daudi cells by all IgG isotypes tested. These results were confirmed using CDC on Wien133 cells, albeit that IgG3-005-E345R displayed limited CDC activity relative to the other isotypic variants. These data indicate that besides IgG1, an oligomerization enhancing mutation such as E345R can also be applied to promote CDC activity of IgG2, IgG3 and IgG4 antibodies.

Example 19

CDC by IgG1-005 and IgG1-005-E345R in an Ex Vivo CDC Assay on Patient-Derived CD38-Positive B Cell Chronic Lymphocytic Leukemia (CLL) Cells Cryopreserved primary cells from CLL patient samples were obtained from the hematopathology biobank from CDB-IDIBAPS-Hospital Clinic (Dr. Elias Campo, Hematopathology Unit, Department of Pathology, Hospital Clinic, Institut d'Investigacions Biomèdiques August Pi i Sunyer (IDIBAPS), University of Barcelona, Barcelona, Spain), or from clinical studies by the National Heart, Lung, and Blood Institute (NHLBI) (Dr. Adrian Wiestner, NHLBI, Hematology Branch of the National Institutes of Health (NIH), Bethesda). Informed consent was obtained from all patients in accordance with the Institutional Ethics Committee of the Hospital Clinic (Barcelona, Spain) or the Institutional Review Board of the NIH and the Declaration of Helsinki. All samples were genetically and immunophenotypically characterized.

The CLL samples were categorized into two groups according to their CD38 expression as determined by FACS: five samples were included in the CD38 high group (between 50% and 98% of the CD38 expression on Daudi cells) and four samples were included in the CD38 low group (between 0.5% and 3% of the CD38 expression on Daudi cells).

Fluorescently labeled CLL cells (labeling with 5 µM Calcein AM) were incubated with a concentration series of antibody (0.01-10 µg/mL in 10-fold dilutions). Next, normal human serum was added to the antibody-opsonized cells (100,000 cells/well) as a source of complement (10% final concentration) and incubated for 45 min at 37° C. Supernatants were recovered and fluorescence was read in a Synergy™ HT fluorometer as a measure for cell lysis. Cell killing was calculated as follows:

Specific lysis=100×(sample−spontaneous lysis)/(max lysis−spontaneous lysis)

where max lysis is determined by a sample of cells treated with 1% Triton, and spontaneous lysis is determined from a sample where cells were incubated in the presence of 10% NHS without antibody.

Figure 20A:
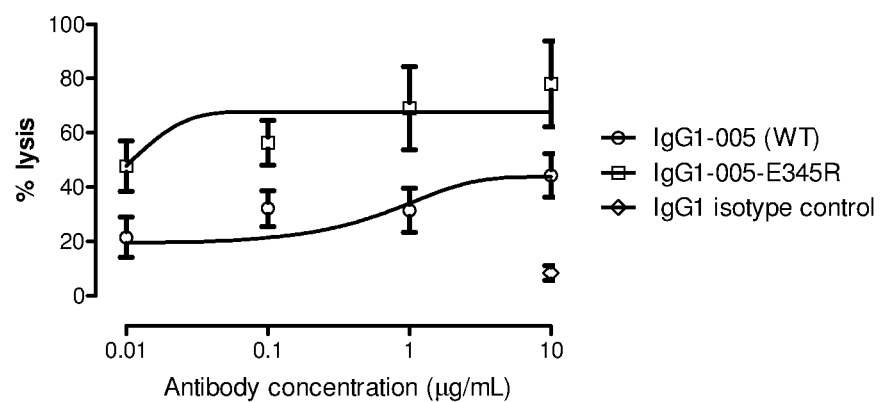
FIGS. 20A and 20B: Introduction of the Fc-Fc stabilizing E345R mutation in wild type CD38 antibody 005 results in enhanced killing of primary CLL cells in an ex vivo CDC assay (average±standard error of the mean).
Figure 20B:
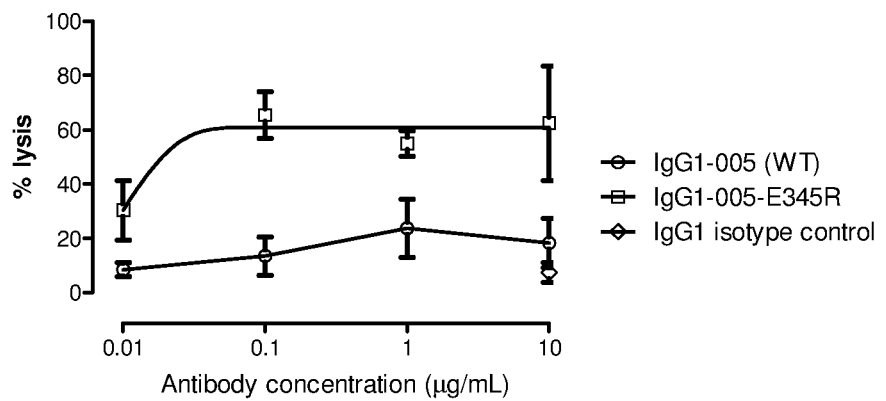

FIG. 20 shows that IgG1-005-E345R strongly enhanced CDC efficacy compared to wild type IgG1-005 on both CLL primary cells with high CD38 expression and CLL primary cells with low CD38 expression.

Example 20

IgG1-005-E345R/E430G/S440Y Forms Non-Covalent, Hexameric Complexes in Solution The IgG1-005-E345R/E430G/S440Y triple mutant was prepared using the Quikchange site-directed mutagenesis kit (Stratagene, US). Briefly, forward and reverse primers encoding the desired mutation E345R were used to replicate full length plasmid DNA template encoding the IgG1-005 heavy chain with IgG1m(f) allotype. The resulting DNA mixture was digested using DpnI to remove source plasmid DNA and used to transform *E. coli*. Mutant plasmid DNA isolated from resulting colonies was checked by DNA sequencing (Agowa, Germany). The E430G mutation was introduced into the IgG1-005-E345R backbone using the same strategy. The S440Y mutation was introduced into the IgG1-005-E345R/E430G backbone using the same strategy. Plasmid DNA mixtures encoding both heavy and light chain of antibodies were transiently transfected to Freestyle HEK293F cells (Invitrogen, US) using 293fectin (Invitrogen, US) essentially as described by the manufacturer. The resulting antibody is a homodimer containing the E345R/E430G/S440Y triple mutation in both heavy chains.

IgG1-005 and IgG1-005-E345R/E430G/S440Y antibodies were purified by protein A affinity chromatography. The cell culture supernatants were filtered over a 0.20 µM dead-end filter, followed by loading on a 5 mL Protein A column (rProtein A FF, GE Healthcare, Uppsala, Sweden) and elution of the IgG with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis, samples were sterile filtered over a 0.20 µM dead-end filter. Purified proteins were analyzed by SDS-PAGE, native PAGE, HP-SEC, multiple angle light scattering (MALS), and dynamic light scattering (DLS).

Figure 21:
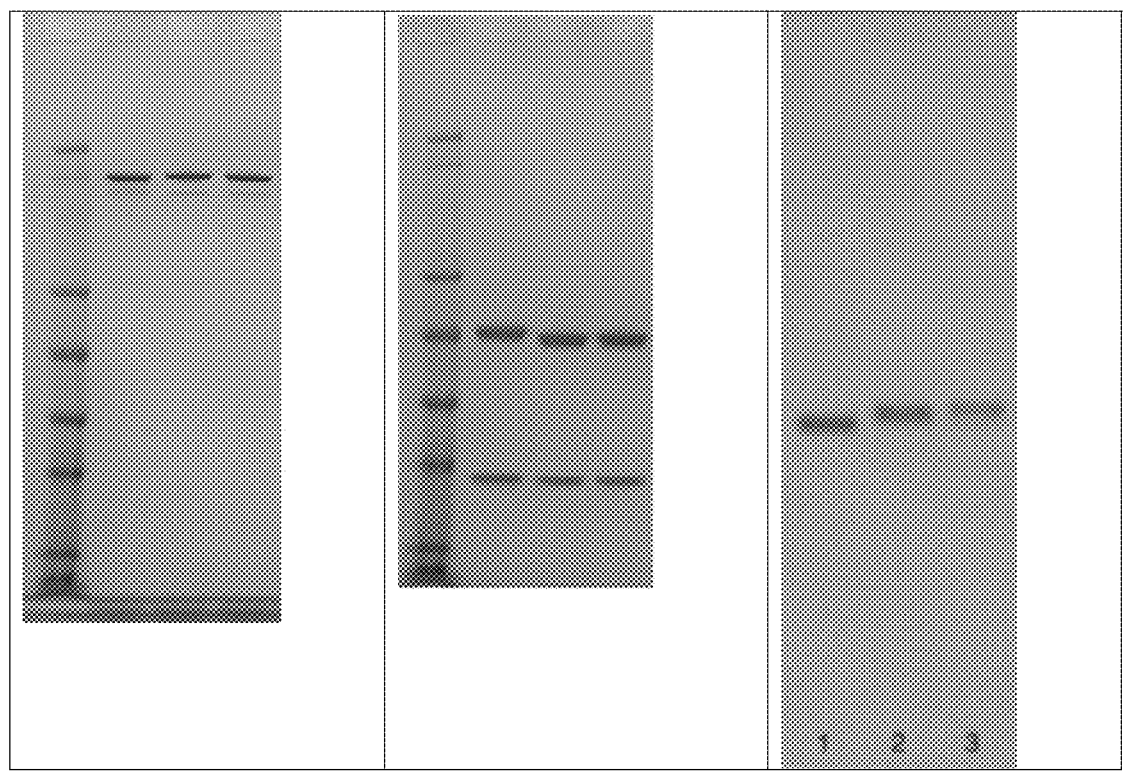
FIG. 21: PAGE analysis of antibody variant IgG1-005-E345R/E430G/S440Y. Left panel: SDS-PAGE, non-reducing conditions. Middle panel: SDS-PAGE, reducing conditions. Right panel: native PAGE. Note: lane 1: IgG1-b12 control antibody. Lane 2: IgG1-005-E345R/E430G. Lane 3: IgG1-005-E345R/E430G/S440Y.

SDS-PAGE was performed under reducing and non-reducing conditions on 4-12% NuPAGE Bis-Tris gels (Invitrogen, Breda, The Netherlands) using a modified Laemmli method (Laemmli 1970 Nature 227(5259): 680-5), where the samples were run at neutral pH. The SDS-PAGE gels were stained with Coomassie and digitally imaged using the GeneGenius (Synoptics, Cambridge, UK). FIG. 21 shows that IgG1-005-E345R/E430G/S440Y displayed behavior typical of IgG1 antibodies with disulfide bridged heavy and light chains. A single molecular species with apparent MW of approximately 150 kDa was visible under non-reducing conditions, while under reducing conditions a heavy chain with apparent MW of 50 kDa and light chain of 26 kDa were visible. We concluded that, under denaturing conditions, a monomeric molecule is formed displaying behavior highly similar to wild type IgG1 antibodies.

Native PAGE was performed under non-reducing conditions using a Sebia Hydragel 15/30 protein gel (Westburg, Leusden, The Netherlands), acid violet-staining and run on a Hydrasys instrument (Sebia, Vilvoorde, Belgium). FIG. 21 shows that IgG1-005-E345R/E430G/S440Y ran at a height similar to that of the unrelated IgG1-b12 control antibody, albeit slightly more diffuse. The observed diffuse staining could be caused by formation of unstable complexes, but under these PAGE conditions, the IgG1-005-E345R/E430G/S440Y behaved predominantly like a monomeric IgG1 molecule.

Figure 22:
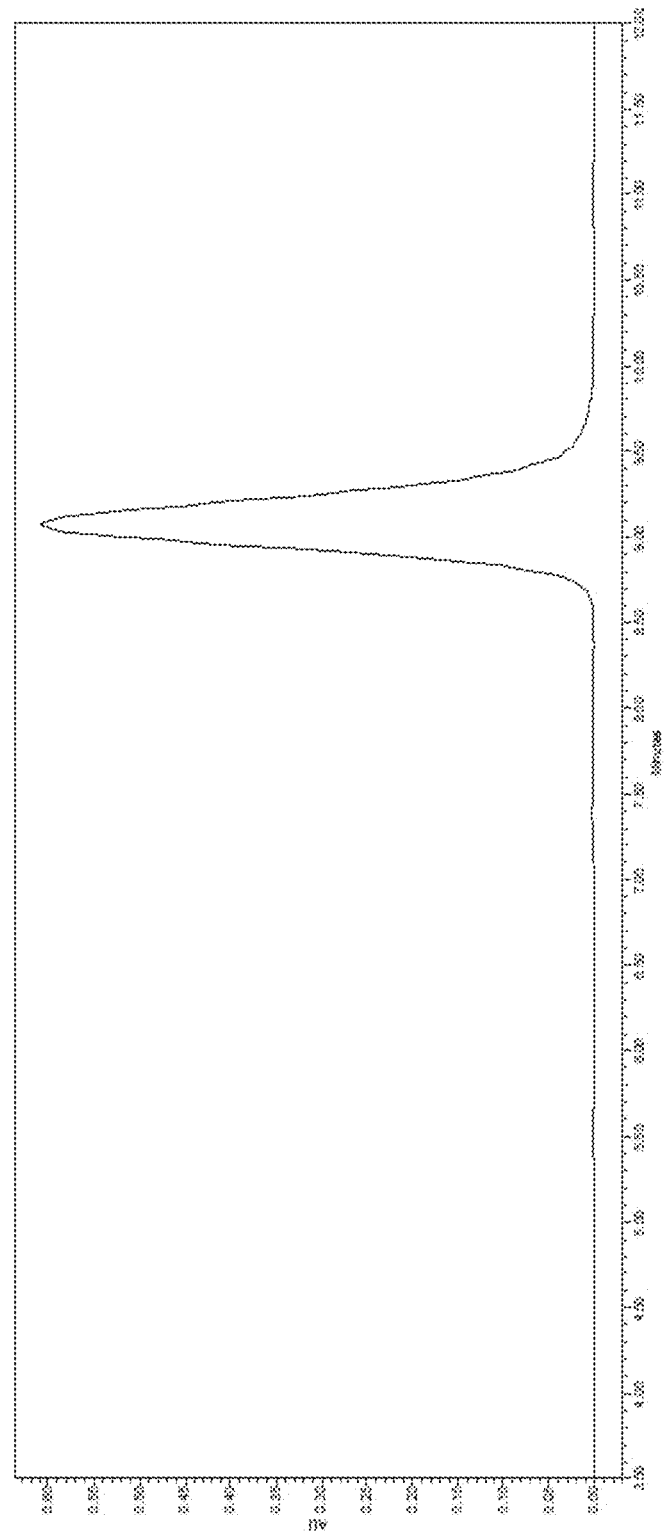
FIG. 22: HP-SEC analysis of wild type IgG1-005 antibody. Fraction monomer (i.e. single antibodies) was estimated at >99%.
Figure 23:
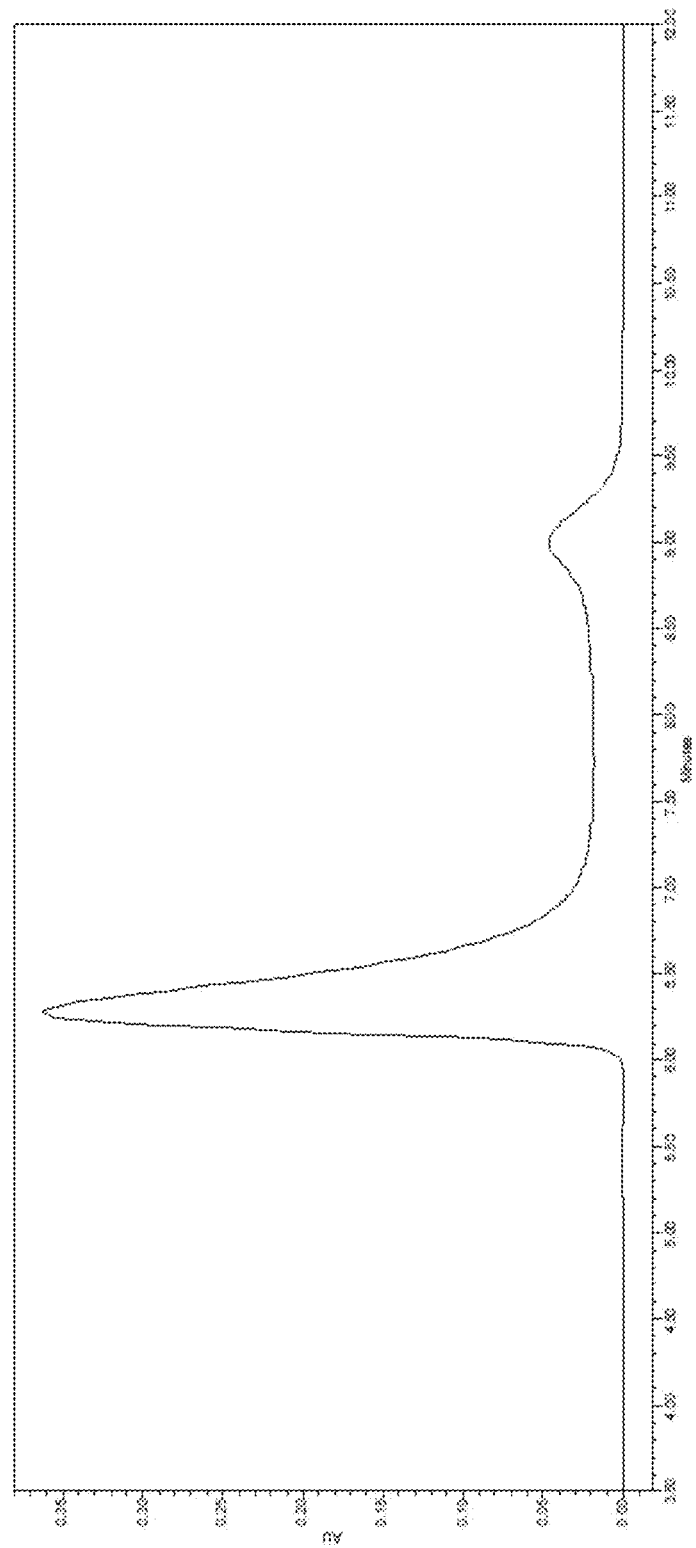
FIG. 23: HP-SEC analysis of antibody variant IgG1-005-E345R/E430G/S440Y. Fraction oligomer was estimated at approximately 79%.

HP-SEC fractionation was performed using a Waters Alliance 2975 separation unit (Waters, Etten-Leur, The Netherlands) connected to a TSK HP-SEC column (G3000SW$_{xl}$; Toso Biosciences, via Omnilabo, Breda, The Netherlands), a Waters 2487 dual λ absorbance detector (Waters), and a Mini Dawn Treos MALS detection unit (Wyatt). 50 µL samples containing 1.25 µg/mL protein were separated at 1 mL/min in 0.1 M $Na_2SO_4$/0.1 M sodium phosphate buffered at pH 6.8. Results were processed using Empower software version 2002 and expressed per peak as percentage of total peak area. FIG. 22 shows that >99% of wild type IgG1-005 consisted of intact monomeric IgG, with practically no aggregates formed. FIG. 23 shows that the triple mutant IgG1-005-E345R/E430G/S440Y shows a large fraction oligomer which was estimated at 79%, while 21% of the population eluted in a peak observed at the expected elution time for a monomeric species.

Figure 24:
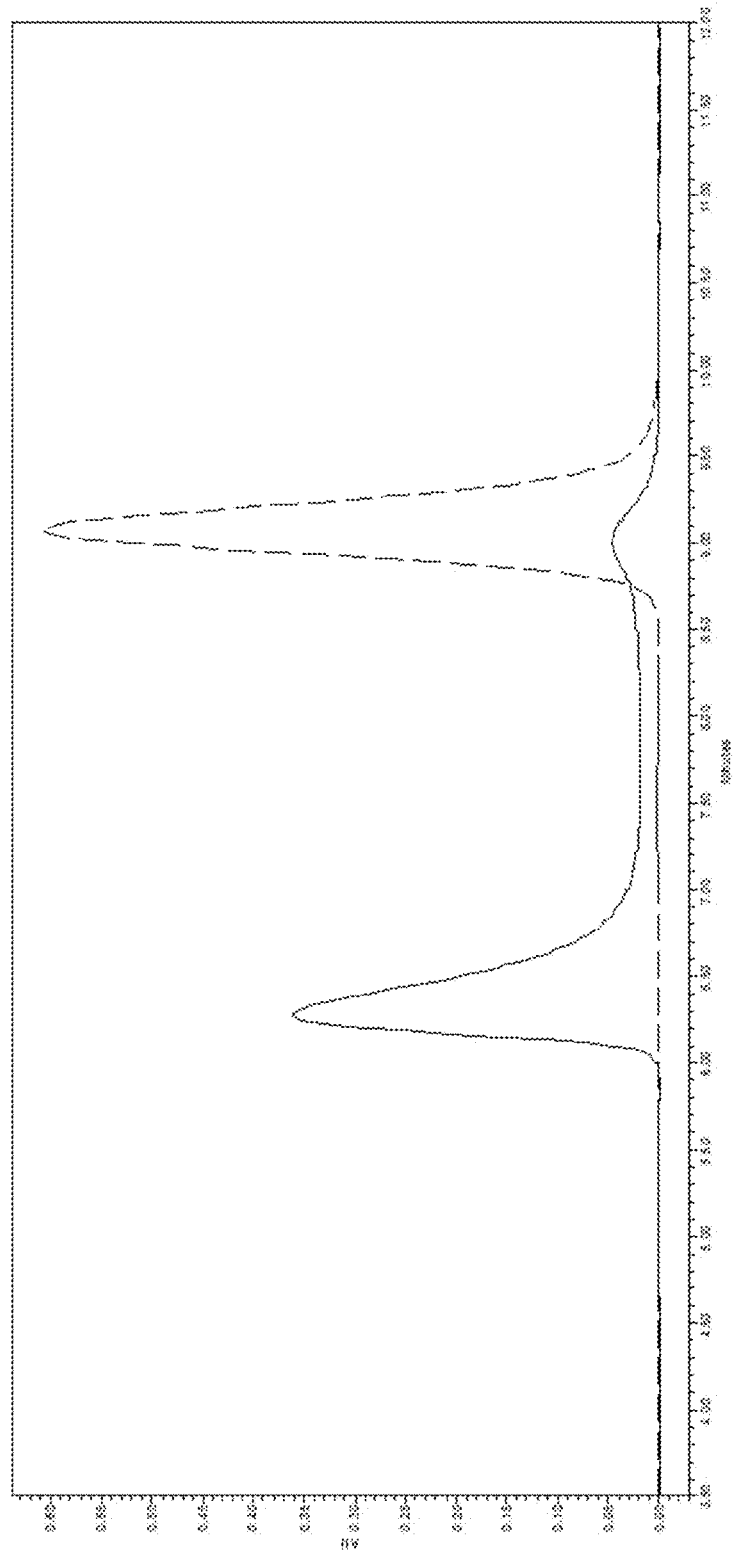
FIG. 24: Overlay of the HP-SEC profiles of wild type IgG1-005 antibody (dashed line) and IgG1-005-E345R/E430G/S440Y (solid line).

An overlay of the HP-SEC profiles of wild type IgG1-005 and IgG1-005-E345R/E430G/S440Y is shown in FIG. 24 and further illustrates the difference in behavior between the two antibodies. IgG1-005-E345R/E430G/S440Y clearly formed high MW complexes, though these complexes seemed to be sensitive to HP-SEC separation, as indicated by the significant amount of protein eluting between the two peaks. Possibly the shear caused by HP-SEC separation may destabilize the non-covalent complexes formed by assembly of IgG1-005-E345R/E430G/S440Y monomers.

To assess the size of the observed oligomeric complex in the IgG1-005-E345R/E430G/S440Y sample, the average molecular weight of the HP-SEC eluate was determined by multiple angle light scattering (MALS). While the minor monomeric peak eluted with an apparent average MW of 143 kDa (145.4 kDa expected), the multimeric peak eluted with an apparent average MW of 772 kDa, or approximately 5.4 monomeric subunits. The MW of the complex is probably underestimated due to the instability of the complex under these conditions. For example, a co-eluting mixture of 88% hexameric species and 12% monomeric species would result in an observed average complex size of 5.4 monomer units.

To assess the apparent molecular weight in solution, in the absence of the shear possibly induced by interactions with the HP-SEC matrix, dynamic light scattering (DLS) analysis was performed. 45 µL of 0.2 µM filtered IgG1-005 (3.80 mg/mL) or IgG1-005-E345R/E430G/S440Y (2.86 mg/mL) in PBS pH 7.4 was analyzed using a DynaPro-801 instrument (Protein Solutions Inc/Wyatt, Dernbach, Germany) in a 100 µL quartz cuvette, recording twenty consecutive measurements per experiment, in three independent experiments. Calibrated using the MW of BSA as a reference, the apparent MW of IgG1-005 was 141.7 kDa (145.4 expected), while IgG1-005-E345R/E430G/S440Y displayed a MW of approximately 875.6 kDa, or 6.17 monomeric subunits. No indication of oligomerization was observed for the IgG1-005 antibody, while IgG1-005-E345R/E430G/S440Y suggested highly efficient complex formation.

In summary, the biophysical data indicate that mutant IgG1-005-E345R/E430G/S440Y forms disulfide-bridged IgG1-like molecules that are monomeric, i.e. single dimeric protein, under denaturing conditions as observed by SDS-PAGE and form hexameric complexes in solution as observed by DLS. The shear imposed by native PAGE was sufficient to fully dissociate the complexes, while HP-SEC partially destabilized predominantly hexameric complexes, as indicated by the presence of a minor fraction of monomers.

Example 21

Functional Assays with IgG1-005, IgG1-005-E345R/E430G/S440Y and IgG1-005-E345R

C1q Binding ELISA

C1q binding by wild-type IgG1-005, triple mutant IgG1-005-E345R-E430G-S440Y and IgG1-005-E345R was tested in an ELISA in which the purified antibodies were immobilized on the plastic surface, bringing about random antibody multimerization. Pooled human serum was used as a source of C1q.

96-well Microlon ELISA plates (Greiner, Germany) were coated overnight at 4° C. with a dilution series of the antibodies in PBS (range 0.007-25.0 µg/mL in 2.5-fold dilutions). Plates were washed and blocked with 200 µL/well 0.5×PBS supplemented with 0.025% Tween 20 and 0.1% gelatine. With washings in between incubations, plates were sequentially incubated with 3% pooled human serum (Sanquin, product # M0008) for 1 h at 37° C., with 100 µL/well rabbit anti-human C1q (DAKO, product # A0136, 1/4.000) for 1 h at RT, and with 100 µL/well swine anti-rabbit IgG-HRP (DAKO, P0399, 1:10.000) as detecting antibody for 1 h at RT. Development was performed for circa 30 min with 1 mg/mL 2,2'-azino-bis(3-ethylbenzothiazoline-6-sulfonic acid) (ABTS; Roche, Mannheim, Germany). The reaction was stopped by the addition of 100 µL 2% oxalic acid. Absorbance was measured at 405 nm in a microplate reader (Biotek, Winooski, Vt.). Log transformed data were analyzed by fitting sigmoidal dose-response curves with variable slope using GraphPad Prism software. From the sigmoidal dose response curves the EC50 values were calculated.

Figure 25:
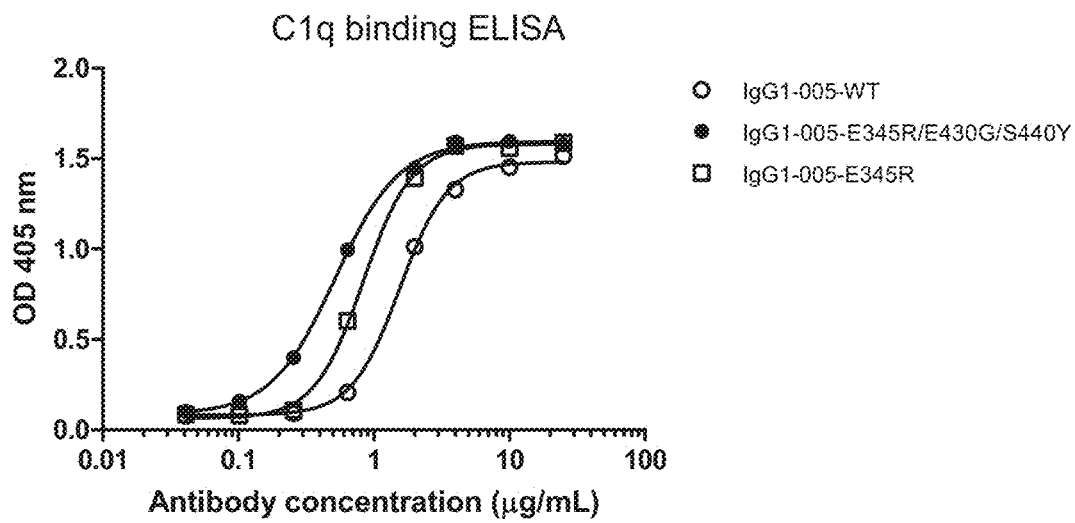
FIG. 25: C1q binding ELISA with IgG1-005, IgG1-005-E345R/E430G/S440Y and IgG1-005-E345R. Concentration series of the indicated antibodies were coated to the wells and incubated with a fixed concentration C1q.

FIG. 25 and Table 8 show that IgG1-005-E345R/E430G/S440Y showed more efficient C1q binding than WT IgG1-005 and IgG1-005-E345R as measured by ELISA (lower EC50 value). Coating efficacy was tested for the three antibodies and was found to be similar (not shown).

TABLE 8

| $EC_{50}$ for C1q binding in ELISA | |
|---|---|
| Antibody | $EC_{50}$ (µg/mL) |
| IgG1-005-WT | 1.551 |
| IgG1-005-E345R/E430G/S440Y | 0.52 |
| IgG1-005-E345R | 0.836 |

CDC Assay on CD38-Positive Ramos Cells 0.1×106 Ramos cells were pre-incubated in round-bottom 96-well plates with a concentration series of purified antibodies (10, 3, 1, 0.3, 0.1, 0.03, 0.01, 0.005, 0.0025, 0.0013, 0.0006 and 0.0003 µg/mL) in a total volume of 100 µL for 15 min on a shaker at RT. Next, 25 µL normal human serum was added as a source of complement (20% final concentration) and incubated in a 37° C. incubator for 45 min. The reaction was stopped by putting the plates on ice. 10 µL propidium iodide was added and cell lysis was determined by FACS.

Figure 26:
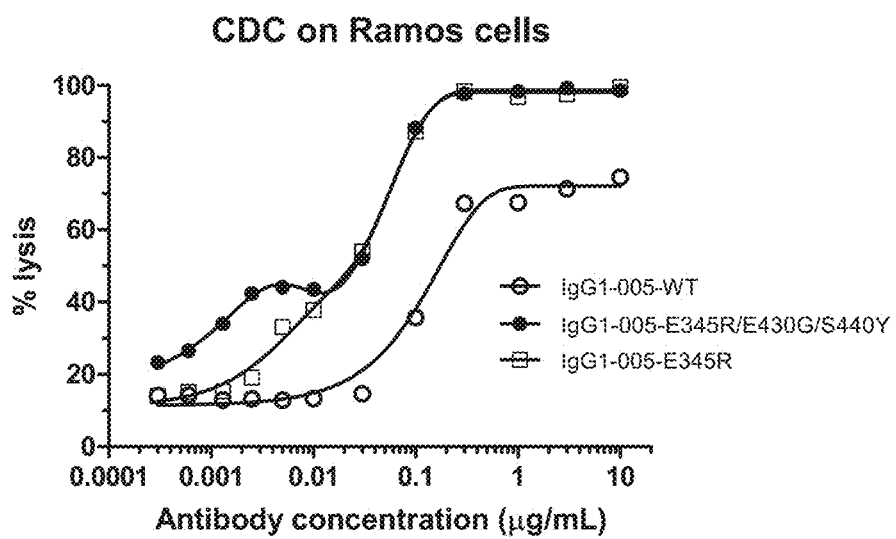
FIG. 26: CDC efficacy by a concentration series of IgG1-005-WT, IgG1-005-E345R/E430G/S440Y and IgG1-005-E345R on CD38-positive Ramos cells.

A three-phase model was used to fit the IgG1-005-E345R/E430G/S440Y data and the medium EC50 value was calculated (Table 9). IgG1-005-WT and IgG1-005-E345R could be fitted by fitting sigmoidal dose-response curves with variable slope. From the sigmoidal dose response curve the EC50 value was calculated (Table 9). GraphPad Prism software was used to fit the data (FIG. 26). IgG1-005-E345R/E430G/S440Y showed enhanced CDC activity compared to wild type IgG1-005 and IgG1-005-E345R antibodies on Ramos cells. The three-phase model of IgG1-005-E345R/E430G/S440Y can be explained by the fact that at low concentrations (between 0.0003 and 0.03 µg/mL) the antibodies within a stable hexamer do not all have to bind a target to induce efficient CDC. Effectively, cell surface C1q binding sites are created by IgG1-005-E345R/E430G/S440Y binding already at low antibody concentrations, because clustering of antigens is not needed for antibody hexamerization.

TABLE 9

EC50 for CDC

| Antibody | EC$_{50}$ (µg/mL) |
|---|---|
| IgG1-005-WT | 0.116 |
| IgG1-005-E345R/E430G/S440Y | 0.005 (medium EC50) |
| IgG1-005-E345R | 0.026 |

ADCC Reporter Assay Using CD38-Positive Raji Cells

ADCC activity of anti-CD38 antibodies opsonized on Raji target cell was measured using an ADCC bioluminescent reporter assay (Promega Madison, Wis., USA) in which biological pathway activation in the effector cells is quantified.

Figure 27:
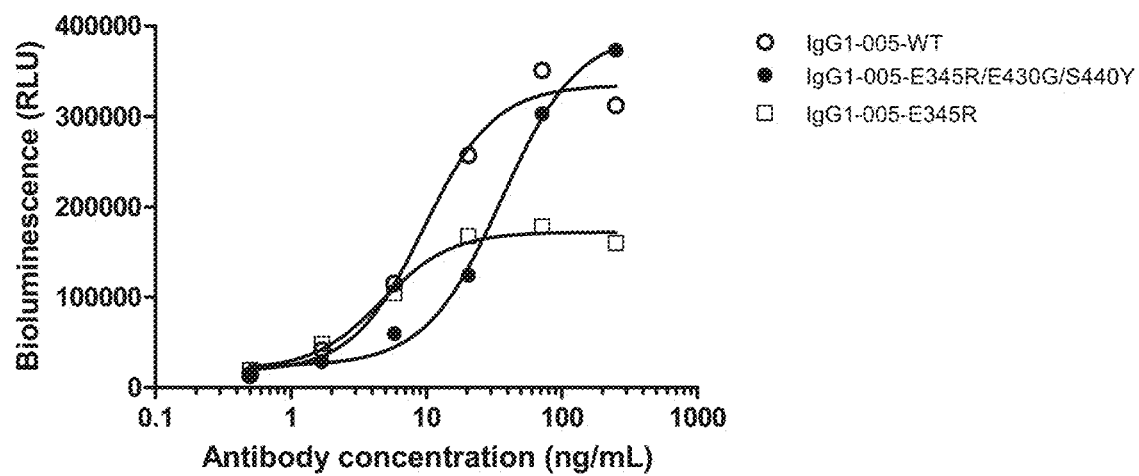
FIG. 27: ADCC Reporter assay using CD38-positive Raji cells and a concentration series of IgG1-005-WT, IgG1-005-E345R/E430G/S440Y and IgG1-005-E345R

The reporter assay uses as effector cells Jurkat cells stably transfected with the gene for FcγRIIIa receptor, V158 (high affinity) variant, and the firefly luciferase reported gene cloned after an NFAT (nuclear factor of activated T-cells) response element driving luciferase expression. Antibody binding to the FcγRIIIa receptor on the effector cells induces NFAT-mediated gene transcription and thus luciferase expression which is quantified by luminescence readout. Raji cells were incubated with a concentration series of purified antibodies (250, 71.4, 20.4, 5.8, 1.7 and 0.5 ng/mL). See for further description of the materials and methods the technical manual provided by Promega. IgG1-005-E345R/E430G/S440Y induced NFAT pathway activation after FcγRIIIa receptor engagement. FIG. 27 shows that Raji cells opsonized with IgG1-005-E345R/E430G/S440Y induced FcgRIIIa-mediated activation of effector cells as measured in the reported assay. The EC50 value for IgG1-005-E345R/E430G/S440Y was higher than for wild type IgG1-005 and IgG1-005-E345R (Table 10). However, the maximal signal for IgG1-005-E345R/E430G/S440Y was higher than for wild type IgG1-005 and IgG1-005-E345R (Table 10).

TABLE 10

EC50 and maximal signal for ADCC reporter assay

| Antibody | EC$_{50}$ (ng/mL) | Maximal signal (RLU) |
|---|---|---|
| IgG1-005-WT | 9.5 | 334878 |
| IgG1-005-E345R/E430G/S440Y | 36 | 393802 |
| IgG1-005-E345R | 4.7 | 172293 |

Example 22

Pharmacokinetic (PK) Analysis of IgG1-005-E345R/E430G/S440Y Compared to Wild Type IgG1-005

The mice in this study were housed in a barrier unit of the Central Laboratory Animal Facility (Utrecht, The Netherlands) and kept in filter-top cages with water and food provided ad libitum. All experiments were approved by the Utrecht University animal ethics committee. SCID mice (C.B-17/IcrCrl-scid-BR, Charles-River) were injected intravenously with 500 µg antibody (wild type IgG1-005 or IgG1-005-E345R/E430G/S440Y) using 3 mice per group.

50 µL blood samples were collected from the saphenous vein at 10 minutes, 4 hours, 1 day, 2 days, 7 days, 14 days and 21 days after antibody administration. Blood was collected into heparin containing vials and centrifuged for 5 minutes at 10,000 g. Plasma was stored at −20° C. until determination of antibody concentrations.

Specific human IgG concentrations were determined using a total hIgG and CD38 specific sandwich ELISA. For the total hIgG ELISA, mouse mAb anti-human IgG-kappa clone MH16 (# M1268, CLB Sanquin, The Netherlands), coated to 96-well Microlon ELISA plates (Greiner, Germany) at a concentration of 2 µg/mL was used as capturing antibody. After blocking plates with PBS supplemented with 0.2% bovine serum albumin, samples were added, serially diluted ELISA buffer (PBS supplemented with 0.05% Tween 20 and 0.2% bovine serum albumin), and incubated on a plate shaker for 1 h at room temperature (RT). Plates were subsequently incubated with goat anti-human IgG immunoglobulin (#109-035-098, Jackson, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm. For the specific CD38 ELISA, His-tagged CD38 extracellular domain was coated to 96-well Microlon ELISA plates (Greiner, Germany) at a concentration of 2 µg/mL. After blocking plates with ELISA buffer, samples serially diluted with ELISA buffer were added, and incubated on a plate shaker for 1 h at room temperature (RT). Plates were subsequently incubated with 30 ng/ml mouse anti human IgG1-HRP, (Sanquin M1328, clone MH161-1) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

Figure 28:
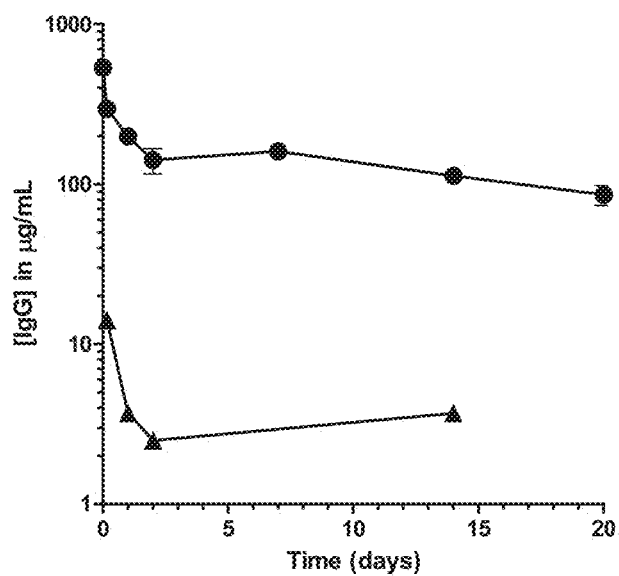
FIG. 28: Plasma human IgG concentrations in SCID mice in time as determined by total human IgG ELISA. Black circles: wild type IgG1-005; black triangles: IgG1-005-E345R/E430G/S440Y.
Figure 29:
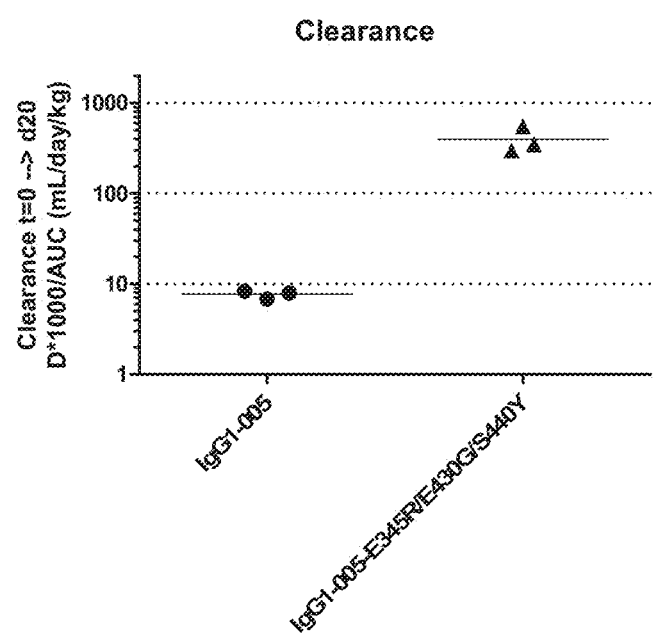
FIG. 29: Clearance rate of administered human IgG in SCID mice as determined by the anti-CD38 ELISA. Black circles: wild type IgG1-005; black triangles: IgG1-005-E345R/E430G/S440Y.

FIG. 28 shows that the plasma human IgG concentrations were considerably lower for mutant IgG1-005-E345R/E430G/S440Y than for IgG1-005 wild type at all tested timepoints. FIG. 29 shows that the clearance rate of IgG1-005-E345R/E430G/S440Y was approximately 50× higher than that of WT IgG1-005.

Example 23

The Oligomeric State of IgG1-005-E345R/E430G/S440Y can be Controlled by Buffer Composition HP-SEC fractionation of IgG1-005 and IgG1-005-E345R/E430G/S440Y antibodies was performed using a Waters Alliance 2975 separation unit (Waters, Etten-Leur, The Netherlands) connected to a TSK HP-SEC column (G3000SW$_{xl}$; Toso Biosciences, via Omnilabo, Breda, The Netherlands), a Waters 2487 dual λ absorbance detector (Waters), and a Mini Dawn Treos MALS detection unit (Wyatt). 50 µL samples containing 1.0 µg/mL protein were separated at 1 mL/min under different buffer conditions. Results were processed using Empower software version 2002 and expressed per peak as percentage of total peak area.

Figure 30:
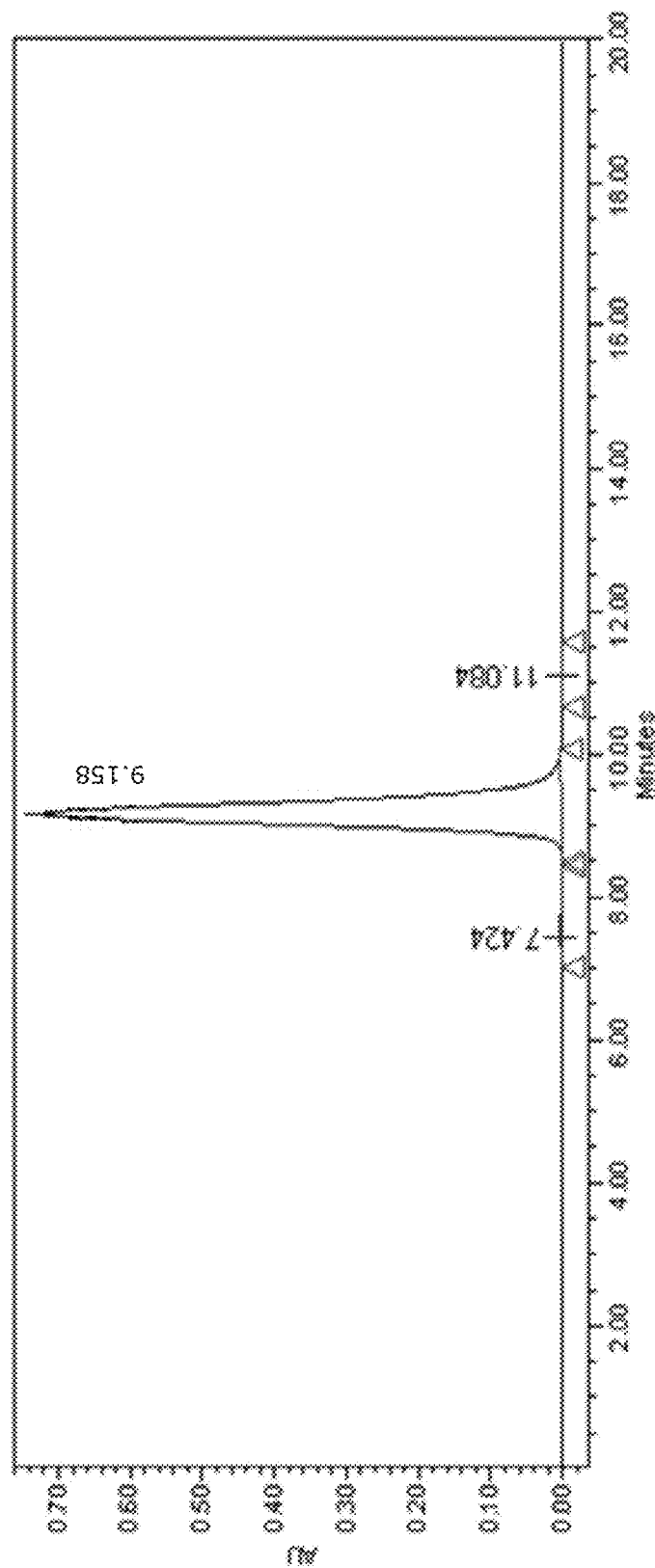
FIG. 30: HP-SEC profile of IgG1-005 in 0.1 M $Na_2SO_4$/0.1 M sodium phosphate pH 6.8.
Figure 31:
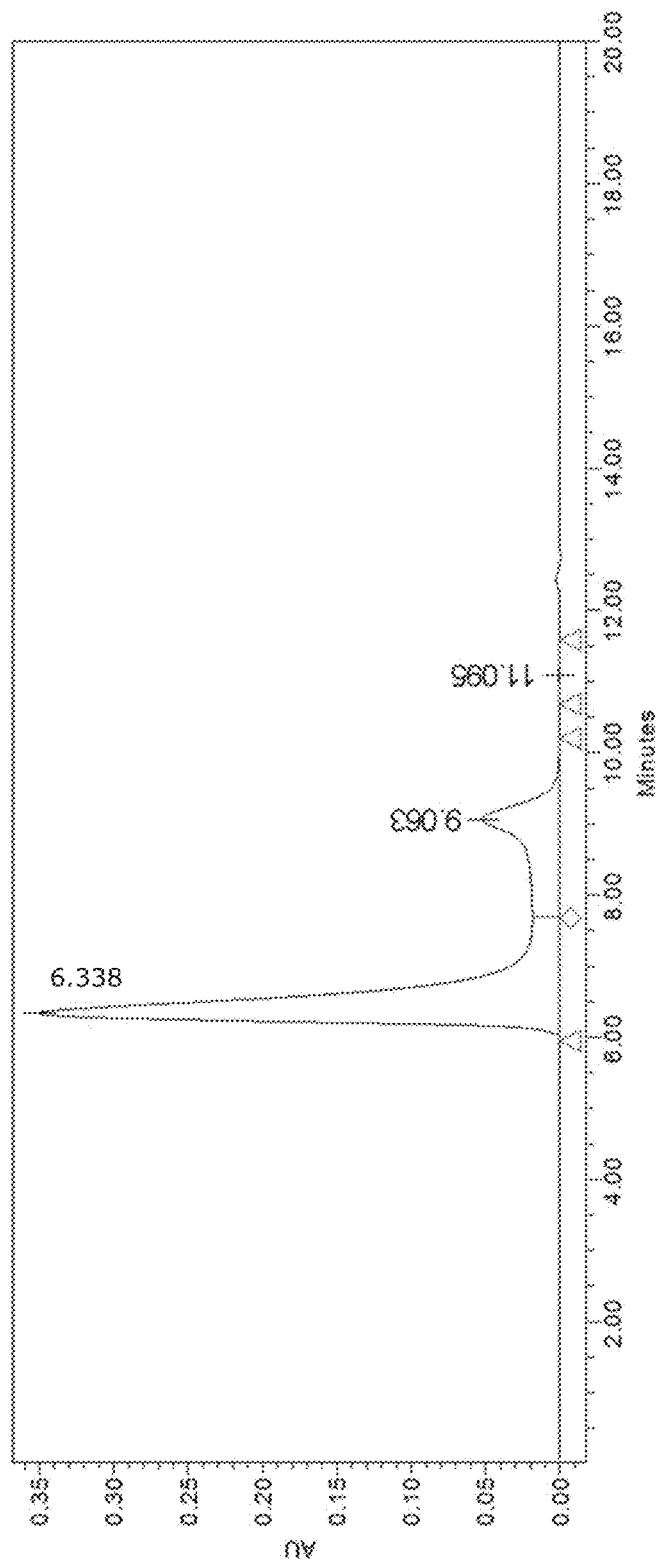
FIG. 31: HP-SEC profile of IgG1-005-E345R/E430G/S440Y in 0.1 M $Na_2SO_4$/0.1 M sodium phosphate pH 6.8.

FIG. 30 shows the HP-SEC elution profiles recorded in 0.1 M Na$_2$SO$_4$/0.1 M sodium phosphate buffered at pH 6.8. At pH 6.8, >99% of wild type IgG1-005 antibodies eluted as monomeric species. In contrast, the HP-SEC profile of IgG1-005-E345R/E430G/S440Y in this buffer shown in FIG. 31 shows a fraction oligomer of 77%, while 23% of the population eluted as a monomeric species. As described in Example 19, the remaining minor fraction of monomer might be caused by column-induced dissociation, since no trace of IgG1-005-E345R/E430G/S440Y monomer was observed during batch-mode analysis using dynamic light scattering under these conditions.

Figure 32:
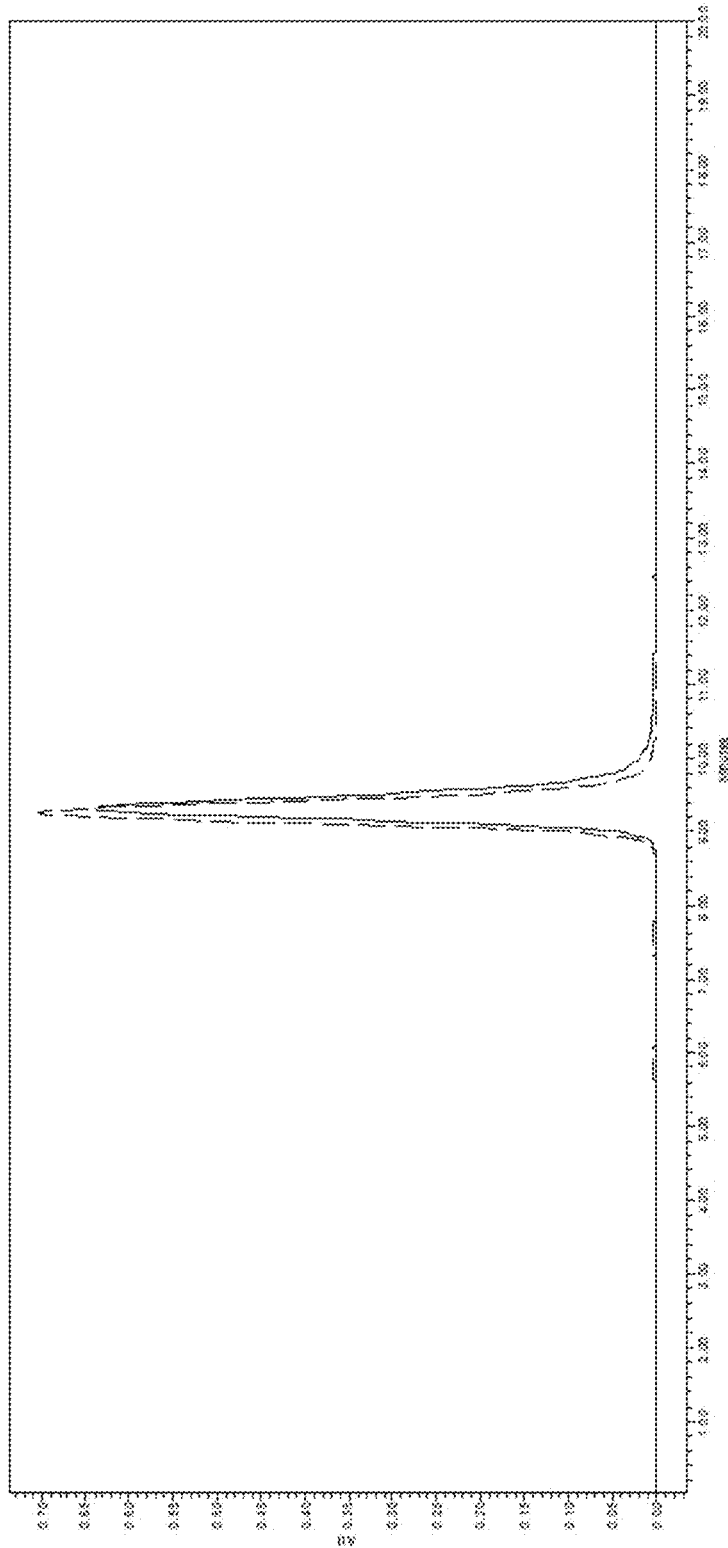
FIG. 32: Overlay of HP-SEC profiles of IgG1-005 in 0.15 M NaCl/0.1 M citrate pH 6.8 (dashed line) and pH 5.0 (solid line).

FIG. 32 shows an overlay of the HP-SEC elution profiles of IgG1-005 recorded in 0.15 M NaCl/0.1 M citrate buffered at pH 6.8 (dashed line) and pH 5.0 (solid line). The HP-SEC profile of IgG1-005 in citrate buffer both at pH 6.8 and pH 5.0 was highly comparable to the behavior in phosphate buffer at pH 6.8, with >99% of the protein eluting as monomeric species.

Figure 33:
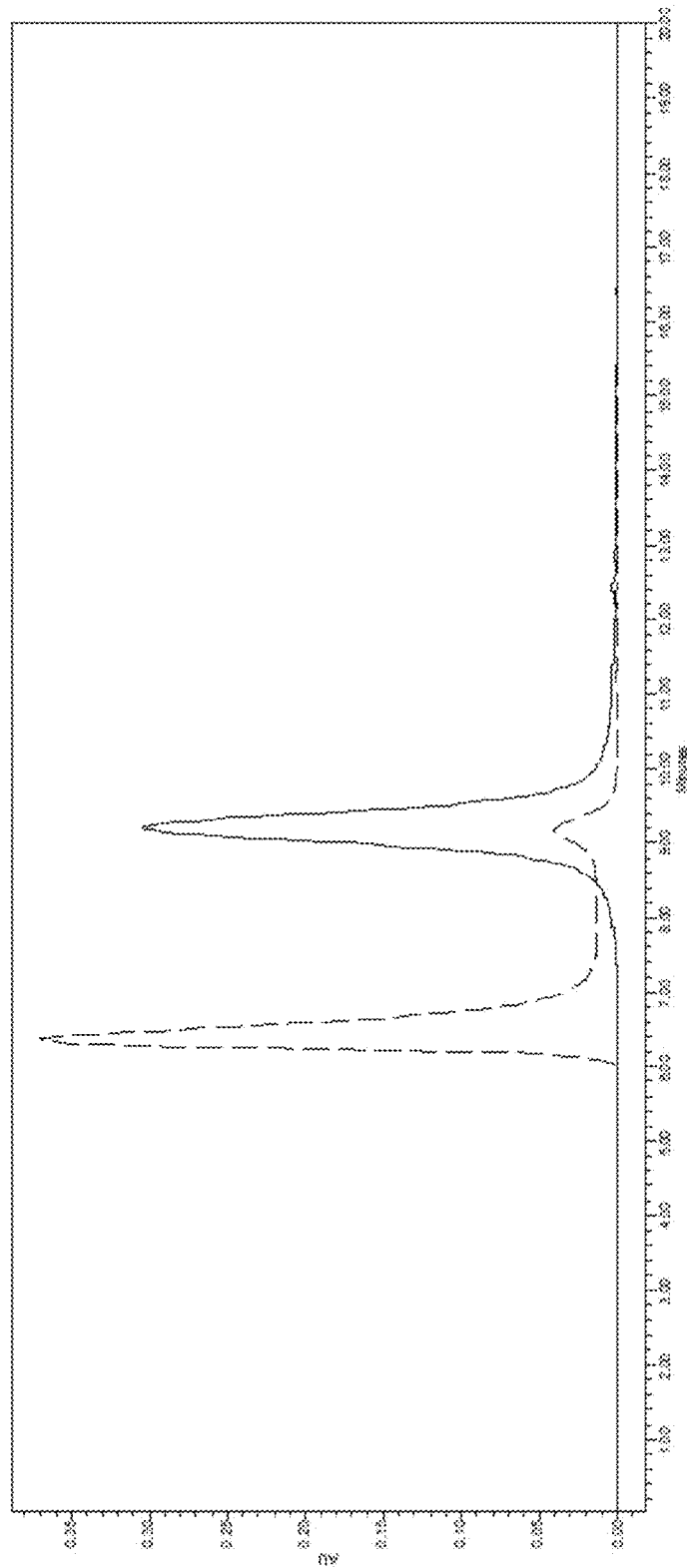
FIG. 33: HP-SEC profile of IgG1-005-E345R/E430G/S440Y in 0.15 M NaCl/0.1 M citrate pH 6.8 (dashed line) and pH 5.0 (solid line).
Figure 34A:
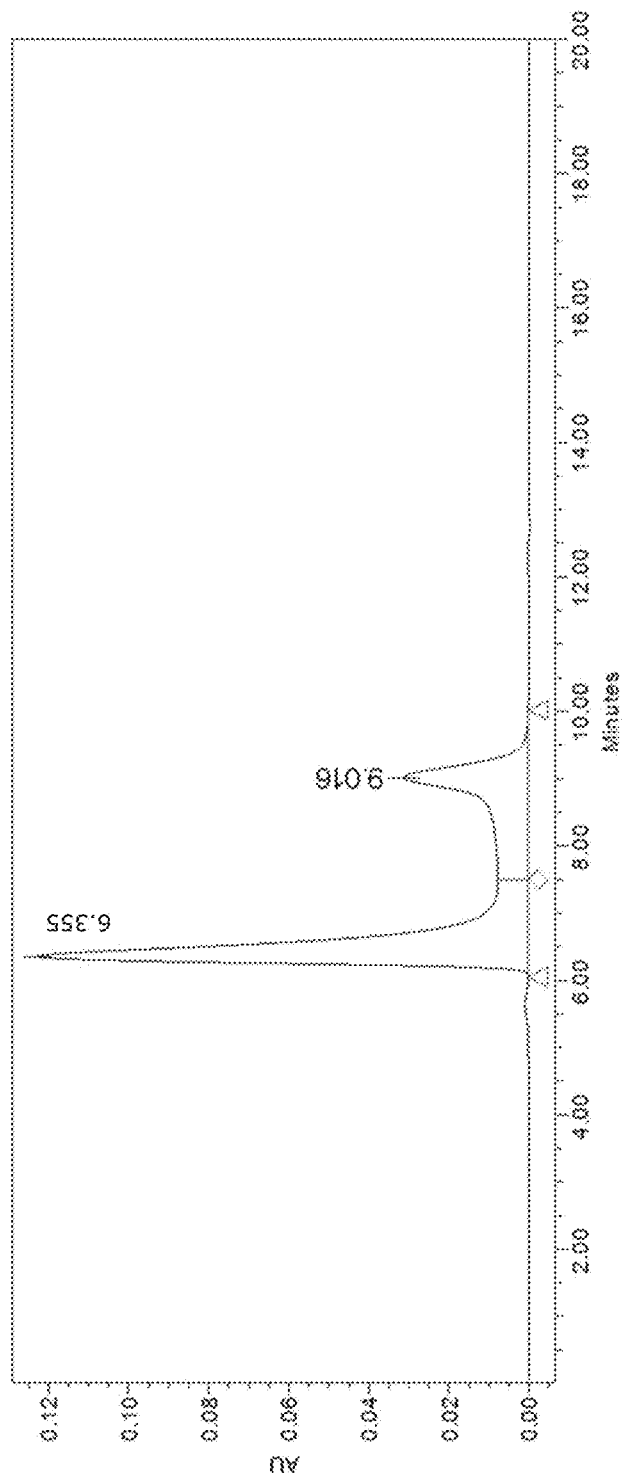
Figure 34B:
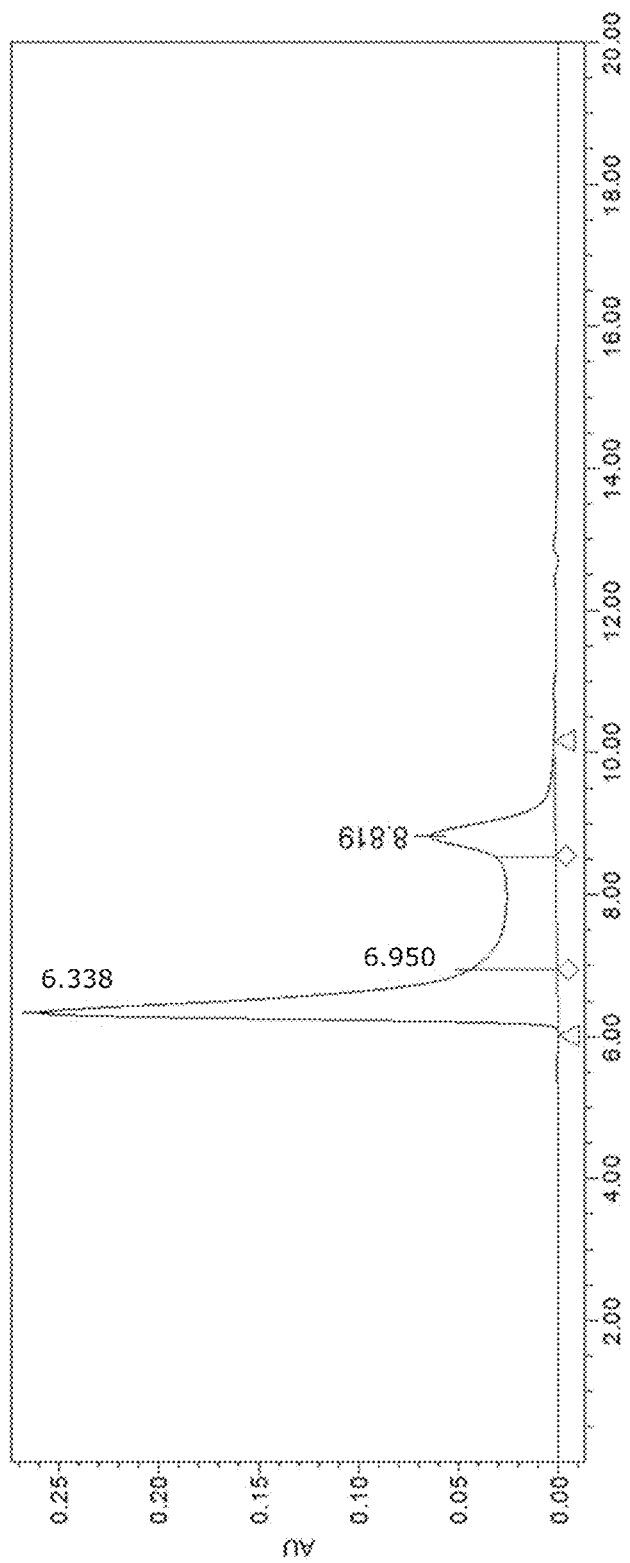
Figure 34C:
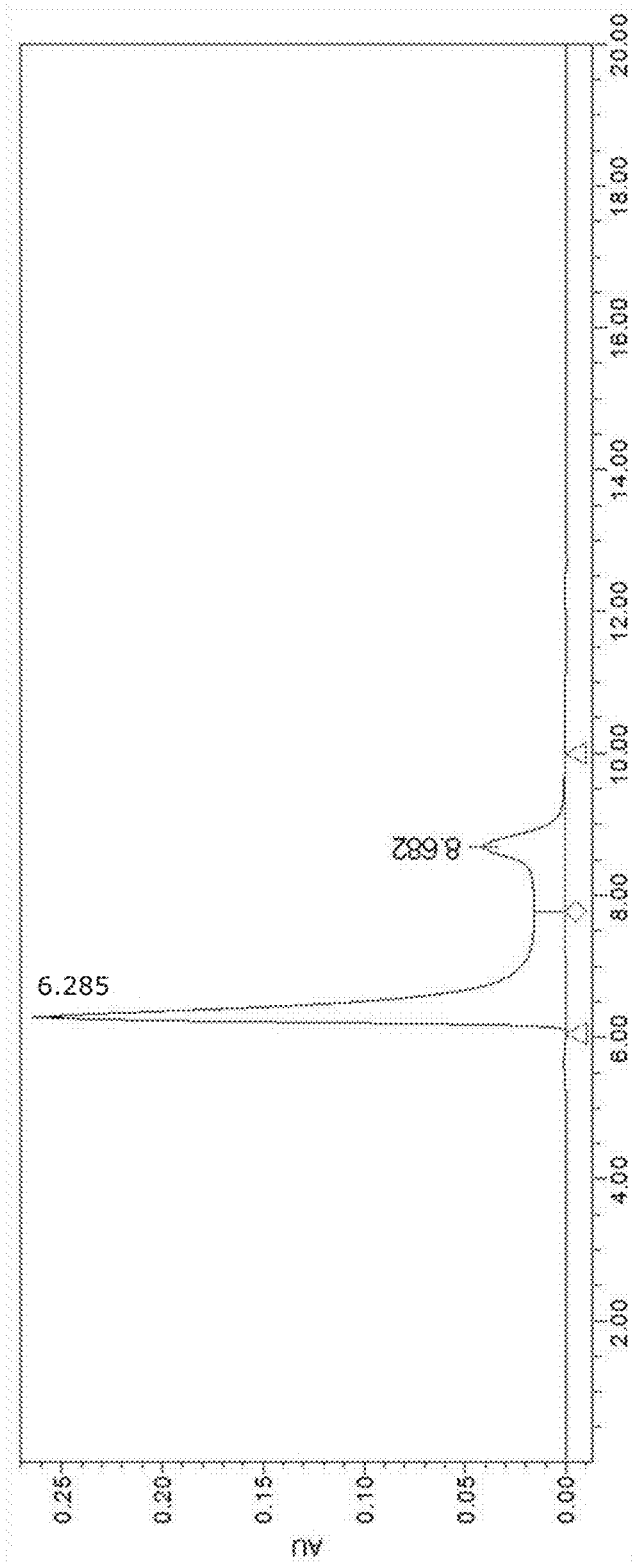
Figure 35A:
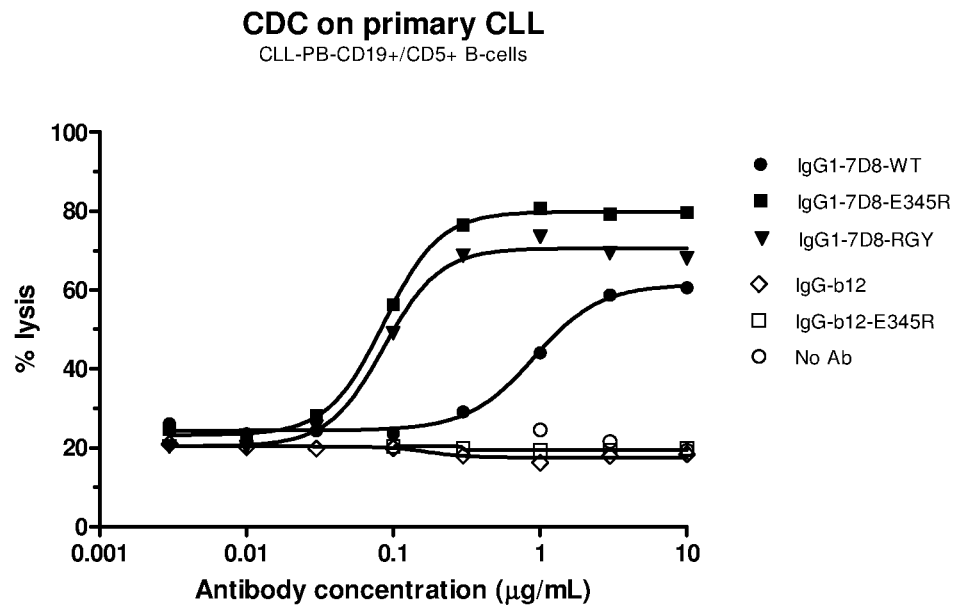
FIGS. 35A and 35B: E345R/E430G/S440Y triple mutant CD20 antibodies show enhanced killing of primary CD20-positive CLL cells in an ex vivo assay with 7D8-derived antibodies (FIG. 35A) and rituximab-derived antibodies (FIG. 35B).
Figure 35B:
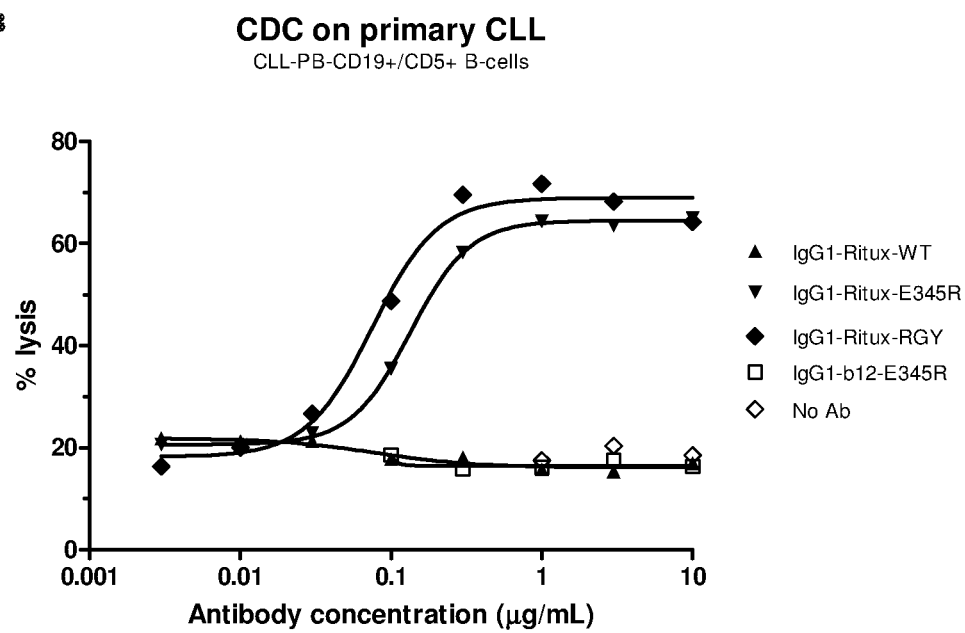
Figure 36A:
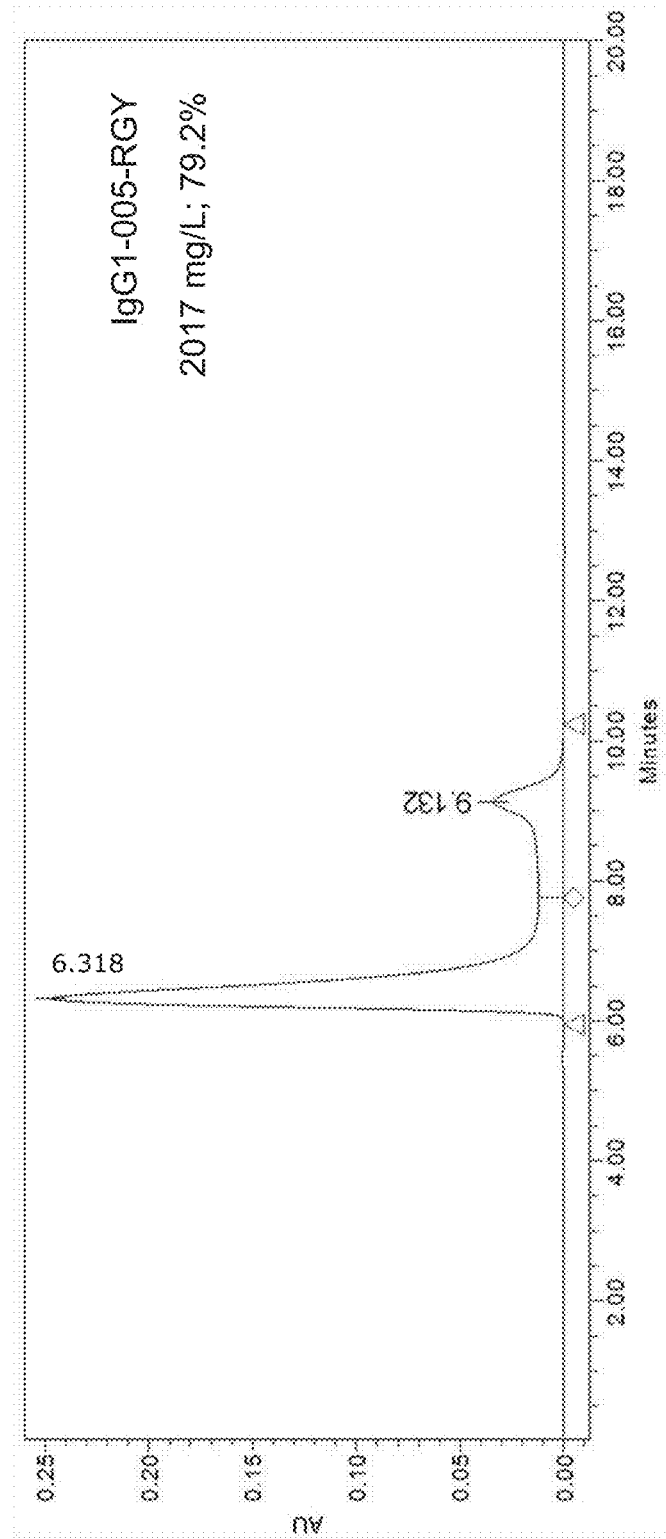
FIGS. 36A-36D: HP-SEC analysis of IgG1-005-RGY (FIG. 36A), IgG2-005-RGY (FIG. 36B), IgG3-005-RGY (FIG. 36C) and IgG4-005-RGY (FIG. 36D). Percentages indicate total multimers as fraction of total peak area.
Figure 36B:
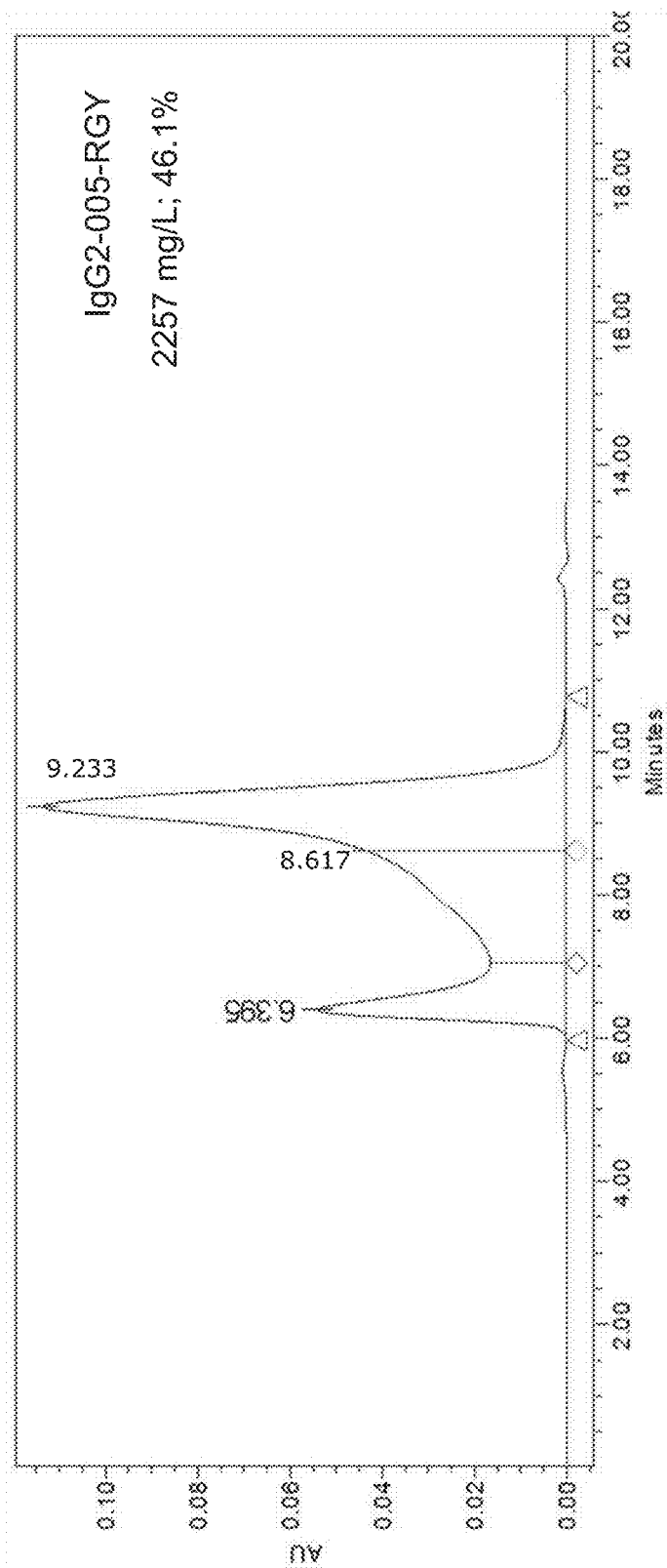
Figure 36C:
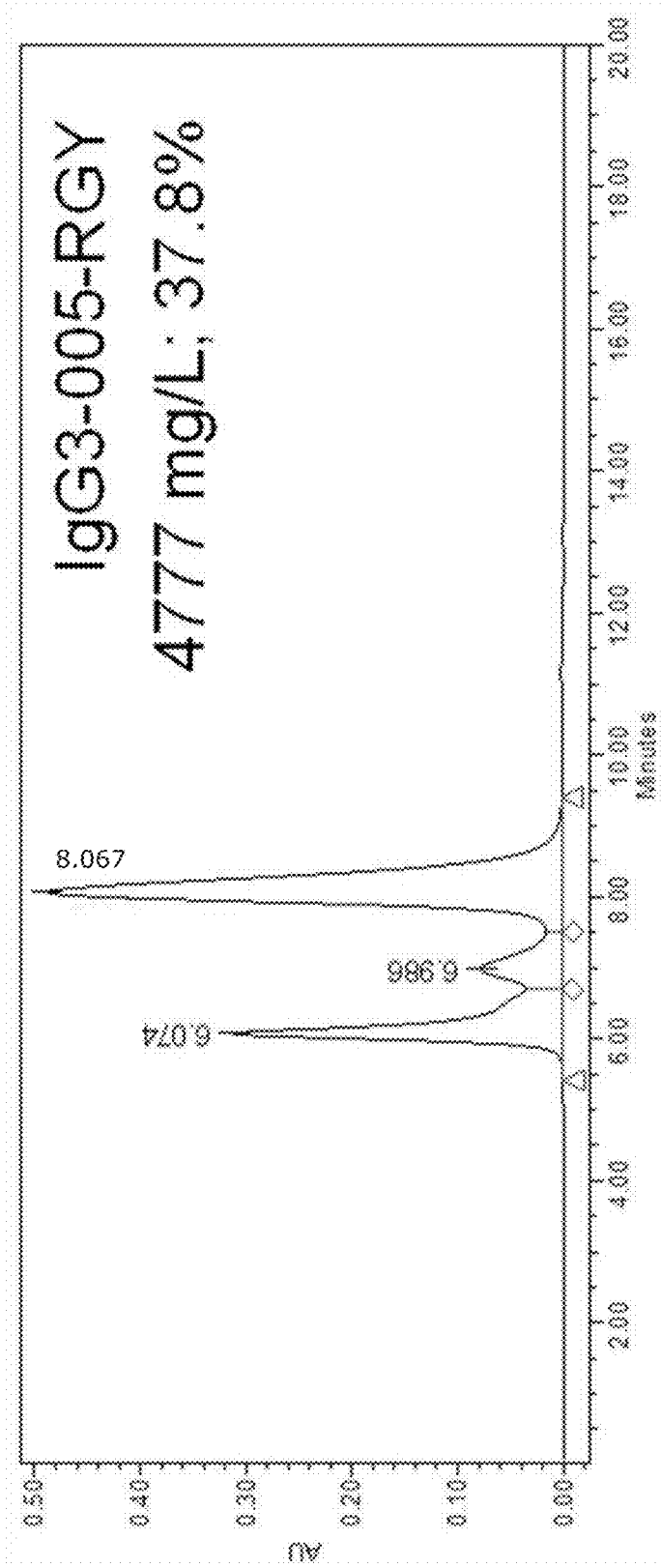
Figure 36D:
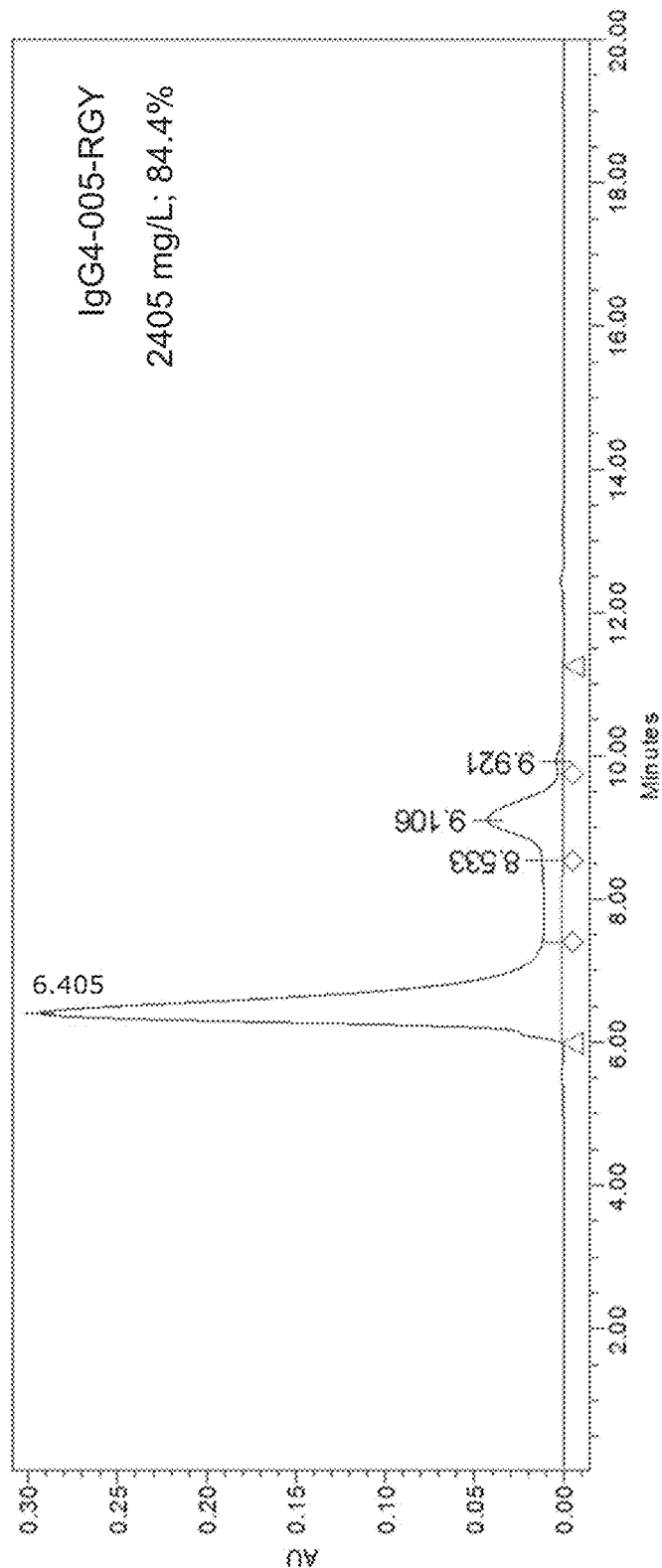
Figure 37A:
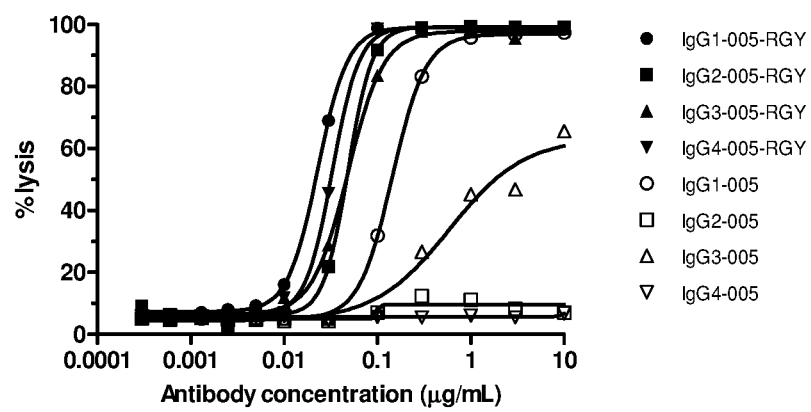
FIGS. 37A and 37B: CDC efficacy by a concentration series of 005 antibody variants in different IgG isotype backbones on CD38-positive Daudi (FIG. 37A) and Wien133 (FIG. 37B) cells.
Figure 37B:
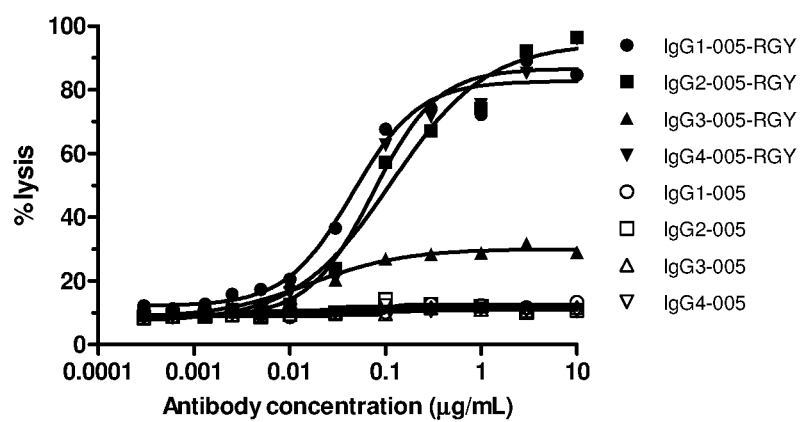

FIG. 33 shows an overlay of the HP-SEC elution profiles of IgG1-005-E345R/E430G/S440Y recorded in 0.15 M NaCl/0.1 M citrate buffered at pH 6.8 (dashed line) and pH 5.0 (solid line). Consistent with the behavior in phosphate at pH 6.8, in citrate pH 6.8 the antibody displayed 84% oligomerization. In stark contrast, lowering the pH to 5.0 dramatically reversed the oligomerization of IgG1-005-E345R/E430G/S440Y. The fraction multimer dropped to less than 1%, with >99% of the protein eluting as a monomeric species. The disassembly of oligomers was specific to low pH conditions and not caused by using citrate as a buffer component, as shown by the efficient oligomerization in citrate buffered at pH 6.8.

In summary, lowering the pH from 6.8 to 5.0 suffices to completely disassemble solution-phase antibody hexamers, an effect that might be explained by the charge modification of histidine amino acids present at the Fc:Fc interface crucial for hexameric antibody assembly. In addition, this behavior was specific to antibody variants containing mutations that induced Fc mediated self assembly, like IgG1-005-E345R/E430G/S440Y, while wild type antibodies remained monomeric at both pH levels.

Example 24

Introduction of the Fc-Fc Stable Hexamer Mutations E345R/E430G/S440Y Will Result in Increased Bactericidal Activity of IgG Antibodies Against Bacteria that Express Fc-Binding Surface Proteins The complement cascade system is an important host defense mechanism against pathogens and can be divided in three different activation routes to recognize pathogens: i) the antibody-mediated classical pathway, which is activated upon C1q binding to the pathogen-bound antibody, ii) the lectin and iii) the alternative pathway, in which the complement system directly recognizes and is triggered by the pathogen in the absence of antibody. The three pathways converge at the step of C3 cleavage and C3b deposition. Microorganisms have developed multiple mechanisms of complement evasion, one of which is mediated by Protein A [Joiner Ann. Rev. Microbiol. (1988) 42:201-30; Foster Nat Rev Microbiol (2005) December; 3(12):948-58]. Protein A was first identified in the cell wall of *Staphylococcus aureus* and is well known for its binding to the Fc region of IgG (Deisenhofer et al., Biochem (1981) 20, 2361-70; Uhlen et al., J. Biol. Chem (1984) 259, 1695-1702). So far, the antiphagocytotic effect of Protein A and its role in the pathogenesis of *S. aureus* was explained by the interaction between Protein A and IgG, which results in an incorrect antibody orientation to be recognized by the neutrophil Fc receptor (Foster Nat Rev Microbiol (2005) December; 3(12):948-58). In example 4, it was shown that CDC mediated by B cell-specific IgG1 antibodies was inhibited by the competing Fc-binding peptide DCAWHLGELVWCT. The peptide targets the consensus binding site on IgG Fc that coincides with the binding site for Protein A, Protein G and rheumatoid factor (Delano et al., Science 2000 Feb. 18; 287(5456):1279-83). Based on these data, it was speculated that the Protein A-mediated bacterial complement evasion mechanism could work by competing for Fc binding, resulting in destabilization of the Fc-Fc interaction of a microbe-specific antibody, and consequently inhibition of antibody-mediated complement activation. Moreover, in example 4, it was also shown that B cell-specific IgG1 antibodies containing the CDC-enhancing E345R mutation were less sensitive to inhibition of CDC by the competing Fc-binding peptide DCAWHLGELVWCT than the parent wild type antibodies. By extrapolating these results to Fc binding proteins expressed on microbes, increased stabilization of the IgG1 Fc-Fc interactions by the E345R mutation would make microbe-specific antibodies less prone to complement inhibition by an escape strategy of the pathogen via Fc binding competition by microbial surface proteins, such as Protein A. Consequently, introduction of the E345R mutation in IgG antibodies directed against a bacterium would result in increased C3b deposition on bacteria and increased bactericidal activity compared to the parent wild type antibodies. It is expected, that a stabilized hexamer (IgG-E345R/E430G/S440Y) that is already oligomerized before binding to a microbe target would be even more resilient to e.g. Protein A binding than IgG antibodies containing the single E345R mutation. Consequently, introduction of the E345R/E430G/S440Y mutations in IgG antibodies directed against microbes would result in increased C3b deposition on microbes and increased microbial activity compared to the parent wild type antibodies.

To test if IgG1-005-E345R/E430/S440Y oligomerization can inhibit binding to protein A, purified protein preparations of IgG1-005 and IgG1-005-E345R/E430/S440Y were analyzed by two orthogonal methods:

1) IgG concentration determination by measuring absorbance at 280 nm wavelength using a Nanodrop ND-1000 spectrophotometer (Isogen Life Science, Maarssen, The Netherlands).

2. IgG concentration determination using an Octet QK instrument (Fortebio, Menlo Park, USA), in Octet Sample Diluent and using ready-to-use protein A sensortips (Fortebio, Menlo Park, USA) in direct comparison with an IgG standard (Siemens) reference curve.

By determining the ratio between the concentration determined by A280 over the concentration determined using Octet-Protein A, it was observed that IgG1-005-E345R/E430/S440Y is indeed less prone to bind Protein A than IgG1-005 (table 11).

TABLE 11

Antibody concentrations by absorbance at 280 nm and Octet-Protein A

| Antibody | A280 (µg/ml) | Octet-Protein A (µg/ml) | A280/Protein A × 100 (%) |
|---|---|---|---|
| IgG1-005-E345R-E430G-S440Y | 2905 | 2052.5 | 0.71 |
| IgG1-005 | 3818 | 3619.6 | 0.95 |

As an in vitro measure for complement-mediated bacterial killing, both phagocytosis by neutrophils and the generation of C3a in the plasma, which coincides with C3b deposition on the bacteria, can be determined. Indeed, it has been described that C3b deposition on *S. aureus* results in enhanced phagocytosis and correlates with bacterial killing (Rooijakkers et. al., Nature Immunology 2005: 6, 920-927).

*S. aureus* will be labelled with FITC by incubating an exponentially growing bacterial culture with 100 µg/mL FITC for 1 h at 37° C. in 0.1 M carbonate buffer (pH 9.6).

Human polymorph nuclear cells (PMN) will be isolated using a Ficoll gradient. FITC-labelled bacteria will be opsonized with a concentration series of specific antibodies with or without the mutation E345R/E430G/S440Y. Phagocytosis will be performed in vitro by incubating $1\times10^8$ opsonized FITC-labelled bacteria with human PMN in the presence of 25% IgG-depleted serum as complement source for 25 min at 37° C. in a total volume of 200 µL under vigorous shaking. The cells will be fixed and erythrocytes lyzed by incubation with BD FACS lysing solution for 15 min at room temperature. After washing, phagocytosis will be measured by FACS. The neutrophil population will be selected through forward and side scatter gating and phagocytosis will be expressed as the mean fluorescence in the neutrophil population. Alternatively, C3a generation will be measured in the samples by ELISA as a measure for complement activation and C3b deposition.

It is expected that the *S. aureus*-specific antibodies containing the E345R/E430G/S440Y mutation will induce more complement activation and phagocytosis by neutrophils than the parent wild type antibodies. An example of an antibody that could be used in such experiments is the chimeric monoclonal IgG1 pagibaximab (BSYX-A110; Biosynexus), targeting Lipoteichoic acid (LTA) that is embedded in the cell wall of staphylococci (Baker, Nat Biotechnol. 2006 December; 24(12):1491-3; Weisman et al., Int Immunopharmacol. 2009 May; 9(5):639-44).

Example 25

The Formation of Non-Covalent Hexameric IgG Complexes by Introducing the E345R/E430G/S440Y Triple Mutation Occurs Irrespective of the Fab Domain The formation in solution of non-covalently bound, hexameric antibody complexes by introducing the E345R/E430G/S440Y (RGY) triple mutation was demonstrated for CD38 antibody 005 in Example 20. In this experiment formation of non-covalent hexameric IgG complexes of other human IgG1 antibodies that differ in their Fab domains: CD20 antibodies 7D8 and rituximab, EGFR antibody 2F8 and *C. albicans* mannan antibody M1g1. The generation and purification of the triple mutant antibodies and HP-SEC analyses were performed essentially as described in Example 20.

FIG. 34 shows that all triple mutant antibodies showed a large fraction oligomer: IgG1-7D8-RGY (67.2%) (FIG. 34A), IgG1-ritux-RGY (83.6%) (FIG. 34B), IgG1-2F8-RGY (74.5%) (FIG. 34C), and IgG1-M1-RGY (74.5%) (FIG. 34D). These data indicate that the concept of E345R/E430G/S440Y for inducing self-assembly of antibodies into hexamers in solution can be generally applied to IgG1 sequences, irrespective of Fab domain primary structure.

Example 26

CDC by CD20 Antibodies Containing the E345R/E430G/S440Y Triple Mutation in an Ex Vivo CDC Assay on Patient-Derived CD20-Positive CLL Cells Frozen CLL PB CD19+/CD5+ B cells (Relapsed/Refractory) isolated from CLL peripheral blood mononuclear cells were purchased from Allcells, Emeryville, Calif. CDC was performed as described in Example 21, with the exception that 20,000 cells per 96-well plate were used. CD20 expression was determined as 39,000 Specific Antibody-Binding Capacity (sABC) by QIFIKIT, Dako, Glostrup, Denmark. FIG. 35 shows that CD20 antibodies containing the E345R/E430G/S440Y triple mutation showed functional CDC activity on CD20-positive primary CLL cells. Introduction of the E345R/E430G/S440Y mutation resulted in more efficient CDC-mediated killing (lower EC50) of primary CLL cells by 7D8 (FIG. 35A) and enabled potent CDC by rituximab, which did not show any killing activity in the WT format (FIG. 35B).

Example 27

Introduction of E345R/E430G/S440Y Triple Mutation for Induction of Hexamerization and Increased CDC can be Applied to Different Antibody Isotypes Isotypic variants of the CD38 antibody IgG1-005 were generated with constant domains of human IgG2, IgG3 or IgG4 yielding IgG2-005, IgG3-005 and IgG4-005 by methods known in the art. Furthermore, the triple mutation E345R/E430G/S440Y was introduced in all these antibodies, yielding IgG2-005-RGY, IgG3-005-RGY and IgG4-005-RGY.

HP-SEC analysis of the different isotypes was performed as described in Example 20.

FIG. 36 shows that the tested isoforms containing the E345R/E430G/S440Y triple mutation formed hexameric complexes in solution: IgG1-005-RGY (79.2% multimeric) (FIG. 36A), IgG2-005-RGY (46.1% multimeric) (FIG. 36B), IgG3-005-RGY (37.8% multimeric) (FIG. 36C), and IgG4-005-RGY (84.4% multimeric) (FIG. 36D).

CDC efficacy of the different isotypes was compared by testing unpurified antibody concentration series (0.0003-10 μg/mL in 2-fold dilutions) in an in vitro CDC assay as described in Example 18. FIG. 37 shows that introduction of the RGY triple mutation enabled potent CDC on Daudi cells (FIG. 37A) by all IgG isotypes tested. These results were confirmed using CDC on Wien133 cells (FIG. 37B), albeit that IgG3-005-RGY displayed limited CDC activity relative to other isotypic variants. These data for the RGY triple mutants are similar as shown for E345R mutants in Example 18, FIG. 19.

Example 28

Combinations of Mutations for Inducing the Formation of Non-Covalent Oligomeric Complexes in Solution Example 20 describes that antibody IgG1-005 containing the three mutations E345R, E430G, and S440Y (RGY) forms oligomeric complexes in solution. Antibodies containing variants of this triple mutation with an amino acid substitution at either one of these three positions were tested for their capacity to form oligomeric complexes in solution. As an example of the class of possible E345R substitutions, consisting of E345 to A/C/D/F/G/H/I/K/L/M/N/P/Q/R/S/T/V/W/Y, E345K was tested in combination with E430G/S440Y. As an example of the class of possible E430G substitutions, consisting of E430 to A/C/D/F/G/H/I/K/L/M/N/P/Q/R/S/T/V/W/Y, E430S was tested in combination with E345R/S440Y. The class of possible S440Y substitutions consists of proteins with an amino acid in at least one position selected from the group consisting of S440, Y436, D/E356, T359, E382, N434, Q438, I253 and S254, that is Y or W; not Y; not D or E; not T; not E; not N; not Q; not I; and not S, for each position, respectively. As an example of this class of S440Y substitutions, Y436I and S440W were tested in combination with E345R/E430G. Mutation combinations E345K/E430G/S440Y (denoted RGY), E345R/E430S/S440Y (denoted RSY), E345R/E430G/S440W (denoted RGW), or E345R/E430G/Y436I (denoted RGI) were introduced in the CD38 antibody IgG1-005 by methods known in the art, yielding IgG1-005-KGY, IgG1-005-RSY, IgG1-005-RGW, and IgG1-005-RGI, respectively.

Figure 38A:
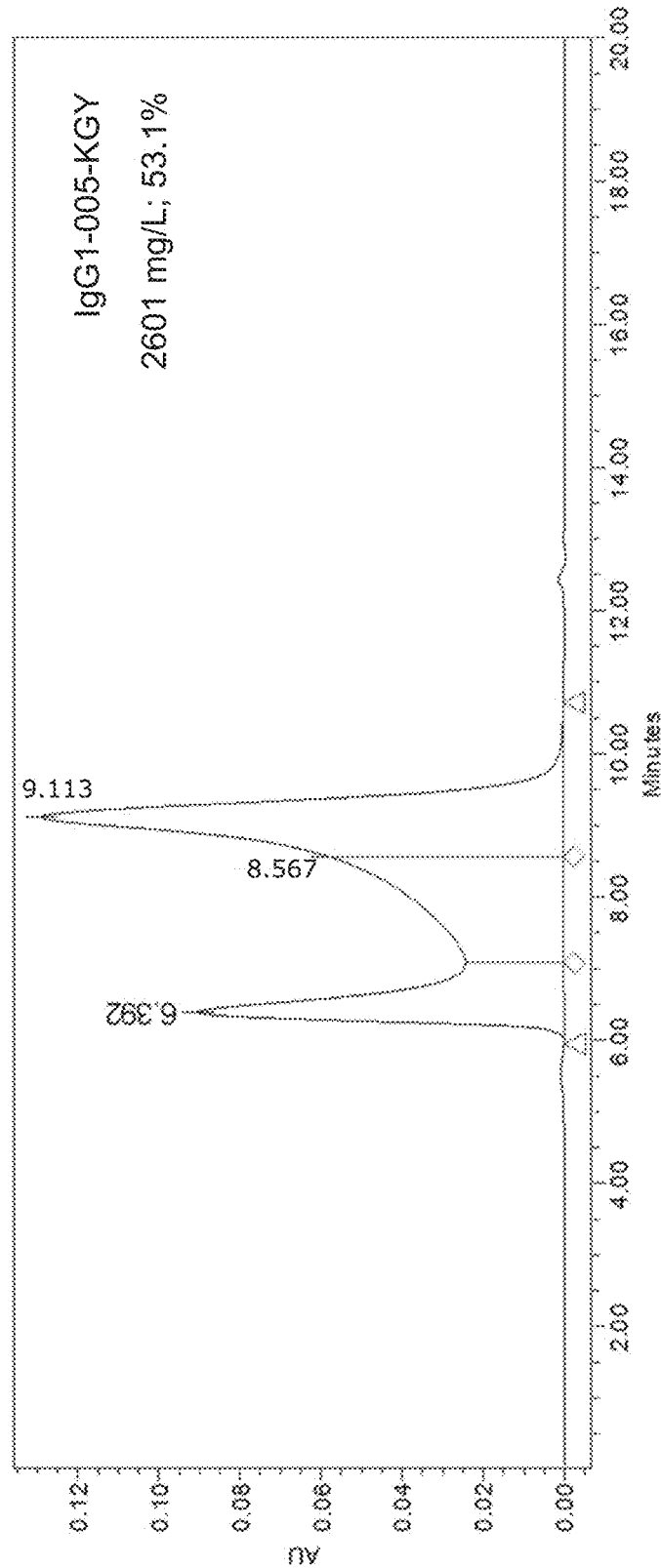
Figure 38B:
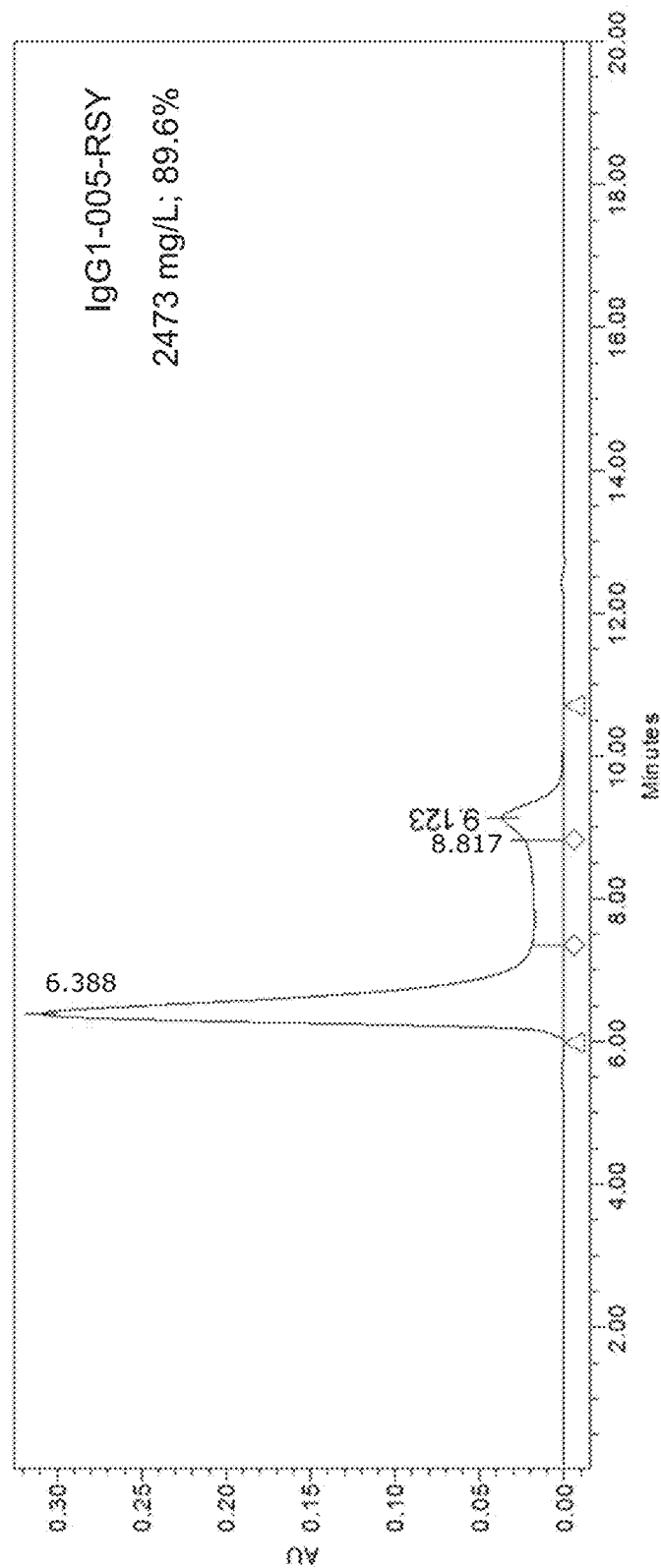
Figure 38D:
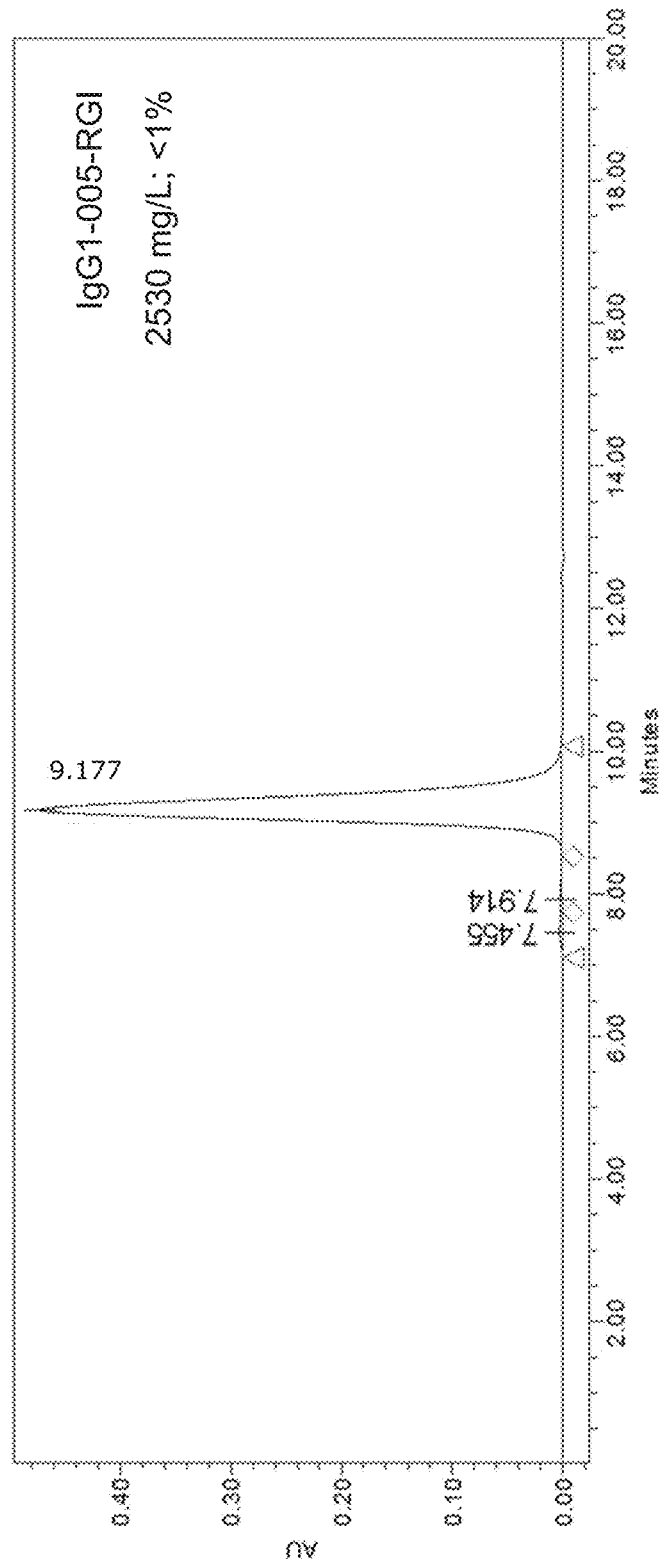

HP-SEC analysis was performed as described in Example 20. FIG. 38 shows that similar to IgG1-005-RGY (Example 20, FIG. 23), IgG1-005-KGY (FIG. 38A), IgG1-005-RSY (FIG. 38B), and IgG1-005-RGW (FIG. 38C) formed oligomeric complexes in solution with varying efficiency. For mutants IgG1-005-KGY and IgG1-005-RGW, the observed A280 signal migrating in between the oligomer and monomer peaks suggested that the HP-SEC method may contribute to destabilization of oligomeric complexes, as described in Example 20.

Figure 39A:
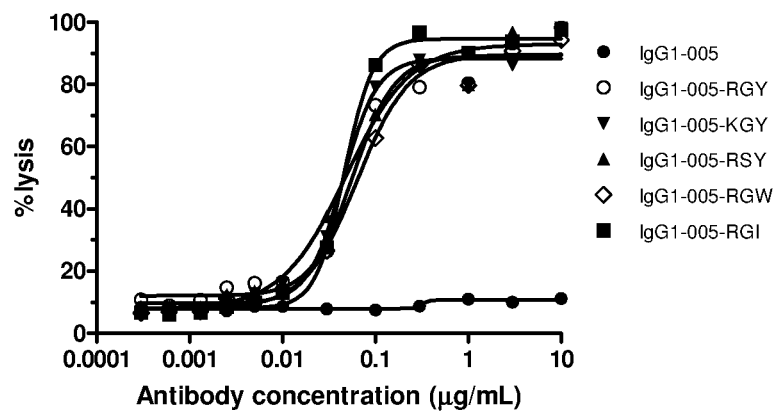
FIGS. 39A and 39B: CDC efficacy by a concentration series of IgG1-005-RGY, IgG1-005-KGY, IgG1-005-RSY, IgG1-005-RGW, and IgG1-005-RGI on CD38-positive Wien133 (FIG. 39A) and Ramos (FIG. 39B) cells.
Figure 39B:
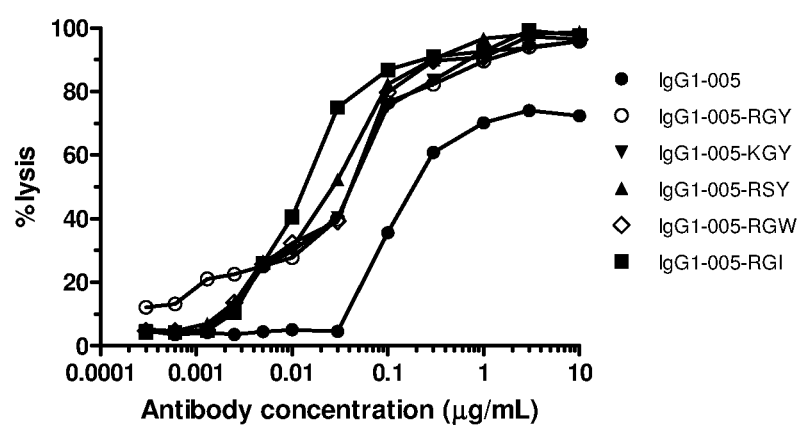

CDC efficacy of the antibodies was compared by testing unpurified antibody concentration series (0.0003-10 µg/mL in 3-fold dilutions) in an in vitro CDC assay as described in Example 18. FIG. 39A shows that all tested triple mutation combinations endowed IgG-005 with the capacity to kill Wien133 cells in an in vitro CDC assay, where wild type IgG-005 does not show any killing. FIG. 39B shows that also Ramos cells were killed more efficiently by the tested triple mutant antibodies as compared to wild type IgG1-005.

These data show that oligomerization in solution and/or induction of CDC can be induced by IgG1-005-KGY, IgG1-005-RSY, IgG1-005-RGW and IgG1-005-RGI, suggesting that mutations selected from any possible naturally occurring amino acid E345R substitutions, any possible naturally occurring amino acid E430G substitutions, or the amino acids tryptophan or tyrosine may be possible amino acid substitutions for S440, can substitute for E345R, E430G, and S440Y, respectively. Furthermore, the HP-SEC data suggest that such substitutions can modulate the interaction strength between the Fc-containing polypeptide subunits of the oligomeric complex.

Example 29

Antibodies Containing E345R/E430G/S440Y Triple Mutations can be Assembled into Hetero-Oligomeric Rings Example 5, FIG. 7 demonstrates that antibodies containing one of the two complementary mutations K439E or S440K, illustrated in FIG. 4, are inhibited in their CDC activity, whereas they could form complexes capable of CDC activation when mixed. Example 20 describes the construction of antibody IgG1-005-E345R/E430G/S440Y (here referred to as IgG1-005-RGY), which formed oligomeric, most likely hexameric, complexes in solution, that also showed enhanced CDC activity compared to wild type IgG1-005 (Example 21, FIG. 26). Example 28 describes that also IgG1-005-KGY, IgG1-005-RSY, IgG1-005-RGW and IgG-005-RGI showed enhanced CDC compared to IgG1-005. To test if solution-phase oligomerization could be restricted to mixtures of non-self-interacting antibodies, antibody variants of IgG1-005-RGY were generated that each contained one of the two complementary mutations K439E or S440K that prohibited self-oligomerization.

Mutation K439E was introduced into IgG1-005-E345R/E430G/S440Y by methods known in the art, yielding IgG1-005-E345R/E430G/K439E/S440Y (IgG1-005-RGEY). Mutation S440K was introduced into IgG1-005-E345R/E430G by methods known in the art, yielding IgG1-005-E345R/E430G/S440K (IgG1-005-RGK). Mutations Y436I and S440K were introduced into IgG1-005-E345R/E430G by methods known in the art, yielding IgG1-005-E345R/E430G/Y436I/S440K (IgG1-005-RGIK). The rationale to include Y436I in IgG1-005-RGIK was to compensate for the absence of the oligomerization enhancing mutation S440Y.

Figure 40:
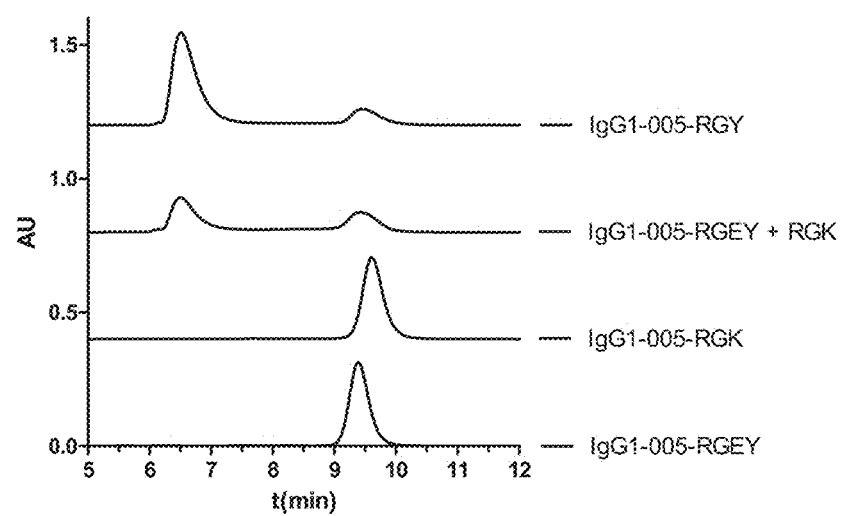
FIG. 40: HP-SEC analysis of IGG1-005-RGE, IgG1-005-RGK and a mixture of IgG1-005-RGE+IgG1-005-RGK (AU indicates "arbitrary units").

HP-SEC analysis of the different antibody variants and equimolar antibody mixtures was performed as described in Example 20, but using PBS (12.6 mM sodium phosphate, 140 mM NaCl, pH 7.4; B. Braun, Oss, The Netherlands) as the mobile phase. FIG. 40 shows that the introduction of K439E in IgG1-005-RGY prohibited self-oligomerization of IgG1-005-RGEY (2.7% multimers). Likewise, substituting S440Y in IgG1-005-RGY with mutation S440K prohibited self-oligomerization of IgG1-005-RGK (2.2% multimers). Remarkably, a mixture of the solution-phase monomeric (i.e. single dimeric antibodies) IgG1-005-RGEY plus IgG1-005-RGK formed oligomeric species with equivalent HP-SEC mobility as IgG1-005-RGY (65% multimers), albeit with lower efficiency than IgG1-005-RGY (84% multimers).

Figure 41:
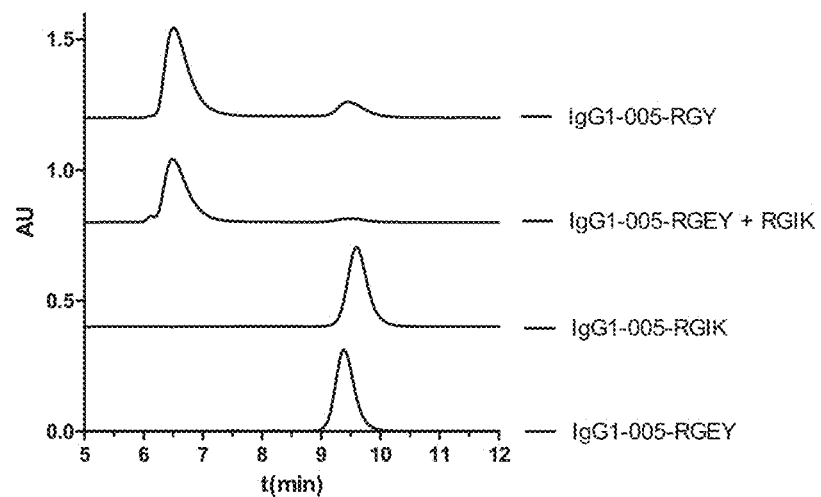
FIG. 41: HP-SEC analysis of IgG1-005-RGE, IgG1-005-RGIK and a mixture of IgG1-005-RGE+IgG1-005-RGIK (AU indicates "arbitrary units").

FIG. 41 shows that the introduction of Y436I plus S440K into IgG1-005-E345R/E430G prohibited self-oligomerization of IgG1-005-RGIK (1.8% multimers). Again, a mixture of the solution-phase monomeric IgG1-005-RGEY plus IgG1-005-RGIK formed oligomeric species with equivalent HP-SEC mobility as IgG1-005-RGY, but now with high efficiency (93% multimers).

Figure 42:
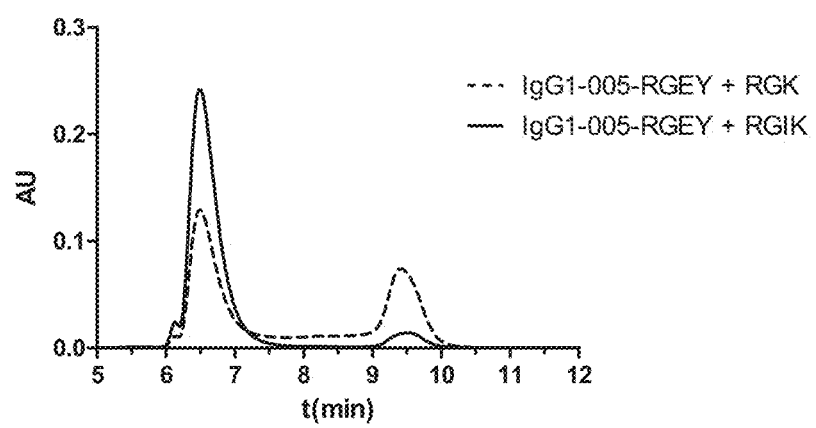
FIG. 42: Overlay of HP-SEC traces of mixture IgG1-005-RGE+IgG1-005-RGK and mixture IgG1-005-RGE+IgG1-005-RGIK (AU indicates "arbitrary units").

FIG. 42 shows a direct comparison of mixture IgG1-005-RGEY plus IgG1-005-RGK with mixture IgG1-005-RGEY plus IgG1-005-RGIK, demonstrating that IgG1-005-RGIK (65% multimers) could induce heteromeric oligomerization with IgG1-005-RGEY more efficiently than IgG1-005-RGK (93% multimers). The presence of the extra oligomerization and CDC-enhancing mutation Y436I in IgG1-005-RGIK apparently stabilized the formation of complexes with IgG1-005-E345R/E430G/K439E/S440Y.

In summary, IgG1-005 antibodies containing mutations E345R/E430G and the additional self-oligomerization inhibiting mutations K439E/S440Y, or S440K, or Y436I/S440K, could be reassembled into multimeric complexes, by mixing antibody molecules with complementary mutations (K439E in one, S440K in the other antibody).

Example 30

Figure 43:
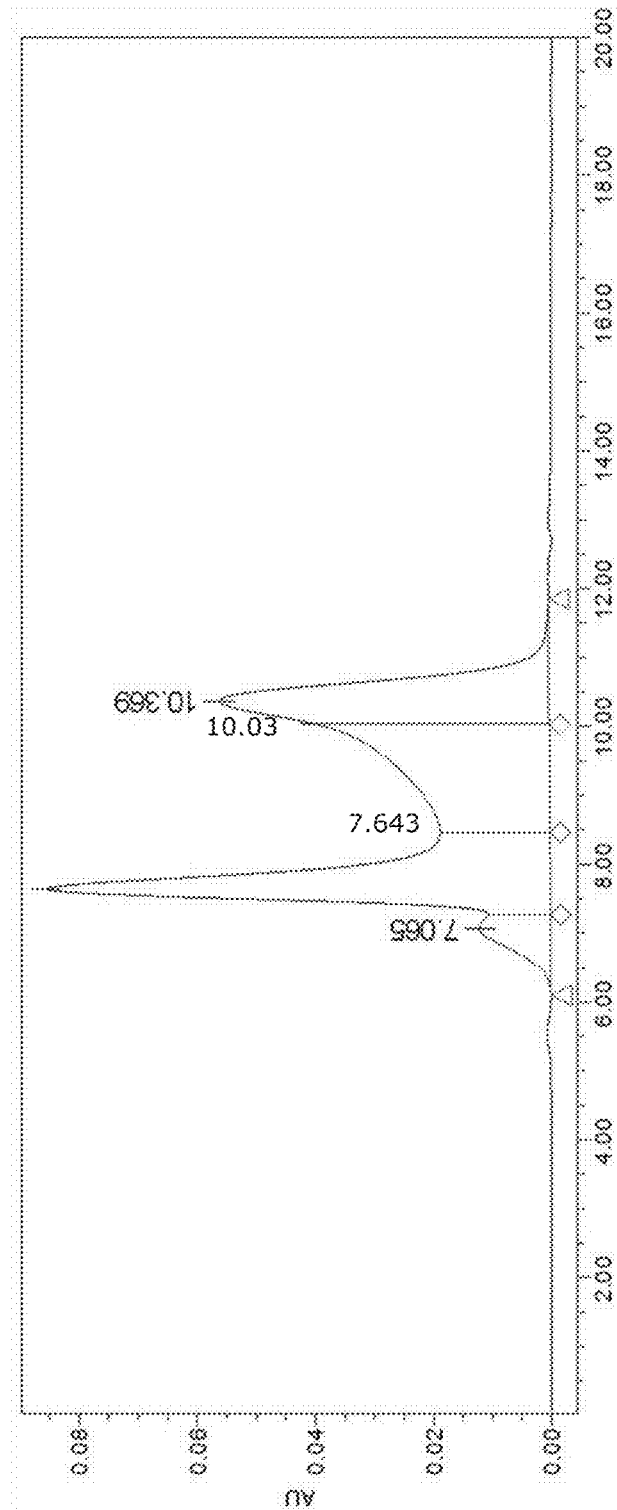
FIG. 43: HP-SEC analysis of triple mutant Fc fragment (Fc-RGY).

Fc Fragments can be Recruited to the Cell Surface by Cell Binding Antibodies, if Both Components Contain the E345R/E430G/S440Y Triple Mutations The three mutations E345R, E430G and S440Y were introduced in a IgG1m(f) Fc fragment by methods known in the art, creating Fc-RGY. Protein was expressed and purified as described in Example 20. HP-SEC analysis of the Fc-RGY sample was performed as described in Example 20. FIG. 43 shows that under the used HP-SEC conditions, Fc-RGY showed approximately 28% monomers and 72% oligomers distributed over multiple states, as measured by fraction of peak area to total area.

Next it was tested whether Fc-RGY fragments could be recruited in oligomeric complexes with IgG1-RGY antibodies in solution. Therefore, 6 µg/mL Alexa-647-labeled Fc-RGY (Fc-RGY-A647,) was mixed 1:1 with a concentration series (0.001-3 µg/mL in 3-fold dilutions) of an EGFR-specific or CD20-specific antibody. Immediately after mixing, the samples were added to 0.1×10⁶ EGFR-positive A431 or CD20-positive Daudi cells and incubated for 45 minutes at 4° C. After washing the cells twice with RPMI1640/0.1% BSA (3 minutes, 1200 rpm), the cells were resuspended in PBS/0.1% BSA/0.02% azide and analyzed on a FACS Canto II (BD Biosciences).

Figure 44A:
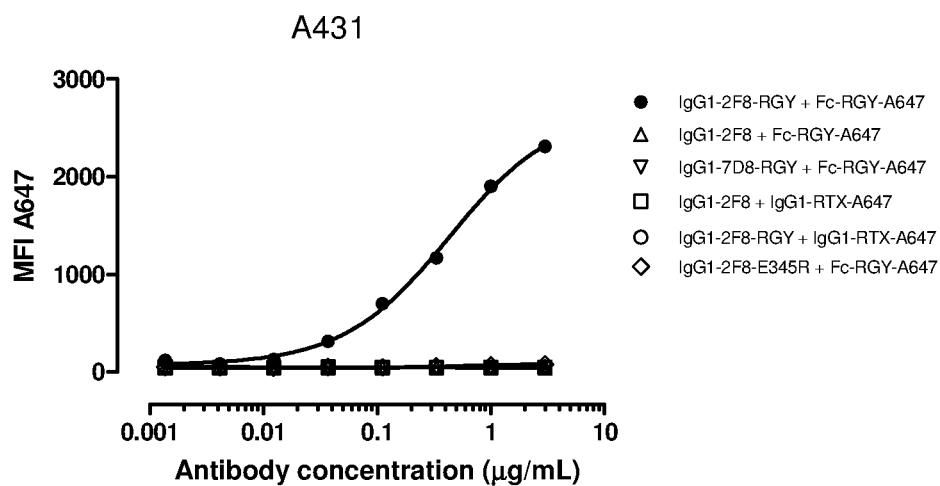
FIGS. 44A and 44B: FACS analysis of A431 (FIG. 44A) and Daudi (FIG. 44B) cells incubated with mixtures of Fc-RGY-647 with full length IgG1-RGY antibodies.

FIG. 44A shows that mixing Fc-RGY-A647 with EGFR-specific IgG1-2F8-RGY antibody resulted in a dose-dependent fluorescent signal on EGFR-positive A431 cells. In contrast, the CD20-specific IgG1-7D8-RGY was not able to recruit Fc-RGY-A647 to the CD20-negative A431 cells. None of the other tested control combinations of Fc-RGY-A647 mixed with either IgG1-2F8 or IgG1-2F8-E345R resulted in a fluorescent signal. Also, neither of the control combinations of CD20-specific IgG1-RTX-A647 mixed with IgG1-2F8 nor IgG1-2F8-RGY induced a fluorescent signal on A431 cells.

These data indicate that the labeled Fc-RGY fragment was specifically recruited to the A431 cells by incorporation into oligomeric complexes with IgG1-2F8-RGY antibodies that bind EGFR on A431 cells.

Figure 44B:
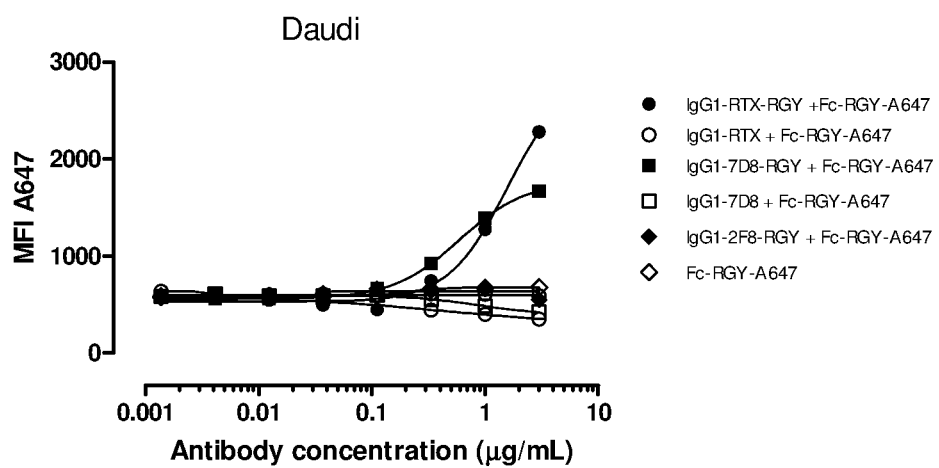

Similarly, FIG. 44B shows that the CD20-specific antibodies IgG1-7D8-RGY and IgG1-RTX-RGY were able to recruit Fc-RGY-A647 fragments to CD20-positive Daudi cells. In contrast, the EGFR-specific IgG1-2F8-RGY was not able to recruit Fc-RGY-A647 to the EGFR-negative Daudi cells. Negative control samples of either Fc-RGY-A647 alone, or Fc-RGY-A647 mixed with IgG1-7D8 or IgG1-RTX, did not yield a fluorescent signal on Daudi cells.

In summary, these data show that Fc-RGY molecules can form complexes in solution, and can be recruited to cells by RGY-containing antibodies that specifically bind the cells.

Example 31

Figure 45A:
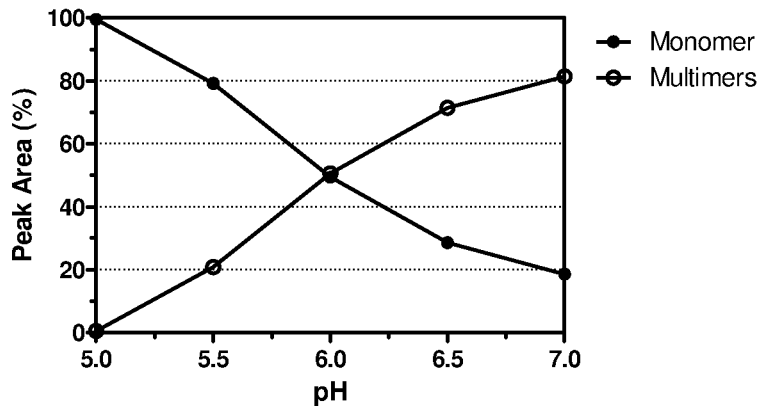
FIGS. 45A and 45B: HP-SEC analysis of IgG1-005-RGY at different pH levels. Percentages indicate total oligomers as fraction of total peak area.

Reversable Oligomerization of Antibody Molecules with Fc-Fc Interaction Enhancing Mutations can be Controlled by pH Example 23 showed that antibody IgG1-005-E345R/E430G/S440Y, here abbreviated to IgG1-005-RGY, was capable of hexamerization at pH 6.8, while lowering the pH to 5.0 dissolved the hexameric complex in individual monomeric subunits. To characterize this property in detail, 50 mM citric acid and 100 mM Na₂HPO₄ were mixed in different ratios to generate mobile phase buffers at pH 5.0, 5.5, 6.0, 6.5 and 7.0. IgG1-005-RGY samples were exchanged into these buffers and separated by HP-SEC using the matching mobile phase. FIG. 45A shows that lowering the pH resulted in disassembly of multimeric complexes into monomeric subunits; that a pH of approximately 5.0 was needed to eliminate multimers from the mixture; and that at pH 6.0, approximately half of the complexes had disassembled.

Figure 45B:
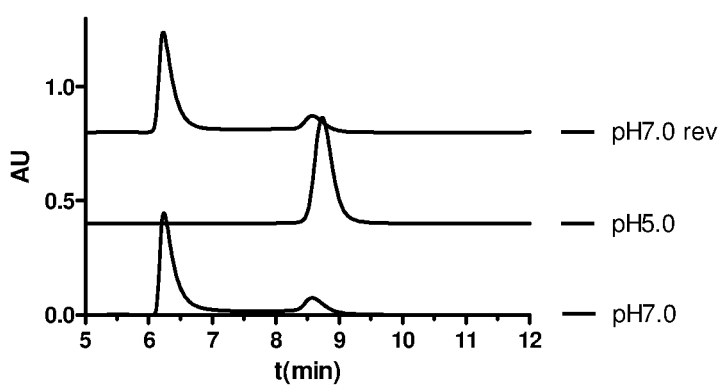

The ability to control the antibody oligomeric state by lowering and raising the pH in a reversible fashion could be useful for applications in upstream or downstream processing during manufacturing. To test if pH-mediated disassembly was reversible, a sample with antibody hexamers was brought to pH 5.0 and split into two samples, one of which was brought back to pH 7.0. FIG. 45B shows that the sample that was exposed to pH 5.0 and subsequently brought back to pH 7.0 (pH 7.0 rev), formed antibody complexes with an efficiency highly similar to the reference sample kept at pH7.0.

Example 32

IgG1-RGY Protein Purification and Downstream Processing Efficiency can be Controlled by Choice of Buffer pH Condition Protein A purification is a cornerstone of antibody downstream processing and implemented in a large number of antibody manufacturing processes. Because the protein A binding site partially overlaps with the Fc:Fc interaction interface mediating hexamerization of IgG1-005-E345R/E430G/S440Y, here abbreviated to IgG1-005-RGY, loading of protein A columns was attempted at pH 7.4, permissive of hexamerization and at pH 5.0, which blocks hexamerization as demonstrated in Example 23.

In example 20, the cloning of antibody IgG1-005-E345R/E430G/S440Y, here abbreviated to IgG1-005-RGY, was described. IgG1-005-RGY was expressed in EXPI293F cells essentially as described by the manufacturer (Invitrogen), after which the supernatant was collected by centrifugation at 300 g for 10 min. Supernatant was concentrated 4-fold using a MiniKros M155-260-01P Hollow Fiber Tangential Flow Filtration device with a 50 kDa cutoff membrane (SpectrumLabs, Rancho Dominguez Calif., USA), yielding supernatant with a protein concentration of 1.1 g/L. The supernatant was split in two parts, one of which was kept at the original pH of 7.5, while the other batch was pH adjusted to pH 5.0 by dropwise addition of 1.0 M citric acid-NaOH pH 3.0. Both batches were filtered over a 0.20 μM dead-end filter.

The supernatant batch kept at pH 7.5 was loaded at a low flow rate of 109 cm/h to mimic downstream processing conditions at manufacturing scale, on a 1.0 mL Protein A column (HiTrap MabSelectSuRe, GE Healthcare, Uppsala, Sweden), which was consecutively washed with PBS (12.6 mM sodium phosphate, 140 mM NaCl, pH 7.4; B. Braun, Oss, The Netherlands), after which bound IgG protein was eluted using 0.1 M citric acid-NaOH, pH 3.0. The eluate was immediately neutralized with 2 M Tris-HCl, pH 9.0 and dialyzed overnight to PBS. After dialysis, the sample was sterile filtered over a 0.20 μM dead-end filter.

The batch brought to pH 5.0 was loaded at a flow rate of 109 cm/h on the same 1.0 mL Protein A column (HiTrap MabSelectSuRe), which was consecutively washed with 20 mM citric acid/citrate pH 5.0, after which bound IgG protein was eluted using 0.1 M citric acid-NaOH, pH 3.0. The eluate was immediately neutralized with 2 M Tris-HCl, pH 9.0 and dialyzed overnight to PBS. After dialysis, the sample was sterile filtered over a 0.20 μM dead-end filter.

Flow-throughs of both protein purifications were collected and purified using a 5.0 mL MabSelect SuRe column yielding approximately 50 mg of protein, demonstrating that the 1.0 mL MabSelectSuRe column had been saturated effectively.

The yields of IgG1-005-RGY were determined by measuring A280 of the dialyzed elution samples using a Nanodrop device (ThermoScientific, Wilmington Del., USA). Protein A purification at 1.0 mL scale at pH 7.0 yielded 21.45 mg of IgG1-005-RGY, while purification at pH 5.0 yielded 29.14 mg of IgG1-005-RGY. In conclusion, the protein yield was increased approximately 36% by performing the binding of antibody to protein A under conditions keeping IgG1-005-RGY monomeric.

Example 33

Programmed Cell Death (PDC) by Stable Hexameric IgG2-005

To test if different isotypic variants of IgG antibodies containing the triple mutation E345R/E430G/S440Y could induce programmed cell death (PCD), antibody IgG2-005-E345R/E430G/S440Y (IgG2-005-RGY) was generated by methods known in the art. 1.0×10⁵ Ramos cells expressing CD38 were cultured for 24 hours in 96-well, U-bottom plates (Nalgene Nunc) in the presence of a dilution series (10, 3, 1, 0.3, 0.1, 0.03, 0.01, 0.005, and 0.0025 μg/mL) of wild type IgG2-005, IgG2-005-RGY, hexameric IgM-005 or human control antibodies IgG1-2F8 and IgG1-2F8-RGY, recognizing EGFR, which is not expressed on Ramos cells. PCD was quantified after these 24 hours by staining with annexin V-FITC (Annexin binding assay; BD Biosciences, San Diego, Calif., USA) according to the manufacturer's instructions. The amount of annexin V-FITC-positive cells was determined using a FACS (BD).

Figure 46:
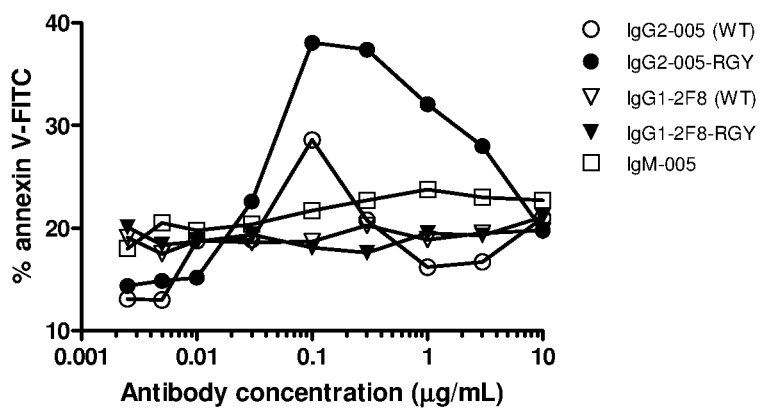
FIG. 46: Programmed cell death is induced in different isotypic variants of IgG antibodies by introduction of the triple mutation RGY.

FIG. 46 shows that IgG2-005-RGY demonstrated enhanced programmed cell death capacity compared to wild type IgG2-005 and control antibodies IgG1-2F8 and IgG1-2F8-RGY. Hexameric IgM did not induce PCD under the conditions tested.

Example 34

IgG-005-RGY Against CD38 Out Performs Hexameric IgM-005 in a CDC Assay on B Cells To compare the CDC efficacy of IgG1-005-RGY to that of IgM, the VH domain of IgG1-005 was cloned into an IgM backbone by methods know in the art, and expressed in the absence of J-chain to produce IgM hexamers against CD38. The construction of IgG1-005-E345R/E430G/S440Y (here referred to as IgG1-005-RGY) was described in Example 20.

Figure 47:
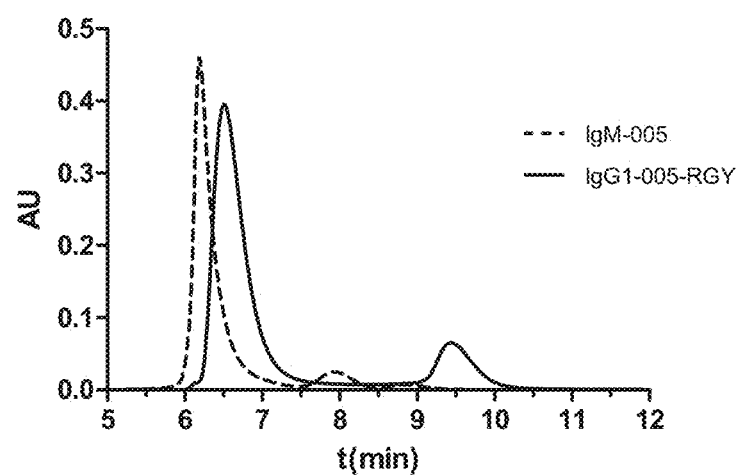
FIG. 47: HP-SEC analysis of IgG1-005-RGY (solid line) and hexameric IgM-005 (dashed line).

HP-SEC analysis of the different antibodies was performed as described in Example 20, but using PBS (12.6 mM sodium phosphate, 140 mM NaCl, pH 7.4; B. Braun, Oss, The Netherlands) as the mobile phase. FIG. 47 shows that IgM-005 expressed in the absence of J-chain yielded a molecule with slightly higher mobility in HP-SEC than IgG1-005-RGY, as could be expected due to the higher molecular weight of hexameric IgM compared to hexameric IgG1-005-RGY.

Figure 48A:
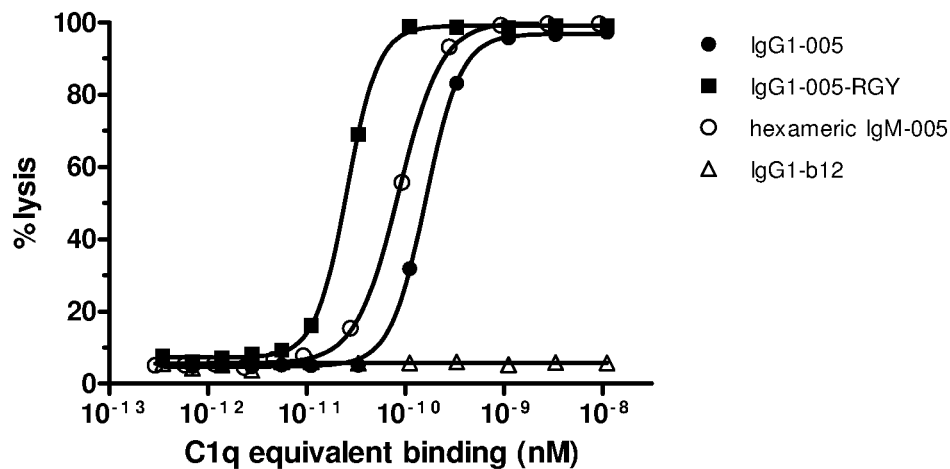
FIGS. 48A and 48B: CDC efficacy by a concentration series of IgG1-005, IgG1-005-RGY, IgM-005 on CD38-positive Daudi (FIG. 48A) and Wien133 (FIG. 48B) cells.
Figure 48B:
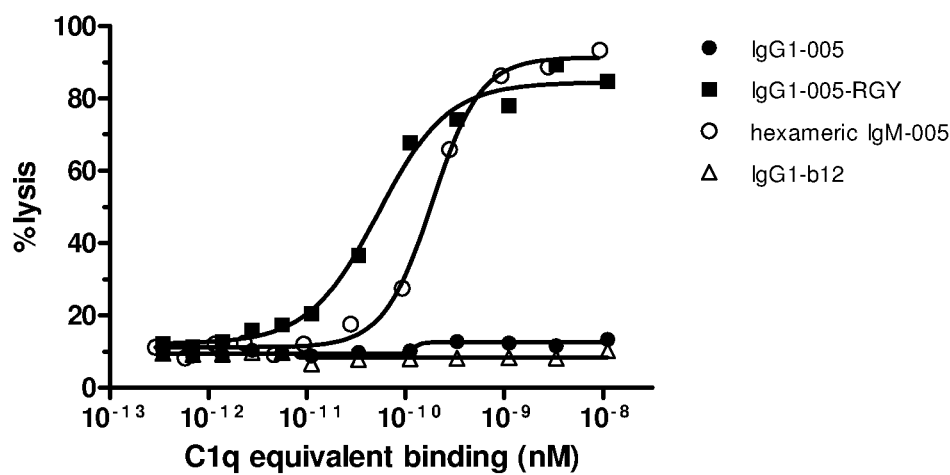

CDC efficacy of IgG1-005-RGY was compared to wild type IgG1-005 and hexameric IgM-005 by testing antibody concentration series (0.0003-10 μg/mL in 2-fold dilutions) in an in vitro CDC assay as described in Example 18. FIG. 48 shows that IgG1-005-RGY showed more potent CDC activity on Daudi and Wien133 cells than hexameric IgM-005. Wild-type IgG1-005 showed lower CDC efficacy than IgG1-005-RGY and IgM-005 on Daudi cells, and no killing activity on Wien133 cells. IgG1-b12 was used as a non-cell binding negative control antibody. Monomeric (i.e. single dimeric protein) IgG1-005, hexameric IgG1-005-RGY and hexameric IgM-005 concentrations are indicated as C1q binding equivalents to enable comparison of non-covalent IgG and covalent IgM complexes with different molecular weight.

In summary, IgG1-005-RGY could induce complement-mediated lysis of target cells more efficiently than IgM-005 at antibody concentrations binding equivalent amounts of C1q.

Example 35

Introduction of the Triple Mutations E345R/E430G/S440Y into Anti-EGFR Antibody IgG1-2F8 Enhances Efficacy of CDC-Mediated Lysis of EGFR-Positive Solid Tumor Cell Lines To test if introduction of the triple mutations E345R/E430G/S440Y into a solid tumor target antibody could lead to activation of complement-mediated lysis, IgG1-2F8-E345R/E430G/S440Y (here referred to as IgG1-2F8-RGY) was generated by methods known in the art.

CDC efficacy by IgG1-2F8-RGY was tested on EGFR-positive A431 and Difi tumor cell lines and was compared to wild type IgG1-2F8 and the control antibodies IgG1-005 and IgG1-005-RGY. The control antibodies recognize CD38, which is expressed on neither A431 nor Difi cells.

After the solid tumor cells were detached by using trypsin-EDTA in phosphate-buffered saline (PBS), the cells were washed and passed through a 40 μm nylon cell strainer (DB Falcon™) and resuspended in PBS at a concentration of 1.0×10⁶ cells/mL. Cells were stained for 30 minutes at 37° C. using SYBR Green (SYBR Green 57563 in DMSO, Invitrogen, 25000× diluted). After centrifugation (1200 rpm, 5 minutes at RT), cells were resuspended in RPMI1640/0.1% BSA at a concentration of 3.0×10⁵ cells/mL. Antibody serial dilutions (0.0003-10 μg/mL) were prepared in RPMI/0.1% BSA supplemented with TOPRO-3 (TOPRO-3 iodide T3605, diluted 1600×). Cells were seeded at 30,000 cells per well into flat bottom 96 wells plates (black 96-Well ABI™ 4315480 FMAT Plates); after addition of the antibody serial dilutions, plates were incubated for 15' on a shaker (300 rpm, RT). Normal Human Serum (NHS, Sanquin) was added at 20% final concentration. Plates were incubated for 45 minutes at 37° C. The amounts of dead cells (TOPRO-3 positive) and total cells (SYBR Green positive) were determined using a Celigo® imaging cytometer (Brooks Life Science Systems). Results were analyzed using GraphPad Prism 5.04.

Figure 49A:
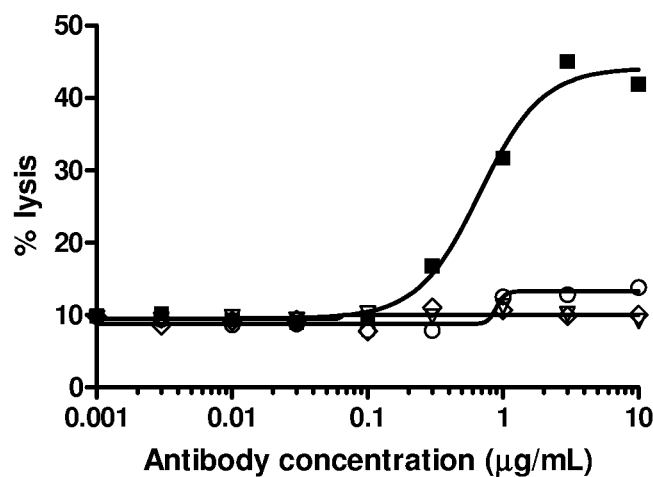
FIGS. 49A and 49B: In vitro CDC assay with IgG1-2F8-RGY on solid tumor cell lines A431 cells (FIG. 49A) and Difi (FIG. 49B).
Figure 49B:
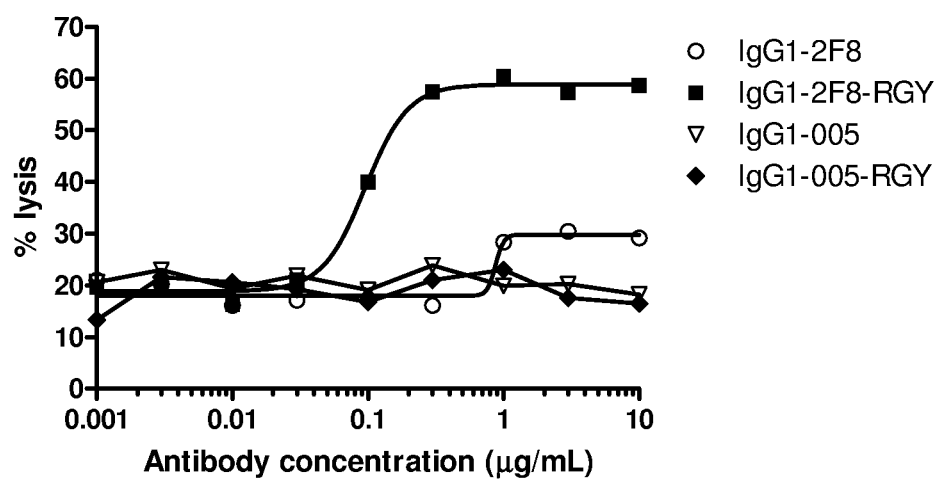

FIG. 49 shows that the efficacy to induce complement-mediated lysis of EGFR-positive solid tumor cells was considerably higher for IgG1-2F8-RGY than wild type IgG1-2F8.

Example 36

IgG1-005-RGY Shows Target-Independent Complement Activation in Contrast to Wild Type IgG1-005

Figure 50:
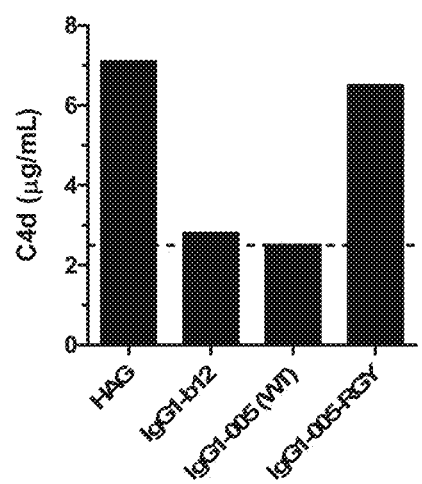
FIG. 50: C4d produced by antibodies in normal human serum as a measure for complement activation in solution.

In example 20, the cloning of antibody IgG1-005-E345R/E430G/S440Y, here abbreviated to IgG1-005-RGY, was described. To test if IgG1-005-RGY could activate complement in solution in the absence of target cells, the formation of C4d, a marker for classical complement pathway activation, was analyzed. Complement activation was determined by measuring C4d concentrations after incubating 100 μg/mL antibody in 90% normal human serum for 1 hour at 37° C. in low protein binding 96 wells polypropylene microplates (U-shaped and sterile; Greiner 650261). C4d concentrations were measured in an ELISA (MicroVue C4d EIA kit, Quidel Corporation) according to the manufacturer's instructions. A heat aggregated IgG (HAG) sample was used as positive control for complement activation in solution. FIG. 50 shows that HAG induced efficient C4d production, while wild type IgG-005 did not show complement activation under these conditions. In contrast, IgG1-005-RGY induced elevated C4d levels, indicative of complement activation in solution.

EQUIVALENTS

Those skilled in the art will recognize, or be able to ascertain using no more than routine experimentation, many equivalents of the specific embodiments of the invention described herein. Such equivalents are intended to be encompassed by the following claims. Any and all combination of embodiments disclosed in dependent claims is also contemplated to be within the scope of the invention.

The invention claimed is:

1. A dimeric protein comprising a first Fc polypeptide and a second Fc polypeptide, each Fc polypeptide comprising at least $C_H2$ and $C_H3$ regions of a human IgG1, IgG2, IgG3, or IgG4, wherein in one or both Fc polypeptides
   (a) the amino acid in the position corresponding to E345 in a human IgG1 heavy chain is R or K,
   (b) the amino acid in the position corresponding to E430 in a human IgG1 heavy chain is G or S, and
   (c) the amino acid in the position corresponding to S440 in a human IgG1 heavy chain is Y or W,
   wherein the numbering is according to the EU Index as set forth in Kabat.

2. The dimeric protein of claim 1, wherein in one or both Fc polypeptides, the amino acids at the positions corresponding to E345, E430, and S440 are R, G, and Y, respectively; K, G, and Y, respectively; R, S, and Y, respectively; or R, G, and W, respectively.

3. The dimeric protein of claim 1, wherein one or both Fc polypeptides further comprises a region capable of covalent binding between said first and second Fc polypeptides.

4. The dimeric protein of claim 1, wherein one or both Fc polypeptides further comprises a hinge region of an immunoglobulin heavy chain.

5. The dimeric protein of claim 3, wherein said first and second Fc polypeptides are interconnected via hinge region disulphide bonds.

6. The dimeric protein of claim 1, which is an antibody.

7. The dimeric protein of claim 6, wherein one or both Fc polypeptides comprise a full-length heavy chain constant region.

8. The dimeric protein of claim 1, further comprising a drug, toxin, radiolabel, radioopaque agent, paramagnetic agent, fluorescent agent, phosphorescent agent, ultrasound enhancing agent, or polyethyleneglycol (PEG).

9. The dimeric protein of claim 1, which is a homodimer or a heterodimer.

10. The dimeric protein of claim 1, which is a heterodimer.

11. The dimeric protein of claim 1, which is predominantly in oligomeric form in a phosphate buffer at a pH of about 6.8.

12. The dimeric protein of claim 1, which is predominantly in monomeric form at a pH of less than 6.0.

13. An oligomer comprising at least two non-covalently associated dimeric proteins, each according to claim 1.

14. A hexamer comprising six non-covalently associated dimeric proteins, each according to claim 1.

15. The hexamer of claim 14, wherein at least one dimeric protein of the hexamer is an antibody.

16. A hexamer comprising six non-covalently associated molecules, at least one of which is a dimeric protein according to claim 1, and at least one of which is an antibody comprising an Fc domain comprising at least CH2, CH3 and hinge regions.

17. The hexamer of claim 16, wherein the antibody is a monoclonal or polyclonal antibody.

18. A composition comprising the dimeric protein of claim 1, and a pharmaceutically acceptable carrier.

19. A composition comprising the dimeric protein of claim 1, one or more antibodies, and a pharmaceutically acceptable carrier.

20. A composition comprising first and second dimeric proteins according to claim 1, and a pharmaceutically acceptable carrier.

21. A composition comprising at least three dimeric proteins according to claim 1.

22. The composition of claim 20, wherein in one or both of said first and second Fc polypeptides of said first and second dimeric proteins, the amino acids at the positions corresponding to E345, E430, and S440 in a human IgG1 heavy chain are R, G, and Y, respectively.

23. The composition of claim 20, wherein at least one of the first and second dimeric proteins is an antibody.

24. The composition of claim 23, wherein both the first and the second dimeric proteins are antibodies.

25. The composition of claim 24, wherein the first and second antibodies bind to the same epitope of the same antigen.

26. The composition of claim 25, wherein the first and second antibodies comprise the same variable heavy and light chain region sequences.

27. The composition of claim 20, wherein the pharmaceutically acceptable carrier is an aqueous buffered solution, wherein the pH is at least about 6.5.

28. The composition of claim 20, wherein the pharmaceutically acceptable carrier is an aqueous buffered solution, wherein the pH is less than pH 6.5.

29. The composition of claim 28, comprising an acetate, histidine, glycine, citrate, nicotinate, lactate, or succinate buffer system.

30. A kit-of-parts comprising at least one dimeric protein according to claim 1.

31. The dimeric protein of claim 1, wherein in one or both Fc polypeptides, the amino acids in the positions corresponding to E345, E430, and S440 are R, G, and Y, respectively.

32. The dimeric protein of claim 1, wherein in one or both Fc polypeptides, the amino acids in the positions corresponding to E345, E430, and S440 are K, G, and Y, respectively.

33. The dimeric protein of claim 1, wherein in one or both Fc polypeptides, the amino acids in the positions corresponding to E345, E430, and S440 are R, S, and Y, respectively.

34. The dimeric protein of claim 1, wherein in one or both Fc polypeptides, the amino acids in the positions corresponding to E345, E430, and S440 are R, G, and W, respectively.

35. A polypeptide comprising an Fc region of a human IgG1, IgG2, IgG3, or IgG4, wherein:
    (a) the amino acid in the position corresponding to E345 in a human IgG1 heavy chain is selected from the group consisting of R and K,
    (b) the amino acid in the position corresponding to E430 in a human IgG1 heavy chain is selected from the group consisting of G and T, and
    (c) the amino acid in the position corresponding to S440 in a human IgG1 heavy chain is selected from the group consisting of Y and W,
    wherein the numbering is according to the EU Index as set forth in Kabat.

36. The dimeric protein of claim 1, wherein one or both Fc polypeptides comprise at least CH2 and CH3 regions of human IgG1.

37. A dimeric protein comprising a first Fc polypeptide and a second Fc polypeptide, each Fc polypeptide comprising at least $C_H2$ and $C_H3$ regions of a human IgG1, IgG2, IgG3, or IgG4, wherein in one or both Fc polypeptides, the amino acids at positions corresponding to E345, E430, and S440 in a human IgG1 heavy chain are
    (a) R, G, and Y, respectively;
    (b) K, G, and Y, respectively;
    (c) R, S, and Y, respectively; or
    (d) R, G, and W, respectively.

38. An antibody comprising a first Fc polypeptide and a second Fc polypeptide, each Fc polypeptide comprising at least $C_H2$ and $C_H3$ regions of a human IgG1, IgG2, IgG3, or IgG4, wherein in one or both Fc polypeptides
    (a) the amino acid in the position corresponding to E345 in a human IgG1 heavy chain is selected from the group consisting of R and K,
    (b) the amino acid in the position corresponding to E430 in a human IgG1 heavy chain is selected from the group consisting of G, and S, and
    (c) the amino acid in the position corresponding to S440 in a human IgG1 heavy chain is selected from the group consisting of Y and W,
    wherein the numbering is according to the EU Index as set forth in Kabat.

39. The antibody of claim 38, wherein in one or both Fc polypeptides, the amino acids at positions corresponding to E345, E430, and S440 in a human IgG1 heavy chain are
    (a) R, G, and Y, respectively;
    (b) K, G, and Y, respectively;
    (c) R, S, and Y, respectively; or
    (d) R, G, and W, respectively.

40. The antibody of claim 38, wherein each Fc polypeptide comprises at least the $C_H2$ and $C_H3$ regions of a human IgG1.

41. The antibody of claim 38, which is predominantly in monomeric form at a pH of less than 6.0.

42. The antibody of claim 38, which is predominantly in oligomeric form in a phosphate buffer at a pH of about 6.8.

43. The composition of claim 20, wherein in one or both of said first and second Fc polypeptides of said first dimeric protein the amino acids at position corresponding to E345, E430 and S440 in a human IgG1 heavy chain are
(a) R, and Y, respectively;
(b) K, G, and Y, respectively;
(c) R, S, and Y, respectively; or
(d) R, G, and W, respectively.

44. The composition of claim 18, wherein
(a) in both Fc polypeptides of the dimeric protein, the amino acids corresponding to E345, E430 and S440 in human IgG1 heavy chain are R, G and Y, respectively; and
(b) the composition further comprises a second dimeric protein comprising a first Fc polypeptide and a second Fc polypeptide, each Fc polypeptide comprising at least $C_H2$ and $C_H3$ regions of a human IgG1, IgG2, IgG3, or IgG4, wherein in both Fc polypeptides of the second dimeric protein the amino acids corresponding to E345, E430 and S440 in a human IgG1 heavy chain are R, G and K, respectively.

45. The composition of claim 18, wherein in one or both Fc polypeptides, the amino acids at the positions corresponding to E345, E430, and S440 are R, G, and Y, respectively; K, G, and Y, respectively; R, S, and Y, respectively; or R, G, and W, respectively.

* * * * *

UNITED STATES PATENT AND TRADEMARK OFFICE
CERTIFICATE OF CORRECTION

PATENT NO. : 11,180,572 B2
APPLICATION NO. : 14/413178
DATED : November 23, 2021
INVENTOR(S) : Rob N. De Jong et al.

It is certified that error appears in the above-identified patent and that said Letters Patent is hereby corrected as shown below:

In the Claims

At Column 135, Claim number 43, Line number 6, please insert -- G, -- after "R,"

Signed and Sealed this
Seventh Day of June, 2022

*Katherine Kelly Vidal*

Katherine Kelly Vidal
*Director of the United States Patent and Trademark Office*